US009043994B2

(12) United States Patent
Stern et al.

(10) Patent No.: US 9,043,994 B2
(45) Date of Patent: Jun. 2, 2015

(54) CRE-LOX BASED GENE KNOCKDOWN CONSTRUCTS AND METHODS OF USE THEREOF

(75) Inventors: Patrick Stern, Cambridge, MA (US); Richard Hynes, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 787 days.

(21) Appl. No.: 12/076,001

(22) Filed: Mar. 12, 2008

(65) Prior Publication Data

US 2009/0187997 A1 Jul. 23, 2009

Related U.S. Application Data

(60) Provisional application No. 60/906,511, filed on Mar. 13, 2007, provisional application No. 60/935,154, filed on Jul. 27, 2007.

(51) Int. Cl.
*A01K 67/027* (2006.01)
*C12N 15/85* (2006.01)

(52) U.S. Cl.
CPC ......... *A01K 67/0275* (2013.01); *A01K 2207/05* (2013.01); *A01K 2217/058* (2013.01); *A01K 2217/206* (2013.01); *A01K 2227/105* (2013.01); *C12N 15/8509* (2013.01); *C12N 2800/30* (2013.01); *C12N 2840/007* (2013.01); *C12N 2840/102* (2013.01)

(58) Field of Classification Search
USPC ............. 435/6.11, 91.1, 91.31, 455, 375, 6.1, 435/320.1, 350, 477; 514/44; 536/23.1, 536/24.5
See application file for complete search history.

(56) References Cited

U.S. PATENT DOCUMENTS

| | | | |
|---|---|---|---|
| 5,795,737 A | 8/1998 | Seed et al. | |
| 5,804,387 A | 9/1998 | Cormack et al. | |
| 5,874,304 A | 2/1999 | Zolotukhin | |
| 5,922,687 A | 7/1999 | Mann et al. | |
| 5,985,847 A | 11/1999 | Carson et al. | |
| 6,953,688 B2 | 10/2005 | Ferrick et al. | |
| 7,074,611 B2* | 7/2006 | Chambon et al. | 435/320.1 |
| 7,090,976 B2 | 8/2006 | Anderson et al. | |
| 7,612,195 B2 | 11/2009 | Grueneberg et al. | |
| 2001/0049144 A1 | 12/2001 | Rivera et al. | |
| 2005/0075492 A1 | 4/2005 | Chen et al. | |
| 2005/0130919 A1 | 6/2005 | Xu et al. | |
| 2005/0201991 A1 | 9/2005 | Andrews et al. | |
| 2005/0289659 A1 | 12/2005 | Jacks et al. | |
| 2007/0044164 A1* | 2/2007 | Dickins et al. | 800/14 |
| 2007/0065912 A1* | 3/2007 | Carson et al. | 435/69.1 |
| 2009/0004668 A1* | 1/2009 | Chen et al. | 435/6 |
| 2009/0187997 A1 | 7/2009 | Stern et al. | |
| 2009/0217397 A1 | 8/2009 | Stern et al. | |
| 2012/0214242 A1 | 8/2012 | Stern et al. | |

FOREIGN PATENT DOCUMENTS

| | | |
|---|---|---|
| WO | WO 9742320 | 11/1997 |
| WO | WO 9821355 | 5/1998 |
| WO | WO 0011092 | 3/2000 |
| WO | WO 0129208 A1 * | 4/2001 |
| WO | WO 2004/029219 A2 | 4/2004 |
| WO | WO 2005/007877 A2 | 1/2005 |
| WO | WO 2006/003215 A2 | 1/2006 |
| WO | WO 2007/149246 | 12/2007 |

OTHER PUBLICATIONS

Denning and Priddle. Reproduction, 126:1-11, 2003.*
Pera et al. Journal of Cell Science 113: 5-10 , 2000.*
Stern et al., PNAS, 105(37): 13895-13900, 2008.*
Araki et al. Nucleic Acids Res., 30(19): 1-8, 2002.*
Doench et al., Genes and development, vol. 18, No. 5, pp. 504-511 (2004).*
Opalinska et al., Nature rev., vol. 1, pp. 503-514 (2004).*
Spivak et al, 1991, J. Virol., 65:6800-6810.
N. Sternberg et al, J. Mol. Biol., 187:197-212 (1986).
McGeoch et al, 1988, J. Gen. Virol., 69:1531-1574.
Klamut et al., (1990) Mol. Cell Biol.163-205.
Buskin and Hauschka, (1989) Mol. Cell Biol. 9:2627.
Mar and Ordahl, (1988) Proc. Natl. Acad. Sci. USA. 85:6404.
Mader, S. and White, J.H. (1993) Proc. Natl. Acad. Sci. USA 90:5603-5607.
Spencer, D.M. et al 1993) Science 262:1019-1024.
Manome, Y. Et al. (1993) Biochemistry 32:10607-10613.
Datta, R. et al. (1992) Proc. Natl. Acad, Sci. USA 89: 1014-10153.
Bennet (1998), infra; Crameri et al. Nature Biotechnol. 14:315-319 (1996).
Lee et al Gene 216:55-65 (1998).
Furth et al. (1992), Anal Biochem 205:365-368.
Chang et al., J. Virol. (2001) 75:3469-3473.
Liu et al., Gene Ther. (1999) 6:1258-1266.
Wolff et al., Science (1990) 247: 1465-1468.
Zhang et al., Hum. Gene Ther. (1999) 10:1735-1737.
Zhang et al., Gene Ther. (1999) 7:1344-1349.
Acsadi et al., New Biot. (1991) 3:71-81.
Hickman et al., Hum. Gen. Ther. (1994) 5:1477-1483.
Hayashi S. and McMahon AP. Dev Biol. Apr. 15, 2002;244(2):305-18.
Tang et al. Nature 356:152-154 (1992).
Qui L. et al. A Construct with fluorescent Indicators for Conditional Expression of miRNA. BMC Biotechnology. Oct. 2008, vol. 8. pp. 1-38, see entire document.
Stegmeier F. et al. A lentiviral microRNA-based system for single-copy polymerase II-regulated RNA interference in mammalian cells. PNAS. Sep. 2005, vol. 102. No. 37, pp. 13212-13217, see entire document.

(Continued)

*Primary Examiner* — Jane Zara
(74) *Attorney, Agent, or Firm* — Wolf, Greenfield & Sacks, P.C.

(57) ABSTRACT

The present invention relates to vectors, compositions and methods for conditional, Cre-lox regulated, RNA interference. The vectors allow for spatial and temporal control of miRNA expression in vivo.

11 Claims, 18 Drawing Sheets

(56) References Cited

OTHER PUBLICATIONS

Horlick and Benfield 1989 Mol. Cell Biol 9:2396.

International Search Report and Written Opinion dated Sep. 8, 2008 for Application No. PCT/US2007/013601.

International Preliminary Report on Patentability dated Dec. 16, 2008 for Application No. PCT/US2007/013601.

International Search Report and Written Opinion dated Nov. 19, 2008 for Application No. PCT/US2008/003225.

International Preliminary Report on Patentability dated Sep. 15, 2009 for Application No. PCT/US2008/003225.

[No. Author Listed], RNAi Codex, p53 in *Mus musculus* that targets nucleotides 1224-1245 of NM0116440. Accessed and retrieved from RNAi Codex at http://codex.cshl.edu/ on Feb. 21, 2013.

Berezikov et al., Many novel mammalian microRNA candidates identified by extensive cloning and RAKE analysis. Genome Res. Oct. 2006;16(10):1289-98. Epub Sep. 5, 2006.

Chang et al., Lessons from Nature: microRNA-based shRNA libraries. Nat Methods. Sep. 2006;3(9):707-14.

Dickins et al., Probing tumor phenotypes using stable and regulated synthetic microRNA precursors. Nat Genet. Nov. 2005;37(11):1289-95. Epub Oct. 2, 2005.

Donnelly et al., The 'cleavage' activities of foot-and-mouth disease virus 2A site-directed mutants and naturally occurring '2A-like' sequences. J Gen Virol. May 2001;82(Pt. 5):1027-41.

GenBank Submission; NIH/NCBI, Accession No. AY_445633.1. Delaitre et al., Nov. 19, 2003.

GenBank Submission; NIH/NCBI, Accession No. NM_011640.3. "*Mus musculus* transformation related protein 53 (Trp53), transcript variant 1, mRNA," first submitted on Jan. 25, 2000, accessed http://www.ncbi.nih.gov/ on May 23, 2010, three printout pages are enclosed.

Grez et al., Embryonic stem cell virus, a recombinant murine retrovirus with expression in embryonic stem cells. Proc Natl Acad Sci U S A. Dec. 1990;87(23):9202-6.

He et al., MicroRNAs: small RNAs with a big role in gene regulation. Nat Rev Genet. Jul. 2004;5(7):522-31.

Kamanu et al., Exploration of miRNA families for hypotheses generation. Scientific Reports. Oct. 15, 2013;3:2940. doi: 10.1038/srep02940.

Kilby et al., Site-specific recombinases: tools for genome engineering. Trends Genet. Dec. 1993;9(12):413-21.

Mogil et al., Heritability of nociception I: responses of 11 inbred mouse strains on 12 measures of nociception. Pain. Mar. 1999;80(1-2):67-82.

Monroe et al., RAG2:GFP knockin mice reveal novel aspects of RAG2 expression in primary and peripheral lymphoid tissues. Immunity. Aug. 1999;11(2):201-12.

Pang et al., RN Adb 2.0—an expanded database of mammalian non-coding RNAs. Nucleic Acids Res. Jan. 2007;35(Database issue):D178-82. Epub Dec. 1, 2006.

Rescher et al., Annexins—unique membrane binding proteins with diverse functions. J Cell Sci. Jun. 1, 2004;117(Pt 13):2631-9.

Ritchie et al., RNA stem-loops: to be or not to be cleaved by RNAse III. RNA. Apr. 2007;13(4):457-62. Epub Feb. 13, 2007.

Sauer, Site-specific recombination: developments and applications. Curr Opin Biotechnol. Oct. 1994;5(5):521-7.

Schnutgen et al., A directional strategy for monitoring Cre-mediated recombination at the cellular level in the mouse. Nat Biotechnol. May 2003;21(5):562-5. Epub Mar. 31, 2003.

Shin et al., A single lentiviral vector platform for microRNA-based conditional RNA interference and coordinated transgene expression. Proc Natl Acad Sci U S A. Sep. 12, 2006;103(37):13759-64. Epub Aug. 31, 2006.

Sigmund, Viewpoint: are studies in genetically altered mice out of control? Arterioscler Thromb Vasc Biol. Jun. 2000;20(6):1425-9.

\* cited by examiner

MSCV FLIP vector pLB2 FLIP vector

FLIP Vector for Knockdown of 1 or 2 Genes

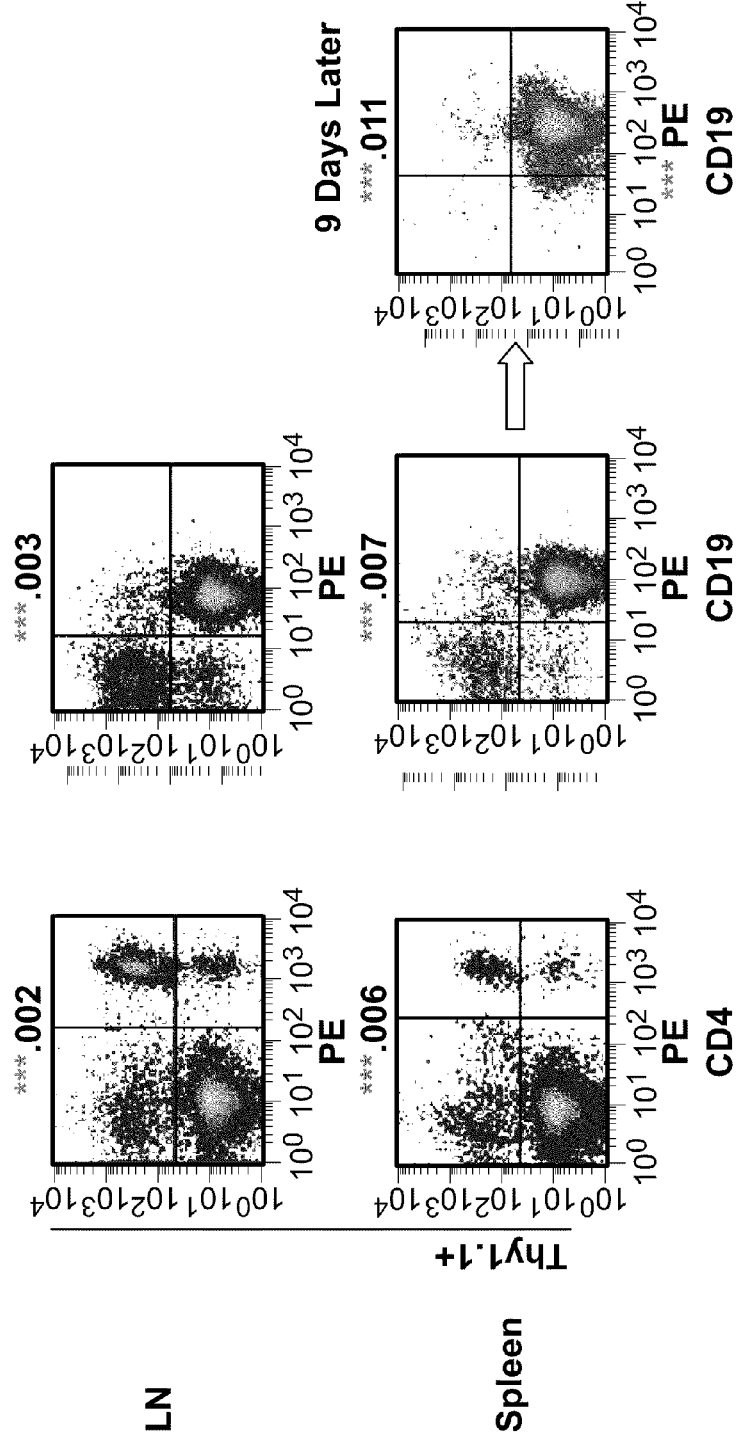
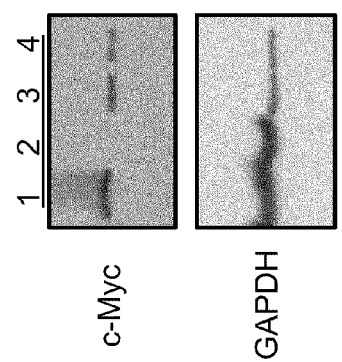
Figure 11A
Figure 11B

SEQUENCE LISTING

<160> NUMBER OF SEQ ID NOS: 28

<210> SEQ ID NO 1
<211> LENGTH: 466
<212> TYPE: DNA
<213> ORGANISM: Artificial
<220> FEATURE:
<223> OTHER INFORMATION: GFP-miR30 flanked by NotI-PmeI and splice donor
      and acceptor sequences

<400> SEQUENCE: 1

```
agtagcggcc caattgcagg tgagtgggcg gccgcaagcc ttgttaagtg ctcgcttcgg      60
cagcacatat actatgtttg aatgaggctt cagtacttta cagaatcgtt gcctgcacat     120
cttggaaaca cttgctggga ttacttcttc aggttaaccc aacagaaggc tcgagaaggt     180
atattgctgt tgacagtgag cgagctcccg tgaattggaa tcctagtgaa gccacagatg     240
taggattcca attcagcggg agcctgccta ctgcctcgga attcaagggg ctactttagg     300
agcaattatc ttgtttacta aaactgaata ccttgctatc tctttgatac attttttacaa    360 agctgaatta aaatggtata aattaaatca cttttttcaa ttggaagact aatgcgttta     420
aaccCCtgac tctcccctttt ttttttttcct ccaggtatgc ataaac                  466
```

<210> SEQ ID NO 2
<211> LENGTH: 467
<212> TYPE: DNA
<213> ORGANISM: Artificial
<220> FEATURE:
<223> OTHER INFORMATION: GFP-miR30 flanked by NotI-PmeI and splice donor
      and acceptor sequences

<400> SEQUENCE: 2

```
agtagcggcc caattgcagg tgagtgggcg gccgcaagcc ttgttaagtg ctcgcttcgg      60
cagcacatat actatgtttg aatgaggctt cagtacttta cagaatcgtt gcctgcacat     120
cttggaaaca cttgctggga ttacttcttc aggttaaccc aacagaaggc tcgagaaggt     180
atattgctgt tgacagtgag cgccgacatt tcaccatcat tatttagtga agccacagat     240
gtaaataatg atggtgaaat gtcgttgcct actgcctcgg aattcaaggg gctactttag     300
gagcaattat cttgtttact aaaactgaat accttgctat ctctttgata cattttttaca    360 aagctgaatt aaaatggtat aaattaaatc acttttttca attggaagac taatgcgttt     420 aaaccCCctga ctctcccctt ttttttttcc tccaggtatg cataaac                  467
```

<210> SEQ ID NO 3
<211> LENGTH: 10849
<212> TYPE: DNA
<213> ORGANISM: Artificial
<220> FEATURE:
<223> OTHER INFORMATION: pLB2 construct comprising the FLIP cassette
      containing miR30 targeting FireFly luciferase

<400> SEQUENCE: 3

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac     240
attgattatt gactagtcat gttctttcct gcgttatccc ctgattctgt ggataaccgt     300
attaccgcct ttgagtgagc tgataccgct cgccgcagcc gaacgaccga gcgcagcgag     360
```

```
tcagtgagcg aggaagcgga agagcgccca atacgcaaac cgcctctccc cgcgcgttgg    420
ccgattcatt aatgcagctg gcacgacagg tttcccgact ggaaagcggg cagtgagcgc    480
aacgcaatta atgtgagtta gctcactcat taggcacccc aggctttaca ctttatgctt    540
ccggctcgta tgttgtgtgg aattgtgagc ggataacaat ttcacacagg aaacagctat    600
gaccatgatt acgccaagcg cgcaattaac cctagcttaa tgtagtctta tgcaatactc    660
ttgtagtctt gcaacatggt aacgatgagt tagcaacatg ccttacaagg agagaaaaag    720
caccgtgcat gccgattggt ggaagtaagg tggtacgatc gtgccttatt aggaaggcaa    780
cagacgggtc tgacatggat tggacgaacc actgaattgc cgcattgcag agatattgta    840
tttaagtgcc tagctcgata caataaacgg gtctctctgg ttagaccaga tctgagcctg    900
ggagctctct ggctaactag ggaacccact gcttaagcct caataaagct tgccttgagt    960
gcttcaagta gtgtgtgccc gtctgttgtg tgactctggt aactagagat ccctcagacc   1020
cttttagtca gtgtggaaaa tctctagcag tggcgcccga acagggactt gaaagcgaaa   1080
gggaaaccag aggagctctc tcgacgcagg actcggcttg ctgaagcgcg cacggcaaga   1140
ggcgaggggc ggcgactggt gagtacgcca aaattttga ctagcggagg ctagaaggag   1200
agagatgggt gcgagagcgt cagtattaag cggggagaa ttagatcgcg atgggaaaaa   1260
attcggttaa ggccaggggg aaagaaaaaa tataaattaa acatatagt atgggcaagc   1320
agggagctag aacgattcgc agttaatcct ggcctgttag aaacatcaga aggctgtaga   1380
caaatactgg gacagctaca accatcccctt cagacaggat cagaagaact tagatcatta   1440
tataatacag tagcaacccct ctattgtgtg catcaaagga tagagataaa agacaccaag   1500
gaagctttag acaagataga ggaagagcaa aacaaaagta agaccaccgc acagcaagcg   1560
gccggccgcg ctgatcttca gacctggagg aggagatatg agggacaatt ggagaagtga   1620
attatataaa tataaagtag taaaaattga accattagga gtagcaccca ccaaggcaaa   1680
gagaagagtg gtgcagagag aaaaaagagc agtgggaata ggagctttgt tccttgggtt   1740
cttgggagca gcaggaagca ctatgggcgc agcgtcaatg acgctgacgg tacaggccag   1800
acaattattg tctggtatag tgcagcagca gaacaatttg ctgagggcta ttgaggcgca   1860
acagcatctg ttgcaactca gtctggggg catcaagcag ctccaggcaa gaatcctggc   1920
tgtggaaaga tacctaaagg atcaacagct cctggggatt tggggttgct ctggaaaact   1980
catttgcacc actgctgtgc cttggaatgc tagttggagt aataaatctc tggaacagat   2040
ttggaatcac acgacctgga tggagtggga cagagaaatt aacaattaca caagcttaat   2100
acactcctta attgaagaat cgcaaaacca gcaagaaaag aatgaacaag aattattgga   2160
attagataaa tgggcaagtt tgtggaattg gtttaacata acaaattggc tgtggtatat   2220
aaaattattc ataatgatag taggaggctt ggtaggttta agaatagttt ttgctgtact   2280
ttctatagtg aatagagtta ggcagggata ttcaccatta tcgtttcaga cccacctccc   2340
aaccccgagg ggacccgaca ggcccgaagg aatagaagaa gaaggtggag agagagacag   2400
agacagatcc attcgattag tgaacggatc ggcactgcgt gcgccaattc tgcagacaaa   2460
tggcagtatt catccacaat tttaaaagaa aaggggggat tggggggtac agtgcagggg   2520
aaagaatagt agacataata gcaacagaca tacaaactaa agaattacaa aaacaaatta   2580
caaaaattca aaattttcgg gtttattaca gggacagcag agatccagtt tggttagtac   2640
cgggcccggt gctttgctct gagccagccc accagtttgg aatgactcct ttttatgact   2700
tgaattttca gtataaagt ctagtgctaa atttaatttg aacaactgta tagttttgc    2760
```

```
tggttgggggg aaggaaaaaa aatggtggca gtgttttttt cagaattaga agtgaaatga    2820
aaacttgttg tgtgtgagga tttctaatga catgtggtgg ttgcatactg agtgaagccg    2880
gtgagcattc tgccatgtca cccctcgtg  ctcagtaatg tactttacag aaatcctaaa    2940
ctcaaaagat tgatataaac catgcttctt gtgtatatcc ggtctcttct ctgggtagtc    3000
tcactcagcc tgcatttctg ccagggcccg ctctagatct agacggttga tctggcctcc    3060
gcgccgggtt ttggcgcctc ccgcgggcgc ccccctcctc acggcgagcg ctgccacgtc    3120
agacgaaggg cgcaggagcg ttcctgatcc ttccgcccgg acgctcagga cagcggcccg    3180
ctgctcataa gactcggcct tagaacccca gtatcagcag aaggacattt taggacggga    3240
cttgggtgac tctagggcac tggttttctt tccagagagc ggaacaggcg aggaaaagta    3300
gtcccttctc ggcgattctg cggagggatc tccgtggggc ggtgaacgcc gatgattata    3360
taaggacgcg ccgggtgtgg cacagctagt tccgtcgcag ccgggatttg ggtcgcggtt    3420
cttgtttgtg gatcgctgtg atcgtcactt ggtgagttgc gggctgctgg gctgccgggg    3480
gctttcgtgg ccgccgggcc gctcggtggg acggaagcgt gtggagagac cgccaagggc    3540
tgtagtctgg gtccgcgagc aaggttgccc tgaactgggg gttgggggga gcgcacaaaa    3600
tggcggctgt tcccgagtct tgaatggaag acgcttgtaa ggcgggctgt gaggtcgttg    3660
aaacaaggtg gggggcatgg tgggcggcaa gaacccaagg tcttgaggcc ttcgctaatg    3720
cgggaaagct cttattcggg tgagatgggc tggggcacca tctgggacc  ctgacgtgaa    3780 gtttgtcact gactggagaa ctcgggtttg tcgtctggtt gcggggcgg  cagttatgcg    3840 gtgccgttgg gcagtgcacc cgtacctttg ggagcgcgcg cctcgtcgtg tcgtgacgtc    3900
acccgttctg ttggcttata atgcaggggtg gggccacctg ccggtaggtg tgcggtaggc    3960
ttttctccgt cgcaggacgc agggttcggg cctagggtag gctctcctga atcgacaggc    4020
gccggacctc tggtgagggg agggataagt gaggcgtcag tttctttggt cggttttatg    4080
tacctatctt cttaagtagc tgaagctccg gttttgaact atgcgctcgg ggttggcgag    4140
tgtgttttgt gaagttttt  aggcacctt  tgaaatgtaa tcatttgggt caatatgtaa    4200
ttttcagtgt tagactagta aattgtccgc taaattctgg ccgttttgg  cttttttgtt    4260 agacgaagta cgcgctagcc gttaataagc ctcgatgcgg atccataact tcgtatagga    4320
taccttatac gaagttatct caggtaccgc caccatgacc gagtacaagc ccacggtgcg    4380
cctcgccacc cgcgacgacg tccccagggc cgtacgcacc ctcgccgccg cgttcgccga    4440
ctaccccgcc acgcgccaca ccgtcgatcc ggaccgccac atcgagcggg tcaccgagct    4500
gcaagaactc ttcctcacgc gcgtcgggct cgacatcggc aaggtgtggg tcgcggacga    4560
cggcgccgcg gtgcggtct  ggaccacgcc ggagagcgtc gaagcggggg cggtgttcgc    4620
cgagatcggc ccgcgcatgg ccgagttgag cggttcccgg ctggccgcgc agcaacagat    4680
ggaaggcctc ctggcgccgc accgccaa  ggagcccgcg tggttcctgg ccaccgtcgg    4740
cgtctcgccc gaccaccagg gcaagggtct gggcagcgcc gtcgtgctcc ccggagtgga    4800
ggcggccgag cgcgcggggg tgcccgcctt cctggagacc tccgcgcccc gcaacctccc    4860
cttctacgag cggctcggct tcaccgtcac cgccgacgtc gaggtgcccg aaggaccgcg    4920
cacctggtgc atgacccgca agcccggtgc cctgtacaag aaacagaaaa ttgtggcacc    4980
agtgaaacag actttgaatt ttgaccttct caagttggcg ggagacgtcg agtccaaccc    5040
tgggcccatg aacccagcca tcagcgtcgc tctcctgctc tcagtcttgc aggtgtcccg    5100
```

| | |
|---|---|
| agggcagaag gtgaccagcc tgacagcctg cctggtgaac caaaaccttc gcctggactg | 5160 |
| ccgccatgag aataacacca aggataactc catccagcat gagttcagcc tgacccgaga | 5220 |
| gaagaggaag cacgtgctct caggcaccct cgggataccc gagcacacgt accgctcccg | 5280 |
| cgtcaccctc tccaaccagc cctatatcaa ggtccttacc ctagccaact tcaccaccaa | 5340 |
| ggatgagggc gactactttt gtgagcttcg agtctcgggc gcgaatccca tgagctccaa | 5400 |
| taaaagtatc agtgtgtata gagacaaact ggtcaagtgt ggcggcataa gcctgctggt | 5460 |
| tcagaacaca tcctggatgc tgctgctgct gctttccctc tccctcctcc aagccctgga | 5520 |
| cttcatttct ctgtgatcta gaagccataa cttcgtatag tacacattat acgaagttat | 5580 |
| gtttaaacgc attagtcttc caattgaaaa aagtgattta atttatacca ttttaattca | 5640 |
| gctttgtaaa aatgtatcaa agagatagca aggtattcag ttttagtaaa caagataatt | 5700 |
| gctcctaaag tagccccttg aattccgagg cagtaggcag gctcccgctg aattggaatc | 5760 |
| ctacatctgt ggcttcacta ggattccaat tcacgggagc tcgctcactg tcaacagcaa | 5820 |
| tataccttct cgagccttct gttgggttaa cctgaagaag taatcccagc aagtgtttcc | 5880 |
| aagatgtgca gcaacgatt ctgtaaagta ctgaagcctc attcaaacat agtatatgtg | 5940 |
| ctgccgaagc gagcacttaa caaggcttgc ggccgctact tgtacagctc gtccatgccg | 6000 |
| agagtgatcc cggcggcggt cacgaactcc agcaggacca tgtgatcgcg cttctcgttg | 6060 |
| gggtctttgc tcagggcgga ctgggtgctc aggtagtggt tgtcgggcag cagcacgggg | 6120 |
| ccgtcgccga tgggggtgtt ctgctggtag tggtcggcga gctgcacgct gccgtcctcg | 6180 |
| atgttgtggc ggatcttgaa gttcaccttg atgccgttct tctgcttgtc ggccatgata | 6240 |
| tagacgttgt ggctgttgta gttgtactcc agcttgtgcc ccaggatgtt gccgtcctcc | 6300 |
| ttgaagtcga tgcccttcag ctcgatgcgg ttcaccaggg tgtcgccctc gaacttcacc | 6360 |
| tcggcgcggg tcttgtagtt gccgtcgtcc ttgaagaaga tggtgcgctc ctggacgtag | 6420 |
| ccttcgggca tggcggactt gaagaagtcg tgctgcttca tgtggtcggg gtagcggctg | 6480 |
| aagcactgca cgccgtaggt cagggtggtc acgagggtgg gccagggcac gggcagcttg | 6540 |
| ccggtggtgc agatgaactt cagggtcagc ttgccgtagg tggcatcgcc ctcgccctcg | 6600 |
| ccggacacgc tgaacttgtg gccgtttacg tcgccgtcca gctcgaccag gatgggcacc | 6660 |
| accccggtga acagctcctc gcccttgctc accatggtgg cgaccggtat aacttcgtat | 6720 |
| aaggtatcct atacgaagtt atccattcag gctgtgctag catcaatggc atggcacaaa | 6780 |
| gcttagccat aacttcgtat aatgtgtact atacgaagtt atccctgttt aagggttccg | 6840 |
| gttccactag gtacaattcg atatcaagct tatcgataat caacctctgg attacaaaat | 6900 |
| ttgtgaaaga ttgactggta ttcttaacta tgttgctcct tttacgctat gtggatacgc | 6960 |
| tgctttaatg cctttgtatc atgctattgc ttcccgtatg gctttcattt tctcctcctt | 7020 |
| gtataaatcc tggttgctgt ctctttatga ggagttgtgg cccgttgtca ggcaacgtgg | 7080 |
| cgtggtgtgc actgtgtttg ctgacgcaac ccccactggt tggggcattg ccaccacctg | 7140 |
| tcagctcctt tccgggactt tcgctttccc cctccctatt gccacggcgg aactcatcgc | 7200 |
| cgcctgcctt gcccgctgct ggacaggggc tcggctgttg gcactgacaa ttccgtggt | 7260 |
| gttgtcgggg aaatcatcgt cctttccttg gctgctcgcc tgtgttgcca cctggattct | 7320 |
| gcgcgggacg tccttctgct acgtcccttc ggccctcaat ccagcggacc ttccttcccg | 7380 |
| cggcctgctg ccggctctgc ggcctcttcc gcgtcttcgc cttcgccctc agacgagtcg | 7440 |
| gatctcccttt tgggccgcct ccccgcatcg ataccgtcga cctcgatcga gacctagaaa | 7500 |

```
aacatggagc aatcacaagt agcaatacag cagctaccaa tgctgattgt gcctggctag    7560
aagcacaaga ggaggaggag gtgggttttc cagtcacacc tcaggtacca agcatggggt    7620
aaagtactgt tctcatcaca tcatatcaag gttatatacc atcaatattg ccacagatgt    7680
tacttagcct tttaatattt ctctaattta gtgtatatgc aatgatagtt ctctgatttc    7740
tgagattgag tttctcatgt gtaatgatta tttagagttt ctctttcatc tgttcaaatt    7800
tttgtctagt tttattttt actgatttgt aagacttctt tttataatct gcatattaca    7860
attctcttta ctggggtgtt gcaaatattt tctgtcattc tatggcctga cttttcttaa    7920
tggtttttta attttaaaaa taagtcttaa tattcatgca atctaattaa caatcttttc    7980
tttgtggtta ggactttgag tcataagaaa tttttctcta cactgaagtc atgatggcat    8040
gcttctatat tattttctaa aagatttaaa gttttgcctt ctccatttag acttataatt    8100
cactggaatt tttttgtgtg tatggtatga catatgggtt cccttttatt ttttacatat    8160
aaatatattt ccctgttttt ctaaaaaaga aaaagatcat cattttccca ttgtaaaatg    8220
ccatattttt ttcataggtc acttacatat atcaatgggt ctgtttctga gctctactct    8280
attttatcag cctcactgtc tatccccaca catctcatgc tttgctctaa atcttgatat    8340
ttagtggaac attctttccc attttgttct acaagaatat ttttgttatt gtcttttggg    8400
cttctatata cattttagaa tgaggttggc aaggtaccct taagaccaat gacttacaag    8460
gcagctgtag atcttagcca ctttttaaaa gaaaaggggg gactggaagg gctaattcac    8520
tcccagctgc ttttttgcctg tactgggtct ctctggttag accagatctg agcctgggag    8580
ctctctggct aactagggaa cccactgctt aagcctcata aagctcgact gtgccttcta    8640
gttgccagcc atctgttgtt tgcccctccc ccgtgccttc cttgaccctg aaggtgccac    8700
ctcccactgt cctttcctaa taaaatgagg aaattgcatc gcattgtctg agtaggtgtc    8760
attctattct gggggggtggg gtggggcagg acagcaaggg ggaggattgg gaagacaata    8820
gcaggcatgc tggggatgcg gtccggactg tactgggtct ctctggttag accagatctg    8880
agcctgggag ctctctggct aactagggaa cccactgctt aagcctcaat aaagcttgcc    8940
ttgagtgctt caagtagtgt gtgcccgtct gttgtgtgac tctggtaact agagatccct    9000
cagacccttt tagtcagtgt ggaaaatctc tagcagcatg tgagcaaaag gccagcaaaa    9060
ggccaggaac cgtaaaaagg ccgcgttgct ggcgtttttc cataggctcc gcccccctga    9120
cgagcatcac aaaaatcgac gctcaagtca gaggtggcga aacccgacag gactataaag    9180
ataccaggcg tttccccctg gaagctccct cgtgcgctct cctgttccga ccctgccgct    9240
taccggatac ctgtccgcct ttctcccttc gggaagcgtg gcgctttctc atagctcacg    9300
ctgtaggtat ctcagttcgg tgtaggtcgt tcgctccaag ctgggctgtg tgcacgaacc    9360
ccccgttcag cccgaccgct gcgccttatc cggtaactat cgtcttgagt ccaacccggt    9420
aagacacgac ttatcgccac tggcagcagc cactggtaac aggattagca gagcgaggta    9480
tgtaggcggt gctacagagt tcttgaagtg gtggcctaac tacggctaca ctagaagaac    9540
agtatttggt atctgcgctc tgctgaagcc agttaccttc ggaaaaagag ttggtagctc    9600
ttgatccggc aaacaaacca ccgctggtag cggtggtttt tttgtttgca agcagcagat    9660
tacgcgcaga aaaaaaggat ctcaagaaga tcctttgatc ttttctacgg ggtctgacgc    9720
tcagtggaac gaaaactcac gttaagggat tttggtcatg agattatcaa aaaggatctt    9780
cacctagatc cttttaaatt aaaaatgaag ttttaaatca atctaaagta tatatgagta    9840
```

-continued

```
aacttggtct gacagttacc aatgcttaat cagtgaggca cctatctcag cgatctgtct    9900
atttcgttca tccatagttg cctgactccc cgtcgtgtag ataactacga tacgggaggg    9960
cttaccatct ggccccagtg ctgcaatgat accgcgagac ccacgctcac cggctccaga   10020
tttatcagca ataaaccagc cagccggaag ggccgagcgc agaagtggtc ctgcaactttt  10080
atccgcctcc atccagtcta ttaattgttg ccgggaagct agagtaagta gttcgccagt   10140
taatagtttg cgcaacgttg ttgccattgc tacaggcatc gtggtgtcac gctcgtcgtt   10200
tggtatggct tcattcagct ccggttccca acgatcaagg cgagttacat gatccccat    10260
gttgtgcaaa aaagcggtta gctccttcgg tcctccgatc gttgtcagaa gtaagttggc   10320
cgcagtgtta tcactcatgg ttatggcagc actgcataat tctcttactg tcatgccatc   10380
cgtaagatgc ttttctgtga ctggtgagta ctcaaccaag tcattctgag aatagtgtat   10440
gcggcgaccg agttgctctt gcccggcgtc aatacgggat aataccgcgc cacatagcag   10500
aactttaaaa gtgctcatca ttggaaaacg ttcttcgggg cgaaaactct caaggatctt   10560
accgctgttg agatccagtt cgatgtaacc cactcgtgca cccaactgat cttcagcatc   10620
ttttactttc accagcgttt ctgggtgagc aaaaacagga aggcaaaatg ccgcaaaaaa   10680
gggaataagg gcgacacgga aatgttgaat actcatactc ttcctttttc aatattattg   10740
aagcatttat cagggttatt gtctcatgag cggatacata tttgaatgta tttagaaaaa   10800
taaacaaata ggggttccgc gcacatttcc ccgaaaagtg ccacctgac               10849
```

<210> SEQ ID NO 4
<211> LENGTH: 2530
<212> TYPE: DNA
<213> ORGANISM: Artificial
<220> FEATURE:
<223> OTHER INFORMATION: pFLIP insert comprising an RNAi to p53

<400> SEQUENCE: 4

```
tccataactt cgtataggat acctatacg aagttatctc aggtaccgcc accatgaccg      60
agtacaagcc cacggtgcgc ctcgccaccc gcgacgacgt ccccagggcc gtacgcaccc    120
tcgccgccgc gttcgccgac taccccgcca cgcgccacac cgtcgatccg gaccgccaca    180
tcgagcgggt caccgagctg caagaactct tcctcacgcg cgtcgggctc gacatcggca    240
aggtgtgggt cgcggacgac ggcgccgcgg tggcggtctg gaccacgccg gagagcgtcg    300
aagcggggc ggtgttcgcc gagatcggcc cgcgcatggc cgagttgagc ggttcccggc     360
tggccgcgca gcaacagatg gaaggcctcc tggcgccgca ccgcccaag gagcccgcgt     420
ggttcctggc caccgtcggc gtctcgcccg accaccaggg caagggtctg ggcagcgccg    480
tcgtgctccc cggagtggag gcggccgagc gcgccgggt gccgccttc ctggagacct     540
ccgcgccccg caacctcccc ttctacgagc ggctcggctt caccgtcacc gccgacgtcg    600
aggtgcccga aggaccgcgc acctggtgca tgacccgcaa gcccggtgcc ctgtacaaga    660
aacagaaaat tgtggcacca gtgaaacaga ctttgaattt tgaccttctc aagttggcgg    720
gagacgtcga gtccaaccct gggcccatga acccagccat cagcgtcgct ctcctgctct    780
cagtcttgca ggtgtcccga gggcagaagg tgaccagcct gacagcctgc tggtgaacc    840
aaaaccttcg cctggactgc cgccatgaga ataacaccaa ggataactcc atccagcatg    900
agttcagcct gacccgagag aagaggaagc acgtgctctc aggcaccctc gggatacccg    960
agcacacgta ccgctcccgc gtcaccctct ccaaccagcc ctatatcaag gtccttaccc   1020
tagccaactt caccaccaag gatgagggcg actactttg tgagcttcga gtctcgggcg   1080
```

```
cgaatcccat gagctccaat aaaagtatca gtgtgtatag agacaaactg gtcaagtgtg    1140
gcggcataag cctgctggtt cagaacacat cctggatgct gctgctgctg ctttccctct    1200
ccctcctcca agccctggac ttcatttctc tgtgatctag aagccataac ttcgtatagt    1260
acacattata cgaagttatg tttaaacgca ttagtcttcc aattgaaaaa agtgatttaa    1320
tttataccat tttaattcag ctttgtaaaa atgtatcaaa gagatagcaa ggtattcagt    1380
tttagtaaac aagataattg ctcctaaagt agcccttga attccgaggc agtaggcatc    1440
cactacaagt acatgtgtaa tacatctgtg gcttcactat tacacatgta cttgtagtgg    1500
gcgctcactg tcaacagcaa tataccttct cgagccttct gttgggttaa cctgaagaag    1560
taatcccagc aagtgtttcc aagatgtgca ggcaacgatt ctgtaaagta ctgaagcctc    1620
attcaaacat agtatatgtg ctgccgaagc gagcacttaa caaggcttgc ggccgctact    1680
tgtacagctc gtccatgccg agagtgatcc cggcggcggt cacgaactcc agcaggacca    1740
tgtgatcgcg cttctcgttg gggtctttgc tcagggcgga ctgggtgctc aggtagtggt    1800
tgtcgggcag cagcacgggg ccgtcgccga tgggggtgtt ctgctggtag tggtcggcga    1860
gctgcacgct gccgtcctcg atgttgtggc ggatcttgaa gttcaccttg atgccgttct    1920
tctgcttgtc ggccatgata tagacgttgt ggctgttgta gttgtactcc agcttgtgcc    1980
ccaggatgtt gccgtcctcc ttgaagtcga tgcccttcag ctcgatgcgg ttcaccaggg    2040
tgtcgccctc gaacttcacc tcggcgcggg tcttgtagtt gccgtcgtcc ttgaagaaga    2100
tggtgcgctc ctggacgtag ccttcgggca tggcggactt gaagaagtcg tgctgcttca    2160
tgtggtcggg gtagcggctg aagcactgca cgccgtaggt cagggtggtc acgagggtgg    2220
gccagggcac gggcagcttg ccggtggtgc agatgaactt cagggtcagc ttgccgtagg    2280
tggcatcgcc ctcgccctcg ccggacacgc tgaacttgtg gccgtttacg tcgccgtcca    2340
gctcgaccag gatgggcacc accccggtga acagctcctc gcccttgctc accatggtgg    2400
cgaccggtat aacttcgtat aaggtatcct atacgaagtt atccattcag gctgtgctag    2460
catcaatggc atggcacaaa gcttagccat aacttcgtat aatgtgtact atacgaagtt    2520
atcccgggtt                                                           2530
```

<210> SEQ ID NO 5
<211> LENGTH: 1205
<212> TYPE: DNA
<213> ORGANISM: Artificial
<220> FEATURE:
<223> OTHER INFORMATION: GFP-miR30 flanked by a single loxP site

<400> SEQUENCE: 5

```
atggataact tcgtatagga taccttatac gaagttatac cggtcgccac catggtgagc      60
aagggcgagg agctgttcac cggggtggtg cccatcctgg tcgagctgga cggcgacgta     120
aacggccaca agttcagcgt gtccggcgag ggcgagggcg atgccaccta cggcaagctg     180
accctgaagt tcatctgcac caccggcaag ctgcccgtgc cctggcccac cctcgtgacc     240
accctgacct acggcgtgca gtgcttcagc cgctaccccg accacatgaa gcagcacgac     300
ttcttcaagt ccgccatgcc cgaaggctac gtccaggagc gcaccatctt cttcaaggac     360
gacggcaact acaagacccg cgccgaggtg aagttcgagg gcgacaccct ggtgaaccgc     420
atcgagctga agggcatcga cttcaaggag gacggcaaca tcctggggca caagctggag     480
tacaactaca acagccacaa cgtctatatc atggccgaca agcagaagaa cggcatcaag     540
```

| | |
|---|---|
| gtgaacttca agatccgcca caacatcgag gacggcagcg tgcagctcgc cgaccactac | 600 |
| cagcagaaca cccccatcgg cgacggcccc gtgctgctgc ccgacaacca ctacctgagc | 660 |
| acccagtccg ccctgagcaa agaccccaac gagaagcgcg atcacatggt cctgctggag | 720 |
| ttcgtgaccg ccgccgggat cactctcggc atggacgagc tgtacaagta gcggccgcaa | 780 |
| gccttgttaa gtgctcgctt cggcagcaca tatactatgt ttgaatgagg cttcagtact | 840 |
| ttacagaatc gttgcctgca catcttggaa acacttgctg ggattacttc ttcaggttaa | 900 |
| cccaacagaa ggctcgagaa ggtatattgc tgttgacagt gagcgcccac tacaagtaca | 960 |
| tgtgtaatag tgaagccaca gatgtattac acatgtactt gtagtggatg cctactgcct | 1020 |
| cggaattcaa ggggctactt taggagcaat tatcttgttt actaaaactg aataccttgc | 1080 |
| tatctctttg atacattttt acaaagctga attaaaatgg tataaattaa atcacttttt | 1140 |
| tcaattggaa gactaatgcg tttaaacata acttcgtata atgtgtacta tacgaagtta | 1200 |
| tggct | 1205 |

<210> SEQ ID NO 6
<211> LENGTH: 10570
<212> TYPE: DNA
<213> ORGANISM: Artificial
<220> FEATURE:
<223> OTHER INFORMATION: pLB2 comprising the FLIP cassette

<400> SEQUENCE: 6

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgctgcttc gcgatgtacg ggccagatat acgcgttgac | 240 |
| attgattatt gactagtcat gttctttcct gcgttatccc ctgattctgt ggataaccgt | 300 |
| attaccgcct ttgagtgagc tgataccgct cgccgcagcc gaacgaccga cgcagcgag | 360 |
| tcagtgagcg aggaagcgga agagcgccca atacgcaaac cgcctctccc cgcgcgttgg | 420 |
| ccgattcatt aatgcagctg gcacgacagg tttcccgact ggaaagcggg cagtgagcgc | 480 |
| aacgcaatta atgtgagtta gctcactcat taggcacccc aggctttaca ctttatgctt | 540 |
| ccggctcgta tgttgtgtgg aattgtgagc ggataacaat ttcacacagg aaacagctat | 600 |
| gaccatgatt acgccaagcg cgcaattaac cctagcttaa tgtagtctta tgcaatactc | 660 |
| ttgtagtctt gcaacatggt aacgatgagt tagcaacatg ccttacaagg agagaaaaag | 720 |
| caccgtgcat gccgattggt ggaagtaagg tggtacgatc gtgccttatt aggaaggcaa | 780 |
| cagacgggtc tgacatggat tggacgaacc actgaattgc cgcattgcag agatattgta | 840 |
| tttaagtgcc tagctcgata caataaacgg gtctctctgg ttagaccaga tctgagcctg | 900 |
| ggagctctct ggctaactag gaacccact gcttaagcct caataaagct tgccttgagt | 960 |
| gcttcaagta gtgtgtgccc gtctgttgtg tgactctggt aactagagat ccctcagacc | 1020 |
| cttttagtca gtgtggaaaa tctctagcag tggcgcccga acagggactt gaaagcgaaa | 1080 |
| gggaaaccag aggagctctc tcgacgcagg actcggcttg ctgaagcgcg cacggcaaga | 1140 |
| ggcgaggggc ggcgactggt gagtacgcca aaaattttga ctagcggagg ctagaaggag | 1200 |
| agagatgggg gcgagagcgt cagtattaag cggggagaa ttagatcgcg atgggaaaaa | 1260 |
| attcggttaa ggccagggg aaagaaaaaa tataaattaa aacatatagt atgggcaagc | 1320 |
| agggagctag aacgattcgc agttaatcct ggcctgttag aaacatcaga aggctgtaga | 1380 |

```
caaatactgg gacagctaca accatcccctt cagacaggat cagaagaact tagatcatta   1440
tataatacag tagcaacccct ctattgtgtg catcaaagga tagagataaa agacaccaag   1500
gaagctttag acaagataga ggaagagcaa aacaaaagta agaccaccgc acagcaagcg   1560
gccggccgcg ctgatcttca gacctggagg aggagatatg agggacaatt ggagaagtga   1620
attatataaa tataaagtag taaaaattga accattagga gtagcaccca ccaaggcaaa   1680
gagaagagtg gtgcagagag aaaaaagagc agtgggaata ggagctttgt tccttgggtt   1740
cttgggagca gcaggaagca ctatgggcgc agcgtcaatg acgctgacgg tacaggccag   1800
acaattattg tctggtatag tgcagcagca gaacaatttg ctgagggcta ttgaggcgca   1860
acagcatctg ttgcaactca cagtctgggg catcaagcag ctccaggcaa gaatcctggc   1920
tgtggaaaga tacctaaagg atcaacagct cctggggatt tggggttgct ctggaaaact   1980
catttgcacc actgctgtgc cttggaatgc tagttggagt aataaatctc tggaacagat   2040
ttggaatcac acgacctgga tggagtggga cagagaaatt aacaattaca caagcttaat   2100
acactcctta attgaagaat cgcaaaacca gcaagaaaag aatgaacaag aattattgga   2160
attagataaa tgggcaagtt tgtggaattg gtttaacata acaaattggc tgtggtatat   2220
aaaattattc ataatgatag taggaggctt ggtaggttta agaatagttt ttgctgtact   2280
ttctatagtg aatagagtta ggcagggata ttcaccatta tcgtttcaga cccacctccc   2340
aaccccgagg ggacccgaca ggcccgaagg aatagaagaa gaaggtggag agagagacag   2400
agacagatcc attcgattag tgaacggatc ggcactgcgt gcgccaattc tgcagacaaa   2460
tggcagtatt catccacaat tttaaaagaa aaggggggat tggggggtac agtgcagggg   2520
aaagaatagt agacataata gcaacagaca tacaaactaa agaattacaa aaacaaatta   2580
caaaaattca aaattttcgg gtttattaca gggacagcag agatccagtt tggttagtac   2640
cgggcccgt gctttgctct gagccagccc accagtttgg aatgactcct ttttatgact   2700
tgaattttca agtataaagt ctagtgctaa atttaatttg aacaactgta tagttttttgc   2760
tggttggggg aaggaaaaaa aatggtggca gtgtttttttt cagaattaga agtgaaatga   2820
aaacttgttg tgtgtgagga tttctaatga catgtggtgg ttgcatactg agtgaagccg   2880
gtgagcattc tgccatgtca ccccctcgtg ctcagtaatg tactttacag aaatcctaaa   2940
ctcaaaagat tgatataaac catgcttctt gtgtatatcc ggtctcttct ctgggtagtc   3000
tcactcagcc tgcatttctg ccagggcccg ctctagatct agacggttga tctggcctcc   3060
gcgccgggtt ttggcgcctc ccgcgggcgc cccctcctc acggcgagcg ctgccacgtc   3120
agacgaaggg cgcaggagcg ttcctgatcc ttccgcccgg acgctcagga cagcggcccg   3180
ctgctcataa gactcggcct agaaccccca gtatcagcag aaggacattt taggacggga   3240
cttgggtgac tctagggcac tggttttctt tccagagagc ggaacaggcg aggaaaagta   3300
gtccccttctc ggcgattctg cggagggatc tccgtgggc ggtgaacgcc gatgattata   3360
taaggacgcg ccgggtgtgg cacagctagt tccgtcgcag ccgggatttg ggtcgcggtt   3420
cttgtttgtg gatcgctgtg atcgtcactt ggtgagttgc gggctgctgg gctggccggg   3480
gctttcgtgg ccgccgggcc gctcggtggg acggaagcgt gtggagagac cgccaagggc   3540
tgtagtctgg gtccgcgagc aaggttgccc tgaactgggg gttgggggga gcgcacaaaa   3600
tggcggctgt tcccgagtct tgaatggaag acgcttgtaa ggcgggctgt gaggtcgttg   3660
aaacaaggtg gggggcatgg tgggcggcaa gaacccaagg tcttgaggcc ttcgctaatg   3720
```

```
cgggaaagct cttattcggg tgagatgggc tggggcacca tctggggacc ctgacgtgaa    3780
gtttgtcact gactggagaa ctcgggtttg tcgtctggtt gcgggggcgg cagttatgcg    3840
gtgccgttgg gcagtgcacc cgtaccttty ggagcgcgcg cctcgtcgtg tcgtgacgtc    3900
acccgttctg ttggcttata atgcaggtgt ggggccacctg ccggtaggtg tgcggtaggc   3960
ttttctccgt cgcaggacgc agggttcggg cctagggtag gctctcctga atcgacaggc    4020
gccggacctc tggtgagggg agggataagt gaggcgtcag tttctttggt cggttttatg    4080
tacctatctt cttaagtagc tgaagctccg gttttgaact atgcgctcgg ggttggcgag    4140
tgtgttttgt gaagttttt aggcacctt tgaaatgtaa tcatttggt caatatgtaa       4200
ttttcagtgt tagactagta aattgtccgc taaattctgg ccgttttggg cttttttgtt    4260
agacgaagta cgcgctagcc gttaataagc ctcgatgcgg atccataact tcgtatagga    4320
taccttatac gaagttatct caggtaccgc caccatgacc gagtacaagc ccacggtgcg    4380
cctcgccacc cgcgacgacg tccccagggc cgtacgcacc ctcgccgccg cgttcgccga    4440
ctaccccgcc acgcgccaca ccgtcgatcc ggaccgccac atcgagcggg tcaccgagct    4500
gcaagaactc ttcctcacgc gcgtcgggct cgacatcggc aaggtgtggg tcgcggacga    4560
cggcgccgcg gtggcggtct ggaccacgcc ggagagcgtc gaagcggggg cggtgttcgc    4620
cgagatcggc ccgcgcatgg ccgagttgag cggttcccgg ctggccgcgc agcaacagat    4680
ggaaggcctc ctggcgccgc accggcccaa ggagcccgcg tggttcctgg ccaccgtcgg    4740
cgtctcgccc gaccaccagg gcaagggtct gggcagcgcc gtcgtgctcc ccggagtgga    4800
ggcggccgag cgcgccgggg tgcccgcctt cctggagacc tccgcgcccc gcaacctccc    4860
cttctacgag cggctcggct tcaccgtcac cgccgacgtc gaggtgcccg aaggaccgcg    4920
cacctggtgc atgacccgca agcccggtgc cctgtacaag aaacagaaaa ttgtggcacc    4980
agtgaaacag actttgaatt ttgaccttct caagttggcg ggagacgtcg agtccaaccc    5040
tgggcccatg aacccagcca tcagcgtcgc tctcctgctc tcagtcttgc aggtgtcccg    5100
agggcagaag gtgaccagcc tgacagcctg cctggtgaac caaaaccttc gcctggactg    5160
ccgccatgag aataacacca aggataactc catccagcat gagttcagcc tgacccgaga    5220
gaagaggaag cacgtgctct caggcaccct cgggataccc gagcacacgt accgctcccg    5280
cgtcaccctc tccaaccagc cctatatcaa ggtccttacc ctagccaact tcaccaccaa    5340
ggatgagggc gactactttt gtgagcttcg agtctcgggc gcgaatccca tgagctccaa    5400
taaaagtatc agtgtgtata gagacaaact ggtcaagtgt gcggcataa gcctgctggt    5460
tcagaacaca tcctggatgc tgctgctgct gcttcccctc tccctcctcc aagccctgga    5520
cttcattct ctgtgatcta gaagccataa cttcgtatag tacacattat acgaagttat     5580
gtttatgcat acctggagga aaaaaaaag gggagagtca ggggtttaaa cctggaatga    5640
aaggtcaagg tgtgacgtca gcttgggcgg ccgcccactc acctgcaatt gggccgctac    5700
ttgtacagct cgtccatgcc gagagtgatc ccggcggcgg tcacgaactc cagcaggacc    5760
atgtgatcgc gcttctcgtt ggggtctttg ctcagggcgg actgggtgct caggtagtgg    5820
ttgtcgggca gcagcacggg gccgtcgccg atggggtgt tctgctggta gtggtcggcg    5880
agctgcacgc tgccgtcctc gatgttgtgg cggatcttga agttcacctt gatgccgttc    5940
ttctgcttgt cggccatgat atagacgttg tggctgttgt agttgtactc cagcttgtgc    6000
cccaggatgt tgccgtcctc cttgaagtcg atgcccttca gctcgatgcg gttcaccagg    6060
gtgtcgccct cgaacttcac ctcggcgcgg gtcttgtagt tgccgtcgtc cttgaagaag    6120
```

```
atggtgcgct cctggacgta gccttcgggc atggcggact tgaagaagtc gtgctgcttc   6180
atgtggtcgg ggtagcggct gaagcactgc acgccgtagg tcagggtggt cacgagggtg   6240
ggccagggca cgggcagctt gccggtggtg cagatgaact tcagggtcag cttgccgtag   6300
gtggcatcgc cctcgccctc gccggacacg ctgaacttgt ggccgtttac gtcgccgtcc   6360
agctcgacca ggatgggcac caccccggtg aacagctcct cgcccttgct caccatggtg   6420
gcgaccggta taacttcgta taaggtatcc tatacgaagt tatccattca ggctgtgcta   6480
gcatcaatgg catggcacaa agcttagcca taacttcgta taatgtgtac tatacgaagt   6540
tatccctgtt taagggttcc ggttccacta ggtacaattc gatatcaagc ttatcgataa   6600
tcaacctctg gattacaaaa tttgtgaaag attgactggt attcttaact atgttgctcc   6660
ttttacgcta tgtggatacg ctgctttaat gcctttgtat catgctattg cttcccgtat   6720
ggctttcatt ttctcctcct tgtataaatc ctggttgctg tctctttatg aggagttgtg   6780
gcccgttgtc aggcaacgtg gcgtggtgtg cactgtgttt gctgacgcaa ccccactgg   6840 ttggggcatt gccaccacct gtcagctcct tccgggact tcgctttcc cctccctat   6900 tgccacggcg gaactcatcg ccgcctgcct tgcccgctgc tggacagggg ctcggctgtt   6960
gggcactgac aattccgtgg tgttgtcggg gaaatcatcg tcctttcctt ggctgctcgc   7020
ctgtgttgcc acctggattc tgcgcgggac gtccttctgc tacgtccctt cggccctcaa   7080
tccagcggac cttccttccc gcggcctgct gccggctctg cggcctcttc cgcgtcttcg   7140
ccttcgccct cagacgagtc ggatctccct ttgggccgcc tccccgcatc gataccgtcg   7200
acctcgatcg agacctagaa aaacatggag caatcacaag tagcaataca gcagctacca   7260
atgctgattg tgcctggcta gaagcacaag aggaggagga ggtgggtttt ccagtcacac   7320
ctcaggtacc aagcatgggg taaagtactg ttctcatcac atcatatcaa ggttatatac   7380
catcaatatt gccacagatg ttacttagcc ttttaatatt tctctaattt agtgtatatg   7440
caatgatagt tctctgattt ctgagattga gtttctcatg tgtaatgatt atttagagtt   7500
tctctttcat ctgttcaaat ttttgtctag ttttattttt tactgatttg taagacttct   7560
ttttataatc tgcatattac aattctcttt actggggtgt tgcaaatatt ttctgtcatt   7620
ctatggcctg acttttctta atggttttt aattttaaaa ataagtctta atattcatgc   7680
aatctaatta acaatctttt ctttgtggtt aggactttga gtcataagaa attttctct   7740 acactgaagt catgatggca tgcttctata ttatttctta aaagatttaa agttttgcct   7800
tctccattta gacttataat tcactggaat ttttttgtgt gtatggtatg acatatgggt   7860 tccctttat tttttacata taaatatatt tccctgtttt tctaaaaaag aaaaagatca   7920
tcattttccc attgtaaaat gccatatttt tttcataggt cacttacata tatcaatggg   7980
tctgtttctg agctctactc tattttatca gcctcactgt ctatccccac acatctcatg   8040
ctttgctcta aatcttgata tttagtggaa cattctttcc cattttgttc tacaagaata   8100
tttttgttat tgtcttttgg gcttctatat acatttaga atgaggttgg caaggtacct   8160
ttaagaccaa tgacttacaa ggcagctgta gatcttagcc actttttaaa agaaaagggg   8220
ggactggaag ggctaattca ctcccagctg ctttttgcct gtactgggtc tctctggtta   8280
gaccagatct gagcctggga gctctctggc taactaggga acccactgct taagcctcat   8340
aaagctcgac tgtgccttct agttgccagc catctgttgt ttgcccctcc cccgtgcctt   8400
ccttgaccct ggaaggtgcc actcccactg tccttcccta ataaaatgag gaaattgcat   8460
```

-continued

```
cgcattgtct gagtaggtgt cattctattc tgggggtgg ggtggggcag gacagcaagg    8520
gggaggattg ggaagacaat agcaggcatg ctggggatgc ggtccggact gtactgggtc    8580
tctctggtta gaccagatct gagcctggga gctctctggc taactaggga acccactgct    8640
taagcctcaa taaagcttgc cttgagtgct tcaagtagtg tgtgcccgtc tgttgtgtga    8700
ctctggtaac tagagatccc tcagaccctt ttagtcagtg tggaaaatct ctagcagcat    8760
gtgagcaaaa ggccagcaaa aggccaggaa ccgtaaaaag gccgcgttgc tggcgttttt    8820
ccataggctc cgcccccctg acgagcatca caaaaatcga cgctcaagtc agaggtggcg    8880
aaacccgaca ggactataaa gataccaggc gtttccccct ggaagctccc tcgtgcgctc    8940
tcctgttccg accctgccgc ttaccggata cctgtccgcc tttctccctt cgggaagcgt    9000
ggcgctttct catagctcac gctgtaggta tctcagttcg gtgtaggtcg ttcgctccaa    9060
gctgggctgt gtgcacgaac cccccgttca gcccgaccgc tgcgccttat ccggtaacta    9120
tcgtcttgag tccaacccgg taagacacga cttatcgcca ctggcagcag ccactggtaa    9180
caggattagc agagcgaggt atgtaggcgg tgctacagag ttcttgaagt ggtggcctaa    9240
ctacggctac actagaagaa cagtatttgg tatctgcgct ctgctgaagc cagttacctt    9300
cggaaaaaga gttggtagct cttgatccgg caaacaaacc accgctggta gcggtggttt    9360
ttttgtttgc aagcagcaga ttacgcgcag aaaaaaagga tctcaagaag atcctttgat    9420
cttttctacg gggtctgacg ctcagtggaa cgaaaactca cgttaaggga ttttggtcat    9480
gagattatca aaaaggatct tcacctagat ccttttaaat taaaaatgaa gttttaaatc    9540
aatctaaagt atatatgagt aaacttggtc tgacagttac caatgcttaa tcagtgaggc    9600
acctatctca gcgatctgtc tatttcgttc atccatagtt gcctgactcc ccgtcgtgta    9660
gataactacg atacgggagg gcttaccatc tggccccagt gctgcaatga taccgcgaga    9720
cccacgctca ccggctccag atttatcagc aataaaccag ccagccggaa gggccgagcg    9780
cagaagtggt cctgcaactt tatccgcctc catccagtct attaattgtt gccgggaagc    9840
tagagtaagt agttcgccag ttaatagttt gcgcaacgtt gttgccattg ctacaggcat    9900
cgtggtgtca cgctcgtcgt ttggtatggc ttcattcagc tccggttccc aacgatcaag    9960
gcgagttaca tgatccccca tgttgtgcaa aaaagcggtt agctccttcg gtcctccgat   10020
cgttgtcaga agtaagttgg ccgcagtgtt atcactcatg gttatggcag cactgcataa   10080
ttctcttact gtcatgccat ccgtaagatg cttttctgtg actggtgagt actcaaccaa   10140
gtcattctga gaatagtgta tgcggcgacc gagttgctct tgcccggcgt caatacggga   10200
taataccgcg ccacatagca gaactttaaa agtgctcatc attggaaaac gttcttcggg   10260
gcgaaaactc tcaaggatct taccgctgtt gagatccagt tcgatgtaac ccactcgtgc   10320
acccaactga tcttcagcat cttttacttt caccagcgtt tctgggtgag caaaaacagg   10380
aaggcaaaat gccgcaaaaa agggaataag ggcgacacgg aaatgttgaa tactcatact   10440
cttcctttt caatattatt gaagcattta tcagggttat tgtctcatga gcggatacat   10500
atttgaatgt atttagaaaa ataaacaaat aggggttccg cgcacatttc cccgaaaagt   10560
gccacctgac                                                          10570
```

<210> SEQ ID NO 7
<211> LENGTH: 10912
<212> TYPE: DNA
<213> ORGANISM: Artificial
<220> FEATURE:
<223> OTHER INFORMATION: pLB2 comprising the FLIP cassette with the miR30 targeting FireFly luciferase

<400> SEQUENCE: 7

```
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt cgcctgcttc gcgatgtacg ggccagatat acgcgttgac   240
attgattatt gactagtcat gttctttcct gcgttatccc ctgattctgt ggataaccgt   300
attaccgcct ttgagtgagc tgataccgct cgccgcagcc gaacgaccga cgcagcgag   360
tcagtgagcg aggaagcgga agagcgccca atacgcaaac cgcctctccc cgcgcgttgg   420
ccgattcatt aatgcagctg gcacgacagg tttcccgact ggaaagcggg cagtgagcgc   480
aacgcaatta atgtgagtta gctcactcat taggcacccc aggctttaca ctttatgctt   540
ccggctcgta tgttgtgtgg aattgtgagc ggataacaat ttcacacagg aaacagctat   600
gaccatgatt acgccaagcg cgcaattaac cctagcttaa tgtagtctta tgcaatactc   660
ttgtagtctt gcaacatggt aacgatgagt tagcaacatg ccttacaagg agagaaaaag   720
caccgtgcat gccgattggt ggaagtaagg tggtacgatc gtgccttatt aggaaggcaa   780
cagacgggtc tgacatggat tggacgaacc actgaattgc cgcattgcag agatattgta   840
tttaagtgcc tagctcgata caataaacgg gtctctctgg ttagaccaga tctgagcctg   900
ggagctctct ggctaactag ggaacccact gcttaagcct caataaagct tgccttgagt   960
gcttcaagta gtgtgtgccc gtctgttgtg tgactctggt aactagagat ccctcagacc  1020
cttttagtca gtgtggaaaa tctctagcag tggcgcccga acagggactt gaaagcgaaa  1080
gggaaaccag aggagctctc tcgacgcagg actcggcttg ctgaagcgcg cacggcaaga  1140
ggcgaggggc ggcgactggt gagtacgcca aaaattttga ctagcggagg ctagaaggag  1200
agagatgggt gcgagagcgt cagtattaag cgggggagaa ttagatcgcg atgggaaaaa  1260
attcggttaa ggccagggggg aaagaaaaaa tataaattaa acatatagt atgggcaagc  1320
agggagctag aacgattcgc agttaatcct ggcctgttag aaacatcaga aggctgtaga  1380
caaatactgg gacagctaca accatcccct cagacaggat cagaagaact tagatcatta  1440
tataatacag tagcaacccct ctattgtgtg catcaaagga tagagataaa agacaccaag  1500
gaagctttag acaagataga ggaagagcaa aacaaaagta agaccaccgc acagcaagcg  1560
gccggccgcg ctgatcttca gacctggagg aggagatatg agggacaatt ggagaagtga  1620
attatataaa tataaagtag taaaaattga accattagga gtagcaccca ccaaggcaaa  1680
gagaagagtg gtgcagagag aaaaaagagc agtgggaata ggagctttgt tccttgggtt  1740
cttgggagca gcaggaagca ctatgggcgc agcgtcaatg acgctgacgg tacaggccag  1800
acaattattg tctggtatag tgcagcagca gaacaatttg ctgagggcta ttgaggcgca  1860
acagcatctg ttgcaactca cagtctgggg catcaagcag ctccaggcaa gaatcctggc  1920
tgtggaaaga tacctaaagg atcaacagct cctggggatt tggggttgct ctggaaaact  1980
catttgcacc actgctgtgc cttggaatgc tagttggagt aataaatctc tggaacagat  2040
ttggaatcac acgacctgga tggagtggga cagagaaatt aacaattaca caagcttaat  2100
acactcctta attgaagaat cgcaaaacca gcaagaaaag aatgaacaag aattattgga  2160
attagataaa tgggcaagtt tgtggaattg gtttaacata acaaattggc tgtggtatat  2220
aaaattattc ataatgatag taggaggctt ggtaggttta agaatagttt ttgctgtact  2280
```

-continued

```
ttctatagtg aatagagtta ggcagggata ttcaccatta tcgtttcaga cccacctccc    2340
aaccccgagg ggacccgaca ggcccgaagg aatagaagaa gaaggtggag agagagacag    2400
agacagatcc attcgattag tgaacggatc ggcactgcgt gcgccaattc tgcagacaaa    2460
tggcagtatt catccacaat tttaaaagaa aagggggtat tggggggtac agtgcagggg    2520
aaagaatagt agacataata gcaacagaca tacaaactaa agaattacaa aaacaaatta    2580
caaaaattca aaattttcgg gtttattaca gggacagcag agatccagtt tggttagtac    2640
cgggcccggt gctttgctct gagccagccc accagtttgg aatgactcct ttttatgact    2700
tgaattttca gtataaagt ctagtgctaa atttaatttg aacaactgta tagtttttgc     2760
tggttggggg aaggaaaaaa aatggtggca gtgtttttt cagaattaga agtgaaatga     2820
aaacttgttg tgtgtgagga tttctaatga catgtggtgg ttgcatactg agtgaagccg    2880
gtgagcattc tgccatgtca cccctcgtg ctcagtaatg tactttacag aaatcctaaa    2940
ctcaaaagat tgatataaac catgcttctt gtgtatatcc ggtctcttct ctgggtagtc    3000
tcactcagcc tgcatttctg ccagggcccg ctctagatct agacggttga tctggcctcc    3060
gcgccgggtt ttggcgcctc ccgcgggcgc ccccctcctc acggcgagcg ctgccacgtc    3120
agacgaaggg cgcaggagcg ttcctgatcc ttccgcccgg acgctcagga cagcggcccg    3180
ctgctcataa gactcggcct tagaaccca gtatcagcag aaggacattt taggacggga     3240
cttgggtgac tctagggcac tggttttctt tccagagagc ggaacaggcg aggaaaagta    3300 gtccccttctc ggcgattctg cggagggatc tccgtggggc ggtgaacgcc gatgattata    3360
taaggacgcg ccgggtgtgg cacagctagt tccgtcgcag ccgggatttg ggtcgcggtt    3420
cttgtttgtg gatcgctgtg atcgtcactt ggtgagttgc gggctgctgg gctggccggg    3480
gctttcgtgg ccgccgggcc gctcggtggg acggaagcgt gtggagagac cgccaagggc    3540
tgtagtctgg gtccgcgagc aaggttgccc tgaactgggg gttgggggga gcgcacaaaa    3600
tggcggctgt tcccgagtct tgaatggaag acgcttgtaa ggcgggctgt gaggtcgttg    3660
aaacaaggtg gggggcatgg tgggcggcaa gaacccaagg tcttgaggcc ttcgctaatg    3720
cgggaaagct cttattcggg tgagatgggc tgggcaccaa tctggggacc ctgacgtgaa    3780
gtttgtcact gactggagaa ctcgggtttg tcgtctggtt gcggggcgg cagttatgcg     3840 gtgccgttgg gcagtgcacc cgtacctttg ggagcgcgcg cctcgtcgtg tcgtgacgtc    3900
acccgttctg ttggcttata atgcagggtg gggccacctg ccggtaggtg tgcggtaggc    3960
ttttctccgt cgcaggacgc agggttcggg cctaggtag gctctcctga atcgacaggc     4020
gccggacctc tggtgagggg agggataagt gaggcgtcag tttctttggt cggttttatg    4080
tacctatctt cttaagtagc tgaagctccg gttttgaact atgcgctcgg ggttggcgag    4140
tgtgttttgt gaagtttttt aggcaccttt tgaaatgtaa tcatttgggt caatatgtaa    4200
ttttcagtgt tagactagta aattgtccgc taaattctgg ccgttttgg cttttttgtt     4260 agacgaagta cgcgctagcc gttaataagc ctcgatgcgg atccataact tcgtatagga    4320
taccttatac gaagttatct caggtaccgc caccatgacc gagtacaagc ccacggtgcg    4380
cctcgccacc cgcgacgacg tccccagggc cgtacgcacc ctcgccgccg cgttcgccga    4440
ctaccccgcc acgcgccaca ccgtcgatcc ggaccgccac atcgagcggg tcaccgagct    4500
gcaagaactc ttcctcacgc gcgtcgggct cgacatcggc aaggtgtggg tcgcggacga    4560
cggcgccgcg gtggcggtct ggaccacgcc ggagagcgtc gaagcggggg cggtgttcgc    4620
```

```
cgagatcggc cgcgcatgg ccgagttgag cggttcccgg ctggccgcgc agcaacagat    4680
ggaaggcctc ctggcgccgc accggcccaa ggagcccgcg tggttcctgg ccaccgtcgg    4740
cgtctcgccc gaccaccagg gcaagggtct gggcagcgcc gtcgtgctcc ccggagtgga    4800
ggcggccgag cgcgccgggg tgcccgcctt cctggagacc tccgcgcccc gcaacctccc    4860
cttctacgag cggctcggct tcaccgtcac cgccgacgtc gaggtgcccg aaggaccgcg    4920
cacctggtgc atgacccgca agcccggtgc cctgtacaag aaacagaaaa ttgtggcacc    4980
agtgaaacag actttgaatt ttgaccttct caagttggcg ggagacgtcg agtccaaccc    5040
tgggcccatg aacccagcca tcagcgtcgc tctcctgctc tcagtcttgc aggtgtccga    5100
gggcagaagg tgaccagcct gacagcctgc ctggtgaacc aaaaccttcg cctggactgc    5160
cgccatgaga ataacaccaa ggataactcc atccagcatg agttcagcct gacccgagag    5220
aagaggaagc acgtgctctc aggcaccctc gggatacccg agcacgtaa ccgctcccgc    5280
gtcaccctct ccaaccagcc ctatatcaag gtccttaccc tagccaactt caccaccaag    5340
gatgagggcg actacttttg tgagcttcga gtctcgggcg cgaatccat gagctccaat    5400
aaaagtatca gtgtgtatag agacaaactg tcaagtgtg gcggcataag cctgctggtt    5460
cagaacacat cctggatgct gctgctgctg cttccctct ccctcctcca gccctggac    5520
ttcatttctc tgtgatctag aagccataac ttcgtatagt acacattata cgaagttatg    5580
tttatgcata cctggaggaa aaaaaaagg ggagagtcag gggtttaaac gcattagtct    5640
tccaattgaa aaagtgatt taatttatac cattttaatt cagctttgta aaaatgtatc    5700
aaagagatag caaggtattc agttttagta aacaagataa ttgctcctaa agtagcccct    5760
tgaattccga ggcagtaggc aggctcccgc tgaattggaa tcctacatct gtggcttcac    5820
taggattcca attcacggga gctcgctcac tgtcaacagc aatataccttt ctcgagcctt    5880
ctgttgggtt aacctgaaga agtaatccca gcaagtgttt ccaagatgtg caggcaacga    5940
ttctgtaaag tactgaagcc tcattcaaac atagtatatg tgctgccgaa gcagcactt    6000
aacaaggctt gcggccgccc actcacctgc aattgggccg ctacttgtac agctcgtcca    6060
tgccgagagt gatcccggcg gcggtcacga actccagcag gaccatgtga tcgcgcttct    6120
cgttggggtc tttgctcagg gcggactggg tgctcaggta gtggttgtcg ggcagcagca    6180
cggggccgtc gccgatgggg gtgttctgct ggtagtggtc ggcgagctgc acgctgccgt    6240
cctcgatgtt gtggcggatc ttgaagttca ccttgatgcc gttcttctgc ttgtcggcca    6300
tgatatagac gttgtggctg ttgtagttgt actccagctt gtgccccagg atgttgccgt    6360
cctccttgaa gtcgatgccc ttcagctcga tgcggttcac cagggtgtcg ccctcgaact    6420
tcacctcggc gcgggtcttg tagttgccgt cgtccttgaa gaagatggtg cgctcctgga    6480
cgtagccttc gggcatggcg gacttgaaga agtcgtgctg cttcatgtgg tcggggtagc    6540
ggctgaagca ctgcacgccg taggtcaggg tggtcacgag ggtgggccag gcacgggca    6600
gcttgccggt ggtgcagatg aacttcaggg tcagcttgcc gtaggtggca tcgccctcgc    6660
cctcgccgga cacgctgaac ttgtggccgt ttacgtcgcc gtccagctcg accaggatgg    6720
gcaccacccc ggtgaacagc tcctcgccct tgctcaccat ggtggcgacc ggtataactt    6780
cgtataaggt atcctatacg aagttatcca ttcaggctgt gctagcatca atggcatggc    6840
acaaagctta gccataactt cgtataatgt gtactatacg aagttatccc tgtttaaggg    6900
ttccggttcc actaggtaca attcgatatc aagcttatcg ataatcaacc tctgattac    6960
aaaatttgtg aaagattgac tggtattctt aactatgttg ctccttttac gctatgtgga    7020
```

```
tacgctgctt taatgccttt gtatcatgct attgcttccc gtatggcttt cattttctcc    7080
tccttgtata aatcctggtt gctgtctctt tatgaggagt tgtggcccgt tgtcaggcaa    7140
cgtggcgtgg tgtgcactgt gtttgctgac gcaaccccca ctggttgggg cattgccacc    7200
acctgtcagc tcctttccgg gactttcgct ttcccctcc  ctattgccac ggcggaactc    7260
atcgccgcct gccttgcccg ctgctggaca ggggctcggc tgttgggcac tgacaattcc    7320
gtggtgttgt cggggaaatc atcgtccttt ccttggctgc tcgcctgtgt tgccacctgg    7380
attctgcgcg ggacgtcctt ctgctacgtc ccttcggccc tcaatccagc ggaccttcct    7440
tcccgcggcc tgctgccggc tctgcggcct cttccgcgtc ttcgccttcg ccctcagacg    7500
agtcggatct cccttttggc gcctccccgc atcgataccg tcgacctcga tcgagaccta    7560
gaaaaacatg gagcaatcac aagtagcaat acagcagcta ccaatgctga ttgtgcctgg    7620
ctagaagcac aagaggagga ggaggtgggt tttccagtca cacctcaggt accaagcatg    7680
gggtaaagtc tgttctcatc acatcatatc aaggttatat accatcaata ttgccacaga    7740
tgttacttag ccttttaata tttctctaat ttagtgtata tgcaatgata gttctctgat    7800
ttctgagatt gagtttctca tgtgtaatga ttatttagag tttctctttc atctgttcaa    7860 attttttgtct agtttttatttt tttactgatt tgtaagactt ctttttataa tctgcatatt   7920
acaattctct ttactggggt gttgcaaata ttttctgtca ttctatggcc tgactttttct    7980 taatggtttt ttaattttaa aaataagtct taatattcat gcaatctaat taacaatctt    8040
ttctttgtgg ttaggacttt gagtcataag aaatttttct ctacactgaa gtcatgatgg    8100
catgcttcta tattattttc taaaagattt aaagttttgc cttctccatt tagacttata    8160
attcactgga attttttttgt gtgtatggta tgacatatgg gttccctttt attttttaca    8220
tataaatata tttccctgtt tttctaaaaa agaaaaagat catcattttc ccattgtaaa    8280
atgccatatt tttttcatag gtcacttaca tatatcaatg gtctgtttc  tgagctctac    8340 tctatttttat cagcctcact gtctatcccc acacatctca tgctttgctc taaatcttga    8400
tatttagtgg aacattcttt cccatttttgt tctacaagaa tatttttgtt attgtctttt    8460
gggcttctat atacatttta gaatgaggtt ggcaaggtac ctttaagacc aatgacttac    8520
aaggcagctg tagatcttag ccactttta  aaagaaaagg ggggactgga agggctaatt    8580
cactcccagc tgctttttgc ctgtactggg tctctctggt tagaccagat ctgagcctgg    8640
gagctctctg gctaactagg gaacccactg cttaagcctc ataaagctcg actgtgcctt    8700
ctagttgcca gccatctgtt gtttgcccct ccccgtgcc  ttccttgacc ctggaaggtg    8760
ccactcccac tgtcctttcc taataaaatg aggaaattgc atcgcattgt ctgagtaggt    8820
gtcattctat tctggggggt ggggtggggc aggacagcaa ggggaggat  tgggaagaca    8880 atagcaggca tgctggggat gcggtccgga ctgtactggg tctctctggt tagaccagat    8940
ctgagcctgg gagctctctg gctaactagg gaacccactg cttaagcctc aataaagctt    9000
gccttgagtg cttcaagtag tgtgtgcccg tctgttgtgt gactctggta actagagatc    9060
cctcagaccc ttttagtcag tgtggaaaat ctctagcagc atgtgagcaa aaggccagca    9120
aaaggccagg aaccgtaaaa aggccgcgtt gctggcgttt ttccataggc tccgcccccc    9180
tgacgagcat cacaaaaatc gacgctcaag tcagaggtgg cgaaacccga caggactata    9240
aagataccag gcgtttcccc ctggaagctc cctcgtgcgc tctcctgttc cgaccctgcc    9300
gcttaccgga tacctgtccg cctttctccc ttcgggaagc gtggcgcttt ctcatagctc    9360
```

| | |
|---|---:|
| acgctgtagg tatctcagtt cggtgtaggt cgttcgctcc aagctgggct gtgtgcacga | 9420 |
| accccccgtt cagcccgacc gctgcgcctt atccggtaac tatcgtcttg agtccaaccc | 9480 |
| ggtaagacac gacttatcgc cactggcagc agccactggt aacaggatta gcagagcgag | 9540 |
| gtatgtaggc ggtgctacag agttcttgaa gtggtggcct aactacggct acactagaag | 9600 |
| aacagtattt ggtatctgcg ctctgctgaa gccagttacc ttcggaaaaa gagttggtag | 9660 |
| ctcttgatcc ggcaaacaaa ccaccgctgg tagcggtggt ttttttgttt gcaagcagca | 9720 |
| gattacgcgc agaaaaaaag gatctcaaga agatcctttg atcttttcta cggggtctga | 9780 |
| cgctcagtgg aacgaaaact cacgttaagg gattttggtc atgagattat caaaaaggat | 9840 |
| cttcacctag atccttttaa attaaaaatg aagttttaaa tcaatctaaa gtatatatga | 9900 |
| gtaaacttgg tctgacagtt accaatgctt aatcagtgag gcacctatct cagcgatctg | 9960 |
| tctatttcgt tcatccatag ttgcctgact ccccgtcgtg tagataacta cgatacggga | 10020 |
| gggcttacca tctggcccca gtgctgcaat gataccgcga gacccacgct caccggctcc | 10080 |
| agatttatca gcaataaacc agccagccgg aagggccgag cgcagaagtg gtcctgcaac | 10140 |
| tttatccgcc tccatccagt ctattaattg ttgccgggaa gctagagtaa gtagttcgcc | 10200 |
| agttaatagt ttgcgcaacg ttgttgccat tgctacaggc atcgtggtgt cacgctcgtc | 10260 |
| gtttggtatg gcttcattca gctccggttc ccaacgatca aggcgagtta catgatcccc | 10320 |
| catgttgtgc aaaaaagcgg ttagctcctt cggtcctccg atcgttgtca gaagtaagtt | 10380 |
| ggccgcagtg ttatcactca tggttatggc agcactgcat aattctctta ctgtcatgcc | 10440 |
| atccgtaaga tgcttttctg tgactggtga gtactcaacc aagtcattct gagaatagtg | 10500 |
| tatgcggcga ccgagttgct cttgcccggc gtcaatacgg gataataccg cgccacatag | 10560 |
| cagaacttta aaagtgctca tcattggaaa acgttcttcg gggcgaaaac tctcaaggat | 10620 |
| cttaccgctg ttgagatcca gttcgatgta acccactcgt gcacccaact gatcttcagc | 10680 |
| atcttttact ttcaccagcg tttctgggtg agcaaaaaca ggaaggcaaa atgccgcaaa | 10740 |
| aaagggaata agggcgacac ggaaatgttg aatactcata ctcttccttt ttcaatatta | 10800 |
| ttgaagcatt tatcagggtt attgtctcat gagcggatac atatttgaat gtatttagaa | 10860 |
| aaataaacaa atagggggttc cgcgcacatt tccccgaaaa gtgccacctg ac | 10912 |

<210> SEQ ID NO 8
<211> LENGTH: 10915
<212> TYPE: DNA
<213> ORGANISM: Artificial
<220> FEATURE:
<223> OTHER INFORMATION: pLB2 comprising the FLIP cassette with the
      miR30 targeting 4 integrin

<400> SEQUENCE: 8

| | |
|---|---:|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagtcat gttctttcct gcgttatccc ctgattctgt ggataaccgt | 300 |
| attaccgcct ttgagtgagc tgataccgct cgccgcagcc gaacgaccga gcgcagcgag | 360 |
| tcagtgagcg aggaagcgga agagcgccca atacgcaaac cgcctctccc cgcgcgttgg | 420 |
| ccgattcatt aatgcagctg gcacgacagg tttcccgact ggaaagcggg cagtgagcgc | 480 |

| | |
|---|---|
| aacgcaatta atgtgagtta gctcactcat taggcacccc aggctttaca ctttatgctt | 540 |
| ccggctcgta tgttgtgtgg aattgtgagc ggataacaat ttcacacagg aaacagctat | 600 |
| gaccatgatt acgccaagcg cgcaattaac cctagcttaa tgtagtctta tgcaatactc | 660 |
| ttgtagtctt gcaacatggt aacgatgagt tagcaacatg ccttacaagg agagaaaaag | 720 |
| caccgtgcat gccgattggt ggaagtaagg tggtacgatc gtgccttatt aggaaggcaa | 780 |
| cagacgggtc tgacatggat tggacgaacc actgaattgc cgcattgcag agatattgta | 840 |
| tttaagtgcc tagctcgata caataaacgg gtctctctgg ttagaccaga tctgagcctg | 900 |
| ggagctctct ggctaactag ggaacccact gcttaagcct caataaagct tgccttgagt | 960 |
| gcttcaagta gtgtgtgccc gtctgttgtg tgactctggt aactagagat ccctcagacc | 1020 |
| cttttagtca gtgtggaaaa tctctagcag tggcgcccga acaggactt gaaagcgaaa | 1080 |
| gggaaaccag aggagctctc tcgacgcagg actcggcttg ctgaagcgcg cacggcaaga | 1140 |
| ggcgaggggc ggcgactggt gagtacgcca aaaattttga ctagcggagg ctagaaggag | 1200 |
| agagatgggt gcgagagcgt cagtattaag cgggggagaa ttagatcgcg atgggaaaaa | 1260 |
| attcggttaa ggccaggggg aaagaaaaaa tataaattaa aacatatagt atgggcaagc | 1320 |
| agggagctag aacgattcgc agttaatcct ggcctgttag aaacatcaga aggctgtaga | 1380 |
| caaatactgg gacagctaca accatcccctt cagacaggat cagaagaact tagatcatta | 1440 |
| tataatacag tagcaaccct ctattgtgtg catcaaagga tagagataaa agacaccaag | 1500 |
| gaagctttag acaagataga ggaagagcaa aacaaaagta agaccaccgc acagcaagcg | 1560 |
| gccggccgcg ctgatcttca gacctggagg aggagatatg agggacaatt ggagaagtga | 1620 |
| attatataaa tataaagtag taaaaattga accattagga gtagcaccca ccaaggcaaa | 1680 |
| gagaagagtg gtgcagagag aaaaaagagc agtgggaata ggagctttgt tccttgggtt | 1740 |
| cttgggagca gcaggaagca ctatgggcgc agcgtcaatg acgctgacgg tacaggccag | 1800 |
| acaattattg tctggtatag tgcagcagca gaacaatttg ctgagggcta ttgaggcgca | 1860 |
| acagcatctg ttgcaactca cagtctgggg catcaagcag ctccaggcaa gaatcctggc | 1920 |
| tgtggaaaga tacctaaagg atcaacagct cctggggatt tggggttgct ctggaaaact | 1980 |
| catttgcacc actgctgtgc cttggaatgc tagttggagt aataaatctc tggaacagat | 2040 |
| ttggaatcac acgacctgga tggagtggga cagagaaatt aacaattaca caagcttaat | 2100 |
| acactcctta attgaagaat cgcaaaacca gcaagaaaag aatgaacaag aattattgga | 2160 |
| attagataaa tgggcaagtt tgtggaattg gtttaacata acaaattggc tgtggtatat | 2220 |
| aaaattattc ataatgatag taggaggctt ggtaggttta agaatagttt ttgctgtact | 2280 |
| ttctatagtg aatagagtta ggcagggata ttcaccatta tcgtttcaga cccacctccc | 2340 |
| aaccccgagg ggacccgaca ggcccgaagg aatagaagaa gaaggtggag agagagacag | 2400 |
| agacagatcc attcgattag tgaacggatc ggcactgcgt gcgccaattc tgcagacaaa | 2460 |
| tggcagtatt catccacaat tttaaaagaa aggggggat tgggggtac agtgcagggg | 2520 |
| aaagaatagt agacataata gcaacagaca tacaaactaa agaattacaa aaacaaatta | 2580 |
| caaaaattca aaattttcgg gtttattaca gggacagcag agatccagtt tggttagtac | 2640 |
| cgggcccggt gctttgctct gagccagccc accagtttgg aatgactcct ttttatgact | 2700 |
| tgaattttca agtataaagt ctagtgctaa atttaatttg aacaactgta gttttttgc | 2760 |
| tggttggggg aaggaaaaaa aatggtggca gtgtttttt cagaattaga agtgaaatga | 2820 |
| aaacttgttg tgtgtgagga tttctaatga catgtggtgg ttgcatactg agtgaagccg | 2880 |

```
gtgagcattc tgccatgtca cccctcgtg ctcagtaatg tactttacag aaatcctaaa    2940
ctcaaaagat tgatataaac catgcttctt gtgtatatcc ggtctcttct ctgggtagtc    3000
tcactcagcc tgcatttctg ccagggcccg ctctagatct agacggttga tctggcctcc    3060
gcgccgggtt ttggcgcctc ccgcgggcgc cccctcctc acggcgagcg ctgccacgtc    3120
agacgaaggg cgcaggagcg ttcctgatcc ttccgcccgg acgctcagga cagcggcccg    3180
ctgctcataa gactcggcct tagaacccca gtatcagcag aaggacattt taggacggga    3240
cttgggtgac tctagggcac tggttttctt tccagagagc ggaacaggcg aggaaaagta    3300
gtcccttctc ggcgattctg cggagggatc tccgtgggc ggtgaacgcc gatgattata    3360
taaggacgcg ccgggtgtgg cacagctagt tccgtcgcag ccgggatttg gtcgcggtt    3420 cttgttgtg gatcgctgtg atcgtcactt ggtgagttgc gggctgctgg gctgccgggg    3480
gctttcgtgg ccgccgggcc gctcggtggg acggaagcgt gtggagagac cgccaagggc    3540
tgtagtctgg gtccgcgagc aaggttgccc tgaactgggg gttgggggga gcgcacaaaa    3600
tggcggctgt tcccgagtct tgaatggaag acgcttgtaa ggcgggctgt gaggtcgttg    3660
aaacaaggtg gggggcatgg tgggcggcaa gaacccaagg tcttgaggcc ttcgctaatg    3720
cgggaaagct cttattcggg tgagatgggc tggggcacca tctgggacc ctgacgtgaa    3780 gtttgtcact gactggagaa ctcgggtttg tcgtctggtt gcggggcgg cagttatgcg    3840 gtgccgttgg gcagtgcacc cgtaccttg ggagcgcgcg cctcgtcgtg tcgtgacgtc    3900
acccgttctg ttggcttata atgcaggtg gggccacctg ccggtaggtg tgcggtaggc    3960
ttttctccgt cgcaggacgc agggttcggg cctagggtag gctctcctga atcgacaggc    4020
gccggacctc tggtgagggg agggataagt gaggcgtcag tttctttggt cggttttatg    4080
tacctatctt cttaagtagc tgaagctccg gttttgaact atgcgctcgg ggttggcgag    4140
tgtgttttgt gaagttttt aggcacctt tgaaatgtaa tcatttgggt caatatgtaa    4200
ttttcagtgt tagactagta aattgtccgc taaattctgg ccgttttgg ctttttgtt    4260 agacgaagta cgcgctagcc gttaataagc ctcgatgcgg atccataact tcgtatagga    4320
taccttatac gaagttatct caggtaccgc caccatgacc gagtacaagc ccacggtgcg    4380
cctcgccacc cgcgacgacg tccccagggc cgtacgcacc ctcgccgccg cgttcgccga    4440
ctaccccgcc acgcgccaca ccgtcgatcc ggaccgccac atcgagcggg tcaccgagct    4500
gcaagaactc ttcctcacgc gcgtcgggct cgacatcggc aaggtgtggg tcgcggacga    4560
cggcgccgcg gtggcggtct ggaccacgcc ggagagcgtc gaagcggggg cggtgttcgc    4620
cgagatcggc ccgcgcatgg ccgagttgag cggttcccgg ctggccgcgc agcaacagat    4680
ggaaggcctc ctggcgccgc accggcccaa ggagcccgcg tggttcctgg ccaccgtcgg    4740
cgtctcgccc gaccaccagg gcaagggtct gggcagcgcc gtcgtgctcc ccggagtgga    4800
ggcggccgag cgcgccgggg tgcccgcctt cctggagacc tccgcgcccc gcaacctccc    4860
cttctacgag cggctcggct tcaccgtcac cgccgacgtc gaggtgcccg aaggaccgcg    4920
cacctggtgc atgaccccgca agcccggtgc cctgtacaag aaacagaaaa ttgtggcacc    4980
agtgaaacag actttgaatt ttgaccttct caagttggcg ggagacgtcg agtccaaccc    5040
tgggcccatg aacccagcca tcagcgtcgc tctcctgctc tcagtcttgc aggtgtcccg    5100
agggcagaag gtgaccagcc tgacagcctg cctggtgaac caaaaccttc gcctggactg    5160
ccgccatgag aataacacca aggataactc catccagcat gagttcagcc tgacccgaga    5220
```

```
gaagaggaag cacgtgctct caggcaccct cgggataccc gagcacacgt accgctcccg    5280
cgtcaccctc tccaaccagc cctatatcaa ggtccttacc ctagccaact tcaccaccaa    5340
ggatgagggc gactactttt gtgagcttcg agtctcgggc gcgaatccca tgagctccaa    5400
taaaagtatc agtgtgtata gagacaaact ggtcaagtgt ggcggcataa gcctgctggt    5460
tcagaacaca tcctggatgc tgctgctgct gctttccctc tccctcctcc aagccctgga    5520
cttcatttct ctgtgatcta gaagccataa cttcgtatag tacacattat acgaagttat    5580
gtttatgcat acctggagga aaaaaaaaag gggagagtca ggggtttaaa cgcattagtc    5640
ttccaattga aaaagtgat ttaatttata ccattttaat tcagctttgt aaaaatgtat    5700
caaagagata gcaaggtatt cagttttagt aaacaagata attgctccta aagtagcccc    5760
ttgaatccga ggcagtaggc atgggcatca tgtgatcacc aaatacatct gtggcttcac    5820
tatttggtga tcacatgatg cccgcgctca ctgtcaacag caatatacct tctcgagcct    5880
tctgttgggt taacctgaag aagtaatccc agcaagtgtt tccaagatgt gcaggcaacg    5940
attctgtaaa gtactgaagc ctcattcaaa catagtatat gtgctgccga agcgagcact    6000
taacaaggct tgcggccgcc cactcacctg caattgggcc gctacttgta cagctcgtcc    6060
atgccgagag tgatcccggc ggcggtcacg aactccagca ggaccatgtg atcgcgcttc    6120
tcgttggggt ctttgctcag ggcggactgg gtgctcaggt agtggttgtc gggcagcagc    6180
acggggccgt cgccgatggg ggtgttctgc tggtagtggt cggcgagctg cacgctgccg    6240
tcctcgatgt tgtggcggat cttgaagttc accttgatgc cgttcttctg cttgtcggcc    6300
atgatataga cgttgtggct gttgtagttg tactccagct tgtgccccag gatgttgccg    6360
tcctccttga agtcgatgcc cttcagctcg atgcggttca ccagggtgtc gccctcgaac    6420
ttcacctcgg cgcgggtctt gtagttgccg tcgtccttga agaagatggt gcgctcctgg    6480
acgtagcctt cgggcatggc ggacttgaag aagtcgtgct gcttcatgtg gtcggggtag    6540
cggctgaagc actgcacgcc gtaggtcagg gtggtcacga gggtgggcca gggcacgggc    6600
agcttgccgg tggtgcagat gaacttcagg gtcagcttgc cgtaggtggc atcgccctcg    6660
ccctcgccgg acacgctgaa cttgtggccg tttacgtcgc cgtccagctc gaccaggatg    6720
ggcaccaccc cggtgaacag ctcctcgccc ttgctcacca tggtggcgac cggtataact    6780
tcgtataagg tatcctatac gaagttatcc attcaggctg tgctagcatc aatggcatgg    6840
cacaaagctt agccataact tcgtataatg tgtactatac gaagttatcc ctgtttaagg    6900
gttccggttc cactaggtac aattcgatat caagcttatc gataatcaac ctctggatta    6960
caaaatttgt gaaagattga ctggtattct taactatgtt gctccttta cgctatgtgg    7020 atacgctgct ttaatgcctt tgtatcatgc tattgcttcc cgtatggctt tcattttctc    7080
ctccttgtat aaatcctggt tgctgtctct ttatgaggag ttgtggcccg ttgtcaggca    7140
acgtggcgtg gtgtgcactg tgtttgctga cgcaacccc actggttggg gcattgccac    7200
cacctgtcag ctcctttccg ggactttcgc tttccccctc cctattgcca cggcggaact    7260
catcgccgcc tgccttgccc gctgctggac aggggctcgg ctgttgggca ctgacaattc    7320
cgtggtgttg tcggggaaat catcgtcctt tccttggctg ctcgcctgtg ttgccacctg    7380
gattctgcgc gggacgtcct tctgctacgt cccttcggcc ctcaatccag cggaccttcc    7440
ttcccgcggc ctgctgccgg ctctgcggcc tcttccgcgt cttcgccttc gccctcagac    7500
gagtcggatc tccctttggg ccgcctcccc gcatcgatac cgtcgacctc gatcgagacc    7560
tagaaaaaca tggagcaatc acaagtagca atacagcagc taccaatgct gattgtgcct    7620
```

```
ggctagaagc acaagaggag gaggaggtgg gttttccagt cacacctcag gtaccaagca    7680
tggggtaaag tactgttctc atcacatcat atcaaggtta tataccatca atattgccac    7740
agatgttact tagccttta  atatttctct aatttagtgt atatgcaatg atagttctct    7800
gatttctgag attgagtttc tcatgtgtaa tgattattta gagtttctct ttcatctgtt    7860
caaatttttg tctagtttta ttttttactg atttgtaaga cttctttta  taatctgcat    7920 attacaattc tctttactgg ggtgttgcaa atattttctg tcattctatg gcctgacttt    7980
tcttaatggt tttttaattt taaaaataag tcttaatatt catgcaatct aattaacaat    8040
cttttctttg tggttaggac tttgagtcat aagaaatttt tctctacact gaagtcatga    8100
tggcatgctt ctatattatt ttctaaaaga tttaaagttt tgccttctcc atttagactt    8160
ataattcact ggaattttt  tgtgtgtatg gtatgacata tgggttccct tttattttt    8220 acatataaat atatttccct gttttttctaa aaagaaaaa gatcatcatt ttcccattgt    8280
aaaatgccat attttttca taggtcactt acatatatca atgggtctgt ttctgagctc    8340
tactctattt tatcagcctc actgtctatc cccacacatc tcatgctttg ctctaaatct    8400
tgatatttag tggaacattc tttcccattt tgttctacaa gaatattttt gttattgtct    8460
tttgggcttc tatatacatt ttagaatgag gttggcaagg taccttaag  accaatgact    8520 tacaaggcag ctgtagatct tagccacttt ttaaaagaaa agggggact  ggaagggcta    8580 attcactccc agctgctttt tgcctgtact gggtctctct ggttagacca gatctgagcc    8640
tgggagctct ctggctaact agggaaccca ctgcttaagc ctcataaagc tcgactgtgc    8700
cttctagttg ccagccatct gttgtttgcc cctcccccgt gccttccttg accctggaag    8760
gtgccactcc cactgtcctt tcctaataaa atgaggaaat tgcatcgcat tgtctgagta    8820
ggtgtcattc tattctgggg gtgggtgg   ggcaggacag caaggggag  gattgggaag    8880 acaatagcag gcatgctggg gatgcggtcc ggactgtact gggtctctct ggttagacca    8940
gatctgagcc tgggagctct ctggctaact agggaaccca ctgcttaagc ctcaataaag    9000
cttgccttga gtgcttcaag tagtgtgtgc ccgtctgttg tgtgactctg gtaactagag    9060
atccctcaga ccctttagt  cagtgtggaa aatctctagc agcatgtgag caaaaggcca    9120
gcaaaaggcc aggaaccgta aaaaggccgc gttgctggcg ttttccata  ggctccgccc    9180 ccctgacgag catcacaaaa atcgacgctc aagtcagagg tggcgaaacc cgacaggact    9240
ataaagatac caggcgtttc ccctggaag  ctccctcgtg cgctctcctg ttccgaccct    9300
gccgcttacc ggatacctgt ccgcctttct cccttcggga agcgtggcgc tttctcatag    9360
ctcacgctgt aggtatctca gttcggtgta ggtcgttcgc tccaagctgg gctgtgtgca    9420 cgaaccccc  gttcagcccg accgctgcgc cttatccggt aactatcgtc ttgagtccaa    9480
cccggtaaga cacgacttat cgccactggc agcagccact ggtaacagga ttagcagagc    9540
gaggtatgta ggcggtgcta cagagttctt gaagtggtgg cctaactacg gctacactag    9600
aagaacagta tttggtatct gcgctctgct gaagccagtt accttcggaa aaagagttgg    9660
tagctcttga tccggcaaac aaaccaccgc tggtagcggt ggttttttg  tttgcaagca    9720 gcagattacg cgcagaaaaa aaggatctca agaagatcct ttgatctttt ctacgggtc    9780 tgacgctcag tggaacgaaa actcacgtta agggattttg gtcatgagat tatcaaaaag    9840
gatcttcacc tagatccttt taaattaaaa atgaagtttt aaatcaatct aaagtatata    9900
tgagtaaact tggtctgaca gttaccaatg cttaatcagt gaggcaccta tctcagcgat    9960
```

-continued

```
ctgtctattt cgttcatcca tagttgcctg actccccgtc gtgtagataa ctacgatacg   10020
ggagggctta ccatctggcc ccagtgctgc aatgataccg cgagacccac gctcaccggc   10080
tccagattta tcagcaataa accagccagc cggaagggcc gagcgcagaa gtggtcctgc   10140
aactttatcc gcctccatcc agtctattaa ttgttgccgg gaagctagag taagtagttc   10200
gccagttaat agtttgcgca acgttgttgc cattgctaca ggcatcgtgg tgtcacgctc   10260
gtcgtttggt atggcttcat tcagctccgg ttcccaacga tcaaggcgag ttacatgatc   10320
ccccatgttg tgcaaaaaag cggttagctc cttcggtcct ccgatcgttg tcagaagtaa   10380
gttggccgca gtgttatcac tcatggttat ggcagcactg cataattctc ttactgtcat   10440
gccatccgta agatgctttt ctgtgactgg tgagtactca accaagtcat tctgagaata   10500
gtgtatgcgg cgaccgagtt gctcttgccc ggcgtcaata cgggataata ccgcgccaca   10560
tagcagaact ttaaaagtgc tcatcattgg aaaacgttct cggggcgaaa actctcaag    10620 gatcttaccg ctgttgagat ccagttcgat gtaacccact cgtgcaccca actgatcttc   10680
agcatctttt actttcacca gcgtttctgg gtgagcaaaa acaggaaggc aaaatgccgc   10740
aaaaaaggga ataagggcga cacggaaatg ttgaatactc atactcttcc ttttcaata    10800 ttattgaagc atttatcagg gttattgtct catgagcgga tacatatttg aatgtattta   10860
gaaaaataaa caatagggg ttccgcgcac atttccccga aaagtgccac ctgac         10915
```

<210> SEQ ID NO 9
<211> LENGTH: 33
<212> TYPE: DNA
<213> ORGANISM: Artificial
<220> FEATURE:
<223> OTHER INFORMATION: Reverse primer

<400> SEQUENCE: 9

```
ccaggattta tacaaggagg agaaaatgaa agc                                33
```

<210> SEQ ID NO 10
<211> LENGTH: 25
<212> TYPE: DNA
<213> ORGANISM: Artificial
<220> FEATURE:
<223> OTHER INFORMATION: Forward primer

<400> SEQUENCE: 10

```
ctgagcaaag accccaacga gaagc                                         25
```

<210> SEQ ID NO 11
<211> LENGTH: 34
<212> TYPE: DNA
<213> ORGANISM: Artificial
<220> FEATURE:
<223> OTHER INFORMATION: loxP WT

<400> SEQUENCE: 11

```
ataacttcgt atagcataca ttatacgaag ttat                               34
```

<210> SEQ ID NO 12
<211> LENGTH: 9
<212> TYPE: DNA
<213> ORGANISM: Artificial
<220> FEATURE:
<223> OTHER INFORMATION: ras splice donor sequence

<400> SEQUENCE: 12

```
gacgtaagt                                                           9
```

<210> SEQ ID NO 13
<211> LENGTH: 8
<212> TYPE: RNA
<213> ORGANISM: Artificial
<220> FEATURE:
<223> OTHER INFORMATION: 5' splice donor site

<400> SEQUENCE: 13 agguaagu                                                                   8

<210> SEQ ID NO 14
<211> LENGTH: 4
<212> TYPE: DNA
<213> ORGANISM: Artificial
<220> FEATURE:
<223> OTHER INFORMATION: 3' splice acceptor site

<400> SEQUENCE: 14 cagg                                                                       4

<210> SEQ ID NO 15
<211> LENGTH: 20
<212> TYPE: DNA
<213> ORGANISM: Artificial
<220> FEATURE:
<223> OTHER INFORMATION: p53 sense probe

<400> SEQUENCE: 15
ccactacaag tacatgtgta                                                     20

<210> SEQ ID NO 16
<211> LENGTH: 20
<212> TYPE: DNA
<213> ORGANISM: Artificial
<220> FEATURE:
<223> OTHER INFORMATION: p53 anti-sense probe

<400> SEQUENCE: 16
tacacatgta cttgtagtgg                                                     20

<210> SEQ ID NO 17
<211> LENGTH: 20
<212> TYPE: DNA
<213> ORGANISM: Artificial
<220> FEATURE:
<223> OTHER INFORMATION: PTEN sense probe

<400> SEQUENCE: 17
ggtgaaacta tactttacaa                                                     20

<210> SEQ ID NO 18
<211> LENGTH: 20
<212> TYPE: DNA
<213> ORGANISM: Artificial
<220> FEATURE:
<223> OTHER INFORMATION: PTEN anti-sense probe

<400> SEQUENCE: 18
ttgtaaagta tagtttcacc                                                     20

<210> SEQ ID NO 19
<211> LENGTH: 23
<212> TYPE: DNA
<213> ORGANISM: Artificial
<220> FEATURE:

-continued

<223> OTHER INFORMATION: Mir-181a probe

<400> SEQUENCE: 19
actcaccgac agcgttgaat gtt                                           23

<210> SEQ ID NO 20
<211> LENGTH: 21
<212> TYPE: DNA
<213> ORGANISM: Artificial
<220> FEATURE:
<223> OTHER INFORMATION: Mir-15b probe

<400> SEQUENCE: 20
tgtaaaccat gatgtgctgc t                                             21

<210> SEQ ID NO 21
<211> LENGTH: 8503
<212> TYPE: DNA
<213> ORGANISM: Artificial
<220> FEATURE:
<223> OTHER INFORMATION: MSCV FLIPi Puro2AThy1.1/human c-Myc-miR-p53
       vector

<400> SEQUENCE: 21
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgcccc tcagcagttt ctagagaacca tcagatgttt     240 ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540 accccctgcct agggaccacc gacccccccg ccgggaggta agctggccag cggtcgtttc     600
gtgtctgtct ctgtctttgt gcgtgtttgt gccggcatct aatgtttgcg cctgcgtctg     660
tactagttag ctaactagct ctgtatctgt cggaccccgtg gtggaactga cgagttctga     720 acaccccggcc gcaaccctgg gagacgtccc agggactttg ggggccgttt ttgtggcccg     780
acctgaggaa gggagtcgat gtggaatccg accccgtcag gatatgtggt tctggtagga     840
gacgagaacc taaaacagtt cccgcctccg tctgaatttt tgctttcggt ttggaaccga     900
agccgcgcgt cttgtctgct gcagcgctgc agcatcgttc tgtgttgtct ctgtctgact     960
gtgtttctgt atttgtctga aaattagggc cagactgtta ccactccctt aagtttgacc    1020
ttaggtcact ggaaagatgt cgagcggatc gctcacaacc agtcggtaga tgtcaagaag    1080
agacgttggg ttaccttctg ctctgcagaa tggccaacct taacgtcgg atggccgcga    1140 gacggcacct ttaaccgaga cctcatcacc caggttaaga tcaaggtctt ttcacctggc    1200
ccgcatggac acccagacca ggtccctac atcgtgacct gggaagcctt ggcttttgac    1260 cccctccct gggtcaagcc ctttgtacac cctaagcctc cgcctcctct tcctccatcc    1320
gccccgtctc tcccccttga acctcctcgt tcgacccccgc ctcgatcctc cctttatcca    1380
gccctcactc cttctctagg cgccggaatt agatccataa cttcgtatag gatacctat    1440 acgaagttat ctcaggtacc gccaccatga ccgagtacaa gcccacggtg cgcctcgcca    1500

```
cccgcgacga cgtccccagg gccgtacgca ccctcgccgc cgcgttcgcc gactaccccg    1560
ccacgcgcca caccgtcgat ccggaccgcc acatcgagcg ggtcaccgag ctgcaagaac    1620
tcttcctcac gcgcgtcggg ctcgacatcg gcaaggtgtg ggtcgcggac gacggcgccg    1680
cggtggcggt ctggaccacg ccggagagcg tcgaagcggg ggcggtgttc gccgagatcg    1740
gcccgcgcat ggccgagttg agcggttccc ggctggccgc gcagcaacag atggaaggcc    1800
tcctggcgcc gcaccggccc aaggagcccg cgtggttcct ggccaccgtc ggcgtctcgc    1860
ccgaccacca gggcaagggt ctgggcagcg ccgtcgtgct ccccggagtg gaggcggccg    1920
agcgcgccgg ggtgcccgcc ttcctggaga cctccgcgcc ccgcaacctc cccttctacg    1980
agcggctcgg cttcaccgtc accgccgacg tcgaggtgcc cgaaggaccg cgcacctggt    2040
gcatgacccg caagcccggt gccctgtaca agaaacagaa aattgtggca ccagtgaaac    2100
agactttgaa ttttgacctt ctcaagttgg cgggagacgt cgagtccaac cctgggccca    2160
tgaacccagc catcagcgtc gctctcctgc tctcagtctt gcaggtgtcc cgagggcaga    2220
aggtgaccag cctgacagcc tgcctggtga accaaaacct tcgcctggac tgccgccatg    2280
agaataacac caaggataac tccatccagc atgagttcag cctgacccga gagaagagga    2340
agcacgtgct ctcaggcacc ctcgggatac ccgagcacac gtaccgctcc cgcgtcaccc    2400
tctccaacca gccctatatc aaggtcctta ccctagccaa cttcaccacc aaggatgagg    2460
gcgactactt ttgtgagctt cgagtctcgg gcgcgaatcc catgagctcc aataaaagta    2520
tcagtgtgta tagagacaaa ctggtcaagt gtggcggcat aagcctgctg gttcagaaca    2580
catcctggat gctgctgctg ctgctttccc tctccctcct ccaagccctg gacttcattt    2640
ctctgtgatc tagaagccat aacttcgtat agtacacatt atacgaagtt atgtttatgc    2700
atacctggag gaaaaaaaaa aggggagagt caggggttta aacgcattag tcttccaatt    2760 gaaaaagtg atttaattta taccatttta attcagcttt gtaaaatgt atcaaagaga    2820 tagcaaggta ttcagttta gtaaacaaga taattgctcc taaagtagcc ccttgaattc    2880
cgaggcagta ggcatccact acaagtacat gtgtaataca tctgtggctt cactattaca    2940
catgtacttg tagtgggcgc tcactgtcaa cagcaatata ccttctcgag ccttctgttg    3000
ggttaacctg aagaagtaat cccagcaagt gttttccaaga tgtgcaggca acgattctgt    3060
aaagtactga agcctcattc aaacatagta tatgtgctgc cgaagcgagc acttaacaag    3120
gcttgcggcc gcccactcac ctgcaattgt cacgcacaag agttccgtag ctgttcaagt    3180
ttgtgtttca actgttctcg tcgtttccgc aacaagtcct cttcagaaat gagcttttgc    3240
tcctctgctt ggacggacag gatgtatgct gtggcttttt taaggataac taccttgggg    3300 gcctttcat tgttttccaa ctccgggatc tggtcacgca gggcaaaaaa gctccgtttt    3360
agctcgttcc tcctctggcg ctccaagacg ttgtgtgttc gcctcttgac attctcctcg    3420
gtgtccgagg acctgggggct ggtgcatttt cggttgttgc tgatctgtct caggactctg    3480
acactgtcca acttgaccct cttggcagca ggatagtcct tccgagtgga gggaggcgct    3540
gcgtagttgt gctgatgtgt ggagacgtgg cacctcttga ggaccagtgg gctgtgagga    3600
ggtttgctgt ggcctccagc agaaggtgat ccagactctg accttttgcc aggagcctgc    3660
ctcttttcca cagaaacaac atcgatttct tcctcatctt cttgttcctc ctcagagtcg    3720
ctgctggtgg tgggcggtgt ctcctcatgg agcaccaggg gctcggggct gccctgcggg    3780
gaggactccg tcgaggagag cagagaatcc gaggacggag agaaggcgct ggagtcttgc    3840
gaggcgcagg acttgggcga gctgctgtcg ttgagagggt aggggaagac caccgagggg    3900
```

```
tcgatgcact ctgaggcggc ggcgctcaga tcctgcaggt acaagctgga ggtggagcag    3960
acgctgtggc cgcgggcggg gttcgggctg ccgctgtctt tgcgcgcagc ctggtaggag    4020
gccagcttct ctgagacgag cttggcggcg gccgagaagc cgctccacat acagtcctgg    4080
atgatgatgt ttttgatgaa ggtctcgtcg tccgggtcgc agatgaaact ctggttcacc    4140
atgtctcctc ccagcagctc ggtcaccatc tccagctggt cggccgtgga agctcccg     4200 ccaccgccgt cgttgtctcc ccgaagggag aagggtgtga ccgcaacgta ggagggcgag    4260
cagagcccgg agcggcggct aggggacagg ggcggggtgg gcagcagctc gaatttcttc    4320
cagatatcct cgctgggcgc cggggggctgc agctcgctct gctgctgctg ctggtagaag    4380
ttctcctcct cgtcgcagta gaaatacggc tgcaccgagt cgtagtcgag gtcatagttc    4440
ctgttggtga agctaacgtt gaggggtcta gacatcagca tcaggctggc atagtcaggc    4500
acgtcataag gatagctcat cagcatcagg ctggcatagt caggcacgtc ataaggatag    4560
ctcatcagca tcaggctggc atagtcaggc acgtcataag gatagctatc catggtggcg    4620
accggtataa cttcgtataa ggtatcctat acgaagttat ccattcaggc tgtgctagca    4680
tcaatggcat ggcacaaagc ttagccataa cttcgtataa tgtgtactat acgaagttat    4740
cccgggttaa acgacctgca gccaagctta tcgataaaat aaaagatttt atttagtctc    4800
cagaaaaagg ggggaatgaa agaccccacc tgtaggtttg gcaagctagc ttaagtaacg    4860
ccattttgca aggcatggaa aatacataac tgagaataga aagttcaga tcaaggttag     4920 gaacagagag acagcagaat atgggccaaa caggatatct gtggtaagca gttcctgccc    4980
cggctcaggg ccaagaacag atggtcccca gatgcggtcc cgccctcagc agtttctaga    5040
gaaccatcag atgtttccag ggtgcccaa ggacctgaaa atgaccctgt gccttatttg      5100
aactaaccaa tcagttcgct tctcgcttct gttcgcgcgc ttctgctccc cgagctcaat    5160
aaaagagccc acaacccctc actcggcgcg ccagtcctcc gatagactgc gtcgcccggg    5220
tacccgtgta tccaataaac cctcttgcag ttgcatccga cttgtggtct cgctgttcct    5280
tgggagggtc tcctctgagt gattgactac ccgtcagcgg gggtctttca tgggtaacag    5340
tttcttgaag ttggagaaca acattctgag ggtaggagtc gaatattaag taatcctgac    5400
tcaattagcc actgttttga atccacatac tccaatactc ctgaaatagt tcattatgga    5460
cagcgcagaa gagctgggga gaattaattc gtaatcatgg tcatagctgt ttcctgtgtg    5520
aaattgttat ccgctcacaa ttccacacaa catacgagcc ggaagcataa agtgtaaagc    5580
ctggggtgcc taatgagtga gctaactcac attaattgcg ttgcgctcac tgcccgcttt    5640
ccagtcggga aacctgtcgt gccagctgca ttaatgaatc ggccaacgcg cggggagagg    5700
cggtttgcgt attgggcgct cttccgcttc ctcgctcact gactcgctgc gctcggtcgt    5760
tcggctgcgg cgagcggtat cagctcactc aaaggcggta atacggttat ccacagaatc    5820
aggggataac gcaggaaaga acatgtgagc aaaaggccag caaaaggcca ggaaccgtaa    5880
aaaggccgcg ttgctggcgt ttttccatag gctccgcccc cctgacgagc atcacaaaaa    5940
tcgacgctca agtcagaggt ggcgaaaccc gacaggacta taaagatacc aggcgtttcc    6000
ccctggaagc tccctcgtgc gctctcctgt tccgaccctg ccgcttaccg gatacctgtc    6060
cgcctttctc ccttcgggaa gcgtggcgct ttctcatagc tcacgctgta ggtatctcag    6120
ttcggtgtag tcgttcgct ccaagctggg ctgtgtgcac gaaccccccg ttcagcccga    6180
ccgctgcgcc ttatccggta actatcgtct tgagtccaac ccggtaagac acgacttatc    6240
```

```
gccactggca gcagccactg gtaacaggat tagcagagcg aggtatgtag gcggtgctac    6300
agagttcttg aagtggtggc ctaactacgg ctacactaga aggacagtat ttggtatctg    6360
cgctctgctg aagccagtta ccttcggaaa aagagttggt agctcttgat ccggcaaaca    6420
aaccaccgct ggtagcggtg gtttttttgt ttgcaagcag cagattacgc gcagaaaaaa    6480
aggatctcaa gaagatcctt tgatcttttc tacggggtct gacgctcagt ggaacgaaaa    6540
ctcacgttaa gggattttgg tcatgagatt atcaaaaagg atcttcacct agatcctttt    6600
aaattaaaaa tgaagtttta aatcaatcta agtatatat gagtaaactt ggtctgacag    6660
ttaccaatgc ttaatcagtg aggcacctat ctcagcgatc tgtctatttc gttcatccat    6720
agttgcctga ctccccgtcg tgtagataac tacgatacgg gagggcttac catctggccc    6780
cagtgctgca atgataccgc gagacccacg ctcaccggct ccagatttat cagcaataaa    6840
ccagccagcc ggaagggccg agcgcagaag tggtcctgca actttatccg cctccatcca    6900
gtctattaat tgttgccggg aagctagagt aagtagttcg ccagttaata gtttgcgcaa    6960
cgttgttgcc attgctacag gcatcgtggt gtcacgctcg tcgtttggta tggcttcatt    7020
cagctccggt tcccaacgat caaggcgagt tacatgatcc cccatgttgt gcaaaaaagc    7080
ggttagctcc ttcggtcctc cgatcgttgt cagaagtaag ttggccgcag tgttatcact    7140
catggttatg gcagcactgc ataattctct tactgtcatg ccatccgtaa gatgcttttc    7200
tgtgactggt gagtactcaa ccaagtcatt ctgagaatag tgtatgcggc gaccgagttg    7260
ctcttgcccg gcgtcaatac gggataatac cgcgccacat agcagaactt taaaagtgct    7320
catcattgga aaacgttctt cggggcgaaa actctcaagg atcttaccgc tgttgagatc    7380
cagttcgatg taacccactc gtgcacccaa ctgatcttca gcatctttta ctttcaccag    7440
cgtttctggg tgagcaaaaa caggaaggca aatgccgca aaaaagggaa taagggcgac    7500
acggaaatgt tgaatactca tactcttcct ttttcaatat tattgaagca tttatcaggg    7560
ttattgtctc atgagcggat acatatttga atgtatttag aaaaataaac aaataggggt    7620
tccgcgcaca tttccccgaa aagtgccacc tgacgtctaa gaaaccatta ttatcatgac    7680
attaacctat aaaaatagge gtatcacgag gcccttcgt ctcgcgcgtt tcggtgatga    7740
cggtgaaaac ctctgacaca tgcagctccc ggagacggtc acagcttgtc tgtaagcgga    7800
tgccgggagc agacaagccc gtcagggcgc gtcagcgggt gttggcgggt gtcgggctg    7860 gcttaactat gcggcatcag agcagattgt actgagagtg caccatatgc ggtgtgaaat    7920
accgcacaga tgcgtaagga gaaaatacccg catcaggcgc cattcgccat tcaggctgcg    7980
caactgttgg aagggcgat cggtgcgggc ctcttcgcta ttacgccagc tggcgaaagg    8040
gggatgtgct gcaaggcgat taagttgggt aacgccaggg ttttcccagt cacgacgttg    8100
taaaacgacg gcgcaaggaa gcagcccagt agtaggttga ggccgttgag caccgccgcc    8160
gcaaggaatg gtgcatgcaa ggagatggcg cccaacagtc ccccggccac ggggcctgcc    8220 accatacccca cgccgaaaca agcgctcatg agcccgaagt ggcgagcccg atcttcccca    8280
tcggtgatgt cggcgatata ggcgccagca accgcacctg tggcgccggt gatgccggcc    8340
acgatgcgtc cggcgtagag gcgattagtc caatttgtta aagacaggat atcagtggtc    8400
caggctctag ttttgactca acaatatcac cagctgaagc ctatagagta cgagccatag    8460
ataaaataaa agattttatt tagtctccag aaaaggggg gaa                      8503

<210> SEQ ID NO 22
<211> LENGTH: 7697
```

<212> TYPE: DNA
<213> ORGANISM: Artificial
<220> FEATURE:
<223> OTHER INFORMATION: MSCV FLIP-p53

<400> SEQUENCE: 22

| | | | | | |
|---|---|---|---|---|---|
| tgaaagaccc | cacctgtagg | tttggcaagc | tagcttaagt | aacgccattt | tgcaaggcat | 60 |
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcgg | cgcgccagtc | ctccgataga | ctgcgtcgcc | cgggtacccg | tattcccaat | 420 |
| aaagcctctt | gctgtttgca | tccgaatcgt | ggactcgctg | atccttggga | gggtctcctc | 480 |
| agattgattg | actgcccacc | tcggggtct | ttcatttgga | ggttccaccg | agatttggag | 540 |
| accccctgcct | agggaccacc | gacccccccg | ccgggaggta | agctggccag | cggtcgtttc | 600 |
| gtgtctgtct | ctgtctttgt | gcgtgtttgt | gccggcatct | aatgtttgcg | cctgcgtctg | 660 |
| tactagttag | ctaactagct | ctgtatctgg | cggacccgtg | gtggaactga | cgagttctga | 720 |
| acacccggcc | gcaaccctgg | gagacgtccc | agggactttg | ggggccgttt | ttgtggcccg | 780 |
| acctgaggaa | gggagtcgat | gtggaatccg | accccgtcag | gatatgtggt | tctggtagga | 840 |
| gacgagaacc | taaaacagtt | cccgcctccg | tctgaatttt | tgctttcggt | ttggaaccga | 900 |
| agccgcgcgt | cttgtctgct | gcagcgctgc | agcatcgttc | tgtgttgtct | ctgtctgact | 960 |
| gtgtttctgt | atttgtctga | aaattagggc | cagactgtta | ccactccctt | aagtttgacc | 1020 |
| ttaggtcact | ggaaagatgt | cgagcggatc | gctcacaacc | agtcggtaga | tgtcaagaag | 1080 |
| agacgttggg | ttaccttctg | ctctgcagaa | tggccaacct | ttaacgtcgg | atggccgcga | 1140 |
| gacggcacct | ttaaccgaga | cctcatcacc | caggttaaga | tcaaggtctt | ttcacctggc | 1200 |
| ccgcatggac | acccagacca | ggtcccctac | atcgtgacct | gggaagcctt | ggcttttgac | 1260 |
| cccccctccct | gggtcaagcc | ctttgtacac | cctaagcctc | cgcctcctct | tcctccatcc | 1320 |
| gccccgtctc | tccccctga | acctcctcgt | tcgaccccgc | ctcgatcctc | cctttatcca | 1380 |
| gccctcactc | cttctctagg | cgccggaatt | agatccataa | cttcgtatag | gataccttat | 1440 |
| acgaagttat | ctcaggtacc | gccaccatga | ccgagtacaa | gcccacggtg | cgcctcgcca | 1500 |
| cccgcgacga | cgtccccagg | gccgtacgca | ccctcgccgc | cgcgttcgcc | gactaccccg | 1560 |
| ccacgcgcca | caccgtcgat | ccggaccgcc | acatcgagcg | ggtcaccgag | ctgcaagaac | 1620 |
| tcttcctcac | gcgcgtcggg | ctcgacatcg | gcaaggtgtg | ggtcgcggac | gacgcgccg | 1680 |
| cggtggcggt | ctggaccacg | ccggagagcg | tcgaagcggg | ggcggtgttc | gccgagatcg | 1740 |
| gcccgcgcat | ggccgagttg | agcggttccc | ggctggccgc | gcagcaacag | atggaaggcc | 1800 |
| tcctggcgcc | gcaccggccc | aaggagcccg | cgtggttcct | ggccaccgtc | ggcgtctcgc | 1860 |
| ccgaccacca | gggcaagggt | ctgggcagcc | gcgtcgtgct | ccccggagtg | gaggcggccg | 1920 |
| agcgcgccgg | ggtgcccgcc | ttcctggaga | cctccgcgcc | ccgcaacctc | cccttctacg | 1980 |
| agcggctcgg | cttcaccgtc | accgccgacg | tcgaggtgcc | cgaaggaccg | cgcacctggt | 2040 |
| gcatgacccg | caagcccggt | gcctgtaca | agaaacagaa | aattgtggca | ccagtgaaac | 2100 |
| agactttgaa | ttttgacctt | ctcaagttgg | cgggagacgt | cgagtccaac | cctgggccca | 2160 |

```
tgaacccagc catcagcgtc gctctcctgc tctcagtctt gcaggtgtcc cgagggcaga    2220
aggtgaccag cctgacagcc tgcctggtga accaaaacct tcgcctggac tgccgccatg    2280
agaataacac caaggataac tccatccagc atgagttcag cctgacccga gagaagagga    2340
agcacgtgct ctcaggcacc ctcgggatac ccgagcacac gtaccgctcc cgcgtcaccc    2400
tctccaacca gccctatatc aaggtcctta ccctagccaa cttcaccacc aaggatgagg    2460
gcgactactt ttgtgagctt cgagtctcgg gcgcgaatcc catgagctcc aataaaagta    2520
tcagtgtgta tagagacaaa ctggtcaagt gtggcggcat aagcctgctg gttcagaaca    2580
catcctggat gctgctgctg ctgctttccc tctccctcct ccaagccctg gacttcattt    2640
ctctgtgatc tagaagccat aacttcgtat agtacacatt atacgaagtt atgtttaaac    2700
gcattagtct tccaattgaa aaagtgatt aatttatac cattttaatt cagctttgta    2760
aaaatgtatc aaagagatag caaggtattc agttttagta acaagataa ttgctcctaa    2820
agtagcccct tgaattccga ggcagtaggc atccactaca agtacatgtg taatacatct    2880
gtggcttcac tattacacat gtacttgtag tgggcgctca ctgtcaacag caatatacct    2940
tctcgagcct tctgttgggt taacctgaag aagtaatccc agcaagtgtt tccaagatgt    3000
gcaggcaacg attctgtaaa gtactgaagc ctcattcaaa catagtatat gtgctgccga    3060
agcgagcact taacaaggct tgcggccgct acttgtacag ctcgtccatg ccgagagtga    3120
tccccggcggc ggtcacgaac tccagcagga ccatgtgatc gcgcttctcg ttggggtctt    3180
tgctcagggc ggactgggtg ctcaggtagt ggttgtcggg cagcagcacg gggccgtcgc    3240
cgatgggggt gttctgctgg tagtggtcgg cgagctgcac gctgccgtcc tcgatgttgt    3300
ggcggatctt gaagttcacc ttgatgccgt tcttctgctt gtcggccatg atatagacgt    3360
tgtggctgtt gtagttgtac tccagcttgt gccccaggat gttgccgtcc tccttgaagt    3420
cgatgccctt cagctcgatg cggttcacca gggtgtcgcc ctcgaacttc acctcggcgc    3480
gggtcttgta gttgccgtcg tccttgaaga agatggtgcg ctcctggacg tagccttcgg    3540
gcatggcgga cttgaagaag tcgtgctgct tcatgtggtc ggggtagcgg ctgaagcact    3600
gcacgccgta ggtcagggtg gtcacgaggg tgggccaggg cacgggcagc ttgccggtgg    3660
tgcagatgaa cttcagggtc agcttgccgt aggtggcatc gccctcgccc tcgccggaca    3720
cgctgaactt gtgccgtttt acgtcgccgt ccagctcgac caggatgggc accaccccgg    3780
tgaacagctc ctcgcccttg ctcaccatgg tggcgaccgg tataacttcg tataaggtat    3840
cctatacgaa gttatccatt caggctgtgc tagcatcaat ggcatggcac aaagcttagc    3900
cataacttcg tataatgtgt actatacgaa gttatcccgg gttaaacgac ctgcagccaa    3960
gcttatcgat aaaataaaag attttattta gtctccagaa aaaggggga atgaaagacc    4020
ccacctgtag gtttggcaag ctagcttaag taacgccatt ttgcaaggca tggaaaatac    4080
ataactgaga atagagaagt tcagatcaag gttaggaaca gagagacagc agaatatggg    4140
ccaaacagga tatctgtggt aagcagttcc tgccccggct cagggccaag aacagatggt    4200
ccccagatgc ggtcccgccc tcagcagttt ctagagaacc atcagatgtt tccagggtgc    4260
cccaaggacc tgaaaatgac cctgtgcctt atttgaacta accaatcagt tcgcttctcg    4320
cttctgttcg cgcgcttctg ctccccgagc tcaataaaag agcccacaac ccctcactcg    4380
gcgcgccagt cctccgatag actgcgtcgc ccgggtaccc gtgtatccaa taaaccctct    4440
tgcagttgca tccgacttgt ggtctcgctg ttccttggga gggtctcctc tgagtgattg    4500
actacccgtc agcgggggtc tttcatgggt aacagtttct tgaagttgga gaacaacatt    4560
```

```
ctgagggtag gagtcgaata ttaagtaatc ctgactcaat tagccactgt tttgaatcca    4620
catactccaa tactcctgaa atagttcatt atggacagcg cagaagagct ggggagaatt    4680
aattcgtaat catggtcata gctgtttcct gtgtgaaatt gttatccgct cacaattcca    4740
cacaacatac gagccggaag cataaagtgt aaagcctggg gtgcctaatg agtgagctaa    4800
ctcacattaa ttgcgttgcg ctcactgccc gctttccagt cgggaaacct gtcgtgccag    4860
ctgcattaat gaatcggcca acgcgcgggg agaggcggtt tgcgtattgg gcgctcttcc    4920
gcttcctcgc tcactgactc gctgcgctcg tcgttcggc tgcggcgagc ggtatcagct    4980
cactcaaagg cggtaatacg gttatccaca gaatcagggg ataacgcagg aaagaacatg    5040
tgagcaaaag gccagcaaaa ggccaggaac cgtaaaaagg ccgcgttgct ggcgtttttc    5100
cataggctcc gcccccctga cgagcatcac aaaaatcgac gctcaagtca gaggtggcga    5160
aacccgacag gactataaag ataccaggcg tttccccctg gaagctccct cgtgcgctct    5220
cctgttccga ccctgccgct taccggatac ctgtccgcct ttctcccttc gggaagcgtg    5280
gcgctttctc atagctcacg ctgtaggtat ctcagttcgg tgtaggtcgt tcgctccaag    5340
ctgggctgtg tgcacgaacc ccccgttcag cccgaccgct gcgccttatc cggtaactat    5400
cgtcttgagt ccaacccggt aagacacgac ttatcgccac tggcagcagc cactggtaac    5460
aggattagca gagcgaggta tgtaggcggt gctacagagt tcttgaagtg gtggcctaac    5520
tacggctaca ctagaaggac agtatttggt atctgcgctc tgctgaagcc agttaccttc    5580
ggaaaaagag ttggtagctc ttgatccggc aaacaaacca ccgctggtag cggtggtttt    5640
tttgtttgca agcagcagat tacgcgcaga aaaaaggat ctcaagaaga tcctttgatc    5700
ttttctacgg ggtctgacgc tcagtggaac gaaaactcac gttaagggat tttggtcatg    5760
agattatcaa aaaggatctt cacctagatc cttttaaatt aaaaatgaag ttttaaatca    5820
atctaaagta tatatgagta aacttggtct gacagttacc aatgcttaat cagtgaggca    5880
cctatctcag cgatctgtct atttcgttca tccatagttg cctgactccc cgtcgtgtag    5940
ataactacga tacgggaggg cttaccatct ggccccagtg ctgcaatgat accgcgagac    6000
ccacgctcac cggctccaga tttatcagca ataaaccagc cagccggaag ggccgagcgc    6060
agaagtggtc ctgcaacttt atccgcctcc atccagtcta ttaattgttg ccgggaagct    6120
agagtaagta gttcgccagt taatagtttg cgcaacgttg ttgccattgc tacaggcatc    6180
gtggtgtcac gctcgtcgtt tggtatggct tcattcagct ccggttccca acgatcaagg    6240
cgagttacat gatcccccat gttgtgcaaa aaagcggtta gctccttcgg tcctccgatc    6300
gttgtcagaa gtaagttggc cgcagtgtta tcactcatgg ttatggcagc actgcataat    6360
tctcttactg tcatgccatc cgtaagatgc ttttctgtga ctggtgagta ctcaaccaag    6420
tcattctgag aatagtgtat gcggcgaccg agttgctctt gcccggcgtc aatacgggat    6480
aataccgcgc cacatagcag aactttaaaa gtgctcatca ttggaaaacg ttcttcgggg    6540
cgaaaactct caaggatctt accgctgttg agatccagtt cgatgtaacc cactcgtgca    6600
cccaactgat cttcagcatc ttttactttc accagcgttt ctgggtgagc aaaaacagga    6660
aggcaaaatg ccgcaaaaaa gggaataagg gcgacacgga aatgttgaat actcatactc    6720
ttcctttttc aatattattg aagcatttat cagggttatt gtctcatgag cggatacata    6780
tttgaatgta tttagaaaaa taaacaaata ggggttccgc gcacatttcc ccgaaaagtg    6840
ccacctgacg ctaagaaacc attattatca tgacattaac ctataaaaat aggcgtatca    6900
```

```
cgaggccctt tcgtctcgcg cgtttcggtg atgacggtga aaacctctga cacatgcagc    6960
tcccggagac ggtcacagct tgtctgtaag cggatgccgg gagcagacaa gcccgtcagg    7020
gcgcgtcagc gggtgttggc gggtgtcggg gctggcttaa ctatgcggca tcagagcaga    7080
ttgtactgag agtgcaccat atgcggtgtg aaataccgca cagatgcgta aggagaaaat    7140
accgcatcag gcgccattcg ccattcaggc tgcgcaactg ttgggaaggg cgatcggtgc    7200
gggcctcttc gctattacgc cagctggcga aggggggatg tgctgcaagg cgattaagtt    7260
gggtaacgcc agggttttcc cagtcacgac gttgtaaaac gacggcgcaa ggaagcagcc    7320
cagtagtagg ttgaggccgt tgagcaccgc cgccgcaagg aatggtgcat gcaaggagat    7380
ggcgcccaac agtcccccgg ccacggggcc tgccaccata cccacgccga acaagcgct     7440
catgagcccg aagtggcgag cccgatcttc cccatcggtg atgtcggcga tataggcgcc    7500
agcaaccgca cctgtggcgc cggtgatgcc ggccacgatg cgtccggcgt agaggcgatt    7560
agtccaattt gttaaagaca ggatatcagt ggtccaggct ctagttttga ctcaacaata    7620
tcaccagctg aagcctatag agtacgagcc atagataaaa taaagatttt atttagtct    7680
ccagaaaaag gggggaa                                                    7697
```

<210> SEQ ID NO 23
<211> LENGTH: 7698
<212> TYPE: DNA
<213> ORGANISM: Artificial
<220> FEATURE:
<223> OTHER INFORMATION: MSCV FLIP-PTEN

<400> SEQUENCE: 23

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactgctg atccttggga gggtctcctc     480
agattgattg actgcccacc tcgggggtct ttcatttgga ggttccaccg agatttggag    540
accccctgcct agggaccacc gacccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttctga    720
acacccggcc gcaaccctgg gagacgtccc agggactttg ggggccgttt tgtggcccg     780
acctgaggaa gggagtcgat gtggaatccg acccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtcccctac atcgtgacct gggaagcctt ggcttttgac   1260
```

```
ccccctccct gggtcaagcc ctttgtacac cctaagcctc cgcctcctct tcctccatcc   1320
gccccgtctc tcccccttga acctcctcgt tcgaccccgc ctcgatcctc cctttatcca   1380
gccctcactc cttctctagg cgccggaatt agatccataa cttcgtatag gataccttat   1440
acgaagttat ctcaggtacc gccaccatga ccgagtacaa gcccacggtg cgcctcgcca   1500
cccgcgacga cgtccccagg gccgtacgca ccctcgccgc cgcgttcgcc gactaccccg   1560
ccacgcgcca caccgtcgat ccggaccgcc acatcgagcg ggtcaccgag ctgcaagaac   1620
tcttcctcac gcgcgtcggg ctcgacatcg gcaaggtgtg ggtcgcggac gacggcgccg   1680
cggtggcggt ctggaccacg ccggagagcg tcgaagcggg ggcggtgttc gccgagatcg   1740
gcccgcgcat ggccgagttg agcggttccc ggctggccgc gcagcaacag atggaaggcc   1800
tcctggcgcc gcaccggccc aaggagcccg cgtggttcct ggccaccgtc ggcgtctcgc   1860
ccgaccacca gggcaagggt ctgggcagcg ccgtcgtgct ccccggagtg gaggcggccg   1920
agcgcgccgg ggtgcccgcc ttcctggaga cctccgcgcc ccgcaacctc cccttctacg   1980
agcggctcgg cttcaccgtc accgccgacg tcgaggtgcc cgaaggaccg cgcacctggt   2040
gcatgacccg caagcccggt gccctgtaca agaaacagaa aattgtggca ccagtgaaac   2100 agacttttgaa ttttgacctt ctcaagttgg cgggagacgt cgagtccaac cctgggccca   2160
tgaacccagc catcagcgtc gctctcctgc tctcagtctt gcaggtgtcc cgagggcaga   2220
aggtgaccag cctgacagcc tgcctggtga accaaaacct tcgcctggac tgccgccatg   2280
agaataacac caaggataac tccatccagc atgagttcag cctgacccga gagaaggagg   2340
agcacgtgct ctcaggcacc ctcgggatac ccgagcacac gtaccgctcc cgcgtcaccc   2400
tctccaacca gccctatatc aaggtcctta ccctagccaa cttcaccacc aaggatgagg   2460
gcgactactt ttgtgagctt cgagtctcgg gcgcgaatcc catgagctcc aataaaagta   2520
tcagtgtgta tagagacaaa ctggtcaagt gtggcggcat aagcctgctg gttcagaaca   2580
catcctggat gctgctgctg ctgctttccc tctccctcct ccaagccctg gacttcattt   2640
ctctgtgatc tagaagccat aacttcgtat agtacacatt atacgaagtt atgtttaaac   2700
gcattagtct tccaattgaa aaaagtgatt taatttatac cattttaatt cagctttgta   2760
aaaatgtatc aaagagatag caaggtattc agttttagta aacaagataa ttgctcctaa   2820
agtagcccct tgaattccga ggcagtaggc aaggtgaaac tatactttac aaatacatct   2880
gtggcttcac tatttgtaaa gtatagtttc accgcgctca ctgtcaacag caatataccc   2940
tctcgagcct tctgttgggt taacctgaag aagtaatccc agcaagtgtt tccaagatgt   3000
gcaggcaacg attctgtaaa gtactgaagc tcattcaaa catagtatat gtgctgccga   3060
agcgagcact taacaaggct tgcggccgct acttgtacag ctcgtccatg ccgagagtga   3120
tcccggcggc ggtcacgaac tccagcagga ccatgtgatc gcgcttctcg ttggggtctt   3180
tgctcagggc ggactgggtg ctcaggtagt ggttgtcggg cagcagcacg gggccgtcgc   3240 cgatggggt gttctgctgg tagtggtcgg cgagctgcac gctgccgtcc tcgatgttgt   3300
ggcggatctt gaagttcacc ttgatgccgt tcttctgctt gtcggccatg atatagacgt   3360
tgtggctgtt gtagttgtac tccagcttgt gccccaggat gttgccgtcc tccttgaagt   3420
cgatgccctt cagctcgatg cggttcacca gggtgtcgcc ctcgaacttc acctcggcgc   3480
gggtcttgta gttgccgtcg tccttgaaga gatggtgcg ctcctggacg tagccttcgg   3540
gcatggcgga cttgaagaag tcgtgctgct tcatgtggtc ggggtagcgg ctgaagcact   3600
```

```
gcacgccgta ggtcagggtg gtcacgaggg tgggccaggg cacgggcagc ttgccggtgg    3660
tgcagatgaa cttcagggtc agcttgccgt aggtggcatc gccctcgccc tcgccggaca    3720
cgctgaactt gtggccgttt acgtcgccgt ccagctcgac caggatgggc accaccccgg    3780
tgaacagctc ctcgcccttg ctcaccatgg tggcgaccgg tataacttcg tataaggtat    3840
cctatacgaa gttatccatt caggctgtgc tagcatcaat ggcatggcac aaagcttagc    3900
cataacttcg tataatgtgt actatacgaa gttatcccgg gttaaacgac ctgcagccaa    3960
gcttatcgat aaaataaaag attttattta gtctccagaa aaaggggggga atgaaagacc    4020
ccacctgtag gtttggcaag ctagcttaag taacgccatt ttgcaaggca tggaaaatac    4080
ataactgaga atagagaagt tcagatcaag gttaggaaca gagagacagc agaatatggg    4140
ccaaacagga tatctgtggt aagcagttcc tgccccggct cagggccaag aacagatggt    4200
ccccagatgc ggtcccgccc tcagcagttt ctagagaacc atcagatgtt tccagggtgc    4260
cccaaggacc tgaaaatgac cctgtgcctt atttgaacta accaatcagt tcgcttctcg    4320
cttctgttcg cgcgcttctg ctccccgagc tcaataaaag agcccacaac ccctcactcg    4380
gcgcgccagt cctccgatag actgcgtcgc ccgggtaccc gtgtatccaa taaaccctct    4440
tgcagttgca tccgacttgt ggtctcgctg ttccttggga gggtcctc tgagtgattg    4500
actaccgtc agcggggtc tttcatgggt aacagtttct tgaagttgga gaacaacatt    4560
ctgagggtag gagtcgaata ttaagtaatc ctgactcaat tagccactgt tttgaatcca    4620
catactccaa tactcctgaa atagttcatt atggacagcg cagaagagct ggggagaatt    4680
aattcgtaat catggtcata gctgtttcct gtgtgaaatt gttatccgct cacaattcca    4740
cacaacatac gagccggaag cataaagtgt aaagcctggg gtgcctaatg agtgagctaa    4800
ctcacattaa ttgcgttgcg ctcactgccc gctttccagt cgggaaacct gtcgtgccag    4860
ctgcattaat gaatcggcca acgcgcgggg agaggcggtt tgcgtattgg gcgctcttcc    4920
gcttcctcgc tcactgactc gctgcgctcg gtcgttcggc tgcggcgagc ggtatcagct    4980
cactcaaagg cggtaatacg gttatccaca gaatcagggg ataacgcagg aaagaacatg    5040
tgagcaaaag gccagcaaaa ggccaggaac cgtaaaaagg ccgcgttgct ggcgtttttc    5100
cataggctcc gcccccctga cgagcatcac aaaaatcgac gctcaagtca gaggtggcga    5160
aacccgacag gactataaag ataccaggcg tttccccctg gaagctccct cgtgcgctct    5220
cctgttccga ccctgccgct taccggatac ctgtccgcct ttctcccttc gggaagcgtg    5280
gcgctttctc atagctcacg ctgtaggtat ctcagttcgg tgtaggtcgt tcgctccaag    5340
ctgggctgtg tgcacgaacc ccccgttcag cccgaccgct gcgccttatc cggtaactat    5400
cgtcttgagt ccaacccggt aagacacgac ttatcgccac tggcagcagc cactggtaac    5460
aggattagca gagcgaggta tgtaggcggt gctacagagt tcttgaagtg gtggcctaac    5520
tacggctaca ctagaaggac agtatttggt atctgcgctc tgctgaagcc agttaccttc    5580
ggaaaaagag ttggtagctc ttgatccggc aaacaaacca ccgctggtag cggtggtttt    5640
tttgtttgca agcagcagat tacgcgcaga aaaaaggat ctcaagaaga tcctttgatc    5700
ttttctacgg ggtctgacgc tcagtggaac gaaaactcac gttaagggat tttggtcatg    5760
agattatcaa aaaggatctt cacctagatc cttttaaatt aaaaatgaag ttttaaatca    5820
atctaaagta tatatgagta aacttggtct gacagttacc aatgcttaat cagtgaggca    5880
cctatctcag cgatctgtct atttcgttca tccatagttg cctgactccc cgtcgtgtag    5940
ataactacga tacgggaggg cttaccatct ggccccagtg ctgcaatgat accgcgagac    6000
```

```
ccacgctcac cggctccaga tttatcagca ataaaccagc cagccggaag ggccgagcgc    6060
agaagtggtc ctgcaacttt atccgcctcc atccagtcta ttaattgttg ccgggaagct    6120
agagtaagta gttcgccagt taatagtttg cgcaacgttg ttgccattgc tacaggcatc    6180
gtggtgtcac gctcgtcgtt tggtatggct tcattcagct ccggttccca acgatcaagg    6240
cgagttacat gatccccat gttgtgcaaa aaagcggtta gctccttcgg tcctccgatc    6300
gttgtcagaa gtaagttggc cgcagtgtta tcactcatgg ttatggcagc actgcataat    6360
tctcttactg tcatgccatc cgtaagatgc ttttctgtga ctggtgagta ctcaaccaag    6420
tcattctgag aatagtgtat gcggcgaccg agttgctctt gcccggcgtc aatacgggat    6480
aataccgcgc cacatagcag aactttaaaa gtgctcatca ttggaaaacg ttcttcgggg    6540
cgaaaactct caaggatctt accgctgttg agatccagtt cgatgtaacc cactcgtgca    6600
cccaactgat cttcagcatc ttttactttc accagcgttt ctgggtgagc aaaaacagga    6660
aggcaaaatg ccgcaaaaaa gggaataagg gcgacacgga aatgttgaat actcatactc    6720
ttcctttttc aatattattg aagcatttat cagggttatt gtctcatgag cggatacata    6780
tttgaatgta tttagaaaaa taaacaaata ggggttccgc gcacatttcc ccgaaaagtg    6840
ccacctgacg tctaagaaac cattattatc atgacattaa cctataaaaa taggcgtatc    6900
acgaggccct tcgtctcgc gcgtttcggt gatgacggtg aaaacctctg acacatgcag    6960
ctcccggaga cggtcacagc ttgtctgtaa gcggatgccg ggagcagaca gcccgtcag    7020 ggcgcgtcag cgggtgttgg cgggtgtcgg gctggctta actatgcggc atcagagcag    7080
attgtactga gagtgcacca tatgcggtgt gaaataccgc acagatgcgt aaggagaaaa    7140
taccgcatca ggcgccattc gccattcagg ctgcgcaact gttgggaagg gcgatcggtg    7200
cgggcctctt cgctattacg ccagctggcg aaagggggat gtgctgcaag gcgattaagt    7260
tgggtaacgc cagggttttc ccagtcacga cgttgtaaaa cgacggcgca aggaagcagc    7320
ccagtagtag gttgaggccg ttgagcaccg ccgccgcaag gaatggtgca tgcaaggaga    7380
tggcgcccaa cagtccccg gccacgggggc ctgccaccat acccacgccg aaacaagcgc    7440
tcatgagccc gaagtggcga gccgatcttc cccatcggt gatgtcggcg atataggcgc    7500
cagcaaccgc acctgtggcg ccggtgatgc cggccacgat gcgtccggcg tagaggcgat    7560
tagtccaatt tgttaaagac aggatatcag tggtccaggc tctagttttg actcaacaat    7620
atcaccagct gaagcctata gagtacgagc catagataaa ataaaagatt ttatttagtc    7680
tccagaaaaa ggggggaa                                                 7698

<210> SEQ ID NO 24
<211> LENGTH: 7806
<212> TYPE: DNA
<213> ORGANISM: Artificial
<220> FEATURE:
<223> OTHER INFORMATION: MSCV FLIPi Puro2AGFP / Thy1.1-miR-FF

<400> SEQUENCE: 24
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaatgacc ctgtgcctta tttgaactaa ccaatcagtt    300
```

```
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540 accccctgcct agggaccacc gaccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttctga    720
acacccggcc gcaaccctgg gagacgtccc agggactttg ggggccgttt ttgtggcccg    780
acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc    1020
ttaggtcact ggaaagatgt cgagcggatc gctcacaacc agtcggtaga tgtcaagaag    1080
agacgttggg ttaccttctg ctctgcagaa tggccaacct ttaacgtcgg atggccgcga    1140
gacggcacct ttaaccgaga cctcatcacc caggttaaga tcaaggtctt ttcacctggc    1200
ccgcatggac acccagacca ggtcccctac atcgtgacct gggaagcctt ggcttttgac    1260
cccccctcct gggtcaagcc ctttgtacac cctaagcctc cgcctcctct tcctccatcc    1320
gccccgtctc tcccccttga acctcctcgt tcgaccccgc ctcgatcctc cctttatcca    1380
gccctcactc cttctctagg cgccggaatt agatccataa cttcgtatag gatacccttat    1440 acgaagttat ctcaggtacc gccaccatgg tggagtacaa gcccacggtg cgcctcgcca    1500
cccgcgacga cgtccccagg gccgtacgca ccctcgccgc cgcgttcgcc gactaccccg    1560
ccacgcgcca caccgtcgat ccggaccgcc acatcgagcg ggtcaccgag ctgcaagaac    1620
tcttcctcac gcgcgtcggg ctcgacatcg gcaaggtgtg ggtcgcggac gacggcgccg    1680
cggtggcggt ctggaccacg ccggagagcg tcgaagcggg ggcggtgttc gccgagatcg    1740
gcccgcgcat ggccgagttg agcggttccc ggctggccgc gcagcaacag atggaaggcc    1800
tcctggcgcc gcaccggccc aaggagcccg cgtggttcct ggccaccgtc ggcgtctcgc    1860
ccgaccacca gggcaagggt ctgggcagcg ccgtcgtgct ccccggagtg gaggcggccg    1920
agcgcgccgg ggtgcccgcc ttcctggaga cctccgcgcc ccgcaacctc cccttctacg    1980
agcggctcgg cttcaccgtc accgccgacg tcgaggtgcc cgaaggaccg cgcacctggt    2040
gcatgacccg caagcccggt gccaaacaga aaattgtggc accagtgaaa cagactttga    2100
attttgacct tctcaagttg gcgggagacg tcgagtccaa ccctgggccc ggcccggtcg    2160
ccaccatggt gagcaagggc gaggagctgt tcaccggggt ggtgcccatc ctggtcgagc    2220
tggacggcga cgtaaacggc cacaagttca gcgtgtccgg cgaggggag ggcgatgcca    2280 cctacggcaa gctgaccctg aagttcatct gcaccaccgg caagctgccc gtgccctggc    2340
ccaccctcgt gaccaccctg acctacggcg tgcagtgctt cagccgctac cccgaccaca    2400
tgaagcagca cgacttcttc aagtccgcca tgcccgaagg ctacgtccag gagcgcacca    2460
tcttcttcaa ggacgacggc aactacaaga cccgcgccga ggtgaagttc gagggcgaca    2520
cccTggtgaa ccgcatcgag ctgaagggca tcgacttcaa ggaggacggc aacatcctgg    2580
ggcacaagct ggagtacaac tacaacagcc acaacgtcta tatcatggcc gacaagcaga    2640
agaacggcat caaggtgaac ttcaagatcc gccacaacat cgaggacggc agcgtgcagc    2700
```

```
tcgccgacca ctaccagcag aacacccca tcggcgacgg ccccgtgctg ctgcccgaca    2760
accactacct gagcacccag tccgccctga gcaaagaccc caacgagaag cgcgatcaca    2820
tggtcctgct ggagttcgtg accgccgccg gatcactctc ggcatggacg agctgtacaa    2880
gtagtctaga agccataact tcgtatagta cacattatac gaagtttatg catacctgga    2940
ggaaaaaaaa aaggggagag tcaggggttt aaacgcatta gtcttccaat tgaaaaagt     3000
gatttaattt ataccatttt aattcagctt tgtaaaaatg tatcaaagag atagcaaggt    3060
attcagtttt agtaaacaag ataattgctc ctaaagtagc cccttgaatt ccgaggcagt    3120
aggcaggctc ccgctgaatt ggaatcctac atctgtggct tcactaggat tccaattcac    3180
gggagctcgc tcactgtcaa cagcaatata ccttctcgag ccttctgttg ggttaacctg    3240
aagaagtaat cccagcaagt gtttccaaga tgtgcaggca acgattctgt aaagtactga    3300
agcctcattc aaacatagta tatgtgctgc cgaagcgagc acttaacaag gcttgcggcc    3360
gctacttgta cagctcgtcc atgccgagag tgatcccggc ggcgccactc acctgcaatt    3420
gggccgctca cagagaaatg aagtccaggg cttggaggag ggagagggaa agcagcagca    3480
gcagcatcca ggatgtgttc tgaaccagca ggcttatgcc gccacacttg accagtttgt    3540
ctctatacac actgatactt ttattggagc tcatgggatt cgcgcccgag actcgaagct    3600
cacaaaagta gtcgccctca tccttggtgg tgaagttggc tagggtaagg accttgatat    3660
agggctggtt ggagagggtg acgcgggagc ggtacgtgtg ctcgggtatc ccgagggtgc    3720
ctgagagcac gtgcttcctc ttctctcggg tcaggctgaa ctcatgctgg atggagttat    3780
ccttggtgtt attctcatgg cggcagtcca ggcgaaggtt ttggttcacc aggcaggctg    3840
tcaggctggt caccttctgc cctcgggaca cctgcaagac tgagagcagg agagcgacgc    3900
tgatggctgg gttcatggtg gcgaccggta aacttcgta taaggtatcc tatacgaagt    3960
tatccattca ggctgtgcta gcatcaatgg catggcacaa agcttagcca taacttcgta    4020
taatgtgtac tatacgaagt tatcccgggt taaacgacct gcagccaagc ttatcgataa    4080
aataaaagat tttatttagt ctccagaaaa aggggggaat gaaagacccc acctgtaggt    4140
ttggcaagct agcttaagta acgccatttt gcaaggcatg gaaaatacat aactgagaat    4200
agagaagttc agatcaaggt taggaacaga gagacagcag aatatgggcc aaacaggata    4260
tctgtggtaa gcagttcctg ccccggctca gggccaagaa cagatggtcc ccagatgcgg    4320
tcccgccctc agcagtttct agagaaccat cagatgtttc cagggtgccc caaggacctg    4380
aaaatgaccc tgtgccttat ttgaactaac caatcagttc gcttctcgct tctgttcgcg    4440
cgcttctgct ccccgagctc aataaaagag cccacaaccc ctcactcggc gcgccagtcc    4500
tccgatagac tgcgtcgccc gggtacccgt gtatccaata aaccctcttg cagttgcatc    4560
cgacttgtgg tctcgctgtt ccttgggagg gtctcctctg agtgattgac tacccgtcag    4620
cgggggtctt tcatgggtaa cagtttcttg aagttggaga caacattct gagggtagga    4680
gtcgaatatt aagtaatcct gactcaatta gccactgttt tgaatccaca tactccaata    4740
ctcctgaaat agttcattat ggacagcgca gaagagctgg ggagaattaa ttcgtaatca    4800
tggtcatagc tgtttcctgt gtgaaattgt tatccgctca caattccaca acacatacga    4860
gccggaagca taaagtgtaa agcctgggt gcctaatgag tgagctaact cacattaatt    4920
gcgttgcgct cactgcccgc tttccagtcg ggaaacctgt cgtgccagct gcattaatga    4980
atcggccaac gcgcggggag aggcggtttg cgtattgggc gctcttccgc ttcctcgctc    5040
```

| | |
|---|---|
| actgactcgc tgcgctcggt cgttcggctg cggcgagcgg tatcagctca ctcaaaggcg | 5100 |
| gtaatacggt tatccacaga atcagggggat aacgcaggaa agaacatgtg agcaaaaggc | 5160 |
| cagcaaaagg ccaggaaccg taaaaaggcc gcgttgctgg cgtttttcca taggctccgc | 5220 |
| cccctgacg agcatcacaa aaatcgacgc tcaagtcaga ggtggcgaaa cccgacagga | 5280 |
| ctataaagat accaggcgtt tccccctgga agctccctcg tgcgctctcc tgttccgacc | 5340 |
| ctgccgctta ccggatacct gtccgccttt ctcccttcgg gaagcgtggc gctttctcat | 5400 |
| agctcacgct gtaggtatct cagttcggtg taggtcgttc gctccaagct gggctgtgtg | 5460 |
| cacgaacccc cgttcagcc cgaccgctgc gccttatccg gtaactatcg tcttgagtcc | 5520 |
| aacccggtaa gacacgactt atcgccactg gcagcagcca ctggtaacag gattagcaga | 5580 |
| gcgaggtatg taggcggtgc tacagagttc ttgaagtggt ggcctaacta cggctacact | 5640 |
| agaaggacag tatttggtat ctgcgctctg ctgaagccag ttaccttcgg aaaaagagtt | 5700 |
| ggtagctctt gatccggcaa acaaaccacc gctggtagcg gtggtttttt tgtttgcaag | 5760 |
| cagcagatta cgcgcagaaa aaaaggatct caagaagatc ctttgatctt ttctacgggg | 5820 |
| tctgacgctc agtggaacga aaactcacgt taagggattt tggtcatgag attatcaaaa | 5880 |
| aggatcttca cctagatcct tttaaattaa aaatgaagtt ttaaatcaat ctaaagtata | 5940 |
| tatgagtaaa cttggtctga cagttaccaa tgcttaatca gtgaggcacc tatctcagcg | 6000 |
| atctgtctat ttcgttcatc catagttgcc tgactccccg tcgtgtagat aactacgata | 6060 |
| cgggagggct taccatctgg ccccagtgct gcaatgatac cgcgagaccc acgctcaccg | 6120 |
| gctccagatt tatcagcaat aaaccagcca gccggaaggg ccgagcgcag aagtggtcct | 6180 |
| gcaactttat ccgcctccat ccagtctatt aattgttgcc gggaagctag agtaagtagt | 6240 |
| tcgccagtta atagtttgcg caacgttgtt gccattgcta caggcatcgt ggtgtcacgc | 6300 |
| tcgtcgtttg gtatggcttc attcagctcc ggttcccaac gatcaaggcg agttacatga | 6360 |
| tcccccatgt tgtgcaaaaa agcggttagc tccttcggtc ctccgatcgt tgtcagaagt | 6420 |
| aagttggccg cagtgttatc actcatggtt atggcagcac tgcataattc tcttactgtc | 6480 |
| atgccatccg taagatgctt ttctgtgact ggtgagtact caaccaagtc attctgagaa | 6540 |
| tagtgtatgc ggcgaccgag ttgctcttgc ccggcgtcaa tacgggataa taccgcgcca | 6600 |
| catagcagaa ctttaaaagt gctcatcatt ggaaaacgtt cttcggggcg aaaactctca | 6660 |
| aggatcttac cgctgttgag atccagttcg atgtaaccca ctcgtgcacc caactgatct | 6720 |
| tcagcatctt ttactttcac cagcgtttct gggtgagcaa aaacaggaag gcaaaatgcc | 6780 |
| gcaaaaaagg gaataagggc gacacggaaa tgttgaatac tcatactctt cctttttcaa | 6840 |
| tattattgaa gcatttatca gggttattgt ctcatgagcg gatacatatt tgaatgtatt | 6900 |
| tagaaaaata aacaaatagg ggttccgcgc acatttcccc gaaaagtgcc acctgacgtc | 6960 |
| taagaaacca ttattatcat gacattaacc tataaaaata ggcgtatcac gaggcccttt | 7020 |
| cgtctcgcgc gtttcggtga tgacggtgaa aacctctgac acatgcagct cccggagacg | 7080 |
| gtcacagctt gtctgtaagc ggatgccggg agcagacaag cccgtcaggg cgcgtcagcg | 7140 |
| ggtgttggcg ggtgtcgggg ctggcttaac tatgcggcat cagagcagat tgtactgaga | 7200 |
| gtgcaccata tgcggtgtga aataccgcac agatgcgtaa ggagaaaata ccgcatcagg | 7260 |
| cgccattcgc cattcaggct gcgcaactgt tgggaagggc gatcggtgcg ggcctcttcg | 7320 |
| ctattacgcc agctggcgaa aggggggatgt gctgcaaggc gattaagttg ggtaacgcca | 7380 |
| gggttttccc agtcacgacg ttgtaaaacg acggcgcaag gaagcagccc agtagtaggt | 7440 |

| | |
|---|---:|
| tgaggccgtt gagcaccgcc gccgcaagga atggtgcatg caaggagatg gcgcccaaca | 7500 |
| gtcccccggc cacggggcct gccaccatac ccacgccgaa acaagcgctc atgagcccga | 7560 |
| agtggcgagc ccgatcttcc ccatcggtga tgtcggcgat ataggcgcca gcaaccgcac | 7620 |
| ctgtggcgcc ggtgatgccg gccacgatgc gtccggcgta gaggcgatta gtccaatttg | 7680 |
| ttaaagacag gatatcagtg gtccaggctc tagttttgac tcaacaatat caccagctga | 7740 |
| agcctataga gtacgagcca tagataaaat aaaagatttt atttagtctc cagaaaaagg | 7800 |
| ggggaa | 7806 |

<210> SEQ ID NO 25
<211> LENGTH: 7766
<212> TYPE: DNA
<213> ORGANISM: Artificial
<220> FEATURE:
<223> OTHER INFORMATION: MSCV FLIPi Puro2AGFP / Thy1.1-miR-p53

<400> SEQUENCE: 25

| | |
|---|---:|
| tgaaagaccc cacctgtagg tttggcaagc tagcttaagt aacgccattt tgcaaggcat | 60 |
| ggaaaataca taactgagaa tagagaagtt cagatcaagg ttaggaacag agagacagca | 120 |
| gaatatgggc caaacaggat atctgtggta agcagttcct gccccggctc agggccaaga | 180 |
| acagatggtc cccagatgcg gtcccgccct cagcagtttc tagagaacca tcagatgttt | 240 |
| ccagggtgcc ccaaggacct gaaaatgacc ctgtgcctta tttgaactaa ccaatcagtt | 300 |
| cgcttctcgc ttctgttcgc gcgcttctgc tccccgagct caataaaaga gcccacaacc | 360 |
| cctcactcgg cgcgccagtc ctccgataga ctgcgtcgcc cgggtacccg tattcccaat | 420 |
| aaagcctctt gctgtttgca tccgaatcgt ggactgctg atccttggga gggtctcctc | 480 |
| agattgattg actgcccacc tcgggggtct ttcatttgga ggttccaccg agatttggag | 540 |
| acccctgcct agggaccacc gacccccccg ccgggaggta agctggccag cggtcgtttc | 600 |
| gtgtctgtct ctgtctttgt gcgtgtttgt gccggcatct aatgtttgcg cctgcgtctg | 660 |
| tactagttag ctaactagct ctgtatctgg cggacccgtg gtggaactga cgagttctga | 720 |
| acacccggcc gcaaccctgg gagacgtccc agggactttg ggggccgttt ttgtggcccg | 780 |
| acctgaggaa gggagtcgat gtggaatccg accccgtcag gatatgtggt tctggtagga | 840 |
| gacgagaacc taaaacagtt cccgcctccg tctgaatttt tgctttcggt ttggaaccga | 900 |
| agccgcgcgt cttgtctgct gcagcgctgc agcatcgttc tgtgttgtct ctgtctgact | 960 |
| gtgtttctgt atttgtctga aaattagggc cagactgtta ccactccctt aagtttgacc | 1020 |
| ttaggtcact ggaaagatgt cgagcggatc gctcacaacc agtcggtaga tgtcaagaag | 1080 |
| agacgttggg ttaccttctg ctctgcagaa tggccaacct ttaacgtcgg atggccgcga | 1140 |
| gacggcacct ttaaccgaga cctcatcacc caggttaaga tcaaggtctt tcacctggcc | 1200 |
| ccgcatggac acccagacca ggtccccctac atcgtgacct gggaagcctt ggcttttgac | 1260 |
| cccccctccct gggtcaagcc ctttgtacac cctaagcctc cgcctcctct tcctccatcc | 1320 |
| gccccgtctc tcccccttga acctcctcgt tcgaccccgc ctcgatcctc cctttatcca | 1380 |
| gccctcactc cttctctagg cgccggaatt agatccataa cttcgtatag gatacctat | 1440 |
| acgaagttat ctcaggtacc gccaccatgg tgagtacaa gcccacggtg cgcctcgcca | 1500 |
| cccgcgacga cgtccccagg gccgtacgca cctcgccgc cgcgttcgcc gactaccccg | 1560 |
| ccacgcgcca caccgtcgat ccggaccgcc acatcgagcg ggtcaccgag ctgcaagaac | 1620 |

```
tcttcctcac gcgcgtcggg ctcgacatcg gcaaggtgtg ggtcgcggac gacggcgccg    1680
cggtggcggt ctggaccacg ccggagagcg tcgaagcggg ggcggtgttc gccgagatcg    1740
gcccgcgcat ggccgagttg agcggttccc ggctggccgc gcagcaacag atggaaggcc    1800
tcctggcgcc gcaccggccc aaggagcccg cgtggttcct ggccaccgtc ggcgtctcgc    1860
ccgaccacca gggcaagggt ctgggcagcg ccgtcgtgct ccccggagtg gaggcggccg    1920
agcgcgccgg ggtgcccgcc ttcctggaga cctccgcgcc ccgcaacctc cccttctacg    1980
agcggctcgg cttcaccgtc accgccgacg tcgaggtgcc cgaaggaccg cgcacctggt    2040
gcatgacccg caagcccggt gccaaacaga aaattgtggc accagtgaaa cagactttga    2100
attttgacct tctcaagttg gcgggagacg tcgagtccaa ccctgggccc ggcccggtcg    2160
ccaccatggt gagcaagggc gaggagctgt tcaccggggt ggtgcccatc ctggtcgagc    2220
tggacggcga cgtaaacggc cacaagttca gcgtgtccgg cgagggcgag ggcgatgcca    2280
cctacggcaa gctgaccctg aagttcatct gcaccaccgg caagctgccc gtgccctggc    2340
ccaccctcgt gaccaccctg acctacggcg tgcagtgctt cagccgctac cccgaccaca    2400
tgaagcagca cgacttcttc aagtccgcca tgcccgaagg ctacgtccag gagcgcacca    2460
tcttcttcaa ggacgacggc aactacaaga cccgcgccga ggtgaagttc gagggcgaca    2520
cccTggtgaa ccgcatcgag ctgaagggca tcgacttcaa ggaggacggc aacatcctgg    2580
ggcacaagct ggagtacaac tacaacagcc acaacgtcta tatcatggcc gacaagcaga    2640
agaacggcat caaggtgaac ttcaagatcc gccacaacat cgaggacggc agcgtgcagc    2700
tcgccgacca ctaccagcag aacaccccca tcggcgacgg ccccgtgctg ctgcccgaca    2760
accactacct gagcacccag tccgcccTga gcaaagaccc caacgagaag cgcgatcaca    2820
tggtcctgct ggagttcgtg accgccgccg ggatcactct cggcatggac gagctgtaca    2880
agtagtctag aagccataac ttcgtatagt acacattata cgaagtttat gcatacctgg    2940
aggaaaaaaa aaaggggaga gtcagggggtt taaacgcatt agtcttccaa ttgaaaaaag    3000
tgatttaatt tataccattt taattcagct ttgtaaaaat gtatcaaaga gatagcaagg    3060
tattcagttt tagtaaacaa gataattgct cctaaagtag ccccttgaat tccgaggcag    3120
taggcatcca ctacaagtac atgtgtaata catctgtggc ttcactatta cacatgtact    3180
tgtagtgggc gctcactgtc aacagcaata taccttctcg agccttctgt tgggttaacc    3240
tgaagaagta atcccagcaa gtgtttccaa gatgtgcagg caacgattct gtaaagtact    3300
gaagcctcat tcaaacatag tatatgtgct gccgaagcga gcacttaaca aggcttgcgg    3360
ccgcccactc acctgcaatt gggccgctca cagagaaatg aagtccaggg cttggaggag    3420
ggagagggaa agcagcagca gcagcatcca ggatgtgttc tgaaccagca ggcttatgcc    3480
gccacacttg accagtttgt ctctatacac actgatactt ttattggagc tcatgggatt    3540
cgcgcccgag actcgaagct cacaaaagta gtcgccctca tccttggtgg tgaagttggc    3600
tagggtaagg accttgatat agggctggtt ggagagggtg acgcgggagc ggtacgtgtg    3660
ctcgggtatc ccgagggtgc ctgagagcac gtgcttcctc ttctctcggg tcaggctgaa    3720
ctcatgctgg atggagttat ccttggtgtt attctcatgg cggcagtcca ggcgaaggtt    3780
ttggttcacc aggcaggctg tcaggctggt caccttctgc cctcgggaca cctgcaagac    3840
tgagagcagg agagcgacgc tgatggctgg gttcatggtg cgaccggta aacttcgta     3900
taaggtatcc tatacgaagt tatccattca ggctgtgcta gcatcaatgg catggcacaa    3960
agcttagcca taacttcgta taatgtgtac tatacgaagt tatcccgggt taaacgacct    4020
```

-continued

```
gcagccaagc ttatcgataa aataaaagat tttatttagt ctccagaaaa agggggaat      4080 gaaagacccc acctgtaggt ttggcaagct agcttaagta acgccatttt gcaaggcatg     4140
gaaaatacat aactgagaat agagaagttc agatcaaggt taggaacaga gagacagcag     4200
aatatgggcc aaacaggata tctgtggtaa gcagttcctg ccccggctca gggccaagaa     4260
cagatggtcc ccagatgcgg tcccgccctc agcagtttct agagaaccat cagatgtttc     4320
cagggtgccc caaggacctg aaaatgaccc tgtgccttat ttgaactaac caatcagttc     4380
gcttctcgct tctgttcgcg cgcttctgct ccccgagctc aataaaagag cccacaaccc     4440
ctcactcggc gcgccagtcc tccgatagac tgcgtcgccc gggtacccgt gtatccaata     4500
aaccctcttg cagttgcatc cgacttgtgg tctcgctgtt ccttgggagg gtctcctctg     4560
agtgattgac tacccgtcag cgggggtctt tcatgggtaa cagtttcttg aagttggaga     4620
acaacattct gagggtagga gtcgaatatt aagtaatcct gactcaatta gccactgttt     4680
tgaatccaca tactccaata ctcctgaaat agttcattat ggacagcgca gaagagctgg     4740
ggagaattaa ttcgtaatca tggtcatagc tgtttcctgt gtgaaattgt tatccgctca     4800
caattccaca acaatacga gccggaagca taaagtgtaa agcctggggt gcctaatgag      4860
tgagctaact cacattaatt gcgttgcgct cactgcccgc tttccagtcg gaaacctgt      4920 cgtgccagct gcattaatga atcggccaac gcgcggggag aggcggtttg cgtattgggc     4980
gctcttccgc ttcctcgctc actgactcgc tgcgctcggt cgttcggctg cggcgagcgg     5040
tatcagctca ctcaaaggcg gtaatacggt tatccacaga atcaggggat aacgcaggaa     5100
agaacatgtg agcaaaaggc cagcaaaagg ccaggaaccg taaaaaggcc gcgttgctgg     5160 cgttttttcca taggctccgc cccctgacg agcatcacaa aaatcgacgc tcaagtcaga     5220
ggtggcgaaa cccgacagga ctataaagat accaggcgtt tcccctgga agctccctcg     5280 tgcgctctcc tgttccgacc ctgccgctta ccggatacct gtccgccttt ctcccttcgg     5340
gaagcgtggc gctttctcat agctcacgct gtaggtatct cagttcggtg taggtcgttc     5400
gctccaagct gggctgtgtg cacgaacccc ccgttcagcc cgaccgctgc gccttatccg     5460
gtaactatcg tcttgagtcc aacccggtaa gacacgactt atcgccactg gcagcagcca     5520
ctggtaacag gattagcaga gcgaggtatg taggcggtgc tacagagttc ttgaagtggt     5580
ggcctaacta cggctacact agaaggacag tatttggtat ctgcgctctg ctgaagccag     5640
ttaccttcgg aaaaagagtt ggtagctctt gatccggcaa acaaaccacc gctggtagcg     5700
gtggtttttt tgtttgcaag cagcagatta cgcgcagaaa aaaaggatct caagaagatc     5760
ctttgatctt ttctacgggg tctgacgctc agtggaacga aaactcacgt taagggattt     5820
tggtcatgag attatcaaaa aggatcttca cctagatcct tttaaattaa aaatgaagtt     5880
ttaaatcaat ctaaagtata tatgagtaaa cttggtctga cagttaccaa tgcttaatca     5940
gtgaggcacc tatctcagcg atctgtctat ttcgttcatc catagttgcc tgactccccg     6000
tcgtgtagat aactacgata cgggagggct taccatctgg ccccagtgct gcaatgatac     6060
cgcgagaccc acgctcaccg gctccagatt tatcagcaat aaaccagcca gccgaagggg     6120
ccgagcgcag aagtggtcct gcaactttat ccgcctccat ccagtctatt aattgttgcc     6180
gggaagctag agtaagtagt tcgccagtta atagtttgcg caacgttgtt gccattgcta     6240
caggcatcgt ggtgtcacgc tcgtcgtttg gtatggcttc attcagctcc ggttcccaac     6300
gatcaaggcg agttacatga tcccccatgt tgtgcaaaaa agcggttagc tccttcggtc     6360
```

| | |
|---|---:|
| ctccgatcgt tgtcagaagt aagttggccg cagtgttatc actcatggtt atggcagcac | 6420 |
| tgcataattc tcttactgtc atgccatccg taagatgctt ttctgtgact ggtgagtact | 6480 |
| caaccaagtc attctgagaa tagtgtatgc ggcgaccgag ttgctcttgc ccggcgtcaa | 6540 |
| tacgggataa taccgcgcca catagcagaa ctttaaaagt gctcatcatt ggaaaacgtt | 6600 |
| cttcggggcg aaaactctca aggatcttac cgctgttgag atccagttcg atgtaaccca | 6660 |
| ctcgtgcacc caactgatct tcagcatctt ttactttcac cagcgtttct gggtgagcaa | 6720 |
| aaacaggaag gcaaaatgcc gcaaaaaagg gaataagggc gacacggaaa tgttgaatac | 6780 |
| tcatactctt cctttttcaa tattattgaa gcatttatca gggttattgt ctcatgagcg | 6840 |
| gatacatatt tgaatgtatt tagaaaaata aacaaatagg ggttccgcgc acatttcccc | 6900 |
| gaaaagtgcc acctgacgtc taagaaacca ttattatcat gacattaacc tataaaaata | 6960 |
| ggcgtatcac gaggcccttt cgtctcgcgc gtttcggtga tgacggtgaa aacctctgac | 7020 |
| acatgcagct cccggagacg gtcacagctt gtctgtaagc ggatgccggg agcagacaag | 7080 |
| cccgtcaggg cgcgtcagcg ggtgttggcg ggtgtcgggg ctggcttaac tatgcggcat | 7140 |
| cagagcagat tgtactgaga gtgcaccata tgcggtgtga ataccgcac agatgcgtaa | 7200 |
| ggagaaaata ccgcatcagg cgccattcgc cattcaggct gcgcaactgt tgggaagggc | 7260 |
| gatcggtgcg ggcctcttcg ctattacgcc agctggcgaa aggggatgt gctgcaaggc | 7320 |
| gattaagttg ggtaacgcca gggttttccc agtcacgacg ttgtaaaacg acggcgcaag | 7380 |
| gaagcagccc agtagtaggt tgaggccgtt gagcaccgcc gccgcaagga atggtgcatg | 7440 |
| caaggagatg gcgcccaaca gtcccccggc cacggggcct gccaccatac ccacgccgaa | 7500 |
| acaagcgctc atgagcccga agtggcgagc ccgatcttcc ccatcggtga tgtcggcgat | 7560 |
| ataggcgcca gcaaccgcac ctgtggcgcc ggtgatgccg gccacgatgc gtccggcgta | 7620 |
| gaggcgatta gtccaatttg ttaaagacag gatatcagtg gtccaggctc tagttttgac | 7680 |
| tcaacaatat caccagctga agcctataga gtacgagcca tagataaaat aaaagatttt | 7740 |
| atttagtctc cagaaaaagg ggggaa | 7766 |

<210> SEQ ID NO 26
<211> LENGTH: 7766
<212> TYPE: DNA
<213> ORGANISM: Artificial
<220> FEATURE:
<223> OTHER INFORMATION: MSCV FLIPi Puro2AGFP / Thy1.1-miR-PTEN

<400> SEQUENCE: 26

| | |
|---|---:|
| tgaaagaccc cacctgtagg tttggcaagc tagcttaagt aacgccattt tgcaaggcat | 60 |
| ggaaaataca taactgagaa tagagaagtt cagatcaagg ttaggaacag agagacagca | 120 |
| gaatatgggc caaacaggat atctgtggta agcagttcct gccccggctc agggccaaga | 180 |
| acagatggtc cccagatgcg gtcccgccct cagcagtttc tagagaacca tcagatgttt | 240 |
| ccagggtgcc ccaaggacct gaaatgacc ctgtgcctta tttgaactaa ccaatcagtt | 300 |
| cgcttctcgc ttctgttcgc gcgcttctgc tccccgagct caataaaaga gcccacaacc | 360 |
| cctcactcgg cgcgccagtc ctccgataga ctgcgtcgcc cgggtacccg tattcccaat | 420 |
| aaagcctctt gctgtttgca tccgaatcgt ggactcgctg atccttggga gggtctcctc | 480 |
| agattgattg actgcccacc tcgggggtct tcatttgga ggttccaccg agatttggag | 540 |
| accccctgcct agggaccacc gacccccccg ccggaggta agctggccag cggtcgtttc | 600 |
| gtgtctgtct ctgtctttgt gcgtgtttgt gccggcatct aatgtttgcg cctgcgtctg | 660 |

```
tactagttag ctaactagct ctgtatctgg cggacccgtg gtggaactga cgagttctga    720
acacccggcc gcaaccctgg gagacgtccc agggactttg ggggccgttt ttgtggcccg    780
acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct taacgtcgg atggccgcga    1140 gacggcacct taaccgaga cctcatcacc caggttaaga tcaaggtctt ttcacctggc    1200
ccgcatggac acccagacca ggtcccctac atcgtgacct gggaagcctt ggcttttgac   1260 cccctccct gggtcaagcc ctttgtacac cctaagcctc cgcctcctct tcctccatcc    1320
gccccgtctc tccccttga acctcctcgt tcgaccccgc ctcgatcctc ctttatccca    1380
gccctcactc cttctctagg cgccggaatt agatccataa cttcgtatag gataccttat   1440
acgaagttat ctcaggtacc gccaccatgg tggagtacaa gcccacggtg cgcctcgcca   1500
cccgcgacga cgtccccagg gccgtacgca ccctcgccgc cgcgttcgcc gactacccg    1560 ccacgcgcca caccgtcgat ccggaccgcc acatcgagcg ggtcaccgag ctgcaagaac   1620
tcttcctcac gcgcgtcggg ctcgacatcg gcaaggtgtg ggtcgcggac gacggcgccg   1680
cggtggcggt ctggaccacg ccggagagcg tcgaagcggg ggcggtgttc gccgagatcg   1740
gcccgcgcat ggccgagttg agcggttccc ggctggccgc gcagcaacag atggaaggcc   1800
tcctggcgcc gcaccggccc aaggagcccg cgtggttcct ggccaccgtc ggcgtctcgc   1860
ccgaccacca gggcaagggt ctgggcagcg ccgtcgtgct ccccggagtg gaggcggccg   1920
agcgcgccgg ggtgcccgcc ttcctggaga cctccgcgcc ccgcaacctc cccttctacg   1980
agcggctcgg cttcaccgtc accgccgacg tcgaggtgcc cgaaggaccg cgcacctggt   2040
gcatgacccg caagcccggt gccaaacaga aaattgtggc accagtgaaa cagactttga   2100
attttgacct tctcaagttg gcgggagacg tcgagtccaa ccctgggccc ggcccggtcg   2160
ccaccatggt gagcaagggc gaggagctgt tcaccggggt ggtgcccatc ctggtcgagc   2220
tggacggcga cgtaaacggc cacaagttca gcgtgtccgg cgagggcgag ggcgatgcca   2280
cctacggcaa gctgaccctg aagttcatct gcaccaccgg caagctgccc gtgccctggc   2340
ccaccctcgt gaccaccctg acctacggcg tgcagtgctt cagccgctac cccgaccaca   2400
tgaagcagca cgacttcttc aagtccgcca tgcccgaagg ctacgtccag gagcgcacca   2460
tcttcttcaa ggacgacggc aactacaaga cccgcgccga ggtgaagttc gagggcgaca   2520
cccTggtgaa ccgcatcgag ctgaagggca tcgacttcaa ggaggacggc aacatcctgg   2580
ggcacaagct ggagtacaac tacaacagcc acaacgtcta tatcatggcc gacaagcaga   2640
agaacggcat caaggtgaac ttcaagatcc gccacaacat cgaggacggc agcgtgcagc   2700
tcgccgacca ctaccagcag aacacccca tcggcgacgg ccccgtgctg ctgcccgaca   2760
accactacct gagcacccag tccgccctga gcaaagaccc caacgagaag cgcgatcaca   2820
tggtcctgct ggagttcgtg accgccgccg ggatcactct cggcatggac gagctgtaca   2880
agtagtctag aagccataac ttcgtatagt acacattata cgaagtttat gcatacctgg   2940
aggaaaaaaa aaggggggaga gtcaggggtt taaacgcatt agtcttccaa ttgaaaaaag   3000
```

```
tgatttaatt tataccattt taattcagct ttgtaaaaat gtatcaaaga gatagcaagg    3060
tattcagttt tagtaaacaa gataattgct cctaaagtag cccctttgaat tccgaggcag   3120 taggcaaggt gaaactatac tttacaaata catctgtggc ttcactattt gtaaagtata    3180
gtttcaccgc gctcactgtc aacagcaata taccttctcg agccttctgt tgggttaacc   3240
tgaagaagta atcccagcaa gtgtttccaa gatgtgcagg caacgattct gtaaagtact   3300
gaagcctcat tcaaacatag tatatgtgct gccgaagcga gcacttaaca aggcttgcgg   3360
ccgcccactc acctgcaatt gggccgctca cagagaaatg aagtccaggg cttggaggag   3420
ggagagggaa agcagcagca gcagcatcca ggatgtgttc tgaaccagca ggcttatgcc   3480
gccacacttg accagtttgt ctctatacac actgatactt ttattggagc tcatgggatt   3540
cgcgcccgag actcgaagct cacaaaagta gtcgccctca tccttggtgg tgaagttggc   3600
tagggtaagg accttgatat agggctggtt ggagagggtg acgcgggagc ggtacgtgtg   3660
ctcgggtatc ccgagggtgc ctgagagcac gtgcttcctc ttctctcggg tcaggctgaa   3720
ctcatgctgg atggagttat ccttggtgtt attctcatgg cggcagtcca ggcgaaggtt   3780
ttggttcacc aggcaggctg tcaggctggt caccttctgc cctcgggaca cctgcaagac   3840
tgagagcagg agagcgacgc tgatggctgg gttcatggtg gcgaccggta aacttcgta    3900 taaggtatcc tatacgaagt tatccattca ggctgtgcta gcatcaatgg catggcacaa   3960
agcttagcca taacttcgta taatgtgtac tatacgaagt tatcccgggt taaacgacct   4020
gcagccaagc ttatcgataa aataaaagat tttatttagt ctccagaaaa agggggaat    4080 gaaagacccc acctgtaggt ttggcaagct agcttaagta acgccatttt gcaaggcatg   4140
gaaaatacat aactgagaat agagaagttc agatcaaggt taggaacaga gagacagcag   4200
aatatgggcc aaacaggata tctgtggtaa gcagttcctg ccccggctca gggccaagaa   4260
cagatggtcc ccagatgcgg tcccgccctc agcagtttct agagaaccat cagatgtttc   4320
cagggtgccc caaggacctg aaaatgaccc tgtgccttat ttgaactaac caatcagttc   4380
gcttctcgct tctgttcgcg cgcttctgct ccccgagctc aataaaagag cccacaaccc   4440
ctcactcggc gcgccagtcc tccgatagac tgcgtcgccc gggtacccgt gtatccaata   4500
aaccctcttg cagttgcatc cgacttgtgg tctcgctgtt ccttgggagg gtctcctctg   4560
agtgattgac tacccgtcag cgggggtctt tcatgggtaa cagtttcttg aagttggaga   4620
acaacattct gagggtagga gtcgaatatt aagtaatcct gactcaatta gccactgttt   4680
tgaatccaca tactccaata ctcctgaaat agttcattat ggacagcgca gaagagctgg   4740
ggagaattaa ttcgtaatca tggtcatagc tgtttcctgt gtgaaattgt tatccgctca   4800
caattccaca acacatacga gccggaagca taaagtgtaa agcctggggt gcctaatgag   4860
tgagctaact cacattaatt gcgttgcgct cactgcccgc tttccagtcg ggaaacctgt   4920
cgtgccagct gcattaatga atcggccaac gcgcggggag aggcggtttg cgtattgggc   4980
gctcttccgc ttcctcgctc actgactcgc tgcgctcggt cgttcggctg cggcgagcgg   5040
tatcagctca ctcaaaggcg gtaatacggt tatccacaga atcaggggat aacgcaggaa   5100
agaacatgtg agcaaaaggc cagcaaaagg ccaggaaccg taaaaaggcc gcgttgctgg   5160 cgttttttcca taggctccgc cccctgacg agcatcacaa aaatcgacgc tcaagtcaga   5220
ggtggcgaaa cccgacagga ctataaagat accaggcgtt tccccctgga agctccctcg   5280
tgcgctctcc tgttccgacc ctgccgctta ccggatacct gtccgccttt ctcccttcgg   5340
gaagcgtggc gctttctcat agctcacgct gtaggtatct cagttcggtg taggtcgttc   5400
```

```
gctccaagct gggctgtgtg cacgaacccc ccgttcagcc cgaccgctgc gccttatccg    5460
gtaactatcg tcttgagtcc aacccggtaa gacacgactt atcgccactg gcagcagcca    5520
ctggtaacag gattagcaga gcgaggtatg taggcggtgc tacagagttc ttgaagtggt    5580
ggcctaacta cggctacact agaaggacag tatttggtat ctgcgctctg ctgaagccag    5640
ttaccttcgg aaaaagagtt ggtagctctt gatccggcaa acaaaccacc gctggtagcg    5700
gtggtttttt tgtttgcaag cagcagatta cgcgcagaaa aaaggatct caagaagatc    5760
ctttgatctt ttctacgggg tctgacgctc agtggaacga aaactcacgt taagggattt    5820
tggtcatgag attatcaaaa aggatcttca cctagatcct tttaaattaa aaatgaagtt    5880
ttaaatcaat ctaaagtata tatgagtaaa cttggtctga cagttaccaa tgcttaatca    5940
gtgaggcacc tatctcagcg atctgtctat ttcgttcatc catagttgcc tgactccccg    6000
tcgtgtagat aactacgata cgggagggct taccatctgg ccccagtgct gcaatgatac    6060
cgcgagaccc acgctcaccg gctccagatt tatcagcaat aaaccagcca gccggaaggg    6120
ccgagcgcag aagtggtcct gcaactttat ccgcctccat ccagtctatt aattgttgcc    6180
gggaagctag agtaagtagt tcgccagtta atagtttgcg caacgttgtt gccattgcta    6240
caggcatcgt ggtgtcacgc tcgtcgtttg gtatggcttc attcagctcc ggttcccaac    6300
gatcaaggcg agttacatga tcccccatgt tgtgcaaaaa agcggttagc tccttcggtc    6360
ctccgatcgt tgtcagaagt aagttggccg cagtgttatc actcatggtt atggcagcac    6420
tgcataattc tcttactgtc atgccatccg taagatgctt ttctgtgact ggtgagtact    6480
caaccaagtc attctgagaa tagtgtatgc ggcgaccgag ttgctcttgc ccggcgtcaa    6540
tacgggataa taccgcgcca catagcagaa ctttaaaagt gctcatcatt ggaaaacgtt    6600
cttcggggcg aaaactctca aggatcttac cgctgttgag atccagttcg atgtaaccca    6660
ctcgtgcacc caactgatct tcagcatctt ttactttcac cagcgtttct gggtgagcaa    6720
aaacaggaag gcaaaatgcc gcaaaaaagg gaataagggc gacacggaaa tgttgaatac    6780
tcatactctt cctttttcaa tattattgaa gcatttatca gggttattgt ctcatgagcg    6840
gatacatatt tgaatgtatt tagaaaaata aacaaatagg ggttccgcgc acatttcccc    6900
gaaaagtgcc acctgacgtc taagaaacca ttattatcat gacattaacc tataaaaata    6960
ggcgtatcac gaggcccttt cgtctcgcgc gtttcggtga tgacggtgaa aacctctgac    7020
acatgcagct cccggagacg gtcacagctt gtctgtaagc ggatgccggg agcagacaag    7080
cccgtcaggg cgcgtcagcg ggtgttggcg ggtgtcgggg ctggcttaac tatgcggcat    7140
cagagcagat tgtactgaga gtgcaccata tgcggtgtga ataccgcac agatgcgtaa    7200
ggagaaaata ccgcatcagg cgccattcgc cattcaggct gcgcaactgt tgggaagggc    7260
gatcggtgcg ggcctcttcg ctattacgcc agctggcgaa agggggatgt gctgcaaggc    7320
gattaagttg ggtaacgcca gggttttccc agtcacgacg ttgtaaaacg acggcgcaag    7380
gaagcagccc agtagtaggt tgaggccgtt gagcaccgcc gccgcaagga atggtgcatg    7440
caaggagatg gcgcccaaca gtcccccggc cacggggcct gccaccatac ccacgccgaa    7500
acaagcgctc atgagcccga agtggcgagc ccgatcttcc ccatcggtga tgtcggcgat    7560
ataggcgcca gcaaccgcac ctgtggcgcc ggtgatgccg gccacgatgc gtccggcgta    7620
gaggcgatta gtccaatttg ttaaagacag gatatcagtg gtccaggctc tagttttgac    7680
tcaacaatat caccagctga agcctataga gtacgagcca tagataaaat aaaagatttt    7740
```
atttagtctc cagaaaaagg ggggaa 7766

<210> SEQ ID NO 27
<211> LENGTH: 8157
<212> TYPE: DNA
<213> ORGANISM: Artificial
<220> FEATURE:
<223> OTHER INFORMATION: MSCV FLIPi Puro2AGFP / Thy1.1-miR-Dbl p53 &
      PTEN

<400> SEQUENCE: 27

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540
accctgcct agggaccacc gacccccccg ccgggaggta agctggccag cggtcgtttc      600
gtgtctgtct ctgtctttgt gcgtgtttgt gccggcatct aatgtttgcg cctgcgtctg     660
tactagttag ctaactagct ctgtatctgg cggacccgtg gtggaactga cgagttctga     720
acacccggcc gcaaccctgg gagacgtccc agggactttg ggggccgttt ttgtggcccg     780
acctgaggaa gggagtcgat gtggaatccg accccgtcag gatatgtggt tctggtagga     840
gacgagaacc taaaacagtt cccgcctccg tctgaatttt tgctttcggt ttggaaccga     900
agccgcgcgt cttgtctgct gcagcgctgc agcatcgttc tgtgttgtct ctgtctgact     960
gtgtttctgt atttgtctga aaattagggc cagactgtta ccactcccct aagttttgacc   1020
ttaggtcact ggaaagatgt cgagcggatc gctcacaacc agtcggtaga tgtcaagaag    1080
agacgttggg ttaccttctg ctctgcagaa tggccaacct ttaacgtcgg atggccgcga    1140
gacggcacct ttaaccgaga cctcatcacc caggttaaga tcaaggtctt ttcacctggc    1200
ccgcatggac acccagacca ggtccctac atcgtgacct gggaagcctt ggcttttgac    1260
ccccctccct gggtcaagcc ctttgtacac cctaagcctc cgcctcctct tcctccatcc    1320
gccccgtctc tcccccttga acctcctcgt tcgaccccgc ctcgatcctc cctttatcca    1380
gccctcactc cttctctagg cgccggaatt agatccataa cttcgtatag gataccttat    1440
acgaagttat ctcaggtacc gccaccatgg tgagtacaa gcccacggtg cgcctcgcca    1500
cccgcgacga cgtccccagg gccgtacgca ccctcgccgc cgcgttcgcc gactaccccg    1560
ccacgcgcca caccgtcgat ccggaccgcc acatcgagcg ggtcaccgag ctgcaagaac    1620
tcttcctcac gcgcgtcggg ctcgacatcg gcaaggtgtg ggtcgcggac gacggcgccg    1680
cggtggcggt ctggaccacg ccggagagcg tcgaagcggg ggcggtgttc gccgagatcg    1740
gcccgcgcat ggccgagttg agcggttccc ggctggccgc gcagcaacag atggaaggcc    1800
tcctggcgcc gcaccggccc aaggagcccg cgtggttcct ggccaccgtc ggcgtctcgc    1860
ccgaccacca gggcaagggt ctgggcagcg ccgtcgtgct ccccgagtg gaggcggccg    1920
agcgcgccgg ggtgcccgcc ttcctggaga cctccgcgcc ccgcaacctc cccttctacg    1980
```

```
agcggctcgg cttcaccgtc accgccgacg tcgaggtgcc cgaaggaccg cgcacctggt    2040
gcatgacccg caagcccggt gccaaacaga aaattgtggc accagtgaaa cagactttga    2100
attttgacct tctcaagttg gcgggagacg tcgagtccaa ccctgggccc ggcccggtcg    2160
ccaccatggt gagcaagggc gaggagctgt tcaccggggt ggtgcccatc ctggtcgagc    2220
tggacggcga cgtaaacggc cacaagttca gcgtgtccgg cgagggcgag ggcgatgcca    2280
cctacggcaa gctgaccctg aagttcatct gcaccaccgg caagctgccc gtgccctggc    2340 ccacccctcgt gaccaccctg acctacggcg tgcagtgctt cagccgctac cccgaccaca    2400
tgaagcagca cgacttcttc aagtccgcca tgcccgaagg ctacgtccag gagcgcacca    2460
tcttcttcaa ggacgacggc aactacaaga cccgcgccga ggtgaagttc gagggcgaca    2520
ccctggtgaa ccgcatcgag ctgaagggca tcgacttcaa ggaggacggc aacatcctgg    2580
ggcacaagct ggagtacaac tacaacagcc acaacgtcta tatcatggcc gacaagcaga    2640
agaacggcat caaggtgaac ttcaagatcc gccacaacat cgaggacggc agcgtgcagc    2700
tcgccgacca ctaccagcag aacacccccca tcggcgacgg ccccgtgctg ctgcccgaca    2760
accactacct gagcacccag tccgcccctga gcaaagaccc caacgagaag cgcgatcaca    2820
tggtcctgct ggagttcgtg accgccgccg ggatcactct cggcatggac gagctgtaca    2880
agtagtctag aagccataac ttcgtatagt acacattata cgaagtttat gcatacctgg    2940
aggaaaaaaa aaaggggaga gtcagggggtt taaacgcatt agtcttccaa ttgaaaaaag    3000
tgatttaatt tataccattt taattcagct ttgtaaaaat gtatcaaaga gatagcaagg    3060
tattcagttt tagtaaacaa gataattgct cctaaagtag ccccttgaat tccgaggcag    3120
taggcaaggt gaaactatac tttacaaata catctgtggc ttcactattt gtaaagtata    3180
gtttcaccgc gctcactgtc aacagcaata taccttctcg agccttctgt tgggttaacc    3240
tgaagaagta atcccagcaa gtgtttccaa gatgtgcagg caacgattct gtaaagtact    3300
gaagcctcat tcaaacatag tatatgtgct gccgaagcga gcacttaaca aggcttgcat    3360
ttaaacgcat tagtcttcca attgaaaaaa gtgatttaat ttataccatt ttaattcagc    3420
tttgtaaaaa tgtatcaaag agatagcaag gtattcagtt ttagtaaaca agataattgc    3480
tcctaaagta gccccttgaa ttccgaggca gtaggcatcc actacaagta catgtgtaat    3540
acatctgtgg cttcactatt acacatgtac ttgtagtggg cgctcactgt caacagcaat    3600
ataccttctc gagccttctg ttgggttaac ctgaagaagt aatcccagca agtgtttcca    3660
agatgtgcag gcaacgattc tgtaaagtac tgaagcctca ttcaaacata gtatatgtgc    3720
tgccgaagcg agcacttaac aaggcttgcg ccgcccact cacctgcaat tgggccgctc    3780
acagagaaat gaagtccagg gcttggagga gggagaggga aagcagcagc agcagcatcc    3840
aggatgtgtt ctgaaccagc aggcttatgc cgccacactt gaccagtttg tctctataca    3900
cactgatact tttattggag ctcatgggat tcgcgcccga gactcgaagc tcacaaaagt    3960
agtcgccctc atccttggtg gtgaagttgg ctagggtaag gaccttgata tagggctggt    4020
tggagagggt gacgcgggag cggtacgtgt gctcgggtat cccgagggtg cctgagagca    4080
cgtgcttcct cttctctcgg gtcaggctga actcatgctg gatggagtta tccttggtgt    4140
tattctcatg gcggcagtcc aggcgaaggt tttggttcac caggcaggct gtcaggctgg    4200
tcaccttctg ccctcgggac acctgcaaga ctgagagcag gagagcgacg ctgatggctg    4260
ggttcatggt ggcgaccggt ataacttcgt ataaggtatc ctatacgaag ttatccattc    4320
aggctgtgct agcatcaatg gcatggcaca aagcttagcc ataacttcgt ataatgtgta    4380
```

```
ctatacgaag ttatcccggg ttaaacgacc tgcagccaag cttatcgata aaataaaaga    4440 tttatttag tctccagaaa aagggggaa tgaaagaccc cacctgtagg tttggcaagc      4500
tagcttaagt aacgccattt tgcaaggcat ggaaaataca taactgagaa tagagaagtt    4560
cagatcaagg ttaggaacag agagacagca gaatatgggc caaacaggat atctgtggta    4620
agcagttcct gccccggctc agggccaaga acagatggtc cccagatgcg gtcccgccct    4680
cagcagtttc tagagaacca tcagatgttt ccagggtgcc ccaaggacct gaaaatgacc    4740
ctgtgcctta tttgaactaa ccaatcagtt cgcttctcgc ttctgttcgc gcgcttctgc    4800
tccccgagct caataaaaga gcccacaacc cctcactcgg cgcgccagtc ctccgataga    4860
ctgcgtcgcc cgggtacccg tgtatccaat aaaccctctt gcagttgcat ccgacttgtg    4920
gtctcgctgt tccttgggag gtctcctct gagtgattga ctacccgtca gcggggtct     4980 ttcatgggta acagtttctt gaagttggag acaacattc tgagggtagg agtcgaatat    5040
taagtaatcc tgactcaatt agccactgtt ttgaatccac atactccaat actcctgaaa   5100
tagttcatta tggacagcgc agaagagctg ggagaatta attcgtaatc atggtcatag    5160
ctgtttcctg tgtgaaattg ttatccgctc acaattccac acaacatacg agccggaagc    5220
ataaagtgta aagcctgggg tgcctaatga gtgagctaac tcacattaat tgcgttgcgc    5280
tcactgcccg ctttccagtc gggaaacctg tcgtgccagc tgcattaatg aatcggccaa    5340
cgcgcgggga gaggcggttt gcgtattggg cgctcttccg cttcctcgct cactgactcg    5400
ctgcgctcgg tcgttcggct gcggcgagcg gtatcagctc actcaaaggc ggtaatacgg    5460
ttatccacag aatcagggga taacgcagga agaacatgt gagcaaaagg ccagcaaaag    5520
gccaggaacc gtaaaaaggc cgcgttgctg gcgttttcc ataggctccg ccccctgac     5580 gagcatcaca aaaatcgacg ctcaagtcag aggtggcgaa acccgacagg actataaaga   5640
taccaggcgt tccccctgg aagctccctc gtgcgctctc ctgttccgac cctgccgctt    5700
accggatacc tgtccgcctt tctcccttcg ggaagcgtgg cgctttctca tagctcacgc    5760
tgtaggtatc tcagttcggt gtaggtcgtt cgctccaagc tgggctgtgt gcacgaaccc    5820
cccgttcagc ccgaccgctg cgccttatcc ggtaactatc gtcttgagtc caacccggta    5880
agacacgact tatcgccact ggcagcagcc actggtaaca ggattagcag agcgaggtat    5940
gtaggcggtg ctacagagtt cttgaagtgg tggcctaact acggctacac tagaaggaca    6000
gtatttggta tctgcgctct gctgaagcca gttaccttcg aaaaagagt tggtagctct    6060 tgatccggca aacaaaccac cgctggtagc ggtggttttt ttgtttgcaa gcagcagatt    6120
acgcgcagaa aaaaggatc tcaagaagat cctttgatct tttctacggg gtctgacgct    6180
cagtggaacg aaaactcacg ttaagggatt ttggtcatga gattatcaaa aaggatcttc    6240
acctagatcc ttttaaatta aaatgaagt tttaaatcaa tctaaagtat atatgagtaa    6300
acttggtctg acagttacca atgcttaatc agtgaggcac ctatctcagc gatctgtcta    6360
tttcgttcat ccatagttgc ctgactcccc gtcgtgtaga taactacgat acgggagggc    6420
ttaccatctg gccccagtgc tgcaatgata ccgcgagacc cacgctcacc ggctccagat    6480
ttatcagcaa taaaccagcc agccggaagg gccgagcgca gaagtggtcc tgcaacttta    6540
tccgcctcca tccagtctat taattgttgc cgggaagcta gagtaagtag ttcgccagtt    6600
aatagtttgc gcaacgttgt tgccattgct acaggcatcg tggtgtcacg ctcgtcgttt    6660
ggtatggctt cattcagctc cggttcccaa cgatcaaggc gagttacatg atccccatg     6720
```

```
ttgtgcaaaa aagcggttag ctccttcggt cctccgatcg ttgtcagaag taagttggcc    6780
gcagtgttat cactcatggt tatggcagca ctgcataatt ctcttactgt catgccatcc    6840
gtaagatgct tttctgtgac tggtgagtac tcaaccaagt cattctgaga atagtgtatg    6900
cggcgaccga gttgctcttg cccggcgtca atacgggata ataccgcgcc acatagcaga    6960
actttaaaag tgctcatcat tggaaaacgt tcttcggggc gaaaactctc aaggatctta    7020
ccgctgttga gatccagttc gatgtaaccc actcgtgcac ccaactgatc ttcagcatct    7080
tttactttca ccagcgtttc tgggtgagca aaaacaggaa ggcaaaatgc cgcaaaaaag    7140
ggaataaggg cgacacggaa atgttgaata ctcatactct tccttttttca atattattga    7200 agcatttatc agggttattg tctcatgagc ggatacatat ttgaatgtat ttagaaaaat    7260
aaacaaatag gggttccgcg cacatttccc cgaaaagtgc cacctgacgt ctaagaaacc    7320
attattatca tgacattaac ctataaaaat aggcgtatca cgaggccctt tcgtctcgcg    7380
cgtttcggtg atgacggtga aaacctctga cacatgcagc tcccggagac ggtcacagct    7440
tgtctgtaag cggatgccgg gagcagacaa gcccgtcagg gcgcgtcagc gggtgttggc    7500
gggtgtcggg gctggcttaa ctatgcggca tcagagcaga ttgtactgag agtgcaccat    7560
atgcggtgtg aaataccgca cagatgcgta aggagaaaat accgcatcag gcgccattcg    7620
ccattcaggc tgcgcaactg ttgggaaggg cgatcggtgc gggcctcttc gctattacgc    7680
cagctggcga aaggggggatg tgctgcaagg cgattaagtt gggtaacgcc agggttttcc    7740
cagtcacgac gttgtaaaac gacggcgcaa ggaagcagcc cagtagtagg ttgaggccgt    7800
tgagcaccgc cgccgcaagg aatggtgcat gcaaggagat ggcgcccaac agtccccgg    7860 ccacggggcc tgccaccata cccacgccga aacaagcgct catgagcccg aagtggcgag    7920
cccgatcttc cccatcggtg atgtcggcga tataggcgcc agcaaccgca cctgtggcgc    7980
cggtgatgcc ggccacgatg cgtccggcgt agaggcgatt agtccaattt gttaaagaca    8040
ggatatcagt ggtccaggct ctagttttga ctcaacaata tcaccagctg aagcctatag    8100
agtacgagcc atagataaaa taaaagattt tatttagtct ccagaaaaag gggggaa     8157

<210> SEQ ID NO 28
<211> LENGTH: 44
<212> TYPE: DNA
<213> ORGANISM: Artificial
<220> FEATURE:
<223> OTHER INFORMATION: FLIP cassette with a splice donor and splice
      acceptor flanking the miR30

<400> SEQUENCE: 28
caggtgagtg gccctgactc tcccctttt tttttcctcc aggt                      44
```

CRE-LOX BASED GENE KNOCKDOWN CONSTRUCTS AND METHODS OF USE THEREOF

CROSS REFERENCE TO RELATED APPLICATIONS

This application claims priority of U.S. Provisional Application Ser. No. 60/906,511, filed Mar. 13, 2007, and U.S. Provisional Application Ser. No. 60/935,154, filed Jul. 27, 2007, which are hereby incorporated by reference, in their entirety.

GOVERNMENT INTEREST STATEMENT

This invention was made in whole or in part with government support under grant number U54-CA112967, awarded by the National Institutes of Health. The government may have certain rights in the invention.

FIELD OF THE INVENTION

The present invention relates to improved vectors and their use in a cre-lox based method for conditional RNA interference.

BACKGROUND OF THE INVENTION

RNA interference (RNAi) is an extremely versatile tool for inhibition of gene expression. RNAi is based on the introduction of double stranded RNA (dsRNA) molecules into cells, whereby one strand is complementary to the coding region of a target gene. Through pairing of the specific mRNA with the introduced RNA molecule, the mRNA is degraded by a cellular mechanism. Short (30 bp) interfering RNA duplexes (siRNA) have been shown to be effective, and do not provoke an immune response, extending the application to mammalian cells. Small hairpin RNAs (shRNAs) transcribed in vivo, are able to trigger degradation of corresponding mRNAs similar to the siRNAs. Micro RNAs (miRNAs) are the endogenous form of shRNAs that carry out the gene silencing function in vivo.

shRNA expression has been accomplished using gene expression vectors, with RNA polymerase III (Pol III) or Polymerase II (Pol II) promoters, with expression occurring in mice injected with the shRNA expression vectors, however, gene inhibition was temporally and spatially restricted. Moreover stable integration of the construct is not readily accomplished or validated in current systems.

SUMMARY OF THE INVENTION

In one embodiment, this invention provides a vector comprising:
i. a first pair of loxP sequences, inverted in orientation, with respect to each other;
ii. a first nucleic acid encoding a first selectable marker in sense orientation, wherein said nucleic acid is positioned between said first pair of loxP sequences;
iii. a second nucleic acid encoding a second selectable marker, fused in frame to an miRNA sequence of interest in antisense orientation, said miRNA sequence of interest being flanked by splice donor and splice acceptor sequences, said second nucleic acid is positioned between said first pair of loxP sequences, and said second nucleic acid is 3' with regard to said first nucleic acid;
iv. a second pair of loxP sequences, inverted in orientation, with respect to each other, wherein said first loxP sequenced of said second pair is positioned between said first and said second nucleic acid, and said second loxP sequence in said second pair is positioned 3' with respect to said first pair of loxP sequences, and said second pair of loxP sequences differs from that of said first pair of loxP sequences.

In one embodiment, the first pair of loxP sequences comprises the wildtype sequence, and in another embodiment, the second pair of loxP sequences comprises a mutated loxP. In one embodiment, the first pair of loxP sequences comprises the loxP 5171 sequence and in another embodiment, the second pair of loxP sequences comprises the loxP 2272 sequence.

In one embodiment, the first nucleic acid encodes two selectable markers fused in-frame with respect to each other, which in one embodiment, comprise a first antibiotic resistance cassette fused in frame to a sequence encoding a cell surface marker, which in one embodiment is a c-terminal sequence encoding a Foot-and-mouth-disease virus (FMDV) 2A peptide. In one embodiment, the two selectable markers localize to different cellular compartments, when expressed.

In another embodiment, the vector comprises a promoter operatively linked to the first nucleic acid, and in one embodiment, the promoter is tissue specific, or in another embodiment, the promoter is inducible.

In one embodiment, the miRNA agent is an shRNA. In one embodiment, the miRNA specifically inactivates p53 gene expression or PTEN gene expression, or a combination thereof. In one embodiment, according to this aspect of the invention, the vector comprises a nucleotide sequence corresponding to, or homolgous to SEQ ID Nos: 22, 23, 25, 26 or 27.

In another embodiment, the miRNA specifically inactivates α4 integrin gene expression, and in one embodiment, comprises a nucleotide sequence corresponding to, or homolgous to SEQ ID NO: 2, or in another embodiment, the vector has a nucleotide sequence corresponding to, or homologous to SEQ ID NO: 8

In one embodiment, the second nucleic acid further comprises an oncogene fused in frame to the miRNA sequence of interest in antisense orientation. In another embodiment the vector has a nucleotide sequence corresponding to or homolgous to SEQ ID NO: 21.

In one embodiment, the vector backbone is derived from a retrovirus.

In another embodiment, the vector further comprises a first regulatory sequence operationally linked to the first nucleic acid, and being in an antisense orientation, which in one embodiment is a UbiquitinC promoter sequence. In another embodiment, the vector further comprises a second regulatory sequence, located 5' to said first regulatory sequence, wherein the second regulatory sequence is in a sense orientation. In another embodiment, the vector further comprises a Bovine Growth Hormone polyadenylation signal positioned 3' to said second pair of loxP sites. In another embodiment, the vector further comprises a modified U3 LTR positioned 5' to the polyadenylation signal.

In another embodiment, the vector further comprises a second miRNA sequence of interest in antisense orientation fused to the miRNA sequence of interest. In one embodiment, the second miRNA sequence of interest modulates expression of a gene whose activity is cooperative with that of a gene modulated by the first miRNA sequence of interest. In another embodiment, the second miRNA sequence of interest modulates expression of a gene whose activity antagonizes that of a gene modulated by said first miRNA sequence of interest. In another embodiment, the vector further comprises a third nucleic acid in antisense orientation, positioned between said first pair of loxP sequences, wherein said third nucleic acid encodes a protein of interest. In one embodiment, the first miRNA sequence of interest specifically interacts with a sequence encoding said protein of interest or a homologue thereof. In another embodiment, the vector may be expressed in a mammalian host, and the homologue thereof is an endogenous protein in the host, which in one embodiment is associated with a disease or disorder in said host.

In one embodiment, the miRNA sequence of interest is flanked by restriction endonuclease sites, which are flanked by splice donor and splice acceptor sequences. In one embodiment, the miRNA specifically inactivates firefly luciferase gene expression, and in one embodiment comprises a sequence corresponding to, or homolgous to SEQ ID NO: 1. In one embodiment, the vector comprises a nucleotide sequence corresponding to SEQ ID NO: 3.

In one embodiment, this invention provides a composition or cell comprising a vector of this invention. In one embodiment, this invention provides a kit comprising a vector of this invention.

In one embodiment, the vector in the kits of this invention comprise an miRNA sequence of interest flanked by restriction endonuclease sites, which are flanked by splice donor and splice acceptor sequences. In one embodiment, according to this aspect, the miRNA specifically inactivates firefly luciferase gene expression. In one embodiment, the miRNA comprises a sequence corresponding to, or homolgous to SEQ ID NO: 1, or in one embodiment, the vector comprises a nucleotide sequence corresponding to SEQ ID NO: 3. In one embodiment, according to this aspect, the kit further comprises restriction endonucleases, which are capable of specifically cleaving such sites.

In one embodiment, this invention provides a method of producing an animal genetically inactivated for a coding sequence, the method comprising:
  a. contacting an embryonic stem cell with a vector as herein described;
  b. injecting the embryonic stem cell in (a) to a blastocyst of said animal; and
  c. obtaining an animal in (b) expressing said vector
  whereby, following Cre-mediated recombination in the animal, the miRNA agent is expressed and reduces expression of the coding sequence, thereby being a method of producing an animal genetically inactivated for a coding sequence.

In one embodiment, the second selectable marker is expressed in a plurality of cells of said animal following Cre-mediated recombination, or in another embodiment, the first selectable marker is lost in a plurality of cells of said animal, following Cre-mediated recombination. In another embodiment, Cre-mediated recombination is tissue-specific in said animal.

In another embodiment, this invention provides a method of conditionally reducing expression of a coding sequence in a target cell, the method comprising contacting the target cell with a vector comprising:
  a. a first pair of loxP sequences, inverted in orientation, with respect to each other;
  b. a first nucleic acid encoding a first selectable marker in sense orientation, wherein said nucleic acid is positioned between said first pair of loxP sequences;
  c. a second nucleic acid encoding a second selectable marker, fused in frame to an miRNA sequence of interest in antisense orientation, said miRNA sequence of interest being flanked by splice donor and splice acceptor sequences, said second nucleic acid is positioned between said first pair of loxP sequences, and said second nucleic acid is 3' with regard to said first nucleic acid;
  d. a second pair of loxP sequences, inverted in orientation, with respect to each other, wherein said first loxP sequenced of said second pair is positioned between said first and said second nucleic acid, and said second loxP sequence in said second pair is positioned 3' with respect to said first pair of loxP sequences, and said second pair of loxP sequences differs from that of said first pair of loxP sequences.

In one embodiment, according to this aspect of the invention, the cell is engineered to express a Cre recombinase, or in another embodiment, the cell endogenously expresses a Cre recombinase. In one embodiment, the target cell is contacted with said vector in vivo, in vitro or ex-vivo, and in one embodiment, contact is in vivo, and the Cre recombinase is expressed at specific times during development.

In one embodiment, the miRNA specifically inactivates firefly luciferase gene expression and the method further comprises excising said miRNA which specifically inactivates firefly luciferase gene expression and inserting a second miRNA which specifically inactivates a gene of interest.

In another embodiment, the vector further comprises a second miRNA sequence of interest in antisense orientation fused to the miRNA sequence of interest. According to this aspect, and in one embodiment, the second miRNA sequence of interest modulates expression of a gene whose activity is cooperative with that of a gene modulated by said first miRNA sequence of interest, or in another embodiment, the second miRNA sequence of interest modulates expression of a gene whose activity antagonizes that of a gene modulated by the first miRNA sequence of interest. In one embodiment, the first and second miRNA sequence of interest regulate expression of a tumor suppressor.

In another embodiment, the vector further comprises a third nucleic acid in antisense orientation, positioned between the first pair of loxP sequences, wherein said third nucleic acid encodes a protein of interest. According to this aspect, and in one embodiment, the third nucleic acid encodes an oncogene.

According to this aspect, and in another embodiment, the first miRNA sequence of interest specifically interacts with a sequence encoding an endogenous form of the protein of interest, and in one embodiment, the endogenous form is associated with a disease or disorder in the host.

In another embodiment, this invention provides a non-human animal with reduced expression of a coding sequence, wherein reduced expression is produced according to a method of this invention.

In another embodiment, this invention provides a mammalian cell with reduced expression of a coding sequence, wherein reduced expression is produced according to a method of this invention.

In another embodiment, this invention provides a method of assessing neoplasia in an animal model, said method comprising:
  i. contacting a target cell in a subject animal with a vector comprising:
    first pair of loxP sequences, inverted in orientation, with respect to each other;
    a first nucleic acid encoding a first selectable marker in sense orientation, wherein said nucleic acid is positioned between said first pair of loxP sequences;

a second nucleic acid encoding a second selectable marker, fused in frame to an miRNA sequence of interest with a suspected role in neoplasia or suppression thereof in antisense orientation, said miRNA sequence of interest being flanked by splice donor and splice acceptor sequences, said second nucleic acid is positioned between said first pair of loxP sequences, and said second nucleic acid is 3' with regard to said first nucleic acid;

second pair of loxP sequences, inverted in orientation, with respect to each other, wherein said first loxP sequenced of said second pair is positioned between said first and said second nucleic acid, and said second loxP sequence in said second pair is positioned 3' with respect to said first pair of loxP sequences, and said second pair of loxP sequences differs from that of said first pair of loxP sequences; and ii. evaluating neoplasia or development thereof in said animal;

whereby said method assesses development of neoplasia or suppression thereof in said subject animal as opposed to a control subject.

In some embodiments, the Cre recombinase is expressed in a cell- or tissue-specific manner.

In some embodiments, the first pair of loxP sequences comprises the wildtype sequence, and in some embodiments, the second pair of loxP sequences comprises a mutated loxP. In some embodiments, the first pair of loxP sequences comprises the loxP 5171 sequence and in some embodiments, the second pair of loxP sequences comprises the loxP 2272 sequence.

In some embodiments, the vector comprises a first regulatory sequence operatively linked to said second nucleic acid and said regulatory sequence is in antisense orientation and in some embodiments, the first regulatory sequence is a UbiquitinC promoter sequence. In some embodiments, the vector further comprises a second regulatory sequence, located 5' to said first regulatory sequence, wherein said second regulatory sequence is in sense orientation.

In some embodiments the vector further comprises a Bovine Growth Hormone polyadenylation signal positioned 3' to said second pair of loxP sites and in some embodiments, the vector further comprises a modified U3 LTR positioned 5' to said polyadenylation signal. In some embodiments, the first regulatory sequence is tissue specific or in some embodiments, the first regulatory sequence is inducible.

In some embodiments, the miRNA agent is an shRNA.

In some embodiments, the miRNA specifically inactivates p53 or PTEN gene expression.

In some embodiments, the vector further comprises a second miRNA sequence of interest in antisense orientation fused to the miRNA sequence of interest. In some embodiments, the second miRNA sequence of interest modulates expression of a gene whose activity is cooperative with that of a gene modulated by said first miRNA sequence of interest. In some embodiments, the first and second miRNA sequence of interest regulate expression of a tumor suppressor.

In some embodiments, the first miRNA sequence of interest specifically inactivates one of p53 or PTEN gene expression and said second miRNA sequence of interest specifically inactivates the other.

In some embodiments, the vector comprises a sequence corresponding to or homologous to SEQ ID No: 27.

In some embodiments, the second miRNA sequence of interest modulates expression of a gene whose activity antagonizes that of a gene modulated by said the miRNA sequence of interest.

In some embodiments, the second nucleic acid encodes an oncogene.

In some embodiments, the vector comprises a third nucleic acid in antisense orientation, positioned between the first pair of loxP sequences, wherein the third nucleic acid encodes a protein of interest.

In some embodiments, the third nucleic acid encodes an miRNA specifically inactivating a tumor suppressor.

In some embodiments, the third nucleic acid encodes an miRNA specifically inactivating p53, PTEN or a combination thereof.

In some embodiments, the vector comprises a nucleic acid sequence corresponding to or homologous to SEQ ID NO: 21.

BRIEF DESCRIPTION OF THE DRAWINGS

FIG. 11A plots results of a FACS analysis showing spleen and lymph node marker expression, from mice reconstituted with CD19-Cre (B cell Cre) donor marrow infected with FLIP vector puro2AGFP/c-Myc+miR-p53. Results are of samples isolated fourteen weeks post-transfer. FIG. 11B shows immunoblot results of the spleen and lymph node cells probed for c-Myc expression.

DETAILED DESCRIPTION OF THE INVENTION

The present invention provides, in one embodiment, constructs and enhanced methods for conditionally reducing expression of a coding sequence in a cell or animal, comprising contacting the cell with a vector comprising a first selectable marker in sense orientation, and a second selectable marker fused in frame to an miRNA sequence, in antisense orientation, wherein the miRNA sequence is flanked by splice donor and acceptor sequences, and wherein the marker sequences are flanked by two pairs of loxP sites, which sites are initially inverted in orientation, in cells capable of expressing a Cre recombinase.

Conditionally reduced expression of a coding sequence was demonstrated herein, with the use of a retroviral vector pLB2, which comprises, in some embodiments, a first pair of loxP sequences, inverted in orientation, with respect to each other, a first nucleic acid encoding a first selectable marker in sense orientation, wherein the first nucleic acid is positioned between the first pair of loxP sequences, a second nucleic acid encoding a second selectable marker, fused in frame to an miRNA sequence of interest in antisense orientation, wherein the second nucleic acid is positioned between the first pair of loxP sequences, and the second nucleic acid is 3' with regard to the first nucleic acid, a second pair of loxP sequences, inverted in orientation, with respect to each other. The first loxP sequence of the second pair is positioned between the first and second nucleic acid, and the second loxP sequence of the second pair is positioned 3' with respect to the first pair of loxP sequences, and the second pair of loxP sequences differs from that of said first pair of loxP sequences. In addition, the miRNA sequence of interest is flanked by splice donor and acceptor sites, to comprise an artificial intron.

Figure 3:
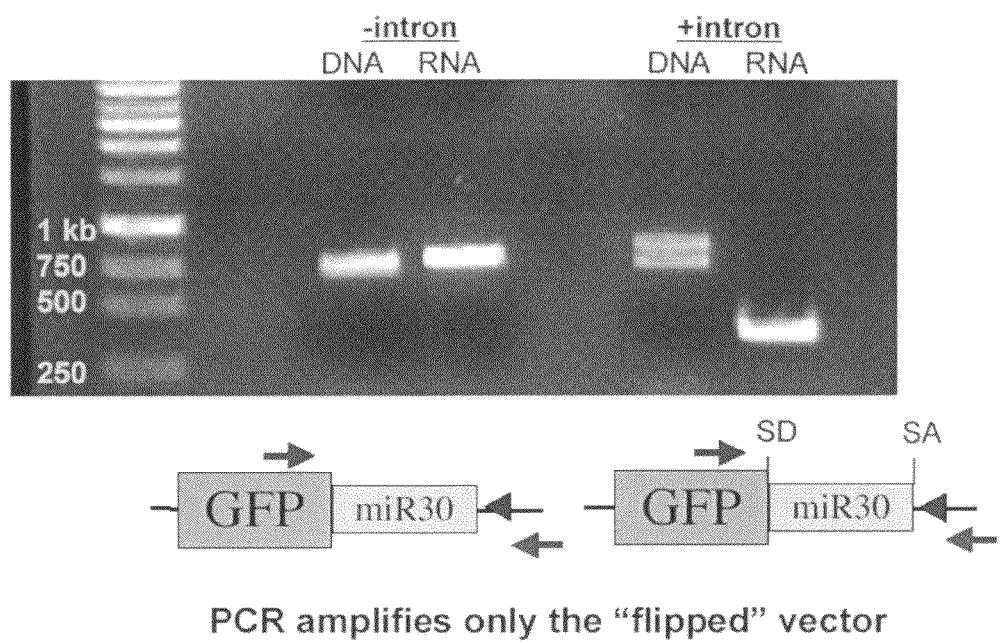
FIG. 3 demonstrates efficient intron splicing from the vector assayed by reverse transcription of cellular mRNA and subsequent PCR, compared to PCR of genomic DNA. The PCR amplified only the transcript derived from the vectors that have been reversed by Cre activity. As is evident from the gel, in constructs without the intron, band sizes are similar, however in constructs with the intron, the band is significantly smaller than that of genomic DNA (genomic amplifies as doublet, an irrelevant finding).
Figure 4:
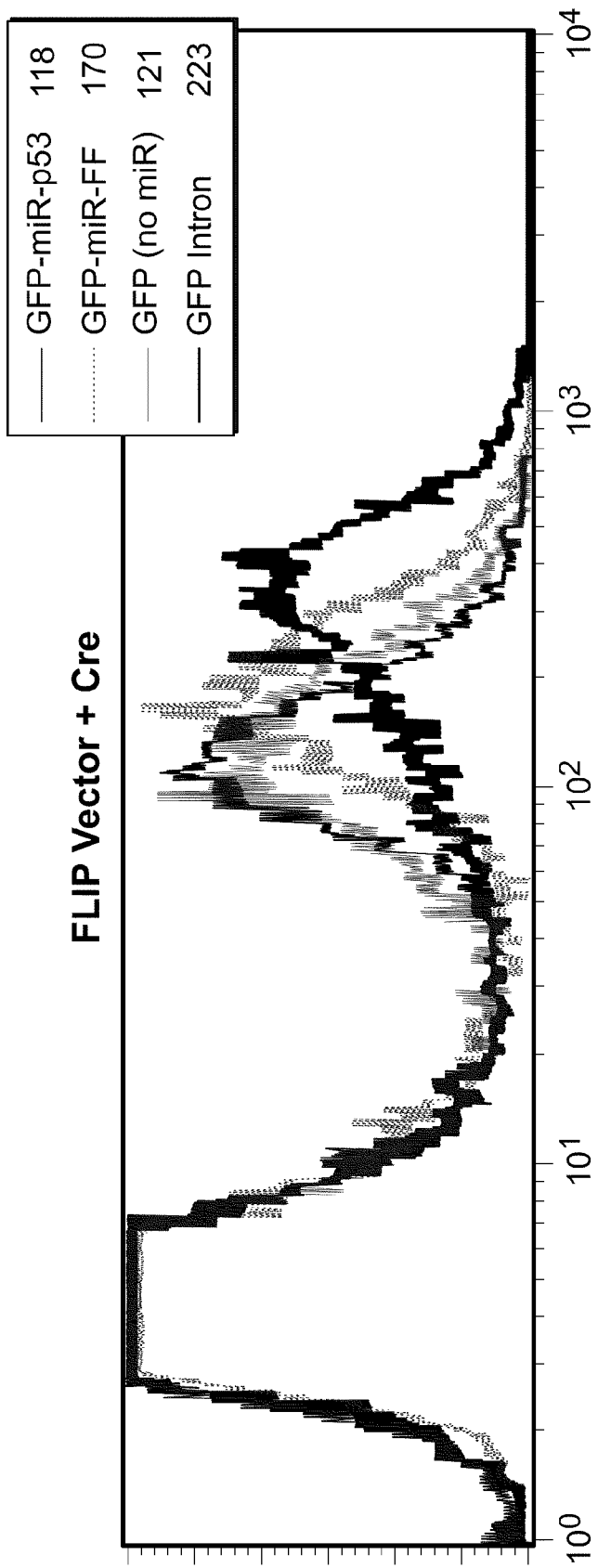
FIG. 4 demonstrates results of FACS analysis of constructs exposed to Cre, for GFP+ cells (all equal number of GFP+ cells). Numbers are Mean Fluorescent Intensity. The Figure indicates that inclusion of the intron increased expression.
Figure 5:
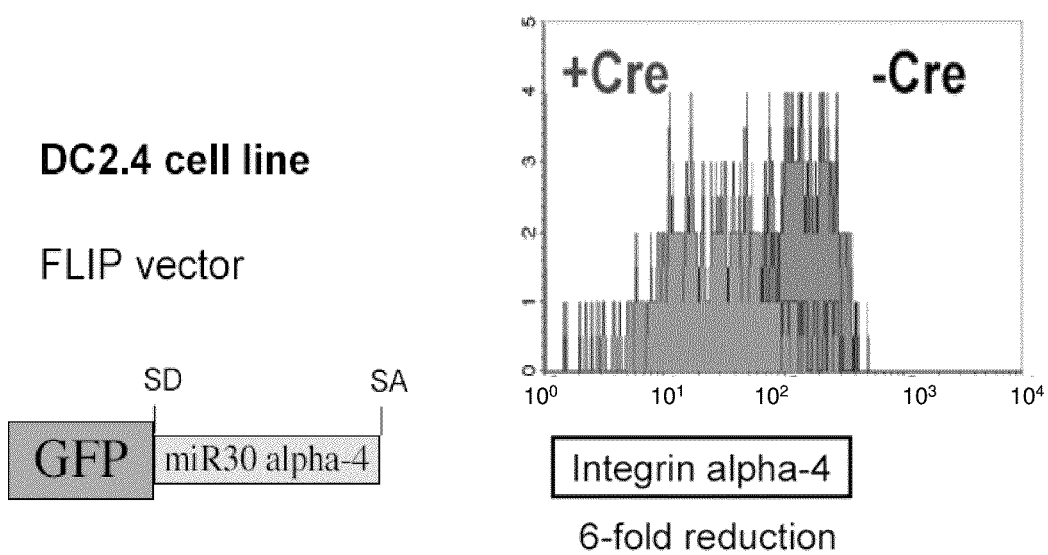
FIG. 5 demonstrates results of FACS analysis for alpha-4 integrin surface expression in DC2.4 cells transduced with a vector comprising a miR30 targeting the integrin, with and without Cre. Cre-mediated reduction of expression was roughly 6-fold.

FIG. 3 demonstrates one embodiment of a pLB2 vector of this invention, showing splicing of the intron, and FIG. 4 shows greater expression of the sequence when flanked by splice donor and acceptor sites, following Cre expression. FIG. 5 demonstrates about a 6-fold knockdown of α4-integrin expression in DC2.4 cells transduced with pLB2, upon expression of Cre.

In one embodiment, this invention provides a method of conditionally reducing expression of a coding sequence in a target cell, said method comprising contacting said target cell with a vector comprising: contacting the target cell with a vector comprising:
  a. a first pair of loxP sequences, inverted in orientation, with respect to each other;
  b. a first nucleic acid encoding a first selectable marker in sense orientation, wherein said nucleic acid is positioned between said first pair of loxP sequences;
  c. a second nucleic acid encoding a second selectable marker, fused in frame to an miRNA sequence of interest in antisense orientation, said miRNA sequence of interest being flanked by splice donor and splice acceptor sequences, said second nucleic acid is positioned between said first pair of loxP sequences, and said second nucleic acid is 3' with regard to said first nucleic acid;
  d. a second pair of loxP sequences, inverted in orientation, with respect to each other, wherein said first loxP sequenced of said second pair is positioned between said first and said second nucleic acid, and said second loxP sequence in said second pair is positioned 3' with respect to said first pair of loxP sequences, and said second pair of loxP sequences differs from that of said first pair of loxP sequences.

In one embodiment, the term "vector" refers to a nucleic acid molecule capable of transporting another nucleic acid to which it has been linked. In one embodiment, the vector is a genomic integrated vector, or "integrated vector", which can become integrated into the chromsomal DNA of the host cell. In another embodiment, the vector is an episomal vector, i.e., a nucleic acid capable of extra-chromosomal replication in an appropriate host, such as, for example a eukaryotic host cell. The vector according to this aspect of the present invention may be, in other embodiments, a plasmid, a bacmid, a phagemid, a cosmid, a phage, a virus or an artificial chromosome.

A nucleic acid of the present invention will generally contain phosphodiester bonds in one embodiment, or in another embodiment, nucleic acid analogs are included, that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone or bases may be done to facilitate the addition of other moieties such as chemical constituents, including 2'O-methyl and 5' modified substituents, or to increase the stability and half-life of such molecules in physiological environments.

The nucleic acids may be single stranded or double stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., Science 273:1386 (1996) and Yoon et al., PNAS USA 93:2071 (1996).

The vectors of this invention comprise, inter alia, an miRNA agent specific for a coding sequence.

The term "miRNA agent" refers, in one embodiment, to an agent that modulates expression of a target gene by an RNA interference mechanism. Micro-RNAs are a very large group of small RNAs produced naturally in organisms, which in one embodiment, regulates the expression of target genes. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors, which are processed to their mature forms by Dicer enzyme.

In one embodiment the miRNA agent comprises double-stranded RNA, which can form a hairpin structure. The miRNA agents employed, in another embodiment, are small ribonucleic acid molecules, or oligoribonucleotides, that are present in duplex structures, such as, in one embodiment, two distinct oligoribonucleotides hybridized to each other, or in another embodiment, a single ribooligonucleotide that assumes a hairpin structure to produce a duplex structure.

In one embodiment, miRNA agent does not exceed about 100 nt in length, and typically does not exceed about 75 nt length, where the length in certain embodiments is less than about 70 nt. In one embodiment, the miRNA agent of this invention has a length about 15 to 40 bp, or in another embodiment, about 20 and 29 bps, or in another embodiment, 25 and 35 bps, or in another embodiment, about 20 and 35 bps, or in another embodiment, about 20 and 40 bps, or in another embodiment, 21 bp, or in another embodiment, 22 bp.

In one embodiment, the nucleic acids/oligonucleotides comprising the miRNA agent may be synthesized on an Applied Bio Systems oligonucleotide synthesizer according to specifications provided by the manufacturer. In another embodiment, the nucleic acids/oligonucleotides or modified oligonucleotides may be synthesized by any number of means as is generally known in the art, and as is described hereinbelow.

In one embodiment, the miRNA agent encodes an interfering ribonucleic acid. In one embodiment, the miRNA agent is a transcriptional template of the interfering ribonucleic acid. According to this aspect of the invention, and in one embodiment, the transcriptional template is typically a DNA that encodes the interfering ribonucleic acid. The DNA may be present in a vector, such as, and in one embodiment, a plasmid vector, or in another embodiment, a viral vector, or any other vector, as will be known to one skilled in the art.

In one embodiment, the term "coding sequence" refers to a nucleic acid sequence that "encodes" a particular polypeptide or peptide. In one embodiment, the coding sequence is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

In one embodiment the term "coding sequence", includes DNA sequences that encode a polypeptide, as well as DNA sequences that are transcribed into inhibitory antisense molecules.

In one embodiment, the term "reducing expression", as it refers to vectors and their use according to the methods of this invention, refers to a diminishment in the level of expression of a gene when compared to the level in the absence of the miRNA agent.

In one embodiment, reduced expression may be affected at the transcriptional or translational level, or a combination thereof. In one embodiment, this invention provides vectors and methods for greater reduction of expression of a coding sequence, as a consequence of greater expression of the miRNA sequence, greater stability of the miRNA sequence, or a combination thereof.

According to this aspect of the invention, reduced expression using the vectors, and/or according to the methods of this invention, is specific. In one embodiment, the reduction in expression is via an ability to inhibit a target gene without manifest effects on other genes of the cell. The consequences of inhibition can be confirmed, in other embodiments, by examination of the outward properties of the cell or organism or by biochemical techniques such as RNA solution hybridization, nuclease protection, Northern hybridization, gene expression monitoring with a microarray, antibody binding, enzyme linked immunosorbent assay (ELISA), Western blotting, radioimmunoassay (RIA), other immunoassays, and fluorescence activated cell analysis (FACS).

In one embodiment, the miRNA agent is an shRNA, which specifically inactivates p53, alpha-4 integrins, or others, as exemplified and described herein.

In one embodiment, the vectors and methods of utilizing the same for reducing expression of a target gene may result in inhibition of target gene expression of greater than 10%, 33%, 50%, 75%, 80%, 85%, 90%, 95% or 99% as compared to a cell subjected to a vector as herein described.

It is to be understood that the term vector refers to any vector as herein described, or any variation thereof, comprising an element of such a vector as herein described, as will be appreciated to one skilled in the art. For example, and in some embodiments, the term vector may be considered to comprise a pLB, pLB2, MSCV or pFLIP vector, or components thereof.

In one embodiment, this invention provides for a method of conditionally reduced expression of a coding sequence in a target cell. In one embodiment, the term "conditionally reduced expression" refers to the flexibility inherent in the methods/vectors of this invention, which enable regulation of reducing expression of a coding sequence in a target cell. In one embodiment, reducing expression via the vectors/methods of this invention is controlled over time, or in a cell or tissue-specific manner, such that production of the miRNA agent is not constant.

Expression of the miRNA agent within a target cell, in one embodiment of this invention, takes advantage of a lox/cre system. In one embodiment, miRNA agent expression is dependent upon the presence of a Cre recombinase. According to this aspect of the invention, Cre recombinase inverts the second nucleic acid from antisense to sense orientation, such that a functional miRNA agent is expressed, and whereby splicing of the miRNA occurs, uncoupling miRNA from reporter expression, in some embodiments.

In one embodiment, the cre recombinase, is derived from a P1 bacteriophage (Abremski and Hoess, J. Biol. Chem. 259 (3):1509-1514 (1984)) which acts on a specific 34 base pair DNA sequence known as "loxP" (locus of crossover), which is, in turn, comprised of two 13 base pair inverted repeats (serving as the recombinase binding sites) flanking an 8 base pair core sequence (Current Opinion in Biotechnology 5:521-527 (1994). Cre catalyzes the rearrangement of DNA sequences that contain loxP sites. Recombination between two loxP sites (catalyzed by the cre protein) causes, in certain cases, the loss of sequences flanked by these sites [for a review see N. Kilby et al, Trends Genet., 9:413-421 (1993)].

In one embodiment, the cre recombinase, is expressed in hematopoietic cells, for example, as described in Zhang C C, et al. Nat. Med. 2006 February; 12(2):240-5. In some embodiments, Cre is estrogen, or estrogen agonist or antagonist induced, for example as described in Hayashi S, McMahon AP. Dev Biol. 2002 Apr. 15; 244(2):305-18. It is to be understood that any Cre Recombinase, or other appropriate recombinase, which can generate the desired expressed products of the vectors of this invention are to be considered a part of this invention.

In some embodiments, the loxP WT has a sequence as follows:

ATAACTTCGTATAGCATACATTATACGAAGTTAT (SEQ ID NO:11)

In some embodiments, this invention utilizes two sets of loxP sites, whose sequences differ. In one embodiment, one pair of the loxP sites may be WT, while the other may be mutated, or in another embodiment, both are mutated.

In one embodiment, mutated loxP sites inclusive of any known in the art, or homologues thereof may be employed in the constructs, materials and/or methods of this invention, for example, mutant sequences exemplified by loxP2272, loxP5171, loxP2271, loxP3171, loxP5272 or loxP5372 as described in Lee et al., Gene, 216:55-65 (1998).

In one embodiment, the loxP sets are oriented initially with inverted orientation, such that regions of the vector undergo inversion, following exposure to a Cre-recombinase. Following such inversion, one of the pairs of loxP sites are co-aligned, thus in the presence of a Cre-recombinase, excision can occur.

In one embodiment, the two pairs of loxP sites are chosen so as to minimize recombination therebetween, as exemplified herein.

Cre works in simple buffers, such as, in one embodiment, with magnesium or, in another embodiment, spermidine as a cofactor, as is well known in the art. The DNA substrates acted on by Cre may be, in one embodiment, in linear, or, in another embodiment, in a supercoiled configuration.

In one embodiment, the Cre sequence is as that described in N. Sternberg et al, J. Mol. Biol., 187:197-212 (1986). In another embodiment, the Cre recombinase may be obtained from commercial sources (for example from Novagen, Catalog No. 69247-1).

In one embodiment, cre recombinase will be expressed in a target cell of this invention. In another embodiment, the target cell will be engineered to express Cre by any means as will be known to one skilled in the art.

In one embodiment, the terms "homology", "homologue" or "homologous", refer to a, which exhibits, in one embodiment at least 70% correspondence with the indicated sequence. In another embodiment, the sequence exhibits at least 72% correspondence with the indicated sequence. In another embodiment, the sequence exhibits at least 75% correspondence with the indicated sequence. In another embodiment, the sequence exhibits at least 80% correspondence with the indicated sequence. In another embodiment, the sequence exhibits at least 82% correspondence with the indicated sequence. In another embodiment, the sequence exhibits at least 85% correspondence with the indicated sequence. In another embodiment, the sequence exhibits at least 87% correspondence with the indicated sequence. In another embodiment, the sequence exhibits at least 90% correspondence with the indicated sequence. In another embodiment, the sequence exhibits at least 92% correspondence with the indicated sequence. In another embodiment, the sequence exhibits at least 95% or more correspondence with the indicated sequence. In another embodiment, the sequence exhibits at least 97% correspondence with the indicated sequence. In another embodiment, the sequence exhibits at least 99% correspondence with the indicated sequence. In another embodiment, the sequence exhibits 95%-100% correspondence with the indicated sequence. Similarly, as used herein, the reference to a correspondence to a particular sequence includes both direct correspondence, as well as homology to that sequence as herein defined.

Homology, as used herein, may refer to sequence identity, or may refer to structural identity, or functional identity. By using the term "homology" and other like forms, it is to be understood that any molecule, that functions similarly, and/or contains sequence identity, and/or is conserved structurally so that it approximates the reference sequence, is to be considered as part of this invention. Homology may be determined in the latter case by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

An additional means of determining homology is via determination of candidate sequence hybridization, methods of which are well described in the art (See, for example, Nucleic Acid Hybridization, Hames and Higgins, Eds. (1985); Molecular Cloning, Sambrook and Russell, eds. (2001), and Current Protocols in Molecular Biology, Ausubel et al. eds, 1989). For example, methods of hybridization may be, in one embodiment, carried out under moderate to stringent conditions, to the complement of a DNA encoding a native peptide or protein of interest. Hybridization conditions may be, for example, overnight incubation at 42° C. in a solution comprising: 10-20% formamide, 5×SSC (150 millimolar (mM) NaCl, 15 mM trisodium citrate), 50 mM sodium phosphate (pH 7.6), 5×Denhardt's solution, 10% dextran sulfate, and 20 micrograms (μg)/milliliter (ml) denatured, sheared salmon sperm DNA. Each method represents a separate embodiment of the present invention. In some embodiments, this invention provides a nucleic acid or a vector or composition or cell comprising the same, with a sequence corresponding to or homologous to any of those set forth in SEQ ID NO: 1-27.

In another embodiment, mutated loxP sites, may be employed in the vectors and/or methods of this invention.

Figure 1A:
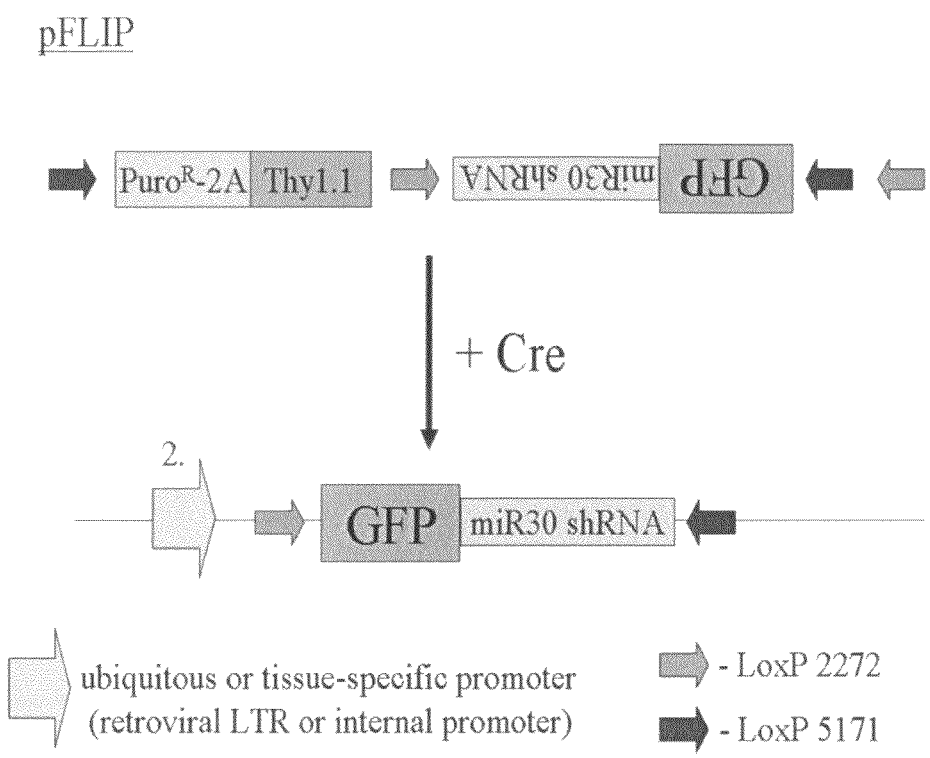
FIG. 1 depicts one embodiment of the organization and expression of constructs of this invention. A. Shematic representation of an embodiment of the pFLIP inserts of this invention. Two pairs of mutated loxP sites and their orientation are depicted, as well as the positioning of the positioning of the selectable marker sequences and miRNA sequence, with respect thereto. Schematic shows elements prior to and following Cre-mediated recombination. B. Schematic depiction of differences in the pLB2 versus pLB vector. C. Schematic depiction of MSCV and pLB2 constructs.
Figure 1B:
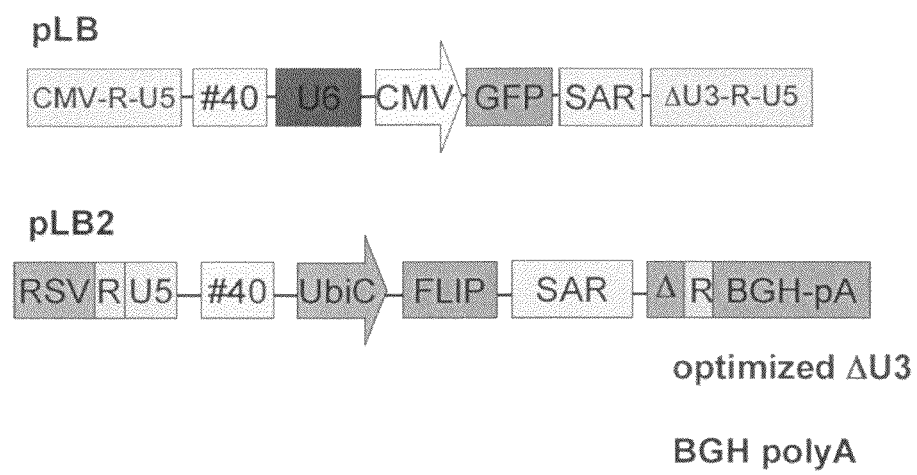

In one embodiment of this invention, a modified pLB vector was constructed, resulting in greater expression, the vector being schematically depicted in FIG. 1B, and referred to herein as pLB2.

In this embodiment of the modified vector (pLB2), the promoter driving the RNA genome was derived from. The packaging signal (Psi), central polypurine tract (cPPT), anti-repressor (Element #40) and scaffold attached region (SAR) were similar to those used in previously described pLB vectors, representing one embodiment of the invention.

In one embodiment, the pLB2 has an internal Ubiquitin-C promoter, driving expression of the FLIP cassette. The FLIP cassette maintains GFP-miR30, or other miR30 fused sequences as herein described in the antisense orientation until reversed by Cre activity.

In some embodiments, pLB2 comprises a modified 3'LTR, as well. In some embodiments, such modification comprises deletions of the U3 to produce self-inactivating vectors (SIN). In some embodiments, pLB2 will comprise from ~200 to a ~420 nucleotide deletion, or in some embodiments, up to the minimum required for integration (~25 nt) and another 20 nt that significantly improved polyadenylation of the integrated viral transcript.

In some embodiments, these untranslated regions aid in protecting the miRNA from rapid breakdown.

In some embodiments, pLB2 will comprise a Bovine Growth Hormone Polyadenylation signal. In another embodiment, the Bovine Growth Hormone polyadenylation signal is positioned 3' to the second pair of loxP sites.

In some embodiments of this invention, pLB2, or the vectors/compositions/kits of this invention comprise, and methods make use of splice donor and splice acceptor sequences flanking at least one miR30, such that the miR30 is contained within an artificial intron.

In some embodiments, such introns may comprise any known in the art, whose use herein results in enhanced miR30 expression, following Cre exposure. In some embodiments, a consensus sequence is utilized, as herein described. In some embodiments, splice donor and acceptor sequences are optimized to yield the greatest fold reduction in gene expression.

In some embodiments, the intron may comprise, or be derived from the 2.0 kb LAT of Herpes Simplex Virus, type I (HSV-1), strain 17. The sequence of this LAT is reported in McGeoch et al, 1988, J. Gen. Virol., 69:1531-1574; the sequence of the 2.0 kb LAT of HSV-1 strain F is reported in Spivak et al, 1991, J. Virol., 65:6800-6810, both of which are incorporated by reference herein.

In some embodiments, the splice donor sequence, is located 5' to the miR30 in the constructs of this invention, may span from about 2 to about 25 nucleotides, and the splice acceptor sequence, located 3' to the miR30 in the constructs of this invention, may span from about 2 to about 25 nucleotides. Corresponding sequences may be obtained from other introns by conventional methods which follow the teachings herein.

In some embodiments, the miR30 will be flanked by restriction endonuclease sites, which in turn are flanked by the splice donor and splice acceptor sequences, respectively. In some embodiments, such restriction endonuclease sites allow for the ready exchange of miR30 sequences in a given vector/construct of this invention.

In some embodiments, the constructs/kits/compositions of this invention may comprise and methods make use of the same, whereby such constructs comprise one or more introns, or hybrids thereof. In one embodiment, multiple miR30s may be flanked by multiple introns and attached in tandem, or in some embodiments, an intron may be optimized, derived from two or more native introns, whereby expression for a particular tissue or sequence is optimally derived.

In some embodiments, the term "intron" as used herein, refers to a non-coding nucleotide sequence of varying length, normally present within many eukaryotic genes, which is removed from a newly transcribed mRNA precursor by the process of splicing. In general, the process of splicing requires that the 5' and 3' ends of the intron be correctly cleaved and the resulting ends of the mRNA be accurately joined, such that a mature mRNA having the proper reading frame for protein synthesis is produced.

Introns have highly conserved sequences at or near each end of the intron which are required for splicing and intron removal. In some embodiments, the term "splice donor site" or "SD" or "5' splice site" refers to the conserved sequence immediately surrounding the exon-intron boundary at the 5' end of the intron, where the exon comprises the nucleic acid 5' to the intron. In some embodiments, the term "splice acceptor site" or "SA" or "3' splice site" herein refers to the sequence immediately surrounding the intron-exon boundary at the 3' end of the intron, where the exon comprises the nucleic acid 3' to the intron. In some embodiments, the term "intron" refers to a nucleic acid comprising a splice donor site and a splice acceptor site including intervening sequences, such as an miRNA as herein described and the presence of restriction endonuclease sites. Many splice donor and splice acceptor sites have been characterized and Ohshima et al., J. Mol. Biol., 195:247-259 (1987) provides a review of these. Examples of efficient splice donor sequences include the wild type (WT) ras splice donor sequence and the GAC:GTAAGT (SEQ ID NO: 12) sequence. In some embodiments, the splice donor site is a "consensus splice donor sequence" and in some embodiments, the splice acceptor site is a "consensus splice acceptor sequence"; these consensus sequences are evolutionarily highly conserved. The consensus sequences for both splice donor and splice acceptor sites in the mRNAs of higher eukaryotes are shown in Molecular Biology of the Cell, 3.sup.rd edition. Alberts et al. (eds.), Garland Publishing, Inc., New York, 1994, on page 373, FIG. 12-53. The consensus sequence for the 5' splice donor site is C/A (C or A) AG:GUAAGU (wherein the colon denotes the site of cleavage and ligation) (SEQ ID NO: 13). The 3' splice acceptor site occurs within the consensus sequence (U/C).sub.11NCAG:G (SEQ ID NO: 14). Other efficient splice donor and acceptor sequences can be readily determined using the techniques for measuring the efficiency of splicing.

In some embodiments, such introns used in the vectors/kits/compositions/methods of this invention provide a splicing efficiency of at least about 75%, or in another embodiment, at least about 80%, or in another embodiment, at least about 85%, or in another embodiment, at least about 90%, or in another embodiment, at least about 95%.

In some embodiments, the term "about" when in reference to a value as described herein is to be understood to encompass the indicated value +/−1%, or in some embodiments, +/−3%, or in some embodiments, +/−3%, or in some embodiments, +/−5%, or in some embodiments, +/−7%, or in some embodiments, +/−10%, or in some embodiments, +/−15%, or in some embodiments, +/−20%, or in some embodiments, +/−25%.

Intron splicing efficiency is readily determined by quantifying the spliced transcripts versus the full-length, unspliced transcripts that contain the intron, using methods known in the art such as by quantitative PCR or Northern blot analysis, using appropriate probes for the transcripts. See, e.g., Sambrook et al., supra, and other general cloning manuals. Reverse transcription-polymerase chain reaction (RT-PCR)

can be used to analyze RNA samples containing mixtures of spliced and unspliced mRNA transcripts. For example, fluorescent-tagged primers designed to span the intron are used to amplify both spliced and unspliced targets. The resultant amplification products are then separated by gel electrophoresis and quantitated by measuring the fluorescent emission of the appropriate band(s). A comparison is made to determine the amount of spliced and unspliced transcripts present in the RNA sample.

In some embodiments, this invention provides a vector comprising any desired grouping of elements, which at least consists of an miR30 and flanking splice donor and splice acceptor sites, in antisense orientation, situated between two sets of loxP sites as herein described, such that upon exposure to a Cre recombinase, or other appropriate recombinase, inversion and excision occurs and expression of the miR30 is accomplished.

In some embodiments, such vectors/compositions/kits of this invention may be said to consist essentially of at least one miR30 contained within an artificial intron, wherein the phrase "consist essentially of" is to convey that other sequences may be incorporated into the vectors/compositions/kits of this invention, including marker sequences, regulatory sequences, including promoter and enhancers, other coding sequences, which may be in antisense orientation, and juxtaposed between loxP sites as herein described, or such sequences may be in sense orientation, and are Cre-independent for their expression.

In one embodiment, the constructs of this invention will comprise a promoter, operatively linked to the first nucleic acid sequence encoding a selection marker. In one embodiment, the term "promoter" refers to a nucleic acid sequence, which regulates expression of a nucleic acid, operably linked thereto. Such promoters are known to be cis-acting sequence elements required for transcription as they serve to bind DNA dependent RNA polymerase, which transcribes sequences present downstream thereof.

The term "operably linked", in one embodiment, refers to a relationship permitting the sequences to function in their intended manner. A vector comprising a regulatory sequence "operably linked" to a coding sequence is ligated in such a way that expression of the nucleic acid sequence is achieved under conditions compatible with the control sequences. "Operably linked" refers, in some embodiments, to a juxtaposition of two or more components, wherein the components so described are in a relationship permitting them to function in their intended manner. For example, a promoter and/or enhancer is operably linked to a coding sequence if it acts in cis to control or modulate the transcription of the linked sequence. Generally, but not necessarily, the DNA sequences that are "operably linked" are contiguous and, where necessary to join two protein coding regions or in the case of a secretory leader, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distances from the promoter. A polyadenylation site is operably linked to a coding sequence if it is located at the downstream end of the coding sequence such that transcription proceeds through the coding sequence into the polyadenylation sequence. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

In one embodiment, the promoter will be an RNA polymerase III promoter.

In one embodiment, a promoter, including an engineered promoter used in the vectors and methods of this invention, may be one known to confer cell-type specific expression of a sequence operatively linked to thereto. For example, and in one embodiment, a promoter specific for myoblast gene expression can be operatively linked to an miRNA for a coding sequence of interest, a reporter gene, or a coding sequence of interest, to confer muscle-specific expression thereof. Muscle-specific regulatory elements which are known in the art include upstream regions from the dystrophin gene (Klamut et al., (1990) Mol. Cell Biol. 10:193), the creatine kinase gene (Horlick and Benfield (1989) Mol. Cell Biol. 9:2396; Buskin and Hauschka, (1989) Mol. Cell Biol. 9:2627) and the troponin gene (Mar and Ordahl, (1988) Proc. Natl. Acad. Sci. USA. 85:6404).

In another embodiment, promoters used in the vectors and methods of this invention, specific for other cell types known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters) may be used, and represent an embodiment of this invention. In another embodiment, a promoter or regulatory element, which can direct constitutive expression of a sequence operatively linked thereto, in a variety of different cell types, such as a viral regulatory element, may be used. Examples of viral promoters commonly used to drive gene expression include those derived from polyoma virus, Adenovirus 2, cytomegalovirus and Simian Virus 40, and retroviral LTRs.

In another embodiment, a regulatory element, which provides inducible expression of a gene linked thereto, may be used. The use of an inducible promoter may allow, in another embodiment, for an additional means of modulating the product of the coding sequence in the cell. Examples of potentially useful inducible regulatory systems for use in eukaryotic cells include hormone-regulated elements (e.g., see Mader, S, and White, J. H. (1993) Proc. Natl. Acad. Sci. USA 90:5603-5607), synthetic ligand-regulated elements (see, e.g., Spencer, D. M. et al 1993) Science 262:1019-1024) and ionizing radiation-regulated elements (e.g., see Manome, Y. Et al. (1993) Biochemistry 32:10607-10613; Datta, R. et al. (1992) Proc. Natl. Acad. Sci. USA 89: 1014-10153). Additional tissue-specific or inducible regulatory systems may be developed for use in accordance with the invention.

In another embodiment, the vector further comprises a first regulatory sequence operationally linked to the first nucleic acid, and being in an antisense orientation, which in one. embodiment is a UbiquitinC promoter sequence. In another embodiment, the vector further comprises a second regulatory sequence, located 5' to said first regulatory sequence, wherein the second regulatory sequence is in a sense orientation.

In one embodiment, the term "capable of expressing a Cre recombinase" refers to a cell that endogenously expresses the Cre recombinase, or in another embodiment, is engineered to express a Cre recombinase.

In one embodiment, the cell is in a culture system, or in another embodiment, in a body of a subject, or in another embodiment, is ex-vivo cultured, and following transfection or transduction with a vector of this invention, is reintroduced to the subject from which the cell was taken. In one embodiment, the cell is a stem or progenitor cell. In another embodiment, the cell is a mature, differentiated cell. In one embodiment, the cell is a human cell in origin, or in another embodiment, the cell is murine in origin.

In one embodiment, the terms "cells," "host cells" or "target cells" are used interchangeably, and refer, in one embodiment, not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In another embodiment, the cell is a diseased cell. In one embodiment, the cell is infected, or in another embodiment, the cell is transformed or neoplastic. In another embodiment, the cell is obtained from a subject with a disease whose etiology is associated with a genetic mutation. In another embodiment, the cell is obtained from a subject with a disease, where an inappropriate immune or inflammatory response has been initiated.

In one embodiment, the target cell of any method of the present invention may be a cancer cell or neoplastic cell. "Neoplastic cell" refers, in one embodiment, to a cell whose normal growth control mechanisms are disrupted (typically by accumulated genetic mutations), thereby providing potential for uncontrolled proliferation. Thus, "neoplastic cell" can include, in one embodiment, both dividing and non-dividing cells. In one embodiment, neoplastic cells may include cells of tumors, neoplasms, carcinomas, sarcomas, leukemias, lymphomas, and others. In another embodiment, "neoplastic cells" may include central nervous system tumors, such as, for example brain tumors. These may include, in other embodiments, glioblastomas, astrocytomas, oligodendrogliomas, meningiomas, neurofibromas, ependymomas, schwannomas or neurofibrosarcomas. In another embodiment, "neoplastic cells" can include either benign or malignant neoplastic cells. In another embodiment, "neoplastic cells" can include any other type of cancer known in the art.

In one embodiment, the target cell may be an infected cell. In another embodiment, the target cell may be a pathogenic cell. In another embodiment, the target cell may mediate autoimmunity or another disease state. In another embodiment, the target cell may comprise a mutated cellular gene necessary for a physiological function. In one embodiment, the mutated product results in disease in the subject. According to this aspect of the invention, the vectors/methods of this invention may be employed to silence a defective gene, and may further be followed by delivery of a wild-type copy of the desired gene.

It is to be understood that any cell comprising a vector of this invention, or utilized for the methods of this invention, is to be considered as part of this invention, and represents an embodiment thereof.

According to this aspect of the invention, and in one embodiment, following Cre-mediated recombination in the target cell, the miRNA agent is expressed and reduces expression of the coding sequence, thereby conditionally reducing expression of a coding sequence in the target cell.

In another embodiment, the vector is a retroviral vector. In one embodiment, the retroviral vector of this invention may correspond to one as exemplified herein.

A retroviral or retrovirus vector, as used herein, is a vector, which comprises at least one component part derivable from a retrovirus. In one embodiment, the component part is involved in the biological mechanisms by which the vector infects cells, expresses genes or is replicated. The term "derivable", in one embodiment, refers to the fact that the sequence need not necessarily be obtained from a retrovirus but instead could be derived therefrom. By way of example, the sequence may be prepared synthetically or by use of recombinant DNA techniques.

The retroviral vectors of this invention may be derived from any member of the family of retroviridae.

In one embodiment, the vectors of this invention are lentivirus, and may be derived from any member of the family of lentiviridae.

In one embodiment, the retroviral vectors of this invention comprise sufficient retroviral genetic information to allow packaging of an RNA genome, in the presence of packaging components, into a viral particle capable of infecting a target cell. In one embodiment, infection of the target cell includes reverse transcription and integration into the target cell genome. The retroviral vectors of this invention may carry, in one embodiment, non-viral coding sequences which are to be delivered by the vector to the target cell. In one embodiment, the retroviral vectors of this invention are incapable of independent replication to produce infectious retroviral particles within the final target cell. In one embodiment, the retroviral vectors of this invention will lack a functional gag-pol and/or env gene and/or other genes essential for replication.

In some embodiments, the vectors of this invention may be integrated into the genome (germ line) of a host mammal, thereby forming a transgenic animal. In some embodiments, such integration into the germ line is desired for the transmission of the construct to offspring, and thus, a strain of mammals containing the constructs can be maintained, as exemplified in an embodiment herein.

Depending upon the characteristics of the miR30 employed, or the intron, for example, a variety of screening procedures are available, which may comprise probe analysis, mRNA analysis, enzyme analysis, functional assays, antibody screens and protein, carbohydrate and lipid analysis, to ascertain, for example gene knockdown, or construct incorporation, as will be appreciated by one skilled in the art.

As exemplified herein, transgenic animals expressing the constructs of this invention may be prepared, representing another embodiment of the invention. In some embodiments, such procedures entail injection of the constructs into early embryos, which may be accomplished by means well known in the art, for example, embryos are placed in a drop of medium (see Quinn, J. Reprod. Fert. 66:161-168 (1982) the disclosure of which is incorporated by reference). The drop of medium is covered with paraffin oil and the embryos are viewed with an inverted microscope using Hoffman optics. Injection of the vectors of this invention may be accomplished by positioning a one cell embryo, or blastula with a holding micropipette and injecting the vector thereto with a finely pulled injection micropipette. The control of the fluid flow through the micropipettes may be accomplished by art-recognized means, for example, the entire system may be filled with paraffin oil allowing positive pressure for injection and negative pressure for holding the embryo to be injected under fine control. Embryo survival after injection may be assessed morphologically.

The embryos surviving microinjection may be placed in HT6 medium in preparation for transfer to the oviducts of 6- to 8-week old female mice. The recipient may be administered PMS i.p. followed later by hCG and placed with a vasectomized male mouse. To aid the recipient in accepting the microinjection embryos the gonadotropic administration and mating may coincide with the schedule of the donor mouse.

The success of the embryo transfer is, in some embodiments judged by the birth of mice about 19-21 days after transfer. Success of the microinjection may be assessed by Southern hybridization analysis of DNA isolated from mouse tail biopsies.

In one embodiment, the vectors and methods of this invention may employ the use of enhancer sequences. In one embodiment, the term "enhancer" refers to a DNA sequence, which binds to other protein components of the transcription initiation complex and may thus facilitate the initiation of transcription directed by its associated promoter.

In another embodiment, the vectors and their use according to the present invention include at least two selectable markers, which may serve to indicate inversion and excision mediated by a Cre-recombinase, as described herein. In one embodiment, the selectable marker comprises an antibiotic resistance cassette, by means well known to one skilled in the art. In one embodiment, the resistance cassette is for conferring resistance to ampicillin, bleomycin, chloramphenicol, gentamycin, hygromycin, kanamycin, lincomycin, methotrexate, phosphinothricin, puromycin, or tetracycline, or derivatives thereof.

In another embodiment, the selectable marker may comprise nucleic acid sequences encoding for a reporter protein, such as, for example, green fluorescent protein (GFP), DS-Red (red fluorescent protein), acetohydroxyacid synthase (AHAS), beta glucoronidase (GUS), secreted alkaline phosphatase (SEAP), beta-galactosidase, chloramphenicol acetyltransferase (CAT), horseradish peroxidase (HRP), luciferase, nopaline synthase (NOS), octopine synthase (OCS), or derivatives thereof, many known in the art, or any number of other reporter proteins known to one skilled in the art.

In some embodiments, the invention provides vectors/kits/compositions and the use of any form or derivative of GFP that emits sufficient fluorescence to enable fluorescence detection of intracellular GFP by flow cytometry using a fluorescence-activated cell sorter (FACS), or by fluorescence microscopy. GFP usable in the invention include wild-type as well as naturally occurring (by spontaneous mutation) or recombinantly engineered mutants and variants, truncated versions and fragments, functional equivalents, derivatives, homologs and fusions, of the naturally occurring or wild-type proteins. A range of mutations in and around the chromophore structure of GFP (around amino acids 64-68) have been described. These mutations result in modifications of the spectral properties, the speed of chromophore formation, the extinction coefficient, and the physical characteristics of the GFP. These forms of GFP may have altered excitation and emission spectra as compared to the wild-type GFP, or may exhibit greater stability. The mutant GFPs may fluoresce with increased intensity or with visibly distinct colors than the wild-type protein, e.g., blue, yellow or red-shifted fluorescent proteins, the DNA containing these genes of which are available commercially (Clontech, Palo Alto, Calif.; Quantum Biotechnologies, Montreal, Canada). Mutants with increased fluorescence over the wild-type GFP provide a much more sensitive detection system. Mutants may have a single excitation peak as opposed to 2 peaks characteristic of the native protein, may be resistant to photobleaching or may exhibit more rapid oxidation to fluorophore. For example, the Aequorea GFP mutant, S65T (Heim et al. Nature 373: 663-664 (1995)), in which Ser65 has been replaced by Thr, offers several advantages over the wild-type GFP in that the mutant provides six-fold greater brightness than wild-type, faster fluorophore formation, no photoisomerization and only very slow photobleaching. Modifications of Ser65 to Thr or Cys result in GFPs that continue to emit maximally at approximately 509 nm but which have a single excitation peak red-shifted to 488 nm and 473 nm respectively. This has several advantages in that it brings the excitation peaks more in line with those already used with fluorescent microscopes and fluorescence-activated cell sorters (FACS) for FITC. Furthermore, chromophore formation of these mutants is more rapid and the extinction coefficient is greater than that of wtGFP (wild-type GFP), which results in a stronger fluorescent signal (Heim et al., 1995, supra). Other GFP mutants have codons optimized for mammalian cell expression as well as exhibiting greater fluorescence than the original GFP gene (see Bennet (1998), infra; Crameri et al. Nature Biotechnol. 14:315-319 (1996)). "Humanized" or otherwise modified versions of GFP, including base substitution to change codon usage, that favor high level expression in mammalian cells, are suitable for use in the constructs of the invention (see, e.g., Hauswirth et al., U.S. Pat. No. 5,874,304; Haas et al. U.S. Pat. No. 5,795,737). GFP mutants that will fluoresce and be detected by illumination with white light are described in WO 9821355. Still other mutant GFPs are described in U.S. Pat. No. 5,804,387 (Cormack et al.) and WO 9742320 (Gaitanaris et al.).

In another embodiment, the vector may further include an origin of replication, and may be a shuttle vector, which can propagate both in bacteria, such as, for example, E. coli (wherein the vector comprises an appropriate selectable marker and origin of replication) and be compatible for propagation in vertebrate cells, or integration in the genome of an organism of choice.

The nucleic acids may be introduced into tissues or host cells by any number of routes, including viral infection, microinjection, or fusion of vesicles. Jet injection may also be used for intramuscular administration, as described by Furth et al. (1992), Anal Biochem 205:365-368. The nucleic acids may be coated onto gold microparticles, and delivered intradermally by a particle bombardment device, or "gene gun" as described in the literature (see, for example, Tang et al. (1992), Nature 356:152-154), where gold microprojectiles are coated with the DNA, then bombarded into skin cells. Expression vectors may be used to introduce the nucleic acids into a cell.

In one embodiment, the vectors of this invention may be fed directly to, injected into, the host organism containing the target gene. The vectors of this invention may be directly introduced into the cell (i.e., intracellularly); or introduced extracellularly into a cavity, interstitial space, into the circulation of an organism, introduced orally, etc. Methods for oral introduction include direct mixing of the vector with food of the organism. Physical methods of introducing the vectors include injection directly into the cell or extracellular injection into the organism of a solution comprising the vector. The vectors may be introduced in an amount, which allows delivery of at least one copy per cell. Higher doses (e.g., at least 5, 10, 100, 500 or 1000 copies per cell) of the vectors may yield more effective inhibition; lower doses may also be useful for specific applications.

In other embodiments, a hydrodynamic administration protocol is employed, and may be as described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349, each of which represents an embodiment of this invention.

In other embodiments, delivery protocols of interest may include, but are not limited to: those described in U.S. Pat. No. 5,985,847, or 5,922,687, WO/11092; Acsadi et al., New Biol. (1991) 3:71-81; Hickman et al., Hum. Gen. Ther. (1994) 5:1477-1483; or Wolff et al., Science (1990) 247: 1465-1468, and others, as will be appreciated by one skilled in the art.

The methods of this invention comprise the step of contacting a target cell with a vector of this invention. In one embodiment, the terms "contacting", "contact" or "contacted" indicate, direct or, in another embodiment, indirect exposure of the cell to a vector, compound or composition comprising the vectors of this invention. It is envisaged that, in another embodiment, indirect supply to the cell may be via provision in a culture medium that surrounds the cell, or via parenteral administration in a body of a subject, whereby the vector ultimately contacts a cell via peripheral circulation (for further detail see, for example, Methods in Enzymology Vol. 1-317, Rubin and Dennis, eds, (1955-2003) and Current Protocols in Molecular Biology, Ausubel, et al, eds (1998), Molecular Cloning: A Laboratory Manual, Sambrook and Russell, eds., (2001), or other standard laboratory manuals). It is to be understood that any direct means or indirect means of intracellular access of a vector, or composition comprising the same of this invention represents an embodiment thereof.

In one embodiment, the target cell is contacted with a vector/composition comprising the same, of this invention, in vivo, in vitro or ex-vivo. In one embodiment, cells may be procured from a subject, contacted with a vector of this invention, and reintroduced into the subject. In one embodiment, the cell is a stem or progenitor cell, and reintroduction into the subject may be followed, in another embodiment, by stimulation of differentiation of the contacted cell, in vivo.

In another embodiment, Cre recombinase is expressed at specific times during development.

In another embodiment, this invention provides for the generation of a non-human animal with reduced expression of a coding sequence, wherein the reduced expression is produced according to the methods, and/or utilizing the vectors of this invention.

Transgenic mice, may, in one embodiment, be derived using the vectors/methods of this invention, according to Hogan, et al., "Manipulating the Mouse Embryo: A Laboratory Manual", Cold Spring Harbor Laboratory (1988) which is incorporated herein by reference. Embryonic stem cells may, in another embodiment, be manipulated according to published procedures (Teratocarcinomas and embryonic stem cells: a practical approach, E. J. Robertson, ed., IRL Press, Washington, D.C., 1987; Zjilstra et al., Nature 342:435-438 (1989); and Schwartzberg et al., Science 246:799-803 (1989), each of which is incorporated herein by reference). Zygotes may be manipulated, in another embodiment, according to known procedures; for example see U.S. Pat. No. 4,873,191, Brinster et al., PNAS 86:7007 (1989); Susulic et al., J. Biol. Chem. 49:29483 (1995), and Cavard et al., Nucleic Acids Res. 16:2099 (1988), hereby incorporated by reference. Tetraploid blastocyst complementation may also be utilized to achieve non-human animals, which express the vectors of this invention, according to methods as exemplified herein, or, as are well known in the art.

In one embodiment, this invention provides a method of producing an animal genetically inactivated for a coding sequence, the method comprising contacting an embryonic stem cell with a vector of this invention which may be used for gene silencing, injecting the contacted embryonic stem cell to a blastocyst of an animal and obtaining an animal expressing the vector, whereby, following Cre-mediated recombination in the animal, the miRNA agent is expressed and reduces expression of the coding sequence, thereby being a method of producing an animal genetically inactivated for a coding sequence.

In another embodiment, the method of conditionally reducing expression of a coding sequence, as described and exemplified herein, may be therapeutic. In one embodiment, the term "therapeutic" refers to the fact that when in contact with a cell in a subject in need, provides a beneficial effect.

In one embodiment, the compositions/vectors and methods of conditionally reducing expression of a coding sequence of this invention prevent inappropriate expression of an encoded protein in a subject. Some examples include endogenous proteins which are mutated, and produces a non-functional protein, or an over-expressed protein, which in another embodiment, may be non-functional, or in another embodiment, pathogenic.

In one embodiment, the encoded protein may include cytokines, such as interferons or interleukins, or their receptors. According to this aspect of the invention, and in one embodiment, inappropriate expression patterns of cytokines may be altered to produce a beneficial effect, such as for example, a biasing of the immune response toward a Th1 type expression pattern, or a Th2 pattern in infection, or in autoimmune disease, wherein altered expression patterns may prove beneficial to the host. In these cases, and in one embodiment, conditionally reducing expression of the inappropriate or non-protective cytokine/receptor may be followed by delivery of an appropriate cytokine, or a vector/nucleic acid for expressing the same.

In another embodiment, the encoded protein may include an enzyme, such as one involved in glycogen storage or breakdown. In another embodiment, the encoded protein may include a transporter, such as an ion transporter, for example CFTR, or a glucose transporter, or other transporters whose inappropriate expression results in a variety of diseases. As described hereinabove, and in another embodiment, conditionally reducing expression of the encoded proteins, according to this aspect of the invention, may be followed by delivery of a wild-type protein, or a plasmid encoding same, or a mutated protein, which results in a therapeutic effect in the subject.

In another embodiment, the encoded protein may include a receptor, such as one involved in signal transduction within a cell. Some examples include as above, cytokine receptors, leptin receptors, transferring receptors, etc., or any receptor wherein altered expression results in inappropriate or inadequate signal transduction in a cell.

It is to be understood that any encoded protein, wherein conditionally reducing expression of the product is therapeutic to a subject is to be considered as part of this invention, and methods/vectors to provide wild-type or otherwise therapeutic versions of the encoded protein to the subject, following conditional reduction of expression of the mutated version, is to be considered as part of this invention, and embodiments thereof.

In another embodiment, the vectors/methods of this invention may be utilized to conditionally reduce expression of an oncogene, whose expression promotes cancer-related events. In one embodiment, the conditionally reduced expression of oncogenes comprising ABLI, BCLI, BCL2, BCL6, CBFA2, CBL, CSFIR, ERBA, ERBB, EBRB2, ETSI, ETSI, ETV6, FOR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, YES, or any form thereof, or combinations thereof, may be effected via the vectors/compositions/methods of this invention. In another embodiment, vectors/methods of this invention may be utilized to conditionally reduce expression of a Prostate Tumor Inducing Gene, which may comprise in one embodiment, PTI-1, PTI-2, PTI-3 or combinations thereof.

In one embodiment, the vectors/methods of this invention may be utilized to conditionally reduce expression of genes whose products promote angiogenesis, such as, for example, and in one embodiment, VEGF, VEGF receptor, erythropoietin, or combinations thereof. In another embodiment, the coding sequence for which conditional reducing expression is desired may comprise a matrix metalloproteinase, wherein reduction of expression prevents, in one embodiment, metastasis of cancerous cells, or, in another embodiment, tissue necrosis in infectious or inflammatory diseases.

In another embodiment, the vectors/compositions/methods of this invention may be utilized to conditionally reduce expression of a mutated rhodopsin gene. Autosomal dominant retinitis pigmentosa (ADRP) is characterized by the substitution of histidine for proline at codon 23 (P23H) in their rhodopsin gene, resulting in photoreceptor cell death from the synthesis of the abnormal gene product. In one embodiment, P23H mutant mRNAs may be targeted for conditional reduction of expression.

In another embodiment, the vectors/compositions/methods of this invention may be utilized to reverse effects of high glucose on progression of diabetic retinopathy. High glucose environments can result in chronically increased nitric oxide (NO) activity, which leads to endothelial cell dysfunction and impaired blood retinal barrier integrity characteristic of diabetic retinopathy.

In one embodiment, NOS synthesis may be conditionally reduced, in a tissue specific manner, in another embodiment, via the use of miRNAs targeted against VEGF, iNOS, or eNOS using the vectors/compositions and methods, as described hereinabove. In another embodiment, glucose transporters may be similarly targeted for therapeutic purposes in diabetic retinopathy.

In another embodiment, the vectors/compositions and methods for reducing expression of a coding sequence may be applied in a subject with a disease, where the disease may comprise, but is not limited to: muscular dystrophy, cancer, cardiovascular disease, hypertension, infection, renal disease, neurodegenerative disease, such as alzheimer's disease, parkinson's disease, huntington's chorea, Creutzfeld-Jacob disease, autoimmune disease, such as lupus, rheumatoid arthritis, endocarditis, Graves' disease or ALD, respiratory disease such as asthma or cystic fibrosis, bone disease, such as osteoporosis, joint disease, liver disease, disease of the skin, such as psoriasis or eczema, ophthalmic disease, otolaryngeal disease, other neurological disease such as Turret syndrome, schizophrenia, depression, autism, or stoke, or metabolic disease such as a glycogen storage disease or diabetes. It is to be understood that any disease whereby reduced expression of a particular protein, which can be accomplished via the use of the vectors or cells or compositions, or via the methods of this invention, is to be considered as part of this invention.

In one embodiment, the vectors and/or methods of this invention inactivate a gene whose product expression results in a disease, disorder or condition. In some embodiments, such vectors may further a second sequence of interest, which are in antisense orientation, as well, and may in some embodiments, be fused to the miRNA sequence as herein described. In some embodiments, the second sequence of interest may itself be flanked by restriction endonuclease sites, splice donor and acceptor sites, or combinations thereof, or in some embodiments, a splice acceptor sequence is positioned 3' to the second sequence, while a splice donor sequence is positioned 5' to the first sequence, such that the splice sequences (and/or restriction endonuclease sites) flank fused miRNAs.

In some embodiments, such second sequences may comprise sequences encoding a therapeutic protein, for example where the sequence which is inactivated is a mutated product, which results in disease, the second sequence may encode the same product, in a therapeutic form, which in turn prevents or treats the disease. For example, in subjects with a mutated CFTR, as herein described, the second sequence may encode a wild type CFTR, or one which restores therapeutic activity in a subject.

In some embodiments, the first miRNA sequence of interest specifically interacts with a sequence encoding an endogenous form of the protein of interest, and in one embodiment, the endogenous form is associated with a disease or disorder in the host.

According to this aspect, and in one embodiment, the second sequence may be another miRNA sequence of interest, which modulates expression of a gene whose activity is cooperative with that of a gene inactivated by the first miRNA sequence of interest. For example, multiple oncogenes may be inactivated in a subject with a particularly aggressive neoplasia, or, in another embodiment, multiple mediators of inflammation may be inactivated in a subject with severe inflammatory disease, or autoimmune disease, or others, as will be appreciated by one skilled in the art.

In another embodiment, the second miRNA sequence may modulate expression of a gene whose activity antagonizes that of a gene modulated by the first miRNA sequence of interest.

In another embodiment, two or more miRNA sequences are expressed in such subjects/are found within the vectors of this invention, and in some embodiments, the vector may further comprise a third nucleic acid in antisense orientation, positioned between the first pair of loxP sequences, wherein the third nucleic acid encodes a protein of interest, which may, in some embodiments be directly related to the products of genes being inactivated, for example, when oncogenes are being inactivated, the third sequence may encode a tumor suppressor. In some embodiments, the encoded protein of interest may be indirectly related, for example, a molecule known to activate the immune response in the subject. In some embodiments, other products may be co-expressed, for example tumor vaccines or antigens directed against/derived from the tumor or neoplasia being treated. In other embodiments, such products may be co-administered, or staggered in administration, or administered at a site distal to delivery of the vectors of this invention, whose therapeutic effect is cooperative.

In another embodiment, the vector will comprise a third sequence, and the methods of this invention make use of the same, or of administration of additional protein/polypeptide/nucleic acids/vectors, which comprise/express any desired protein, for example a therapeutic protein, for example insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P and transcription factors and enzymes (e.g., ACC synthases and oxidases, ACP desaturases and hydroxylases, ADP-glucose pyrophorylases, ATPases, alcohol dehydrogenases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5), the RNA component of telomerase, vascular endothelial growth factor (VEGF), VEGF receptor, tumor necrosis factors nuclear factor kappa B, transcription factors, cell adhesion molecules, Insulin-like growth factor, transforming growth factor beta family members, cell surface receptors, RNA binding proteins (e.g. small nucleolar RNAs, RNA transport factors), translation factors, telomerase reverse transcriptase), or combinations thereof.

In another embodiment, expression of a tumor suppressor gene is desired, such as, for example, APC, BRCA 1, BRCA2, MADH4, MCC, NF 1, NF2, RB 1, TP53, WTI, or combinations thereof, and vectors of this invention comprising and methods making use of such sequences, may in one embodiment, suppress, or in another embodiment, diminish severity, or in another embodiment, prevent metastasis of a cancer, and represent an embodiment of this invention.

In another embodiment, expression of an immunomodulating protein is desired, such as, for example, cytokines, chemokines, complement components, immune system accessory and adhesion molecules or their receptors, such as, for example, GM-CSF, IL-2, IL-12, OX40, OX40L (gp34), lymphotactin, CD40, and CD40L, interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, TRAP, ICAM-1, 2 or 3, cytokine receptors, OX40, OX40-ligand (gp34), or combinations thereof.

In another embodiment, expression of a protein, which suppresses angiogenesis is desired, and vectors comprising same and uses thereof to treat disease states, including cancer, hemangiomas, glaucoma, and other diseases, as will be well known to one skilled in the art, represent embodiments of this invention. In one embodiment, suppression of angiogenesis is accomplished via expressing an endostatin.

In another embodiment, the method of conditionally reducing expression of a coding sequence, as described and exemplified herein, may be for the evaluation of interacting proteins or endogenous mechanisms or interaction of substances therewith. For example, and in one embodiment, reduced expression of a specific tumor suppressor, or multiple suppressors is evaluated in an animal subject, for the creation of an experimental model. According to this aspect and in some embodiments, knockdown of such suppressors may be cell or tissue specific. In some embodiments, according to this aspect, the model may further comprise expression of an oncogene. In some embodiments, the model may further comprise the evaluation of therapies and/or treatment regimens, as a model for appropriate therapeutics.

In another aspect, the reduced expression may be of a specific oncogene in an established animal model of cancer, or multiple oncogenes, for the creation of an experimental model of cancer therapy. According to this aspect and in some embodiments, knockdown of such oncogenes may be cell or tissue specific, and evaluation thereof may provide a mechanism for therapy of a particular cancer, or cancers in general. In some embodiments, according to this aspect, the model may further comprise expression of a tumor suppressor. In some embodiments, the model may further comprise the evaluation of therapies and/or treatment regimens, as a model for appropriate therapeutics, or in some embodiments, evaluation of certain agents, or lifestyle changes which prevent therapy, reduce efficacy thereto, or exacerbate disease.

Similarly, animal models of diseases, such as suspected multi-genic dependent diseases may be evaluated with the vectors, nucleic acids, compositions and methods of this invention, as will be appreciated by one skilled in the art.

In another embodiment, this invention provides a method of assessing neoplasia in an animal model, said method comprising:
  i. contacting a target cell in a subject animal with a vector comprising:
    first pair of loxP sequences, inverted in orientation, with respect to each other;
    a first nucleic acid encoding a first selectable marker in sense orientation, wherein said nucleic acid is positioned between said first pair of loxP sequences;
    second nucleic acid encoding a second selectable marker, fused in frame to an miRNA sequence of interest with a suspected role in neoplasia or suppression thereof in antisense orientation, said miRNA sequence of interest being flanked by splice donor and splice acceptor sequences, said second nucleic acid is positioned between said first pair of loxP sequences, and said second nucleic acid is 3' with regard to said first nucleic acid;
    second pair of loxP sequences, inverted in orientation, with respect to each other, wherein said first loxP sequenced of said second pair is positioned between said first and said second nucleic acid, and said second loxP sequence in said second pair is positioned 3' with respect to said first pair of loxP sequences, and said second pair of loxP sequences differs from that of said first pair of loxP sequences; and
  ii. evaluating neoplasia or development thereof in said animal;
  whereby said method assesses development of neoplasia or suppression thereof in said subject animal as opposed to a control subject.

In some embodiments, the Cre recombinase is expressed in a cell- or tissue-specific manner.

In some embodiments, the first pair of loxP sequences comprises the wildtype sequence, and in some embodiments, the second pair of loxP sequences comprises a mutated loxP. In some embodiments, the first pair of loxP sequences comprises the loxP 5171 sequence and in some embodiments, the second pair of loxP sequences comprises the loxP 2272 sequence.

In some embodiments, the vector comprises a first regulatory sequence operatively linked to said second nucleic acid and said regulatory sequence is in antisense orientation and in some embodiments, the first regulatory sequence is a UbiquitinC promoter sequence. In some embodiments, the vector further comprises a second regulatory sequence, located 5' to said first regulatory sequence, wherein said second regulatory sequence is in sense orientation.

In some embodiments the vector further comprises a Bovine Growth Hormone polyadenylation signal positioned 3' to said second pair of loxP sites and in some embodiments, the vector further comprises a modified U3 LTR positioned 5' to said polyadenylation signal. In some embodiments, the first regulatory sequence is tissue specific or in some embodiments, the first regulatory sequence is inducible.

In some embodiments, the miRNA agent is an shRNA.

In some embodiments, the miRNA specifically inactivates p53 or PTEN gene expression.

In some embodiments, the vector further comprises a second miRNA sequence of interest in antisense orientation fused to the miRNA sequence of interest. In some embodiments, the second miRNA sequence of interest modulates expression of a gene whose activity is cooperative with that of a gene modulated by said first miRNA sequence of interest. In some embodiments, the first and second miRNA sequence of interest regulate expression of a tumor suppressor.

In some embodiments, the first miRNA sequence of interest specifically inactivates one of p53 or PTEN gene expression and said second miRNA sequence of interest specifically inactivates the other.

In some embodiments, the vector comprises a sequence corresponding to or homologous to SEQ ID No: 27.

In some embodiments, the second miRNA sequence of interest modulates expression of a gene whose activity antagonizes that of a gene modulated by said the miRNA sequence of interest.

In some embodiments, the second nucleic acid encodes an oncogene.

In some embodiments, the vector comprises a third nucleic acid in antisense orientation, positioned between the first pair of loxP sequences, wherein the third nucleic acid encodes a protein of interest.

In some embodiments, the third nucleic acid encodes an miRNA specifically inactivating a tumor suppressor.

In some embodiments, the third nucleic acid encodes an miRNA specifically inactivating p53, PTEN or a combination thereof.

In some embodiments, the vector comprises a nucleic acid sequence corresponding to or homologous to SEQ ID NO: 21

In some embodiments, animal models, and/or treatment strategies for the following neoplasias are to be considered as part of this invention, when applying the vectors, nucleic acids, compositions and methods of this invention to create a model and/or treatment for a cancer which may comprise: comprise adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell lung cancer, non small cell lung cancer, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof. It is to be understood that the animal models, and/or treatment strategies for the neoplasias listed herein, and in reference thereto in applying the vectors, nucleic acids, compositions and methods of this invention to create a model and/or treatment for such neoplasias are to be considered for application to preneoplastic or hyperplastic lesions thereof, as well, and represent other embodiments of this invention.

In another embodiment, the methods/vectors/compositions of this invention do not exhibit the limitation of causing constitutive gene silencing or gene expression, in all tissues. According to this aspect of the invention, the methods of this allow for regulated expression of miRNA and thereby regulated expression of a desired coding sequence.

In another embodiment, this invention provides for kits for conditional reduction of expression, or conditional expression of a coding sequence, comprising one or more containers filled with one or more of the ingredients of the aforementioned vectors, or compositions of the invention.

The vectors of the invention may be employed, in another embodiment, in combination with a non-sterile or sterile carrier or carriers for administration to cells, tissues or organisms, such as a pharmaceutical carrier suitable for administration to an individual. Such compositions comprise, for instance, a media additive or a therapeutically effective amount of a recombinant virus of the invention and a pharmaceutically acceptable carrier or excipient. Such carriers may include, but are not limited to, saline, buffered saline, dextrose, water, glycerol, and combinations thereof. The formulation should suit the mode of administration.

The vectors or compositions of the invention may be employed alone or in conjunction with other compounds, such as additional therapeutic compounds.

The pharmaceutical compositions may be administered in any effective, convenient manner including, for instance, administration by intravascular (i.v.), intramuscular (i.m.), intranasal (i.n.), subcutaneous (s.c.), oral, rectal, intravaginal delivery, or by any means in which the recombinant virus/ composition can be delivered to tissue (e.g., needle or catheter). Alternatively, topical administration may be desired for insertion into epithelial cells. Another method of administration is via aspiration or aerosol formulation.

For administration to mammals, and particularly humans, it is expected that the physician will determine the actual dosage and duration of treatment, which will be most suitable for an individual and can vary with the age, weight and response of the particular individual.

The following examples are presented in order to more fully illustrate some embodiments of the invention. They should, in no way be construed, however, as limiting the scope of the invention.

EXAMPLES

Materials and Methods

Generation of Constructs pLB2 was generated by modification of pLB [Kissler S, et al. Nat. Genet. 2006 April; 38(4):479-83] to introduce the FLIP insert, followed by insert fill in and ligation.

The FLIP insert comprises loxP 5171 and loxP 2272 genes, a modified puromycin resistance cassette incorporating the foot-and-mouth-disease virus (FMDV) 2A encoding sequence at its C-terminus, fused in frame to a gene encoding the Thy1.1 surface marker (See Schnutgen F, et. al., Nat. Biotechnol. 2003 May; 21(5):562-5 for methods), and nucleic acids encoding the indicated miR30 and GFP, as outlined in FIG. 1.

An miR30 following GFP was placed in an artificial intron by flanking the miR30 with consensus splice donor and splice acceptor sequences (underlined). The restriction sites NotI-PmeI (in bold) flanked a miR30 specific for firefly luciferase.

(SEQ ID NO: 1)
agta<u>GCGGCCCAATTGCAGGTGAGTGG</u>gcggccgcaagccttgttaagtg
ctcgcttcggcagcacatatactatgtttgaatgaggcttcagtacttta
cagaatcgttgcctgcacatcttggaaacacttgctgggattacttcttc
aggttaacccaacagaaggctcgagAAGGTATATTGCTGTTGACAGTGAG
CGAGCTCCCGTGAATTGGAATCCTAGTGAAGCCACAGATGTAGGATTCCA
ATTCAGCGGGAGCCTGCCTACTGCCTCGgaattcaaggggctactttagg
agcaattatcttgtttactaaaactgaataccttgctatctctttgatac
attttacaaagctgaattaaaatggtataaattaaatcactttttt<u>caa
ttggaagactaatgc</u>gtttaaacCCCTGACTCTCCCCTTTTTTTTTCCT
CCAGGTATGCATaaac.

A similar construct was prepared, comprising a miR30 specific for α4 integrin:

(SEQ ID NO:2)
agta<u>GCGGCCCAATTGCAGGTGAGTGG</u>gcggccgcaagccttgttaagtg
ctcgcttcggcagcacatatactatgtttgaatgaggcttcagtacttta
cagaatcgttgcctgcacatcttggaaaacacttgctgggattacttctt
caggttaacccaacagaaggctcgagAAGGTATATTGCTGTTGACAGTGA
GCGCCGACATTTCACCATCATTATTTAGTGAAGCCACAGATGTAAATAAT
GATGGTGAAATGTCGTTGCCTACTGCCTCGGAattcaaggggctacttta
ggagcaattatcttgtttactaaaactgaataccttgctatctctttgat
acattttacaaagctgaattaaaatggtataaattaaatcacttttttc
<u>aattggaagactaatgc</u>gtttaaacCCCTGACTCTCCCCTTTTTTTTTC
CTCCAGGTATGCATaaac It is noted that the preceding sequences represent sense orientation.

A pLB2 construct comprising the FLIP cassette containing miR30 targeting FireFly luciferase was constructed, with the following sequence:

(SEQ ID NO: 3)
GTCGACGGATCGGGAGATCTCCCGATCCCCTATGGTGCACTCTCAGTACA
ATCTGCTCTGATGCCGCATAGTTAAGCCAGTATCTGCTCCCTGCTTGTGT
GTTGGAGGTCGCTGAGTAGTGCGCGAGCAAAATTTAAGCTACAACAAGGC
AAGGCTTGACCGACAATTGCATGAAGAATCTGCTTAGGGTTAGGCGTTTT

-continued
GCGCTGCTTCGCGATGTACGGGCCAGATATACGCGTTGACATTGATTATT
GACTAGTcatgttctttcctgcgttatcccctgattctgtggataaccgt
attaccgcctttgagtgagctgataccgctcgccgcagccgaacgaccga
gcgcagcgagtcagtgagcgaggaagcggaagagcgcccaatacgcaaac
cgcctctccccgcgcgttggccgattcattaatgcagctggcacgacagg
tttcccgactggaaagcgggcagtgagcgcaacgcaattaatgtgagtta
gctcactcattaggcaccccaggctttacactttatgcttccggctcgta
tgttgtgtggaattgtgagcggataacaatttcacacaggaaacagctat
gaccatgattacgccaagcgcgcaattaaccctagcttaatgtagtctta
tgcaatactcttgtagtcttgcaacatggtaacgatgagttagcaacatg
ccttacaaggagagaaaaagccaccgtgcatgccgattggtggaagtaagg
tggtacgatcgtgccttattaggaaggcaacagacgggtctgacatggat
tggacgaaccactgaattgccgcattgcagagatattgtatttaagtgcc
tagctcgatacaataaacgggtctctctggttagaccagatctgagcctg
ggagctctctggctaactagggaacccactgcttaagcctcaataaagct
tgccttgagtgcttcaagtagtgtgtgcccgtctgttgtgtgactctggt
aactagagatccctcagaccccttttagtcagtgtggaaaatctctagcag
tGGCGCCCGAACAGGGACTTGAAAGCGAAAGGGAAACCAGAGGAGCTCTC
TCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAG
AGAGATGGGTGCGAGAGCGTCAGTATTAAGCGGGGGAGAATTAGATCGCG
ATGGGAAAAAATTCGGTTAAGGCCAGGGGGAAAGAAAAAATATAAATTAA
AACATATAGTATGGGCAAGCAGGGAGCTAGAACGATTCGCAGTTAATCCT
GGCCTGTTAGAAACATCAGAAGGCTGTAGACAAATACTGGGACAGCTACA
ACCATCCCTTCAGACAGGATCAGAAGAACTTAGATCATTATATAATACAG
TAGCAACCCTCTATTGTGTGCATCAAAGGATAGAGATAAAAGACACCAAG
GAAGCTTTAGACAAGATAGAGGAAGAGCAAAACAAAAGTAAGACCACCGC
ACAGCAAGCGGCCGGCCGCGCTGATCTTCAGACCTGGAGGAGGAGATATG
AGGGACAATTGGAGAAGTGAATTATATAAATATAAAGTAGTAAAAATTGA
ACCATTAGGAGTAGCACCCACCAAGGCAAAGAGAAGAGTGGTGCAGAGAG
AAAAAAGAGCAGTGGGAATAGGAGCTTTGTTCCTTGGGTTCTTGGGAGCA
GCAGGAAGCACTATGGGCGCAGCGTCAATGACGCTGACGGTACAGGCCAG
ACAATTATTGTCTGGTATAGTGCAGCAGCAGAACAATTTGCTGAGGGCTA
TTGAGGCGCAACAGCATCTGTTGCAACTCACAGTCTGGGGCATCAAGCAG
CTCCAGGCAAGAATCCTGGCTGTGGAAAGATACCTAAAGGATCAACAGCT
CCTGGGGATTTGGGGTTGCTCTGGAAAACTCATTTGCACCACTGCTGTGC
CTTGGAATGCTAGTTGGAGTAATAAATCTCTGGAACAGATTTGGAATCAC
ACGACCTGGATGGAGTGGGACAGAGAAATTAACAATTACACAAGCTTAAT
ACACTCCTTAATTGAAGAATCGCAAAACCAGCAAGAAAAGAATGAACAAG
AATTATTGGAATTAGATAAATGGGCAAGTTTGTGGAATTGGTTTAACATA
ACAAATTGGCTGTGGTATATAAAATTATTCATAATGATAGTAGGAGGCTT -continued GGTAGGTTTAAGAATAGTTTTTGCTGTACTTTCTATAGTGAATAGAGTTA
GGCAGGGATATTCACCATTATCGTTTCAGACCCACCTCCCAACCCCGAGG
GGACCCGACAGGCCCGAAGGAATAGAAGAAGAAGGTGGAGAGAGAGACAG
AGACAGATCCATTCGATTAGTGAACGGATCGGCACTGCGTGCGCCAATTC
TGCAGACAAATGGCAGTATTCATCCACAATTTTAAAAGAAAAGGGGGAT
TGGGGGGTACAGTGCAGGGGAAAGAATAGTAGACATAATAGCAACAGACA
TACAAACTAAAGAATTACAAAAACAAATTACAAAAATTCAAAATTTTCGG
GTTTATTACAGGGACAGCAGAGATCCAGTTTGGTTAGTACCGGGCCCGGT
GCTTTGCTCTGAGCCAGCCCACCAGTTTGGAATGACTCCTTTTTATGACT
TGAATTTTCAAGTATAAAGTCTAGTGCTAAATTTAATTTGAACAACTGTA
TAGTTTTTGCTGGTTGGGGGAAGGAAAAAAAATGGTGGCAGTGTTTTTT
CAGAATTAGAAGTGAAATGAAAACTTGTTGTGTGTGAGGATTTCTAATGA
CATGTGGTGGTTGCATACTGAGTGAAGCCGGTGAGCATTCTGCCATGTCA
CCCCCTCGTGCTCAGTAATGTACTTTACAGAAATCCTAAACACTCAGCCT
GCATTTCTGCCAGGGCCCGCTCTAGATCTAGACGGTTGATCTggcctccg
cgccgggttttggcgcctcccgcgggcgccccctcctcacggcgagcgc
tgccacgtcagacgaagggcgcaggagcgttcctgatccttccgcccgga
cgctcaggacagcggcccgctgctcataagactcggccttagaaccccag
tatcagcagaaggacattttaggacgggacttgggtgactctagggcact
ggttttcttccagagagcggaacaggcgaggaaaagtagtcccttctcg
gcgattctgcggagggatctcctgtggggcggtgaacgccgatgattata
taaggacgcgccgggtgtggcacagctagttccgtcgcagccgggatttg
ggtcgcggttcttgtttgtggatcgctgtgatcgtcacttggtgagttgc
gggctgctgggctggccggggctttcgtggccgccgggccgctcggtggg
acggaagcgtgtggagagaccgccaagggctgtagtctgggtccgcgagc
aaggttgccctgaactgggggttgggggagcgcacaaaatggcggctgt
tcccgagtcttgaatggaagacgcttgtaaggcgggctgtgaggtcgttg
aaacaaggtgggggcatggtgggcggcaagaacccaaggtcttgaggcc
ttcgctaatgcgggaaagctcttattcgggtgagatgggctggggcacca
tctggggaccctgacgtgaagtttgtcactgactggagaactcgggtttg
tcgtctggttgcggggcggcagttatgcggtgccgttgggcagtgcacc
cgtacctttgggagcgcgcgcctcgtcgtgtcgtgacgtcacccgttctg
ttggcttataatgcagggtggggccacctgccggtaggtgtgcggtaggc
ttttctccgtcgcaggacgcagggttcgggcctagggtaggctctcctga
atcgacaggcgccgacctctggtgagggagggataagtgaggcgtcag
tttctttggtcggttttatgtacctatcttcttaagtagctgaagctccg
gttttgaactatgcgctcggggttggcgagtgtgttttgtgaagtttttt
aggcaccttttgaaatgtaatcatttgggtcaatatgtaattttcagtgt
tagactagtaaattgtccgctaaattctggccgttttggctttttttgtt
agacGAAGTACGCGCTAGCCGTTAATAAGCCTCGATGCggatccataact tcgtataggatacttatacgaagttatctcaggtaccgccaccatgacc
gagtacaagcccacggtgcgcctcgccaccgcgacgacgtccccagggc
cgtacgcaccctcgccgccgcgttcgccgactacccccgccacgcgccaca
ccgtcgatccggaccgccacatcgagcgggtcaccgagctgcaagaactc
ttcctcacgcgcgtcgggctcgacatcggcaaggtgtgggtcgcggacga
cggcgccgcggtggcggtctggaccacgccggagagcgtcgaagcgggg
cggtgttcgccgagatcggcccgcgcatggccgagttgagcggttcccgg
ctggccgcgcagcaacagatggaaggcctcctggcgccgcaccggcccaa
ggagcccgcgtggttcctggccaccgtcggcgtctcgcccgaccaccagg
gcaagggtctgggcagcgccgtcgtgctccccggagtggaggcggccgag
cgcgccggggtgccccgccttcctggagacctccgcgcccgcaacctccc
cttctacgagcggctcggcttcaccgtcaccgccgacgtcgaggtgcccg
aaggaccgcgcacctggtgcatgacccgcaagcccggtgccctgtacaag
aaacagaaaattgtggccagtgaaacagactttgaattttgaccttct
caagttggcgggagacgtcgagtccaaccctgggcccatgaacccagcca
tcagcgtcgctctcctgctctcagtcttgcaggtgtcccgagggcagaag
gtgaccagcctgacagcctgcctggtgaaccaaaccttcgcctggactg
ccgccatgagaataacaccaaggataactccatccagcatgagttcagcc
tgacccgagagaagaggaagcacgtgctctcaggcaccctcgggataccc
gagcacacgtaccgctcccgcgtcaccctctccaaccagccctatatcaa
ggtccttaccctagcaacttcaccaccaaggatgagggcgactactttt
gtgagcttcgagtctcgggcgcgaatcccatgagctccaataaaagtatc
agtgtgtatagagacaaactggtcaagtgtggcggcataagcctgctggt
tcagaacacatcctggatgctgctgctgctgctttccctctcctcctcc
aagcctggacttcatttctctgtgatctagaagccataacttcgtatag
tacacattatacgaagttatgtttaaacgcattagtcttccaattgaaaa
aagtgatttaattttataccatttttaattcagcttttgtaaaaatgtatcaa
agagatagcaaggtattcagttttagtaaacaagataattgctcctaaag
tagccccttgaattcCGAGGCAGTAGGCAGGCTCCCGCTGAATTGGAATC
CTACATCTGTGGCTTCACTAGGATTCCAATTCACGGGAGCTCGCTCACTG
TCAACAGCAATATACCTTctcgagccttctgttgggttaacctgaagaag
taatcccagcaagtgtttccaagatgtgcaggcaacgattctgtaaagta
ctgaagcctcattcaaacatagtatatgtgctgccgaagcgagcacttaa
caaggcttgcggccgctacttgtacagctcgtccatgccgagagtgatcc
cggcggcggtcacgaactccagcaggaccatgtgatcgcgcttctcgttg
gggtctttgctcagggcggactgggtgctcaggtagtggttgtcgggcag
cagcacggggccgtcgccgatgggggtgttctgctggtagtggtcggcga
gctgcacgctgccgtcctcgatgttgtggcggatcttgaagttcaccttg
atgccgttcttctgcttgtcggccatgatatagacgttgtggctgttgta
gttgtactccagcttgtgccccaggatgttgccgtcctccttgaagtcga
tgcccttcagctcgatgcggttcaccagggtgtcgccctcgaacttcacc tcggcgcgggtcttgtagttgccgtcgtccttgaagaagatggtgcgctc
ctggacgtagccttcgggcatggcggacttgaagaagtcgtgctgcttca
tgtggtcggggtagcggctgaagcactgcacgccgtaggtcagggtggtc
acgagggtgggccagggcacgggcagcttgccggtggtgcagatgaactt
cagggtcagcttgccgtaggtggcatcgccctcgccctcgccggacacgc
tgaacttgtggccgtttacgtcgccgtccagctcgaccaggatgggcacc
accccggtgaacagctcctcgcccttgctcaccatggtggcgaccggtat
aacttcgtataaggtatcctatacgaagttatccattcaggctgtgctag
catcaatggcatggcacaaagcttagccataacttcgtataatgtgtact
atacgaagttatcccTGTTTAAGGGTTCCGGTTCCACTAGGTACAATTCG
ATATCAAGCTTATCGATAATCAACCTCTGGATTACAAAATTTGTGAAAGA
TTGACTGGTATTCTTAACTATGTTGCTCCTTTTACGCTATGTGGATACGC
TGCTTTAATGCCTTTGTATCATGCTATTGCTTCCCGTATGGCTTTCATTT
TCTCCTCCTTGTATAAATCCTGGTTGCTGTCTCTTTATGAGGAGTTGTGG
CCCGTTGTCAGGCAACGTGGCGTGGTGTGCACTGTGTTTGCTGACGCAAC
CCCCACTGGTTGGGGCATTGCCACCACCTGTCAGCTCCTTTCCGGGACTT
TCGCTTTCCCCCTCCCTATTGCCACGGCGGAACTCATCGCCGCCTGCCTT
GCCCGCTGCTGGACAGGGGCTCGGCTGTTGGGCACTGACAATTCCGTGGT
GTTGTCGGGGAAATCATCGTCCTTTCCTTGGCTGCTCGCCTGTGTTGCCA
CCTGGATTCTGCGCGGGACGTCCTTCTGCTACGTCCCTTCGGCCCTCAAT
CCAGCGGACCTTCCTTCCCGCGGCCTGCTGCCGGCTCTGCGGCCTCTTCC
GCGTCTTCGCCTTCGCCCTCAGACGAGTCGGATCTCCCTTTGGGCCGCCT
CCCCGCATCGATACCGTCGACCTCGATCGAGACCTAGAAAAACATGGAGC
AATCACAAGTAGCAATACAGCAGCTACCAATGCTGATTGTGCCTGGCTAG
AAGCACAAGAGGAGGAGGAGGTGGGTTTTCCAGTCACACCTCAGGTACCA
AGCATGGGTAAAGTACTGTTCTCATCACATCATATCAAGGTTATATACC
ATCAATATTGCCACAGATGTTACTTAGCCTTTTAATATTTCTCTAATTTA
GTGTATATGCAATGATAGTTCTCTGATTTCTGAGATTGAGTTTCTCATGT
GTAATGATTATTTAGAGTTTCTCTTTCATCTGTTCAAATTTTTGTCAGT
TTTATTTTTTACTGATTTGTAAGACTTCTTTTTATAATCTGCATATTACA
ATTCTCTTTACTGGGGTGTTGCAAATATTTTCTGTCATTCTATGGCTGA
CTTTTCTTAATGGTTTTTTAATTTTAAAAATAAGTCTTAATATTCATGCA
ATCTAATTAACAATCTTTTCTTTGTGGTTAGGACTTTGAGTCATAAGAAA
TTTTTCTCTACACTGAAGTCATGATGGCATGCTTCTATATTATTTTCTAA
AAGATTTAAAGTTTTGCCTTCTCCATTTAGACTTATAATTCACTGGAATT
TTTTTGTGTGTATGGTATGACATATGGGTTCCCTTTTATTTTTTACATAT
AAATATATTTCCCTGTTTTTCTAAAAAAGAAAAAGATCATCATTTTCCCA
TTGTAAAATGCCATATTTTTTTCATAGGTCACTTACATATATCAATGGGT
CTGTTTCTGAGCTCTACTCTATTTTATCAGCCTCACTGTCTATCCCCACA
CATCTCATGCTTTGCTCTAAATCTTGATATTTAGTGGAACATTCTTTCCC ATTTTGTTCTACAAGAATATTTTTGTTATTGTCTTTTGGGCTTCTATATA
CATTTTAGAATGAGGTTGGCAAGGTACCTTTAAGACCAATGACTTACAAG
GCAGCTGTAGATCTTAGCCACTTTTTAAAAGAAAAGGGGGGACTGGAAGG
GCTAATTCACTCCCAGCTGCTTTTTGCCTGTACTGGGTCTCTCTGGTTAG
ACCAGATCTGAGCCTGGGAGCTCTCTGGCTAACTAGGGAACCCACTGCTT
AAGCCTCATAAAGCTCGACTGTGCCTTCTAGTTGCCAGCCATCTGTTGTT
TGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGG
GAAGACAATAGCAGGCATGCTGGGGATGCGGTCCGGACTGTACTGGGTCT
CTCTGGTTAGACCAGATCTGAGCCTGGGAGCTCTCTGGCTAACTAGGGAA
CCCACTGCTTAAGCCTCAATAAAGCTTGCCTTGAGTGCTTCAAGTAGTGT
GCCCGTCTGTTGTGTGACTCTGGTAACTAGAGATCCCTCAGACCCTTTTA
GTCAGTGTGGAAAATCTCTAGCAGCATGTGAGCAAAAGGCCAGCAAAAGG
CCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAA
CCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTT
CTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCC
AACCCGGTAAGACACGACTTATCGCCACTGGCAGCAGCCACTGGTAACAG
GATTAGCAGAGCGAGGTATGTAGGCGGTGCTACAGAGTTCTTGAAGTGGT
GGCCTAACTACGGCTACACTAGAAGAACAGTATTTGGTATCTGCGCTCTG
CTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTA
CGCGCAGAAAAAAAGGATCTCAAGAAGATCCTTTGATCTTTTCTACGGGG
TCTGACGCTCAGTGGAACGAAAACTCACGTTAAGGGATTTTGGTCATGAG
ATTATCAAAAAGGATCTTCACCTAGATCCTTTTAAATTAAAAATGAAGTT
TTAAATCAATCTAAAGTATATATGAGTAAACTTGGTCTGACAGTTACCAA
TGCTTAATCAGTGAGGCACCTATCTCAGCGATCTGTCTATTTCGTTCATC
CATAGTTGCCTGACTCCCCGTCGTGTAGATAACTACGATACGGGAGGGCT
TACCATCTGGCCCCAGTGCTGCAATGATACCGCGAGACCCACGCTCACCG
GCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTC
ATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTC
TCTTACTGTCATGCCATCCGTAAGATGCTTTTCTGTGACTGGTGAGTACT

CAACCAAGTCATTCTGAGAATAGTGTATGCGGCGACCGAGTTGCTCTTGC

CCGGCGTCAATACGGGATAATACCGCGCCACATAGCAGAACTTTAAAAGT

GCTCATCATTGGAAAACGTTCTTCGGGGCGAAAACTCTCAAGGATCTTAC

CGCTGTTGAGATCCAGTTCGATGTAACCCACTCGTGCACCCAACTGATCT

TCAGCATCTTTTACTTTCACCAGCGTTTCTGGGTGAGCAAAAACAGGAAG

GCAAAATGCCGCAAAAAAGGGAATAAGGGCGACACGGAAATGTTGAATAC

TCATACTCTTCCTTTTTCAATATTATTGAAGCATTTATCAGGGTTATTGT

CTCATGAGCGGATACATATTTGAATGTATTTAGAAAAATAAACAAATAGG

GGTTCCGCGCACATTTCCCCGAAAAGTGCCACCTGAC

The pFLIP insert comprising an RNAi to p53 (not in an intron) has a nucleic acid sequence as follows (microRNA-short hairpin to p53 in upper case):

(SEQ ID NO: 4)
tccataacttcgtataggataccttatacgaagttatctcaggtaccgcc accatgaccgagtacaagcccacggtgcgcctcgccaccgcgacgacgt ccccagggccgtacgcaccctcgccgccgcgttcgccgactaccccgcca cgcgccacaccgtcgatccggaccgccacatcgagcgggtcaccgagctg caagaactcttcctcacgcgcgtcgggctcgacatcggcaaggtgtgggt cgcggacgacgcgccgcggtggcggtctggaccacgccggagagcgtcg aagcggggcggtgttcgccgagatcggcccgcgcatggccgagttgagc ggttcccggctggccgcgcagcaacagatggaaggcctcctggcgccgca ccggcccaaggagcccgcgtggttcctggccaccgtcggcgtctcgcccg accaccagggcaagggtctgggcagcgccgtcgtgctccccggagtggag gcggccgagcgcgccggggtgcccgccttcctggagacctccgcgcccg caacctcccccttctacgagcggctcggcttcaccgtcaccgccgacgtcg aggtgcccgaaggaccgcgcacctggtgcatgacccgcaagcccggtgcc ctgtacaagaaacagaaaattgtggcaccagtgaaacagactttgaattt tgaccttctcaagttggcgggagacgtcgagtccaaccctgggcccatga acccagccatcagcgtcgctctcctgctctcagtcttgcaggtgtcccga gggcagaaggtgaccagcctgacagcctgcctggtgaaccaaaaccttcg cctggactgccgccatgagaataacaccaaggataactccatccagcatg agttcagcctgacccgagaagaggaagcacgtgctctcaggcaccctc gggatacccgagcacacgtaccgctcccgcgtcaccctctccaaccagcc ctatatcaaggtccttaccctagccaacttcaccaccaaggatgagggcg actacttttgtgagcttcgagtctcgggcgcgaatcccatgagctccaat aaaagtatcagtgtgtatagagacaaactggtcaagtgtggcggcataag cctgctggttcagaacacatcctggatgctgctgctgctgctttccctct ccctcctccaagccctggacttcatttctctgtgatctagaagccataac ttcgtatagtacacattatacgaagttatGTTTAAACGCATTAGTCTTCC

AATTGAAAAAAGTGATTTAATTTATACCATTTTAATTCAGCTTTGTAAAA

ATGTATCAAAGAGATAGCAAGGTATTCAGTTTTAGTAAACAAGATAATTG

CTCCTAAAGTAGCCCCTTGAATTCCGAGGCAGTAGGCATCCACTACAAGT

ACATGTGTAATACATCTGTGGCTTCACTATTACACATGTACTTGTAGTGG

GCGCTCACTGTCAACAGCAATATACCTTCTCGAGCCTTCTGTTGGGTTAA

CCTGAAGAAGTAATCCCAGCAAGTGTTTCCAAGATGTGCAGGCAACGATT

CTGTAAAGTACTGAAGCCTCATTCAAACATAGTATATGTGCTGCCGAAGC

GAGCACTTAACAAGGCTTGCGGCCGCtacttgtacagctcgtccatgccg agagtgatcccggcggcggtcacgaactccagcaggaccatgtgatcgcg cttctcgttggggtctttgctcagggcggactgggtgctcaggtagtggt tgtcgggcagcagcacggggccgtcgccgatgggggtgttctgctggtag tggtcggcgagctgcacgctgccgtcctcgatgttgtggcggatcttgaa gttcaccttgatgccgttcttctgcttgtcggccatgatatagacgttgt ggctgttgtagttgtactccagcttgtgccccaggatgttgccgtcctcc ttgaagtcgatgcccttcagctcgatgcggttcaccagggtgtcgccctc gaacttcacctcggcgcgggtcttgtagttgccgtcgtccttgaagaaga tggtgcgctcctggacgtagccttcgggcatggcggacttgaagaagtcg tgctgcttcatgtggtcggggtagcggctgaagcactgcacgccgtaggt cagggtggtcacgagggtgggccagggcacgggcagcttgccggtggtgc agatgaacttcagggtcagcttgccgtaggtggcatcgccctcgccctcg ccggacacgctgaacttgtggccgtttacgtcgccgtccagctcgaccag gatgggcaccaccccggtgaacagctcctcgcccttgctcaccatggtgg cgaccggtataacttcgtataaggtatcctatacgaagttatccattcag gctgtgctagcatcaatggcatggcacaaagcttagccataacttcgtat aatgtgtactatacgaagttatcccgggtt.

GFP-miR30 flanked by a single loxP site, as FLIP would look after Cre-mediated recombination, has a sequence as follows:

(SEQ ID NO: 5)
atggATAACTTCGTATAggatacctTATACGAAGTTATaccggtcgccac catggtgagcaagggcgaggagctgttcaccggggtggtgcccatcctgg tcgagctggacggcgacgtaaacggccacaagttcagcgtgtccggcgag ggcgagggcgatgccacctacggcaagctgaccctgaagttcatctgcac caccggcaagctgcccgtgccctggcccaccctcgtgaccaccctgacct acggcgtgcagtgcttcagccgctaccccgaccacatgaagcagcacgac ttcttcaagtccgccatgcccgaaggctacgtccaggagcgcaccatctt cttcaaggacgacggcaactacaagacccgcgccgaggtgaagttcgagg gcgacaccctggtgaaccgcatcgagctgaagggcatcgacttcaaggag gacggcaacatcctggggcacaagctggagtacaactacaacagccacaa cgtctatatcatgccgacaagcagaagaacggcatcaaggtgaacttca agatccgccacaacatcgaggacggcagcgtgcagctcgccgaccactac cagcagaacacccccatcggcgacggccccgtgctgctgcccgacaacca ctacctgagcacccagtccgccctgagcaaagaccccaacgagaagcgcg

```
atcacatggtcctgctggagttcgtgaccgccgccgggatcactctcggc
atggacgagctgtacaagtaGCGGCCGCAAGCCTTGTTAAGTGCTCGCTT
CGGCAGCACATATACTATGTTTGAATGAGGCTTCAGTACTTTACAGAATC
GTTGCCTGCACATCTTGGAAACACTTGCTGGGATTACTTCTTCAGGTTAA
CCCAACAGAAGGCTCGAGAAGGTATATTGCTGTTGACAGTGAGCGCCCAC
TACAAGTACATGTGTAATAGTGAAGCCACAGATGTATTACACATGTACTT
GTAGTGGATGCCTACTGCCTCGGAATTCAAGGGGCTACTTTAGGAGCAAT
TATCTTGTTTACTAAAACTGAATACCTTGCTATCTCTTTGATACATTTTT
ACAAAGCTGAATTAAAATGGTATAAATTAAATCACTTTTTTCAATTGGAA
GACTAATGCGTTTAAACATAACTTCGTATAatgtgtacTATACGAAGTTA
Tggct.
``` pLB2 comprising the FLIP cassette comprising an intron with restriction sites NotI-PmeI and has a sequence as follows:

```
                                              (SEQ ID NO: 6)
GTCGACGGATCGGGAGATCTCCCGATCCCCTATGGTGCACTCTCAGTACA
ATCTGCTCTGATGCCGCATAGTTAAGCCAGTATCTGCTCCCTGCTTGTGT
GTTGGAGGTCGCTGAGTAGTGCGCGAGCAAAATTTAAGCTACAACAAGGC
AAGGCTTGACCGACAATTGCATGAAGAATCTGCTTAGGGTTAGGCGTTTT
GCGCTGCTTCGCGATGTACGGGCCAGATATACGCGTTGACATTGATTATT
GACTAGTcatgttcttcctgcgttatccctgattctgtggataaccgt
attaccgcctttgagtgagctgataccgctcgccgcagccgaacgaccga
gcgcagcgagtcagtgagcgaggaagcggaagagcgcccaatacgcaaac
cgcctctccccgcgcgttggccgattcattaatgcagctggcacgacagg
tttcccgactggaaagcgggcagtgagcgcaacgcaattaatgtgagtta
gctcactcattaggcaccccaggctttacactttatgcttccggctcgta
tgttgtgtggaattgtgagcggataacaatttcacacaggaaacagctat
gaccatgattacgccaagcgcgcaattaaccctagcttaatgtagtctta
tgcaatactcttgtagtcttgcaacatggtaacgatgagttagcaacatg
ccttacaaggagagaaaaagcaccgtgcatgccgattggtggaagtaagg
tggtacgatcgtgccttattaggaaggcaacagacgggtctgacatggat
tggacgaaccactgaattgccgcattgcagagatattgtatttaagtgcc
tagctcgatacaataaacgggtctctctggttagaccagatctgagcctg
ggagctctctggctaactagggaacccactgcttaagcctcaataaagct
tgccttgagtgcttcaagtagtgtgtgcccgtctgttgtgtgactctggt
aactagagatccctcagacccttttagtcagtgtggaaaatctctagcag
tGGCGCCCGAACAGGGACTTGAAAGCGAAAGGGAAACCAGAGGAGCTCTC
TCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAG
AGAGATGGGTGCGAGAGCGTCAGTATTAAGCGGGGGAGAATTAGATCGCG
ATGGGAAAAAATTCGGTTAAGGCCAGGGGGAAAGAAAAAATATAAATTAA
AACATATAGTATGGGCAAGCAGGGAGCTAGAACGATTCGCAGTTAATCCT
GGCCTGTTAGAAACATCAGAAGGCTGTAGACAAATACTGGGACAGCTACA
ACCATCCCTTCAGACAGGATCAGAAGAACTTAGATCATTATATAATACAG
TAGCAACCCTCTATTGTGTGCATCAAAGGATAGAGATAAAAGACACCAAG
GAAGCTTTAGACAAGATAGAGGAAGAGCAAAACAAAAGTAAGACCACCGC
ACAGCAAGCGGCCGGCCGCGCTGATCTTCAGACCTGGAGGAGGAGATATG
AGGGACAATTGGAGAAGTGAATTATATAAATATAAAGTAGTAAAAATTGA
ACCATTAGGAGTAGCACCCACCAAGGCAAAGAGAAGAGTGGTGCAGAGAG
AAAAAAGAGCAGTGGGAATAGGAGCTTTGTTCCTTGGGTTCTTGGGAGCA
GCAGGAAGCACTATGGGCGCAGCGTCAATGACGCTGACGGTACAGGCCAG
ACAATTATTGTCTGGTATAGTGCAGCAGCAGAACAATTTGCTGAGGGCTA
TTGAGGCGCAACAGCATCTGTTGCAACTCACAGTCTGGGGCATCAAGCAG
CTCCAGGCAAGAATCCTGGCTGTGGAAAGATACCTAAAGGATCAACAGCT
CCTGGGGATTTGGGGTTGCTCTGGAAAACTCATTTGCACCACTGCTGTGC
CTTGGAATGCTAGTTGGAGTAATAAATCTCTGGAACAGATTTGGAATCAC
ACGACCTGGATGGAGTGGGACAGAGAAATTAACAATTACACAAGCTTAAT
ACACTCCTTAATTGAAGAATCGCAAAACCAGCAAGAAAAGAATGAACAAG
AATTATTGGAATTAGATAAATGGGCAAGTTTGTGGAATTGGTTTAACATA
ACAAATTGGCTGTGGTATATAAAATTATTCATAATGATAGTAGGAGGCTT
GGTAGGTTTAAGAATAGTTTTTGCTGTACTTTCTATAGTGAATAGAGTTA
GGCAGGGATATTCACCATTATCGTTTCAGACCCACCTCCCAACCCCGAGG
GGACCCGACAGGCCCGAAGGAATAGAAGAAGAAGGTGGAGAGAGAGACAG
AGACAGATCCATTCGATTAGTGAACGGATCGGCACTGCGTGCGCCAATTC
TGCAGACAAATGGCAGTATTCATCCACAATTTTAAAAGAAAAGGGGGGAT
TGGGGGGTACAGTGCAGGGGAAAGAATAGTAGACATAATAGCAACAGACA
TACAAACTAAAGAATTACAAAAACAAATTACAAAAATTCAAAATTTTCGG
GTTTATTACAGGGACAGCAGAGATCCAGTTTGGTTAGTACCGGGCCCGGT
GCTTTGCTCTGAGCCAGCCCACCAGTTTGGAATGACTCCTTTTTATGACT
TGAATTTTCAAGTATAAAGTCTAGTGCTAAATTTAATTTGAACAACTGTA
TAGTTTTTGCTGGTTGGGGGAAGGAAAAAAAATGGTGGCAGTGTTTTTTT
CAGAATTAGAAGTGAAATGAAAACTTGTTGTGTGTGAGGATTTCTAATGA
CATGTGGTGGTTGCATACTGAGTGAAGCCGGTGAGCATTCTGCCATGTCA
CCCCCTCGTGCTCAGTAATGTACTTTACAGAAATCCTAAACTCAAAAGAT
TGATATAAACCATGCTTCTTGTGTATATCCGGTCTCTTCTCTGGGTAGTC
TCACTCAGCCTGCATTTCTGCCAGGGCCCGCTCTAGATCTAGACGGTTGA
TCTggcctccgcgccgggttttggcgcctcccgcgggcgccccctcctc
acgcgagcgctgccacgtcagacgaagggcgcaggagcgttcctgatcc
ttccgcccggacgctcaggacagcggcccgctgctcataagactcggcct
tagaaccccagtatcagcagaaggacattttaggacgggacttgggtgac
tctagggcactggttttctttccagagagcggaacaggcgaggaaaagta
```

-continued

```
gtcccttctcggcgattctgcggagggatctccgtggggcggtgaacgcc
gatgattatataaggacgcgccgggtgtggcacagctagttccgtcgcag
ccgggatttgggtcgcggttcttgtttgtggatcgctgtgatcgtcactt
ggtgagttgcggctgctgggctggccggggcttcgtggccgccgggcc
gctcggtgggacggaagcgtgtggagagaccgccaagggctgtagtctgg
gtccgcgagcaaggttgccctgaactgggggttgggggggagcgcacaaaa
tggcggctgttcccgagtcttgaatggaagacgcttgtaaggcgggctgt
gaggtcgttgaaacaaggtggggggcatggtgggcggcaagaacccaagg
tcttgaggccttcgctaatgcgggaaagctcttattcgggtgagatgggc
tggggcaccatctggggaccctgacgtgaagtttgtcactgactggagaa
ctcgggtttgtcgtctggttgcgggggcggcagttatgcggtgccgttgg
gcagtgcacccgtacctttgggagcgcgcgcctcgtcgtgtcgtgacgtc
acccgttctgttggcttataatgcagggtggggccacctgccggtaggtg
tgcggtaggctttctccgtcgcaggacgcagggttcgggcctagggtag
gctctcctgaatcgacaggcgccgacctctggtgaggggagggataagt
gaggcgtcagtttctttggtcggttttatgtacctatcttcttaagtagc
tgaagctccggttttgaactatgcgctcggggttggcgagtgtgttttgt
gaagttttttaggcaccttttgaaatgtaatcatttgggtcaatatgtaa
ttttcagtgttagactagtaaattgtccgctaaattctggccgttttttgg
cttttttgttagacGAAGTACGCGCTAGCCGTTAATAAGCCTCGATGCgg
atccataacttcgtataggatacctatacgaagttatctcaggtaccgc
caccatgaccgagtacaagcccacggtgcgcctcgccacccgcgacgacg
tcccagggccgtacgcaccctcgccgccgcgttcgccgactaccccgcc
acgcgccacaccgtcgatccggaccgccacatcgagcgggtcaccgagct
gcaagaactcttcctcacgcgcgtcgggctcgacatcggcaaggtgtggg
tcgcggacgacggcgccgcggtggcggtctggaccacgccggagagcgtc
gaagcggggcggtgttcgccgagatcggcccgcgcatggccgagttgag
cggttcccggctggccgcgcagcaacagatggaaggcctcctggcgccgc
accggcccaaggagcccgcgtggttcctggccaccgtcggcgtctcgccc
gaccaccagggcaagggtctgggcagcgccgtcgtgctccccggagtgga
ggcggccgagcgcgccggggtgcccgccttcctggagacctccgcgccc
gcaacctcccctctacgagcggctcggcttcaccgtcaccgccgacgtc
gaggtgcccgaaggaccgcgcacctggtgcatgaccgcaagcccggtgc
cctgtacaagaaacagaaaattgtggcaccagtgaaacagactttgaatt
ttgaccttctcaagttggcgggagacgtcgagtccaaccctgggccatg
aacccagccatcagcgtcgctctcctgctctcagtcttgcaggtgtcccg
agggcagaaggtgaccagcctgacagcctgcctggtgaaccaaaaccttc
gcctggactgccgccatgagaataacaccaaggataactccatccagcat
gagttcagcctgacccgagagaagaggaagcacgtgctctcaggcaccct
cgggatacccgagcacacgtaccgctcccgcgtcaccctctccaaccagc
cctatatcaaggtccttaccctagccaacttcaccaccaaggatgagggc
```

-continued

```
gactacttttgtgagcttcgagtctcgggcgcgaatcccatgagctccaa
taaaagtatcagtgtgtatagagacaaactggtcaagtgtggcggcataa
gcctgctggttcagaacacatcctggatgctgctgctgctgctttccctc
tccctcctccaagccctggacttcatttctctgtgatctagaagccataa
cttcgtatagtacacattatacgaagttatgttttATGCATACCTGGAGGA
AAAAAAAAGGGGAGAGTCAGGGTTTAAACCTGGAATGAAAGGTCAAGGT
GTGACGTCAGCTTGGGCGGCCGCCCACTCACCTGCAATTGGGCCGCtact
tgtacagctcgtccatgccgagagtgatcccggcggcggtcacgaactcc
agcaggaccatgtgatcgcgcttctcgttggggtctttgctcagggcgga
ctgggtgctcaggtagtggttgtcggcagcagcacggggccgtcgccga
tgggggtgttctgctggtagtggtcggcgagctgcacgctgccgtcctcg
atgttgtggcggatcttgaagttcacttgatgccgttcttctgcttgtc
ggccatgatatagacgttgtggctgttgtagttgtactccagcttgtgcc
ccaggatgttgccgtcctccttgaagtcgatgcccttcagctcgatgcgg
ttcaccagggtgtcgccctcgaacttcacctcggcgcgggtcttgtagtt
gccgtcgtccttgaagaagatggtgcgctcctggacgtagccttcgggca
tggcggacttgaagaagtcgtgctgcttcatgtggtcggggtagcggctg
aagcactgcacgccgtaggtcagggtggtcacgagggtgggccagggcac
gggcagcttgccggtggtgcagatgaacttcagggtcagcttgccgtagg
tggcatcgccctcgccctcgccggacacgctgaacttgtggccgtttacg
tcgccgtccagctcgaccaggatgggcaccacccggtgaacagctcctc
gcccttgctcaccatggtggcgaccggtataacttcgtataaggtatcct
atacgaagttatccattcaggctgtgctagcatcaatggcatggcacaaa
gcttagcataacttcgtataatgtgtactatacgaagttatcccTGTTT
AAGGGTTCCGGTTCCACTAGGTACAATTCGATATCAAGCTTATCGATAAT
CAACCTCTGGATTACAAAATTTGTGAAAGATTGACTGGTATTCTTAACTA
TGTTGCTCCTTTTACGCTATGTGGATACGCTGCTTTAATGCCTTTGTATC
ATGCTATTGCTTCCCGTATGGCTTTCATTTTCTCCTCCTTGTATAAATCC
TGGTTGCTGTCTCTTTATGAGGAGTTGTGGCCCGTTGTCAGGCAACGTGG
CGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGC
TCGGCTGTTGGGCACTGACAATTCCGTGGTGTTGTCGGGAAATCATCGT
CCTTTCCTTGGCTGCTCGCCTGTGTTGCCACCTGGATTCTGCGCGGGACG
TCCTTCTGCTACGTCCCTTCGGCCCTCAATCCAGCGGACCTTCCTTCCCG
CGGCCTGCTGCCGGCTCTGCGGCCTCTTCCGCGTCTTCGCCTTCGCCCTC
AGACGAGTCGGATCTCCCTTTGGGCCGCCTCCCCGCATCGATACCGTCGA
CCTCGATCGAGACCTAGAAAAACATGGAGCAATCACAAGTAGCAATACAG
CAGCTACCAATGCTGATTGTGCCTGGCTAGAAGCACAAGAGGAGGAGGAG
GTGGGTTTTCCAGTCACACCTCAGGTACCAAGCATGGGGTAAAGTACTGT
```

```
TCTCATCACATCATATCAAGGTTATATACCATCAATATTGCCACAGATGT
TACTTAGCCTTTTAATATTTCTCTAATTTAGTGTATATGCAATGATAGTT
CTCTGATTTCTGAGATTGAGTTTCTCATGTGTAATGATTATTTAGAGTTT
CTCTTTCATCTGTTCAAATTTTTGTCTAGTTTTATTTTTTACTGATTTGT
AAGACTTCTTTTTATAATCTGCATATTACAATTCTCTTTACTGGGGTGTT
GCAAATATTTCTGTCATTCTATGGCCTGACTTTTCTTAATGGTTTTTTA
ATTTTAAAAATAAGTCTTAATATTCATGCAATCTAATTAACAATCTTTTC
TTTGTGGTTAGGACTTTGAGTCATAAGAAATTTTTCTCTACACTGAAGTC
ATGATGGCATGCTTCTATATTATTTTCTAAAAGATTTAAAGTTTTGCCTT
CTCCATTTAGACTTATAATTCACTGGAATTTTTTTGTGTGTATGGTATGA
CATATGGGTTCCCTTTTATTTTTTACATATAAATATATTTCCCTGTTTTT
CTAAAAAGAAAAAGATCATCATTTTCCCATTGTAAAATGCCATATTTTT
TTCATAGGTCACTTACATATATCAATGGGTCTGTTTCTGAGCTCTACTCT
ATTTTATCAGCCTCACTGTCTATCCCCACACATCTCATGCTTTGCTCTAA
ATCTTGATATTTAGTGGAACATTCTTTCCCATTTTGTTCTACAAGAATAT
TTTTGTTATTGTCTTTTGGGCTTCTATATACATTTTAGAATGAGGTTGGC
AAGGTACCTTTAAGACCAATGACTTACAAGGCAGCTGTAGATCTTAGCCA
CTTTTTAAAAGAAAAGGGGGGACTGGAAGGGCTAATTCACTCCCAGCTGC
TTTTTGCCTGTACTGGGTCTCTCTGGTTAGACCAGATCTGAGCCTGGGAG
CTCTCTGGCTAACTAGGGAACCCACTGCTTAAGCCTCATAAAGCTCGACT
GTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGG
AAATTGCATCGCATTGTCTGAGTAGGTGTCATTCTATTCTGGGGGGTGGG
GTGGGGCAGGACAGCAAGGGGGAGGATTGGGAAGACAATAGCAGGCATGC
TGGGGATGCGGTCCGGACTGTACTGGGTCTCTCTGGTTAGACCAGATCTG
AGCCTGGGAGCTCTCTGGCTAACTAGGGAACCCACTGCTTAAGCCTCAAT
AAAGCTTGCCTTGAGTGCTTCAAGTAGTGTGTGCCCGTCTGTTGTGTGAC
TCTGGTAACTAGAGATCCCTCAGACCCTTTTAGTCAGTGTGGAAAATCTC
TAGCAGCATGTGAGCAAAAGGCCAGCAAAAGGCCAGGAACCGTAAAAAGG
CCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGCT
GCGCCTTATCCGGTAACTATCGTCTTGAGTCCAACCCGGTAAGACACGAC
TTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACA
CTAGAAGAACAGTATTTGGTATCTGCGCTCTGCTGAAGCCAGTTACCTTC
GGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAAC
GAAAACTCACGTTAAGGGATTTTGGTCATGAGATTATCAAAAAGGATCTT
CACCTAGATCCTTTTAAATTAAAAATGAAGTTTTAAATCAATCTAAAGTA
TATATGAGTAAACTTGGTCTGACAGTTACCAATGCTTAATCAGTGAGGCA
CCTATCTCAGCGATCTGTCTATTTCGTTCATCCATAGTTGCCTGACTCCC
CGTCGTGTAGATAACTACGATACGGGAGGGCTTACCATCGGCCCCAGTG
CTGCAATGATACCGCGAGACCCACGCTCACCGGCTCCAGATTTATCAGCA
ATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTA
TCACTCATGGTTATGGCAGCACTGCATAATTCTCTTACTGTCATGCCATC
CGTAAGATGCTTTTCTGTGACTGGTGAGTACTCAACCAAGTCATTCTGAG
AATAGTGTATGCGGCGACCGAGTTGCTCTTGCCCGGCGTCAATACGGGAT
AATACCGCGCCACATAGCAGAACTTTAAAAGTGCTCATCATTGGAAAACG
TTCTTCGGGGCGAAAACTCTCAAGGATCTTACCGCTGTTGAGATCCAGTT
CGATGTAACCCACTCGTGCACCCAACTGATCTTCAGCATCTTTTACTTTC
ACCAGCGTTTCTGGGTGAGCAAAAACAGGAAGGCAAAATGCCGCAAAAA
GGGAATAAGGGCGACACGGAAATGTTGAATACTCATACTCTTCCTTTTTC
AATATTATTGAAGCATTTATCAGGGTTATTGTCTCATGAGCGGATACATA
TTTGAATGTATTTAGAAAAATAAACAAATAGGGGTTCCGCGCACATTTCC
CCGAAAAGTGCCACCTGAC.
``` pLB2 comprising the FLIP cassette with the miR30 targeting FireFly luciferase in the antisense orientation was constructed, with a sequence as follows:

(SEQ ID NO: 7)
```
GTCGACGGATCGGGAGATCTCCCGATCCCCTATGGTGCACTCTCAGTACA
ATCTGCTCTGATGCCGCATAGTTAAGCCAGTATCTGCTCCCTGCTTGTGT
GTTGGAGGTCGCTGAGTAGTGCGCGAGCAAAATTTAAGCTACAACAAGGC
AAGGCTTGACCGACAATTGCATGAAGAATCTGCTTAGGGTTAGGCGTTTT
GCGCTGCTTCGCGATGTACGGGCCAGATATACGCGTTGACATTGATTATT
GACTAGTcatgttctttcctgcgttatccctgattctgtggataaccgt
attaccgcctttgagtgagctgataccgctcgccgcagccgaacgaccga
gcgcagcgagtcagtgagcgaggaagcggaagagcgcccaatacgcaaac
cgcctctccccgcgcgttggccgattcattaatgcagctggcacgacagg
tttcccgactggaaagcgggcagtgagcgcaacgcaattaatgtgagtta
gctcactcattaggcaccccaggctttacactttatgcttccggctcgta
tgttgtgtggaattgtgagcggataacaatttcacacaggaaacagctat
gaccatgattacgccaagcgcgcaattaaccctagcttaatgtagtctta
``` tgcaatactcttgtagtcttgcaacatggtaacgatgagttagcaacatg ccttacaaggagagaaaaagcaccgtgcatgccgattggtggaagtaagg tggtacgatcgtgccttattaggaaggcaacagacgggtctgacatggat tggacgaaccactgaattgccgcattgcagagatattgtatttaagtgcc tagctcgatacaataaacgggtctctctggttagaccagatctgagcctg ggagctctctggctaactagggaacccactgcttaagcctcaataaagct tgccttgagtgcttcaagtagtgtgtgcccgtctgttgtgtgactctggt aactagagatccctcagaccccttttagtcagtgtggaaaatctctagcag tGGCGCCCGAACAGGGACTTGAAAGCGAAAGGGAAACCAGAGGAGCTCTC

TCGACGCAGGACTCGGCTTGCTGAAGCGCGCACGGCAAGAGGCGAGGGGC

GGCGACTGGTGAGTACGCCAAAAATTTTGACTAGCGGAGGCTAGAAGGAG

AGAGATGGGTGCGAGAGCGTCAGTATTAAGCGGGGGAGAATTAGATCGCG

ATGGGAAAAAATTCGGTTAAGGCCAGGGGGAAAGAAAAAATATAAATTAA

AACATATAGTATGGGCAAGCAGGGAGCTAGAACGATTCGCAGTTAATCCT

GGCCTGTTAGAAACATCAGAAGGCTGTAGACAAATACTGGGACAGCTACA

ACCATCCCTTCAGACAGGATCAGAAGAACTTAGATCATTATATAATACAG

TAGCAACCCTCTATTGTGTGCATCAAAGGATAGAGATAAAAGACACCAAG

GAAGCTTTAGACAAGATAGAGGAAGAGCAAAACAAAAGTAAGACCACCGC

ACAGCAAGCGGCCGGCCGCGCTGATCTTCAGACCTGGAGGAGGAGATATG

AGGGACAATTGGAGAAGTGAATTATATAAATATAAAGTAGTAAAAATTGA

ACCATTAGGAGTAGCACCCACCAAGGCAAAGAGAAGAGTGGTGCAGAGAG

AAAAAAGAGCAGTGGGAATAGGAGCTTTGTTCCTTGGGTTCTTGGGAGCA

GCAGGAAGCACTATGGGCGCAGCGTCAATGACGCTGACGGTACAGGCCAG

ACAATTATTGTCTGGTATAGTGCAGCAGCAGAACAATTTGCTGAGGGCTA

TTGAGGCGCAACAGCATCTGTTGCAACTCACAGTCTGGGGCATCAAGCAG

CTCCAGGCAAGAATCCTGGCTGTGGAAAGATACCTAAAGGATCAACAGCT

CCTGGGGATTTGGGGTTGCTCTGGAAAACTCATTTGCACCACTGCTGTGC

CTTGGAATGCTAGTTGGAGTAATAAATCTCTGGAACAGATTTGGAATCAC

ACGACCTGGATGGAGTGGGACAGAGAAATTAACAATTACACAAGCTTAAT

ACACTCCTTAATTGAAGAATCGCAAAACCAGCAAGAAAAGAATGAACAAG

AATTATTGGAATTAGATAAATGGGCAAGTTTGTGGAATTGGTTTAACATA

ACAAATTGGCTGTGGTATATAAAATTATTCATAATGATAGTAGGAGGCTT

GGTAGGTTTAAGAATAGTTTTTGCTGTACTTTCTATAGTGAATAGAGTTA

GGCAGGGATATTCACCATTATCGTTTCAGACCCACCTCCCAACCCCGAGG

GGACCCGACAGGCCCGAAGGAATAGAAGAAGAAGGTGGAGAGAGAGACAG

AGACAGATCCATTCGATTAGTGAACGGATCGGCACTGCGTGCGCCAATTC

TGCAGACAAATGGCAGTATTCATCCACAATTTTAAAAGAAAAGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG

GTTTATTACAGGGACAGCAGAGATCCAGTTTGGTTAGTACCGGGCCCGGT

GCTTTGCTCTGAGCCAGCCCACCAGTTTGGAATGACTCCTTTTTATGACT

TGAATTTTCAAGTATAAAGTCTAGTGCTAAATTTAATTTGAACAACTGTA

TAGTTTTTGCTGGTTGGGGAAGGAAAAAAAATGGTGGCAGTGTTTTTTT

CAGAATTAGAAGTGAAATGAAAACTTGTTGTGTGTGAGGATTTCTAATGA

CATGTGGTGGTTGCATACTGAGTGAAGCCGGTGAGCATTCTGCCATGTCA

CCCCCTCGTGCTCAGTAATGTACTTTACAGAAATCCTAAACTCAAAAGAT

TGATATAAACCATGCTTCTTGTGTATATCCGGTCTCTTCTCTGGGTAGTC

TCACTCAGCCTGCATTTCTGCCAGGGCCCGCTCTAGATCTAGACGGTTGA

TCTggcctccgcgccgggttttggcgcctcccgcgggcgccccctcctc acggcgagcgctgccacgtcagacgaagggcgcaggagcgttcctgatcc ttccgcccggacgctcaggacagcggcccgctgctcataagactcggcct tagaacccagtatcagcagaaggacattttaggacgggacttgggtgac tctagggcactggttttctttccagagagcggaacaggcgaggaaaagta gtcccttctcggcgattctgcggagggatctccgtgggcggtgaacgcc gatgattatataaggacgcgccgggtgtggcacagctagttccgtcgcag ccgggatttgggtcgcggttcttgtttgtggatcgctgtgatcgtcactt ggtgagttgcgggctgctgggctggccggggcttcgtggccgccgggcc gctcggtgggacggaagcgtgtggagagaccgccaagggctgtagtctgg gtccgcgagcaaggttgccctgaactgggggttggggggagcgcacaaaa tggcggctgttcccgagtcttgaatggaagacgcttgtaaggcgggctgt gaggtcgttgaaacaaggtgggggcatggtgggcggcaagaacccaagg tcttgaggccttcgctaatgcgggaaagctcttattcgggtgagatgggc tggggcaccatctggggaccctgacgtgaagtttgtcactgactggagaa ctcgggtttgtcgtctggttgcggggcggcagttatgcggtgccgttgg gcagtgcaccgtaccttgggagcgcgcgcctcgtcgtgtcgtgacgtc acccgttctgttggcttataatgcagggtggggccacctgccggtaggtg tgcggtaggcttttctccgtcgcaggacgcagggttcgggcctagggtag gctctcctgaatcgacaggcgccggacctctggtgaggggagggataagt gaggcgtcagtttctttggtcggttttatgtacctatcttcttaagtagc tgaagctccggttttgaactatgcgctcggggttggcgagtgtgttttgt gaagttttttaggcaccttttgaaatgtaatcatttgggtcaatatgtaa ttttcagtgttagactagtaaattgtccgctaaattctggccgttttgg cttttttgttagacGAAGTACGCGCTAGCCGTTAATAAGCCTCGATGCgg atccataacttcgtataggatccttatacgaagttatctcaggtaccgc caccatgaccgagtacaagcccacggtgcgcctcgccacccgcgacgacg tccccagggccgtacgcaccctcgccgccgcgttcgccgactaccccgcc acgcgccacaccgtcgatccggaccgccacatcgagcgggtcaccgagct gcaagaactcttcctcacgcgcgtcgggctcgacatcggcaaggtgtggg tcgcggacgacggcgccgcggtggcggtctggaccacgccggagagcgtc gaagcggggcggtgttcgccgagatcggcccgcgcatggccgagttgag cggttcccggctggccgcgcagcaacagatggaaggcctcctggcgccgc -continued accggcccaaggagcccgcgtggttcctggccaccgtcggcgtctcgccc
gaccaccagggcaagggtctgggcagcgccgtcgtgctcccggagtgga
ggcggccgagcgcgccggggtgcccgccttcctggagacctccgcgcccc
gcaacctcccccttctacgagcggctcggcttcaccgtcaccgccgacgtc
gaggtgcccgaaggaccgcgcacctggtgcatgacccgcaagcccggtgc
cctgtacaagaaacagaaaattgtggcaccagtgaaacagacttttgaatt
ttgaccttctcaagttggcgggagacgtcgagtccaaccctgggcccatg
aacccagccatcagcgtcgctctcctgctctcagtcttgcaggtgtccga
gggcagaaggtgaccagcctgacagcctgcctggtgaaccaaaaccttcg
cctggactgccgccatgagaataacaccaaggataactccatccagcatg
agttcagcctgacccgagagaagaggaagcacgtgctctcaggcaccctc
gggatacccgagcacacgtaccgctcccgcgtcacccctctccaaccagcc
ctatatcaaggtccttaccctagccaacttcaccaccaaggatgagggcg
actactttgtgagcttcgagtctcgggcgcgaatcccatgagctccaat
aaaagtatcagtgtgtatagagacaaactggtcaagtgtggcggcataag
cctgctggttcagaacacatcctggatgctgctgctgctgctttccctct
ccctcctccaagccctggacttcatttctctgtgatctagaagccataac
ttcgtatagtacacattatacgaagttatgttttATGCATACCTGGAGGAA
AAAAAAAGGGGAGAGTCAGGGgtttaaacgcattagtcttccaattgaa
aaaagtgatttaatttataccattttaattcagctttgtaaaaatgtatc
aaagagatagcaaggtattcagttttagtaaacaagataattgctcctaa
agtagcccttgaattcCGAGGCAGTAGGCAGGCTCCCGCTGAATTGGAA
TCCTACATCTGTGGCTTCACTAGGATTCCAATTCACGGGAGCTCGCTCAC
TGTCAACAGCAATATACCTTctcgagccttctgttgggttaacctgaaga
agtaatcccagcaagtgtttccaagatgtgcaggcaacgattctgtaaag
tactgaagcctcattcaaacatagtatatgtgctgccgaagcgagcactt
aacaaggcttgcggccgcCCACTCACCTGCAATTGGGCCGCtacttgtac
agctcgtccatgccgagagtgatcccggcggcggtcacgaactccagcag
gaccatgtgatcgcgcttctcgttggggtcttttgctcagggcggactggg
tgctcaggtagtggttgtcgggcagcagcacggggccgtcgccgatgggg
gtgttctgctggtagtggtcggcgagctgcacgctgccgtcctcgatgtt
gtggcggatcttgaagttcaccttgatgccgttcttctgcttgtcggca
tgatatagacgttgtggctgttgtagttgtactccagcttgtgccccagg
atgttgccgtcctccttgaagtcgatgcccttcagctcgatgcggttcac
cagggtgtcgccctcgaacttcacctcggcgcgggtcttgtagttgccgt
cgtccttgaagaagatggtgcgctcctggacgtagccttcgggcatggcg
gacttgaagaagtcgtgctgcttcatgtggtcggggtagcggctgaagca
ctgcacgccgtaggtcagggtggtcacgagggtgggccagggcacgggca
gcttgccggtggtgcagatgaacttcagggtcagcttgccgtaggtggca
tcgccctcgccctcgccggacacgctgaacttgtggccgtttacgtcgcc -continued gtccagctcgaccaggatgggcaccaccccggtgaacagctcctcgccct
tgctcaccatggtggcgaccggtataacttcgtataaggtatcctatacg
aagttatccattcaggctgtgctagcatcaatggcatggcacaaagctta
gccataacttcgtataatgtgtactatacgaagttatcccTGTTTAAGGG
TTCCGGTTCCACTAGGTACAATTCGATATCAAGCTTATCGATAATCAACC
TCTGGATTACAAAATTTGTGAAAGATTGACTGGTATTCTTAACTATGTTG
CTCCTTTTACGCTATGTGGATACGCTGCTTTAATGCCTTTGTATCATGCT
ATTGCTTCCCGTATGGCTTTCATTTTCTCCTCCTTGTATAAATCCTGGTT
GCTGTCTCTTTATGAGGAGTTGTGGCCCGTTGTCAGGCAACGTGGCGTGG
TGTGCACTGTGTTTGCTGACGCAACCCCCACTGGTTGGGGCATTGCCACC
ACCTGTCAGCTCCTTTCCGGGACTTTCGCTTTCCCCCTCCCTATTGCCAC
GGCGGAACTCATCGCCGCCTGCCTTGCCCGCTGCTGGACAGGGGCTCGGC
TGTTGGGCACTGACAATTCCGTGGTGTTGTCGGGGAAATCATCGTCCTTT
CCTTGGCTGCTCGCCTGTGTTGCCACCTGGATTCTGCGCGGGACGTCCTT
CTGCTACGTCCCTTCGGCCCTCAATCCAGCGGACCTTCCTTCCCGCGGCC
TGCTGCCGGCTCTGCGGCCTCTTCCGCGTCTTCGCCTTCGCCCTCAGACG
AGTCGGATCTCCCTTTGGGCGCCTCCCCGCATCGATACCGTCAGACCTCG
ATCGAGACCTAGAAAAACATGGAGCAATCACAAGTAGCAATACAGCAGCT
ACCAATGCTGATTGTGCCTGGCTAGAAGCACAAGAGGAGGAGGAGGTGGG
TTTTCCAGTCACACCTCAGGTACCAAGCATGGGGTAAAGTCTGTTCTCAT
CACATCATATCAAGGTTATATACCATCAATATTGCCACAGATGTTACTTA
GCCTTTTAATATTTCTCTAATTTAGTGTATATGCAATGATAGTTCTCTGA
TTTCTGAGATTGAGTTTCTCATGTGTAATGATTATTTAGAGTTTCTCTTT
CATCTGTTCAAATTTTTGTCTAGTTTTATTTTTTACTGATTTGTAAGACT
TCTTTTTATAATCTGCATATTACAATTCTCTTTACTGGGGTGTTGCAAAT
ATTTTCTGTCATTCTATGGCCTGACTTTTCTTAATGGTTTTTTAATTTTA
AAAATAAGTCTTAATATTCATGCAATCTAATTAACAATCTTTTCTTTGTG
GTTAGGACTTTGAGTCATAAGAAATTTTTCTCTACACTGAAGTCATGATG
GCATGCTTCTATATTATTTTCTAAAAGATTTAAAGTTTTGCCTTCTCCAT
TTAGACTTATAATTCACTGGAATTTTTTTGTGTGTATGGTATGACATATG
GGTTCCCTTTTATTTTTTACATATAAATATATTTCCCTGTTTTTCTAAAA
AAGAAAAAGATCATCATTTTCCCATTGTAAAATGCCATATTTTTTTCATA
GGTCACTTACATATATCAATGGGTCTGTTTCTGAGCTCTACTCTATTTTA
TCAGCCTCACTGTCTATCCCCACACATCTCATGCTTTGCTCTAAATCTTG
ATATTTAGTGGAACATTCTTTCCCATTTTGTTCTACAAGAATATTTTTGT
TATTGTCTTTTGGGCTTCTATATACATTTTAGAATGAGGTTGGCAAGGTA
CCTTTAAGACCAATGACTTACAAGGCAGCTGTAGATCTTAGCCACTTTTT
AAAAGAAAAGGGGGACTGGAAGGGCTAATTCACTCCCAGCTGCTTTTTG
CCTGTACTGGGTCTCTCTGGTTAGACCAGATCTGAGCCTGGGAGCTCTCT
GGCTAACTAGGGAACCCACTGCTTAAGCCTCATAAAGCTCGACTGTGCCT
TCTAGTTGCCAGCCATCTGTTGTTTGCCCCTCCCCCGTGCCTTCCTTGAC

```
CCTGGAAGGTGCCACTCCCACTGTCCTTTCCTAATAAAATGAGGAAATTG
CATCGCATTGTCTGAGTAGGTGTCATTCTATTCTGGGGGTGGGGTGGGG
CAGGACAGCAAGGGGGAGGATTGGGAAGACAATAGCAGGCATGCTGGGGA
TGCGGTCCGGACTGTACTGGGTCTCTCTGGTTAGACCAGATCTGAGCCTG
GGAGCTCTCTGGCTAACTAGGGAACCCACTGCTTAAGCCTCAATAAAGCT
TGCCTTGAGTGCTTCAAGTAGTGTGTGCCCGTCTGTTGTGTGACTCTGGT
AACTAGAGATCCCTCAGACCCTTTTAGTCAGTGTGGAAAATCTCTAGCAG
CATGTGAGCAAAAGGCCAGCAAAAGGCCAGGAACCGTAAAAGGCCGCGT
TGCTGGCGTTTTTCCATAGGCTCCGCCCCCCTGACGAGCATCACAAAAAT
CGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCTC
CAAGCTGGGCTGTGTGCACGAACCCCCCGTTCAGCCCGACCGCTGCGCCT
TATCCGGTAACTATCGTCTTGAGTCCAACCCGGTAAGACACGACTTATCG
CCACTGGCAGCAGCCACTGGTAACAGGATTAGCAGAGCGAGGTATGTAGG
CGGTGCTACAGAGTTCTTGAAGTGGTGGCCTAACTACGGCTACACTAGAA
GAACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAAC
TCACGTTAAGGGATTTTGGTCATGAGATTATCAAAAAGGATCTTCACCTA
GATCCTTTTAAATTAAAAATGAAGTTTTAAATCAATCTAAAGTATATATG
AGTAAACTTGGTCTGACAGTTACCAATGCTTAATCAGTGAGGCACCTATC
TCAGCGATCTGTCTATTTCGTTCATCCATAGTTGCCTGACTCCCCGTCGT
GTAGATAACTACGATACGGGAGGGCTTACCATCTGGCCCCAGTGCTGCAA
TGATACCGCGAGACCCACGCTCACCGGCTCCAGATTTATCAGCAATAAAC
CAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGC
CAGTTAATAGTTTGCGCAACGTTGTTGCCATTGCTACAGGCATCGTGGTG
TCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCT
TCGGTCCTCCGATCGTTGTCAGAAGTAAGTTGGCCGCAGTGTTATCACTC
ATGGTTATGGCAGCACTGCATAATTCTCTTACTGTCATGCCATCCGTAAG
ATGCTTTTCTGTGACTGGTGAGTACTCAACCAAGTCATTCTGAGAATAGT
GTATGCGGCGACCGAGTTGCTCTTGCCCGGCGTCAATACGGGATAATACC
GCGCCACATAGCAGAACTTTAAAAGTGCTCATCATTGGAAAACGTTCTTC
GGGGCGAAAACTCTCAAGGATCTTACCGCTGTTGAGATCCAGTTCGATGT
AACCCACTCGTGCACCCAACTGATCTTCAGCATCTTTTACTTTCACCAGC
GTTTCTGGGTGAGCAAAAACAGGAAGGCAAAATGCCGCAAAAAAGGGAAT
AAGGGCGACACGGAAATGTTGAATACTCATACTCTTCCTTTTTCAATATT
ATTGAAGCATTTATCAGGGTTATTGTCTCATGAGCGGATACATATTTGAA
TGTATTTAGAAAAATAAACAAATAGGGGTTCCGCGCACATTTCCCCGAAA
AGTGCCACCTGAC
``` pLB2 comprising the FLIP cassette with the miR30 targeting α4 integrin in the antisense orientation was constructed, with a sequence as follows:

(SEQ ID NO: 8)
```
GTCGACGGATCGGGAGATCTCCCGATCCCCTATGGTGCACTCTCAGTACA
ATCTGCTCTGATGCCGCATAGTTAAGCCAGTATCTGCTCCCTGCTTGTGT
GTTGGAGGTCGCTGAGTAGTGCGCGAGCAAAATTTAAGCTACAACAAGGC
AAGGCTTGACCGACAATTGCATGAAGAATCTGCTTAGGGTTAGGCGTTTT
GCGCTGCTTCGCGATGTACGGGCCAGATATACGCGTTGACATTGATTATT
GACTAGTcatgttctttcctgcgttatccctgattctgtggataaccgt
attaccgcctttgagtgagctgataccgctcgccgcagccgaacgaccga
gcgcagcgagtcagtgagcgaggaagcggaagagcgcccaatacgcaaac
cgcctctccccgcgcgttggccgattcattaatgcagctggcacgacagg
tttcccgactggaaagcgggcagtgagcgcaacgcaattaatgtgagtta
gctcactcattaggcaccccaggctttacactttatgcttccggctcgta
tgttgtgtggaattgtgagcggataacaatttcacacaggaaacagctat
gaccatgattacgccaagcgcgcaattaaccctagcttaatgtagtctta
tgcaatactcttgtagtcttgcaacatggtaacgatgagttagcaacatg
ccttacaaggagagaaaaagcaccgtgcatgccgattggtggaagtaagg
tggtacgatcgtgccttattaggaaggcaacagacgggtctgacatggat
tggacgaaccactgaattgccgcattgcagagatattgtatttaagtgcc
tagctcgatacaataaacgggtctctctggttagaccagatctgagcctg
ggagctctctggctaactagggaacccactgcttaagcctcaataaagct
tgccttgagtgcttcaagtagtgtgtgcccgtctgttgtgtgactctggt
aactagagatccctcagaccctttagtcagtgtggaaaatctctagcag
tGGCGCCCGAACAGGGACTTGAAAGCGAAAGGGAAACCAGAGGAGCTCTC
TCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAG
AGAGATGGGTGCGAGAGCGTCAGTATTAAGCGGGGGAGAATTAGATCGCG
ATGGGAAAAATTCGGTTAAGGCCAGGGGGAAAGAAAAAATATAAATTAA
AACATATAGTATGGGCAAGCAGGGAGCTAGAACGATTCGCAGTTAATCCT
GGCCTGTTAGAAACATCAGAAGGCTGTAGACAAATACTGGGACAGCTACA
ACCATCCCTTCAGACAGGATCAGAAGAACTTAGATCATTATATAATACAG
TAGCAACCCTCTATTGTGTGCATCAAAGGATAGAGATAAAAGACACCAAG
GAAGCTTTAGACAAGATAGAGGAAGAGCAAAACAAAAGTAAGACCACCGC
ACAGCAAGCGGCCGGCCGCGCTGATCTTCAGACCTGGAGGAGGAGATATG
AGGGACAATTGGAGAAGTGAATTATATAAATATAAAGTAGTAAAAATTGA
```

```
ACCATTAGGAGTAGCACCCACCAAGGCAAAGAGAAGAGTGGTGCAGAGAG
AAAAAAGAGCAGTGGGAATAGGAGCTTTGTTCCTTGGGTTCTTGGGAGCA
GCAGGAAGCACTATGGGCGCAGCGTCAATGACGCTGACGGTACAGGCCAG
ACAATTATTGTCTGGTATAGTGCAGCAGCAGAACAATTTGCTGAGGGCTA
TTGAGGCGCAACAGCATCTGTTGCAACTCACAGTCTGGGGCATCAAGCAG
CTCCAGGCAAGAATCCTGGCTGTGGAAAGATACCTAAAGGATCAACAGCT
CCTGGGGATTTGGGGTTGCTCTGGAAAACTCATTTGCACCACTGCTGTGC
CTTGGAATGCTAGTTGGAGTAATAAATCTCTGGAACAGATTTGGAATCAC
ACGACCTGGATGGAGTGGGACAGAGAAATTAACAATTACACAAGCTTAAT
ACACTCCTTAATTGAAGAATCGCAAAACCAGCAAGAAAAGAATGAACAAG
AATTATTGGAATTAGATAAATGGGCAAGTTTGTGGAATTGGTTTAACATA
ACAAATTGGCTGTGGTATATAAAATTATTCATAATGATAGTAGGAGGCTT
GGTAGGTTTAAGAATAGTTTTTGCTGTACTTTCTATAGTGAATAGAGTTA
GGCAGGGATATTCACCATTATCGTTTCAGACCCACCTCCCAACCCCGAGG
GGACCCGACAGGCCCGAAGGAATAGAAGAAGAAGGTGGAGAGAGAGAGAC
AGAGACAGATCCATTCGATTAGTGAACGGATCGGCACTGCGTGCGCCAAT
TCTGCAGACAAATGGCAGTATTCATCCACAATTTTAAAAGAAAAGGGGGG
ATTGGGGGGTACAGTGCAGGGGAAAGAATAGTAGACATAATAGCAACAGA
CATACAAACTAAAGAATTACAAAAACAAATTACAAAAATTCAAAATTTTC
GGGTTTATTACAGGGACAGCAGAGATCCAGTTTGGTTAGTACCGGGCCCG
GTGCTTTGCTCTGAGCCAGCCCACCAGTTTGGAATGACTCCTTTTTATGA
CTTGAATTTTCAAGTATAAAGTCTAGTGCTAAATTTAATTTGAACAACTG
TATAGTTTTTGCTGGTTGGGGAAGGAAAAAAAATGGTGGCAGTGTTTTT
TTCAGAATTAGAAGTGAAATGAAAACTTGTTGTGTGTGAGGATTTCTAAT
GACATGTGGTGGTTGCATACTGAGTGAAGCCGGTGAGCATTCTGCCATGT
CACCCCCTCGTGCTCAGTAATGTACTTTACAGAAATCCTAAACTCAAAAG
ATTGATATAAACCATGCTTCTTGTGTATATCCGGTCTCTTCTCTGGGTAG
TCTCACTCAGCCTGCATTTCTGCCAGGGCCCGCTCTAGATCTAGACGGTT
GATCTggcctccgcgcgggttttggcgcctcccgcgggcgcccccctcc
tcacggcgagcgctgccacgtcagacgaagggcgcaggagcgttcctgat
ccttccgcccgacgctcaggacagcggcccgctgctcataagactcggc
cttagaaccccagtatcagcagaaggacattttaggacgggacttgggtg
actctagggcactggttttctttccagagagcggaacaggcgaggaaaag
tagtcccttctcggcgattctgcgagggatctccgtggggcggtgaacg
ccgatgattatataaggacgcgccgggtgtggcacagctagttccgtcgc
agccgggatttgggtcgcggttcttgtttgtggatcgctgtgatcgtcac
ttggtgagttgcgggctgctgggctggccggggctttcgtggccgccggg
ccgctcggtgggacggaagcgtgtggagagaccgccaagggctgtagtct
gggtccgcgagcaaggttgcctgaactgggggttggggggagcgcacaa
aatggcggctgttcccgagtcttgaatggaagacgcttgtaaggcggct
gtgaggtcgttgaaacaaggtgggggggcatggtgggcggcaagaacccaa
```

```
ggtcttgaggccttcgctaatgcgggaaagctcttattcgggtgagatgg
gctggggcaccatctggggaccctgacgtgaagtttgtcactgactggag
aactcgggtttgtcgtctggttgcggggcggcagttatgcggtgccgtt
gggcagtgcacccgtacctttgggagcgcgcgcctcgtcgtgtcgtgacg
tcacccgttctgttggcttataatgcagggtggggccacctgccggtagg
tgtgcggtaggcttttctccgtcgcaggacgcagggttcgggcctagggt
aggctctcctgaatcgacaggcgccggacctctggtgaggggagggataa
gtgaggcgtcagtttctttggtcggttttatgtacctatcttcttaagta
gctgaagctccggttttgaactatgcgctcggggttggcgagtgtgtttt
gtgaagtttttaggcaccttttgaaatgtaatcatttgggtcaatatgt
aattttcagtgttagactagtaaattgtccgctaaattctggccgttttt
ggcttttttgttagacGAAGTACGCGCTAGCCGTTAATAAGCCTCGATGC
ggatccataacttcgtataggatacctatacgaagttatctcaggtacc
gccaccatgaccgagtacaagcccacggtgcgcctcgccacccgcgacga
cgtccccagggccgtacgcaccctcgccgccgcgttcgccgactaccccg
ccacgcgccacaccgtcgatccggaccgccacatcgagcgggtcaccgag
ctgcaagaactcttcctcacgcgcgtcgggctcgacatcggcaaggtgtg
ggtcgcggacgacggcgccgcggtggcggtctggaccacgcggagagcg
tcgaagcggggcggtgttcgccgagatcggcccgcgcatggccgagttg
agcggttcccggctggccgcgcagcaacagatggaaggcctcctggcgcc
gcaccgccccaaggagcccgcgtggttcctggccaccgtcggcgtctcgc
ccgaccaccagggcaagggtctgggcagcgccgtcgtgctccccggagtg
gaggcggccgagcgcgccggggtgcccgccttcctggagacctccgcgcc
ccgcaacctcccccttctacgagcggctcggcttcaccgtcaccgccgacg
tcgaggtgcccgaaggaccgcgcacctggtgcatgacccgcaagcccgt
gccctgtacaagaaacagaaaattgtggcaccagtgaaacagactttgaa
ttttgaccttctcaagttggcgggagacgtcgagtccaaccctgggccca
tgaacccagccatcagcgtcgctctcctgctctcagtcttgcaggtgtcc
cgagggcagaaggtgaccagcctgacagcctgcctggtgaaccaaaacct
tcgcctggactgccgccatgagaataacaccaaggataactccatccagc
atgagttcagcctgacccgagagaagaggaagcacgtgctctcaggcacc
ctcgggatacccgagcacacgtaccgctcccgcgtcaccctctccaacca
gccctatatcaaggtccttaccctagccaacttcaccaccaaggatgagg
gcgactacttttgtgagcttcgagtctcgggcgcgaatcccatgagctcc
aataaaagtatcagtgtgtatagagacaaactggtcaagtgtggcggcat
aagcctgctggttcagaacacatcctggatgctgctgctgctgctttccc
tctccctcctccaagccctggacttcatttctctgtgatctagaagccat
aacttcgtatagtacacattatacgaagttatgtttATGCATACCTGGAG
GAAAAAAAAAGGGGAGAGTCAGGGgtttaaacgcattagtcttccaatt
gaaaaaagtgatttaatttataccattttaattcagcttttgtaaaaatgt
```

-continued atcaaagagatagcaaggtattcagtttttagtaaacaagataattgctcc
taaagtagccccttgaaTCCGAGGCAGTAGGCATGGGCATCATGTGATCA
CCAAATACATCTGTGGCTTCACTATTTGGTGATCACATGATGCCCGCGCT
CACTGTCAACAGCAATATACCTTctcgagccttctgttgggttaacctga
agaagtaatcccagcaagtgtttccaagatgtgcaggcaacgattctgta
aagtactgaagcctcattcaaacatagtatatgtgctgccgaagcgagca
cttaacaaggcttgcggccgcCCACTCACCTGCAATTGGGCCGCtacttg
tacagctcgtccatgccgagagtgatcccggcggcggtcacgaactccag
caggaccatgtgatcgcgcttctcgttggggtctttgctcagggcggact
gggtgctcaggtagtggttgtcgggcagcagcacggggccgtcgccgatg
ggggtgttctgctggtagtggtcggcgagctgcacgctgccgtcctcgat
gttgtggcggatcttgaagttcaccttgatgccgttcttctgcttgtcgg
ccatgatatagacgttgtggctgttgtagttgtactccagcttgtgcccc
aggatgttgccgtcctccttgaagtcgatgcccttcagctcgatgcggtt
caccagggtgtcgccctcgaacttcacctcggcgcgggtcttgtagttgc
cgtcgtccttgaagaagatggtgcgctcctggacgtagccttcgggcatg
gcggacttgaagaagtcgtgctgcttcatgtggtcggggtagcggctgaa
gcactgcacgccgtaggtcaggtggtcacgagggtgggccagggcacgg
gcagcttgccggtggtgcagatgaacttcagggtcagcttgccgtaggtg
gcatcgccctcgccctcgccggacacgctgaacttgtggccgtttacgtc
gccgtccagctcgaccaggatgggcaccaccccggtgaacagctcctcgc
ccttgctcaccatggtggcgaccggtataacttcgtataaggtatcctat
acgaagttatccattcaggctgtgctagcatcaatggcatggcacaaagc
ttagccataacttcgtataatgtgtactatacgaagttatcccTGTTTAA
GGGTTCCGGTTCCACTAGGTACAATTCGTATATCAAGCTTATCGATAATCA
ACCTCTGGATTACAAAATTTGTGAAAGATTGACTGGTATTCTTAACTATG
TTGCTCCTTTTACGCTATGTGGATACGCTGCTTTAATGCCTTTGTATCAT
GCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCG
TGGTGTGCACTGTGTTTGCTGACGCAACCCCCACTGGTTGGGGCATTGCC
ACCACCTGTCAGCTCCTTTCCGGGACTTTCGCTTTCCCCCTCCCTATTGC
CACGGCGGAACTCATCGCCGCCTGCCTTGCCCGCTGCTGGACAGGGGCTC
GGCTGTTGGGCACTGACAATTCCGTGGTGTTGTCGGGGAAATCATCGTCC
TTTCCTTGGCTGCTCGCCTGTGTTGCCACCTGGATTCTGCGCGGGACGTC
CTTCTGCTACGTCCCTTCGGCCCTCAATCCAGCGGACCTTCCTTCCCGCG
GCCTGCTGCCGGCTCTGCGCCTCTTCCGCGTCTTCGCCTTCGCCCTCAG
ACGAGTCGGATCTCCCTTTGGGCCGCTCCCCGCATCGATACCGTCGACC
TCGATCGAGACCTAGAAAAACATGGAGCAATCACAAGTAGCAATACAGCA
GCTACCAATGCTGATTGTGCCTGGCTAGAAGCACAAGAGGAGGAGGAGGT
GGGTTTTCCAGTCACACCTCAGGTACCAAGCATGGGGTAAAGTACTGTTC
TCATCACATCATATCAAGGTTATATACCATCAATATTGCCACAGATGTTA -continued CTTAGCCTTTTAATATTTCTCTAATTTAGTGTATATGCAATGATAGTTCT
CTGATTTCTGAGATTGAGTTTCTCATGTGTAATGATTATTTAGAGTTTCT
CTTTCATCTGTTCAAATTTTTGTCTAGTTTTATTTTTTACTGATTTGTAA
GACTTCTTTTTATAATCTGCATATTACAATTCTCTTTACTGGGGTGTTGC
AAATATTTTCTGTCATTCTATGGCCTGACTTTTCTTAATGGTTTTTTAAT
TTTAAAAATAAGTCTTAATATTCATGCAATCTAATTAACAATCTTTTCTT
TGTGGTTAGGACTTTGAGTCATAAGAAATTTTTCTCTACACTGAAGTCAT
GATGGCATGCTTCTATATTATTTTCTAAAAGATTTAAAGTTTTGCCTTCT
CCATTTAGACTTATAATTCACTGGAATTTTTTTGTGTGTATGGTATGACA
TATGGGTTCCCTTTTATTTTTTACATATAAATATATTTCCCTGTTTTTCT
AAAAAGAAAAAGATCATCATTTTCCCATTGTAAAATGCCATATTTTTTT
CATAGGTCACTTACATATATCAATGGGTCTGTTTCTGAGCTCTACTCTAT
TTTATCAGCCTCACTGTCTATCCCCACACATCTCATGCTTTGCTCTAAAT
CTTGATATTTAGTGGAACATTCTTTCCCATTTTGTTCTACAAGAATATTT
TTGTTATTGTCTTTTGGGCTTCTATATACATTTTAGAATGAGGTTGGCAA
GGTACCTTTAAGACCAATGACTTACAAGGCAGCTGTAGATCTTAGCCACT
TTTTAAAAGAAAAGGGGGGACTGGAAGGGCTAATTCACTCCCAGCTGCTT
TTTGCCTGTACTGGGTCTCTCTGGTTAGACCAGATCTGAGCCTGGGAGCT
CTCTGGCTAACTAGGGAACCCACTGCTTAAGCCTCATAAAGCTCGACTGT
GCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTG
GGGATGCGGTCCGGACTGTACTGGGTCTCTCTGGTTAGACCAGATCTGAG
CCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTA
GCAGCATGTGAGCAAAAGGCCAGCAAAAGGCCAGGAACCGTAAAAAGGCC
GCGTTGCTGGCGTTTTTCCATAGGCTCCGCCCCCCTGACGAGCATCACAA
AAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGC
GCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCT -continued

```
CAAGAAGATCCTTTGATCTTTTCTACGGGGTCTGACGCTCAGTGGAACGA
AAACTCACGTTAAGGGATTTTGGTCATGAGATTATCAAAAAGGATCTTCA
CCTAGATCCTTTTAAATTAAAAATGAAGTTTTAAATCAATCTAAAGTATA
TATGAGTAAACTTGGTCTGACAGTTACCAATGCTTAATCAGTGAGGCACC
TATCTCAGCGATCTGTCTATTTCGTTCATCCATAGTTGCCTGACTCCCCG
TCGTGTAGATAACTACGATACGGGAGGGCTTACCATCTGGCCCCAGTGCT
GCAATGATACCGCGAGACCCACGCTCACCGGCTCCAGATTTATCAGCAAT
AAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATC
ACTCATGGTTATGGCAGCACTGCATAATTCTCTTACTGTCATGCCATCCG
TAAGATGCTTTTCTGTGACTGGTGAGTACTCAACCAAGTCATTCTGAGAA
TAGTGTATGCGGCGACCGAGTTGCTCTTGCCCGGCGTCAATACGGGATAA
TACCGCGCCACATAGCAGAACTTTAAAAGTGCTCATCATTGGAAAACGTT
CTTCGGGGCGAAAACTCTCAAGGATCTTACCGCTGTTGAGATCCAGTTCG
ATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGG
GAATAAGGGCGACACGGAAATGTTGAATACTCATACTCTTCCTTTTTCAA
TATTATTGAAGCATTTATCAGGGTTATTGTCTCATGAGCGGATACATATT
TGAATGTATTTAGAAAAATAAACAAATAGGGGTTCCGCGCACATTTCCCC
GAAAAGTGCCACCTGAC.
```

The MSCV FLIPi Puro2AThy1.1/human c-Myc-miR-p53 vector (SEQ ID NO: 21) comprised a sequence as follows:

```
TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGAGACCCCTGCCT
AGGGACCACCGACCCCCCCGCCGGGAGGTAAGCTGGCCAGCGGTCGTTTC
GTGTCTGTCTCTGTCTTTGTGCGTGTTTGTGCCGGCATCTAATGTTTGCG
CCTGCGTCTGTACTAGTTAGCTAACTAGCTCTGTATCTGGCGGACCCGTG
```

-continued

```
GTGGAACTGACGAGTTCTGAACACCCGGCCGCAACCCTGGGAGACGTCCC
AGGGACTTTGGGGGCCGTTTTTGTGGCCCGACCTGAGGAAGGGAGTCGAT
GTGGAATCCGACCCCGTCAGGATATGTGGTTCTGGTAGGAGACGAGAACC
TAAAACAGTTCCCGCCTCCGTCTGAATTTTTGCTTTCGGTTTGGAACCGA
AGCCGCGCGTCTTGTCTGCTGCAGCGCTGCAGCATCGTTCTGTGTTGTCT
CTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATC
GCTCACAACCAGTCGGTAGATGTCAAGAAGAGACGTTGGGTTACCTTCTG
CTCTGCAGAATGGCCAACCTTTAACGTCGGATGGCCGCGAGACGGCACCT
TTAACCGAGACCTCATCACCCAGGTTAAGATCAAGGTCTTTTCACCTGGC
CCGCATGGACACCCAGACCAGGTCCCCTACATCGTGACCTGGGAAGCCTT
GGCTTTTGACCCCCCTCCCTGGGTCAAGCCCTTTGTACACCCTAAGCCTC
CGCCTCCTCTTCCTCCATCCGCCCCGTCTCTCCCCCTTGAACCTCCTCGT
TCGACCCCGCCTCGATCCTCCCTTTATCCAGCCCTCACTCCTTCTCTAGG
CGCCGGAATTAGAtccataacttcgtataggatacccttatacgaagttat
ctcaggtaccgccaccatgaccgagtacaagcccacggtgcgcctcgcca
cccgcgacgacgtcccagggccgtacgcaccctcgccgccgcgttcgcc
gactaccccgccacgcgccacaccgtcgatccggaccgccacatcgagcg
ggtcaccgagctgcaagaacttcctcacgcgcgtcgggctcgacatcg
gcaaggtgtgggtcgcggacgacggcgccgcggtggcggtctggaccacg
ccggagagcgtcgaagcggggcggtgttcgccgagatcggcccgcgcat
ggccgagttgagcggttcccggctggccgcgcagcaacagatggaaggcc
tcctggcgccgcaccggcccaaggagcccgcgtggttcctggccaccgtc
ggcgtctcgcccgaccaccagggcaagggtctgggcagcgccgtcgtgct
ccccggagtggaggcggccgagcgcgccggggtgcccgccttcctggaga
cctccgcgccccgcaacctccccttctacgagcggctcggcttcaccgtc
accgccgacgtcgaggtgcccgaaggaccgcgcacctggtgcatgacccg
caagcccggtgccctgtacaagaaacagaaaattgtggcaccagtgaaac
agactttgaattttgaccttctcaagttggcgggagacgtcgagtccaac
cctgggcccatgaacccagccatcagcgtcgctctcctgctctcagtctt
gcaggtgtcccgagggcagaaggtgaccagcctgacagcctgcctggtga
accaaaaccttcgcctggactgccgccatgagaataacaccaaggataac
tccatccagcatgagttcagcctgacccgagagaagaggaagcacgtgct
ctcaggcacctcgggataccgagcacacgtaccgctcccgcgtcaccc
tctccaaccagccctatatcaaggtccttaccctagccaacttcaccacc
aaggatgagggcgactacttttgtgagcttcgagtctcgggcgcgaatcc
catgagctccaataaaagtatcagtgtgtatagagacaaactggtcaagt
gtggcggcataagcctgctggttcagaacacatcctggatgctgctgctg
ctgctttccctctccctcctccaagccctggacttcatttctctgtgatc
tagaagccataacttcgtatagtacacattatacgaagttatGTTTATGC
ATACCTGGAGGAAAAAAAAAGGGGAGAGTCAGGGGTTTAAACGCATTAG
```

-continued

TCTTCCAATTGAAAAAAGTGATTTAATTTATACCATTTTAATTCAGCTTT
GTAAAAATGTATCAAAGAGATAGCAAGGTATTCAGTTTTAGTAAACAAGA
TAATTGCTCCTAAAGTAGCCCCTTGAATTCCGAGGCAGTAGGCATCCACT
ACAAGTACATGTGTAATACATCTGTGGCTTCACTATTACACATGTACTTG
TAGTGGGCGCTCACTGTCAACAGCAATATACCTTCTCGAGCCTTCTGTTG
GGTTAACCTGAAGAAGTAATCCCAGCAAGTGTTTCCAAGATGTGCAGGCA
ACGATTCTGTAAAGTACTGAAGCCTCATTCAAACATAGTATATGTGCTGC
CGAAGCGAGCACTTAACAAGGCTTGCGGCCGCCCACTCACCTGCAATTGT
CACGCACAAGAGTTCCGTAGCTGTTCAAGTTTGTGTTTCAACTGTTCTCG
TCGTTTCCGCAACAAGTCCTCTTCAGAAATGAGCTTTTGCTCCTCTGCTT
GGACGGACAGGATGTATGCTGTGGCTTTTTTAAGGATAACTACCTTGGGG
GCCTTTTCATTGTTTTCCAACTCCGGGATCTGGTCACGCAGGGCAAAAAA
GCTCCGTTTTAGCTCGTTCCTCCTCTGGCGCTCCAAGACGTTGTGTGTTC
GCCTCTTGACATTCTCCTCGGTGTCCGAGGACCTGGGGCTGGTGCATTTT
CGGTTGTTGCTGATCTGTCTCAGGACTCTGACACTGTCCAACTTGACCCT
CTTGGCAGCAGGATAGTCCTTCCGAGTGGAGGAGGCGCTGCGTAGTTGT
GCTGATGTGTGGAGACGTGGCACCTCTTGAGGACCAGTGGGCTGTGAGGA
GGTTTGCTGTGGCCTCCAGCAGAAGGTGATCCAGACTCTGACCTTTTGCC
AGGAGCCTGCCTCTTTTCCACAGAAACAACATCGATTTCTTCCTCATCTT
CTTGTTCCTCCTCAGAGTCGCTGCTGGTGGTGGGCGGTGTCTCCTCATGG
AGCACCAGGGGCTCGGGGCTGCCCTGCGGGGAGGACTCCGTCGAGGAGAG
CAGAGAATCCGAGGACGGAGAGAAGGCGCTGGAGTCTTGCGAGGCGCAGG
ACTTGGGCGAGCTGCTGTCGTTGAGAGGGTAGGGGAAGACCACCGAGGGG
TCGATGCACTCTGAGGCGGCGGCGCTCAGATCCTGCAGGTACAAGCTGGA
GGTGGAGCAGACGCTGTGGCCGCGGGCGGGGTTCGGGCTGCCGCTGTCTT
TGCGCGCAGCCTGGTAGGAGGCCAGCTTCTCTGAGACGAGCTTGGCGGCG
GCCGAGAAGCCGCTCCACATACAGTCCTGGATGATGATGTTTTGATGAAG
GTCTCGTCGTCCGGGTCGCAGATGAAACTCTGGTTCACCATGTCTCCTCC
CAGCAGCTCGGTCACCATCTCCAGCTGGTCGGCCGTGGAGAAGCTCCCGC
CACCGCCGTCGTTGTCTCCCCGAAGGGAGAAGGGTGTGACCGCAACGTAG
GAGGGCGAGCAGAGCCCGGAGCGGCGGCTAGGGGACAGGGGCGGGTGGG
CAGCAGCTCGAATTTCTTCCAGATATCCTCGCTGGGCGCCGGGGCTGCA
GCTCGCTCTGCTGCTGCTGCTGGTAGAAGTTCTCCTCCTCGTCGCAGTAG
AAATACGGCTGCACCGAGTCGTAGTCGAGGTCATAGTTCCTGTTGGTGAA
GCTAACGTTGAGGGGTCTAGACATCAGCATCAGGCTGGCATAGTCAGGCA
CGTCATAAGGATAGCTCATCAGCATCAGGCTGGCATAGTCAGGCACGTCA
TAAGGATAGCTCATCAGCATCAGGCTGGCATAGTCAGGCACGTCATAAGG
ATAGCTATCCATggtggcgaccggtataacttcgtataaggtatcctata
cgaagttatccattcaggctgtgctagcatcaatggcatggcacaaagct
tagccataacttcgtataatgtgtactatacgaagttatcccgggttAAA -continued CGACCTGCAGCCAAGCTTATCGATAAAATAAAAGATTTTATTTAGTCTCC
AGAAAAGGGGGAATGAAAGACCCCACCTGTAGGTTTGGCAAGCTAGCT
TAAGTAACGCCATTTTGCAAGGCATGGAAAATACATAACTGAGAATAGAG
AAGTTCAGATCAAGGTTAGGAACAGAGAGACAGCAGAATATGGGCCAAAC
AGGATATCTGTGGTAAGCAGTTCCTGCCCCGGCTCAGGGCCAAGAACAGA
TGGTCCCCAGATGCGGTCCCGCCCTCAGCAGTTTCTAGAGAACCATCAGA
TGTTTCCAGGGTGCCCCAAGGACCTGAAAATGACCCTGTGCCTTATTTGA
ACTAACCAATCAGTTCGCTTCTCGCTTCTGTTCGCGCGCTTCTGCTCCCC
GAGCTCAATAAAAGAGCCCACAACCCCTCACTCGGCGCGCCAGTCCTCCG
ATAGACTGCGTCGCCCGGGTACCCGTGTATCCAATAAACCCTCTTGCAGT
TGCATCCGACTTGTGGTCTCGCTGTTCCTTGGGAGGGTCTCCTCTGAGTG
ATTGACTACCCGTCAGCGGGGTCTTTCATGGGTAACAGTTTCTTGAAGT
TGGAGAACAACATTCTGAGGGTAGGAGTCGAATATTAAGTAATCCTGACT
CAATTAGCCACTGTTTTGAATCCACATACTCCAATACTCCTGAAATAGTT
CATTATGGACAGCGCAGAAGAGCTGGGGAGAATTAATTCGTAATCATGGT
CATAGCTGTTTCCTGTGTGAAATTGTTATCCGCTCACAATTCCACACAAC
ATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAA
ACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAA
TACGGTTATCCACAGAATCAGGGGATAACGCAGGAAAGAACATGTGAGCA
AAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAA
GTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAA
CTATCGTCTTGAGTCCAACCCGGTAAGACACGACTTATCGCCACTGGCAG
CAGCCACTGGTAACAGGATTAGCAGAGCGAGGTATGTAGGCGGTGCTACA
GAGTTCTTGAAGTGGTGGCCTAACTACGGCTACACTAGAAGGACAGTATT
TGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTT
GATCTTTTCTACGGGGTCTGACGCTCAGTGGAACGAAAACTCACGTTAAG
GGATTTTGGTCATGAGATTATCAAAAAGGATCTTCACCTAGATCCTTTTA
AATTAAAAATGAAGTTTTAAATCAATCTAAAGTATATATGAGTAAACTTG
GTCTGACAGTTACCAATGCTTAATCAGTGAGGCACCTATCTCAGCGATCT
GTCTATTTCGTTCATCCATAGTTGCCTGACTCCCCGTCGTGTAGATAACT
ACGATACGGGAGGGCTTACCATCTGGCCCCAGTGCTGCAATGATACCGCG

```
AGACCCACGCTCACCGGCTCCAGATTTATCAGCAATAAACCAGCCAGCCG
GAAGGGCCGAGCGCAGAAGTGGTCCTGCAACTTTATCCGCCTCCATCCAG
TCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGT
CGTTTGGTATGGCTTCATTCAGCTCCGGTTCCCAACGATCAAGGCGAGTT
ACATGATCCCCATGTTGTGCAAAAAAGCGGTTAGCTCCTTCGGTCCTCC
GATCGTTGTCAGAAGTAAGTTGGCCGCAGTGTTATCACTCATGGTTATGG
CAGCACTGCATAATTCTCTTACTGTCATGCCATCCGTAAGATGCTTTTCT
GTGACTGGTGAGTACTCAACCAAGTCATTCTGAGAATAGTGTATGCGGCG
ACCGAGTTGCTCTTGCCCGGCGTCAATACGGGATAATACCGCGCCACATA
GCAGAACTTTAAAAGTGCTCATCATTGGAAAACGTTCTTCGGGGCGAAAA
CTCTCAAGGATCTTACCGCTGTTGAGATCCAGTTCGATGTAACCCACTCG
TGCACCCAACTGATCTTCAGCATCTTTTACTTTCACCAGCGTTTCTGGGT
GAGCAAAAACAGGAAGGCAAAATGCCGCAAAAAAGGGAATAAGGGCGACA
CGGAAATGTTGAATACTCATACTCTTCCTTTTTCAATATTATTGAAGCAT
TTATCAGGGTTATTGTCTCATGAGCGGATACATATTTGAATGTATTTAGA
AAAATAAACAAATAGGGGTTCCGCGCACATTTCCCCGAAAAGTGCCACCT
GACGTCTAAGAAACCATTATTATCATGACATTAACCTATAAAAATAGGCG
TATCACGAGGCCCTTTCGTCTCGCGCGTTTCGGTGATGACGGTGAAAACC
TCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTG
TCGGGGCTGGCTTAACTATGCGGCATCAGAGCAGATTGTACTGAGAGTGC
ACCATATGCGGTGTGAAATACCGCACAGATGCGTAAGGAGAAAATACCGC
ATCAGGCGCCATTCGCCATTCAGGCTGCGCAACTGTTGGGAAGGGCGATC
GGTGCGGGCCTCTTCGCTATTACGCCAGCTGGCGAAAGGGGGATGTGCTG
CAAGGCGATTAAGTTGGGTAACGCCAGGGTTTTCCCAGTCACGACGTTGT
AAAACGACGGCCAAGGAAGCAGCCCAGTAGTAGGTTGAGGCCGTTGAGC
ACCGCCGCCGCAAGGAATGGTGCATGCAAGGAGATGGCGCCCAACAGTCC
CCCGGCCACGGGGCCTGCCACCATACCCACGCCGAAACAAGCGCTCATGA
GCCCGAAGTGGCGAGCCCGATCTTCCCCATCGGTGATGTCGGCGATATAG
GCGCCAGCAACCGCACCTGTGGCGCCGGTGATGCCGGCCACGATGCGTCC
GGCGTAGAGGCGATTAGTCCAATTTGTTAAAGACAGGATATCAGTGGTCC
AGGCTCTAGTTTTGACTCAACAATATCACCAGCTGAAGCCTATAGAGTAC
GAGCCATAGATAAAATAAAAGATTTTATTTAGTCTCCAGAAAAAGGGGGG
AA
```

The MSCV FLIP-p53 sequence was as follows (SEQ ID NO: 22):

```
TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGGAGACCCCTGCCT
AGGGACCACCGACCCCCCGCCGGGAGGTAAGCTGGCCAGCGGTCGTTTC
GTGTCTGTCTCTGTCTTTGTGCGTGTTTGTGCCGGCATCTAATGTTTGCG
CCTGCGTCTGTACTAGTTAGCTAACTAGCTCTGTATCTGGCGGACCCGTG
GTGGAACTGACGAGTTCTGAACACCCGGCCGCAACCCTGGGAGACGTCCC
AGGGACTTTGGGGGCCGTTTTTGTGGCCCGACCTGAGGAAGGGAGTCGAT
GTGGAATCCGACCCCGTCAGGATATGTGGTTCTGGTAGGAGACGAGAACC
TAAAACAGTTCCCGCCTCCGTCTGAATTTTTGCTTTCGGTTTGGAACCGA
AGCCGCGCGTCTTGTCTGCTGCAGCGCTGCAGCATCGTTCTGTGTTGTCT
CTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATC
GCTCACAACCAGTCGGTAGATGTCAAGAAGAGACGTTGGGTTACCTTCTG
CTCTGCAGAATGGCCAACCTTTAACGTCGGATGGCCGCGAGACGGCACCT
TTAACCGAGACCTCATCACCCAGGTTAAGATCAAGGTCTTTTCACCTGGC
CCGCATGGACACCCAGACCAGGTCCCCTACATCGTGACCTGGGAAGCCTT
GGCTTTTGACCCCCCTCCCTGGGTCAAGCCCTTTGTACACCCTAAGCCTC
CGCCTCCTCTTCCTCCATCCGCCCCGTCTCTCCCCCTTGAACCTCCTCGT
TCGACCCCGCCTCGATCCTCCCTTTATCCAGCCCTCACTCCTTCTCTAGG
CGCCGGAATTAGAtccataacttcgtataggatatccttatacgaagttat
ctcaggtaccgccaccatgaccgagtacaagcccacggtgcgcctcgcca
ccgcgacgacgtccccagggccgtacgcaccctcgccgccgcgttcgcc
gactaccccgccacgcgccacaccgtcgatccggaccgccacatcgagcg
ggtcaccgagctgcaagaactcttcctcacgcgcgtcgggctcgacatcg
gcaaggtgtgggtcgcggacgacggcgccgcggtggcggtctggaccacg
ccggagagcgtcgaagcggggcggtgttcgccgagatcggcccgcgcat
ggccgagttgagcggttcccggctggccgcgcagcaacagatgaaggcc
tcctggcgccgcaccggcccaaggagcccgcgtggttcctggccaccgtc
ggcgtctcgcccgaccaccagggcaagggtctgggcagcgccgtcgtgct
ccccggagtggaggcggccgagcgcgccggggtgcccgccttcctggaga
cctccgcgcccgcaacctcccctctacgagcggctcggcttcaccgtc
accgccgacgtcgaggtgcccgaaggaccgcgcacctggtgcatgacccg
caagcccggtgccctgtacaagaaacagaaaattgtggcaccagtgaaac
agactttgaattttgaccttctcaagttggcgggagacgtcgagtccaac
```

-continued

```
cctgggcccatgaacccagccatcagcgtcgctcctgctctcagtctt
gcaggtgtcccgagggcagaaggtgaccagcctgacagcctgcctggtga
accaaaaccttcgcctggactgccgccatgagaataacaccaaggataac
tccatccagcatgagttcagcctgacccgagagaagaggaagcacgtgct
ctcaggcaccctcgggatacccgagcacacgtaccgctcccgcgtcaccc
tctccaaccagccctatatcaaggtccttaccctagccaacttcaccacc
aaggatgagggcgactactttgtgagcttcgagtctcgggcgcgaatcc
catgagctccaataaaagtatcagtgtgtatagagacaaactggtcaagt
gtggcggcataagcctgctggttcagaacacatcctggatgctgctgctg
ctgctttccctctccctcctccaagccctggacttcattctctgtgatc
tagaagccataacttcgtatagtacacattatacgaagttatGTTTAAAC
GCATTAGTCTTCCAATTGAAAAAAGTGATTTAATTTATACCATTTTAATT
CAGCTTTGTAAAAATGTATCAAAGAGATAGCAAGGTATTCAGTTTTAGTA
AACAAGATAATTGCTCCTAAAGTAGCCCCTTGAATTCCGAGGCAGTAGGC
ATCCACTACAAGTACATGTGTAATACATCTGTGGCTTCACTATTACACAT
GTACTTGTAGTGGGCGCTCACTGTCAACAGCAATATACCTTCTCGAGCCT
TCTGTTGGGTTAACCTGAAGAAGTAATCCCAGCAAGTGTTTCCAAGATGT
GCAGGCAACGATTCTGTAAAGTACTGAAGCCTCATTCAAACATAGTATAT
GTGCTGCCGAAGCGAGCACTTAACAAGGCTTGCGGCCGCtacttgtacag
ctcgtccatgccgagagtgatcccggcggcggtcacgaactccagcagga
ccatgtgatcgcgcttctcgttgggtgtctttgctcagggcggactgggtg
ctcaggtagtggttgtcgggcagcagcacgggccgtcgccgatggggt
gttctgctggtagtggtcggcgagctgcacgctgccgtcctcgatgttgt
ggcggatcttgaagttcaccttgatgccgttcttctgcttgtcggccatg
atatagacgttgtggctgttgtagttgtactccagcttgtgcccaggat
gttgccgtcctccttgaagtcgatgcccttcagctcgatgcggttcacca
gggtgtcgccctcgaacttcacctcggcgcgggtcttgtagttgccgtcg
tccttgaagaagatggtgcgctcctggacgtagccttcgggcatggcgga
cttgaagaagtcgtgctgcttcatgtggtcggggtagcggctgaagcact
gcacgccgtaggtcagggtggtcacgagggtgggccagggcacgggcagc
ttgccggtggtgcagatgaacttcagggtcagcttgccgtaggtggcatc
gccctcgccctcgccggacacgctgaacttgtggccgtttacgtcgcgt
ccagctcgaccaggatgggcaccaccccggtgaacagctcctcgcccttg
ctcaccatggtggcgaccggtataacttcgtataaggtatcctatacgaa
gttatccattcaggctgtgctagcatcaatggcatggcacaaagcttagc
cataacttcgtataatgtgtactatacgaagttatcccgggttAAACGAC
CTGCAGCCAAGCTTATCGATAAAATAAAAGATTTTATTTAGTCTCCAGAA
AAAGGGGGGAATGAAAGACCCCACCTGTAGGTTTGGCAAGCTAGCTTAAG
TAACGCCATTTTGCAAGGCATGGAAAATACATAACTGAGAATAGAGAAGT
TCAGATCAAGGTTAGGAACAGAGAGACAGCAGAATATGGGCCAAACAGGA
TATCTGTGGTAAGCAGTTCCTGCCCCGGCTCAGGGCCAAGAACAGATGGT
```

-continued

```
CCCCAGATGCGGTCCCGCCCTCAGCAGTTTCTAGAGAACCATCAGATGTT
TCCAGGGTGCCCCAAGGACCTGAAAATGACCCTGTGCCTTATTTGAACTA
ACCAATCAGTTCGCTTCTCGCTTCTGTTCGCGCGCTTCTGCTCCCCGAGC
TCAATAAAAGAGCCCACAACCCCTCACTCGGCGCGCCAGTCCTCCGATAG
ACTGCGTCGCCCGGGTACCCGTGTATCCAATAAACCCTCTTGCAGTTGCA
TCCGACTTGTGGTCTCGCTGTTCCTTGGGAGGGTCTCCTCTGAGTGATTG
ACTACCCGTCAGCGGGGGTCTTTCATGGGTAACAGTTTCTTGAAGTTGGA
GAACAACATTCTGAGGGTAGGAGTCGAATATTAAGTAATCCTGACTCAAT
TAGCCACTGTTTTGAATCCACATACTCCAATACTCCTGAAATAGTTCATT
ATGGACAGCGCAGAAGAGCTGGGGAGAATTAATTCGTAATCATGGTCATA
GCTGTTTCCTGTGTGAAATTGTTATCCGCTCACAATTCCACACAACATAC
GAGCCGGAAGCATAAAGTGTAAAGCCTGGGGTGCCTAATGAGTGAGCTAA
CTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACG
GTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCA
GAGGTGGCGAAACCCGACAGGACTATAAAGATACCAGGCGTTTCCCCCTG
GAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTAT
CGTCTTGAGTCCAACCCGGTAAGACACGACTTATCGCCACTGGCAGCAGC
CACTGGTAACAGGATTAGCAGAGCGAGGTATGTAGGCGGTGCTACAGAGT
TCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAAATT
AAAAATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTACGA
TACGGGAGGGCTTACCATCTGGCCCCAGTGCTGCAATGATACCGCGAGAC
CCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTT
```

```
TGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGC
ACTGCATAATTCTCTTACTGTCATGCCATCCGTAAGATGCTTTTCTGTGA
CTGGTGAGTACTCAACCAAGTCATTCTGAGAATAGTGTATGCGGCGACCG
AGTTGCTCTTGCCCGGCGTCAATACGGGATAATACCGCGCCACATAGCAG
AACTTTAAAAGTGCTCATCATTGGAAAACGTTCTTCGGGGCGAAAACTCT
CAAGGATCTTACCGCTGTTGAGATCCAGTTCGATGTAACCCACTCGTGCA
CCCAACTGATCTTCAGCATCTTTTACTTTCACCAGCGTTTCTGGGTGAGC
AAAAACAGGAAGGCAAAATGCCGCAAAAAAGGGAATAAGGGCGACACGGA
AATGTTGAATACTCATACTCTTCCTTTTTCAATATTATTGAAGCATTTAT
CAGGGTTATTGTCTCATGAGCGGATACATATTTGAATGTATTTAGAAAAA
TAAACAAATAGGGGTTCCGCGCACATTTCCCCGAAAAGTGCCACCTGACG
CTAAGAAACCATTATTATCATGACATTAACCTATAAAAATAGGCGTATCA
CGAGGCCCTTTCGTCTCGCGCGTTTCGGTGATGACGGTGAAAACCTCTGA
CACATGCAGCTCCCGGAGACGGTCACAGCTTGTCTGTAAGCGGATGCCGG
GAGCAGACAAGCCCGTCAGGGCGCGTCAGCGGGTGTTGGCGGGTGTCGG
GCTGGCTTAACTATGCGGCATCAGAGCAGATTGTACTGAGAGTGCACCAT
ATGCGGTGTGAAATACCGCACAGATGCGTAAGGAGAAAATACCGCATCAG
GCGCCATTCGCCATTCAGGCTGCGCAACTGTTGGGAAGGGCGATCGGTGC
GGGCCTCTTCGCTATTACGCCAGCTGGCGAAAGGGGGATGTGCTGCAAGG
CGATTAAGTTGGGTAACGCCAGGGTTTTCCCAGTCACGACGTTGTAAAAC
GACGGCGCAAGGAAGCAGCCCAGTAGTAGGTTGAGGCCGTTGAGCACCGC
CGCCGCAAGGAATGGTGCATGCAAGGAGATGGCGCCCAACAGTCCCCCGG
CCACGGGGCCTGCCACCATACCCACGCCGAAACAAGCGCTCATGAGCCCG
AAGTGGCGAGCCCGATCTTCCCCATCGGTGATGTCGGCGATATAGGCGCC
AGCAACCGCACCTGTGGCGCCGGTGATGCCGGCCACGATGCGTCCGGCGT
AGAGGCGATTAGTCCAATTTGTTAAAGACAGGATATCAGTGGTCCAGGCT
CTAGTTTTGACTCAACAATATCACCAGCTGAAGCCTATAGAGTACGAGCC
ATAGATAAAATAAAAGATTTTATTTAGTCTCCAGAAAAAGGGGGGAA.
```

The MSCV FLIP-PTEN construct comprises a sequence as follows (SEQ ID NO: 23):

```
TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGGAGACCCCTGCCT
AGGGACCACCGACCCCCCCGCCGGGAGGTAAGCTGGCCAGCGGTCGTTTC
GTGTCTGTCTCTGTCTTTGTGCGTGTTTGTGCCGGCATCTAATGTTTGCG
CCTGCGTCTGTACTAGTTAGCTAACTAGCTCTGTATCTGGCGGACCCGTG
GTGGAACTGACGAGTTCTGAACACCCGGCCGCAAACCCTGGGAGACGTCCC
AGGGACTTTGGGGGCCGTTTTTGTGGCCCGACCTGAGGAAGGGAGTCGAT
GTGGAATCCGACCCCGTCAGGATATGTGGTTCTGGTAGGAGACGAGAACC
TAAAACAGTTCCCGCCTCCGTCTGAATTTTTGCTTTCGGTTTGGAACCGA
AGCCGCGCGTCTTGTCTGCTGCAGCGCTGCAGCATCGTTCTGTGTTGTCT
CTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATC
GCTCACAACCAGTCGGTAGATGTCAAGAAGAGACGTTGGGTTACCTTCTG
CTCTGCAGAATGGCCAACCTTTAACGTCGGATGGCCGCGAGACGGCACCT
TTAACCGAGACCTCATCACCCAGGTTAAGATCAAGGTCTTTTCACCTGGC
CCGCATGGACACCCAGACCAGGTCCCCTACATCGTGACCTGGGAAGCCTT
GGCTTTTGACCCCCCTCCCTGGGTCAAGCCCTTTGTACACCCTAAGCCTC
CGCCTCCTCTTCCTCCATCCGCCCCGTCTCTCCCCCTTGAACCTCCTCGT
TCGACCCCGCCTCGATCCTCCCTTTATCCAGCCCTCACTCCTTCTCTAGG
CGCCGGAATTAGAtccataacttcgtataggatacccttatacgaagttat
ctcaggtaccgccaccatgaccgagtacaagcccacggtgcgcctcgcca
cccgcgacgacgtccccagggccgtacgcaccctcgccgccgcgttcgcc
gactaccccgccacgcgccacaccgtcgatccggaccgccacatcgagcg
ggtcaccgagctgcaagaactcttcctcacgcgcgtcgggctcgacatcg
gcaaggtgtgggtcgcggacgacggcgccgcggtggcggtctggaccacg
ccggagagcgtcgaagcggggcggtgttcgccgagatcggcccgcgcat
ggccgagttgagcggttcccggctggccgcgcagcaacagatggaaggcc
tcctggcgccgcaccggcccaaggagcccgcgtggttcctggccaccgtc
ggcgtctcgcccgaccaccagggcaagggtctgggcagcgccgtcgtgct
ccccggagtggaggcggccgagcgcgccggggtgcccgccttcctggaga
cctccgcgccccgcaacctcccccttctacgagcggctcggcttcaccgtc
accgccgacgtcgaggtgcccgaaggaccgcgcacctggtgcatgacccg
caagcccggtgcctgtacaagaaacagaaaattgtggcaccagtgaaac
agactttgaattttgaccttctcaagttggcgggagacgtcgagtccaac
cctgggcccatgaacccagccatcagcgtcgctctcctgctctcagtctt
gcaggtgtcccgagggcagaaggtgaccagcctgacagcctgcctggtga
accaaaaccttcgcctggactgccgccatgagaataacaccaaggataac
tccatccagcatgagttcagcctgacccgagagaagaggaagcacgtgct
ctcaggcacctcgggatacccgagcacacgtaccgctcccgcgtcaccc
tctccaaccagccctatatcaaggtccttaccctagccaacttcaccacc
```

-continued aaggatgagggcgactactttttgtgagcttcgagtctcgggcgcgaatcc
catgagctccaataaaagtatcagtgtgtatagagacaaactggtcaagt
gtggcggcataagcctgctggttcagaacacatcctggatgctgctgctg
ctgctttccctctccctcctccaagccctggacttcatttctctgtgatc
tagaagccataacttcgtatagtacacattatacgaagttatGTTTAAAC
GCATTAGTCTTCCAATTGAAAAAAGTGATTTAATTTATACCATTTTAATT
CAGCTTTGTAAAAATGTATCAAAGAGATAGCAAGGTATTCAGTTTTAGTA
AACAAGATAATTGCTCCTAAAGTAGCCCCTTGAATTCCGAGGCAGTAGGC
AAGGTGAAACTATACTTTACAAATACATCTGTGGCTTCACTATTTGTAAA
GTATAGTTTCACCGCGCTCACTGTCAACAGCAATATACCTTCTCGAGCCT
TCTGTTGGGTTAACCTGAAGAAGTAATCCCAGCAAGTGTTTCCAAGATGT
GCAGGCAACGATTCTGTAAAGTACTGAAGCCTCATTCAAACATAGTATAT
GTGCTGCCGAAGCGAGCACTTAACAAGGCTTGCGGCCGCtacttgtacag
ctcgtccatgccgagagtgatcccggcggcggtcacgaactccagcagga
ccatgtgatcgcgcttctcgttggggtctttgctcagggcggactgggtg
ctcaggtagtggttgtcgggcagcagcacggggccgtcgccgatgggggt
gttctgctggtagtggtcggcgagctgcacgctgccgtcctcgatgttgt
ggcggatcttgaagttcacttgatgccgttcttctgcttgtcggccatg
atatagacgttgtggctgttgtagttgtactccagcttgtgccccaggat
gttgccgtcctccttgaagtcgatgcccttcagctcgatgcggttcacca
gggtgtcgccctcgaacttcacctcggcgcgggtcttgtagttgccgtcg
tccttgaagaagatggtgcgctcctggacgtagccttcgggcatggcgga
cttgaagaagtcgtgctgcttcatgtggtcggggtagcggctgaagcact
gcacgccgtaggtcagggtggtcacgagggtgggccagggcacgggcagc
ttgccggtggtgcagatgaacttcagggtcagcttgccgtaggtggcatc
gccctcgccctcgccggacacgctgaacttgtggccgtttacgtcgccgt
ccagctcgaccaggatgggcaccaccccggtgaacagctcctcgcccttg
ctcaccatggtggcgaccggtataacttcgtataaggtatcctatacgaa
gttatccattcaggctgtgctagcatcaatggcatggcacaaagcttagc
cataacttcgtataatgtgtactatacgaagttatcccgggttAAACGAC
CTGCAGCCAAGCTTATCGATAAAATAAAAGATTTTATTTAGTCTCCAGAA
AAAGGGGGGAATGAAAGACCCCACCTGTAGGTTTGGCAAGCTAGCTTAAG
TAACGCCATTTTGCAAGGCATGGAAAATACATAACTGAGAATAGAGAAGT
TCAGATCAAGGTTAGGAACAGAGAGACAGCAGAATATGGGCCAAACAGGA
TATCTGTGGTAAGCAGTTCCTGCCCCGGCTCAGGGCAAGAACAGATGGT
CCCCAGATGCGGTCCCGCCCTCAGCAGTTTCTAGAGAACCATCAGATGTT
TCCAGGGTGCCCCAAGGACCTGAAAATGACCCTGTGCCTTATTTGAACTA
ACCAATCAGTTCGCTTCTCGCTTCTGTTCGCGCGCTTCTGCTCCCCGAGC
TCAATAAAAGAGCCCACAACCCCTCACTCGGCGCGCCAGTCCTCCGATAG
ACTGCGTCGCCCGGGTACCCGTGTATCCAATAAACCCTCTTGCAGTTGCA -continued TCCGACTTGTGGTCTCGCTGTTCCTTGGGAGGGTCTCCTCTGAGTGATTG
ACTACCCGTCAGCGGGGGTCTTTCATGGGTAACAGTTTCTTGAAGTTGGA
GAACAACATTCTGAGGGTAGGAGTCGAATATTAAGTAATCCTGACTCAAT
TAGCCACTGTTTTGAATCCACATACTCCAATACTCCTGAAATAGTTCATT
ATGGACAGCGCAGAAGAGCTGGGGAGAATTAATTCGTAATCATGGTCATA
GCTGTTTCCTGTGTGAAATTGTTATCCGCTCACAATTCCACACAACATAC
GAGCCGGAAGCATAAAGTGTAAAGCCTGGGGTGCCTAATGAGTGAGCTAA
CTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACG
GTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCA
GAGGTGGCGAAACCCGACAGGACTATAAAGATACCAGGCGTTTCCCCCTG
GAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTAT
CGTCTTGAGTCCAACCCGGTAAGACACGACTTATCGCCACTGGCAGCAGC
CACTGGTAACAGGATTAGCAGAGCGAGGTATGTAGGCGGTGCTACAGAGT
TCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAAATT
AAAAATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTACGA
TACGGGAGGGCTTACCATCTGGCCCCAGTGCTGCAATGATACCGCGAGAC
CCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTT
TGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGC
ACTGCATAATTCTCTTACTGTCATGCCATCCGTAAGATGCTTTTCTGTGA
CTGGTGAGTACTCAACCAAGTCATTCTGAGAATAGTGTATGCGGCGACCG
AGTTGCTCTTGCCCGGCGTCAATACGGGATAATACCGCGCCACATAGCAG AACTTTAAAAGTGCTCATCATTGGAAAACGTTCTTCGGGGCGAAAACTCT
CAAGGATCTTACCGCTGTTGAGATCCAGTTCGATGTAACCCACTCGTGCA
CCCAACTGATCTTCAGCATCTTTTACTTTCACCAGCGTTTCTGGGTGAGC
AAAAACAGGAAGGCAAAATGCCGCAAAAAAGGGAATAAGGGCGACACGGA
AATGTTGAATACTCATACTCTTCCTTTTTCAATATTATTGAAGCATTTAT
CAGGGTTATTGTCTCATGAGCGGATACATATTTGAATGTATTTAGAAAAA
TAAACAAATAGGGGTTCCGCGCACATTTCCCCGAAAAGTGCCACCTGACG
TCTAAGAAACCATTATTATCATGACATTAACCTATAAAAATAGGCGTATC
ACGAGGCCCTTTCGTCTCGCGCGTTTCGGTGATGACGGTGAAAACCTCTG
ACACATGCAGCTCCCGGAGACGGTCACAGCTTGTCTGTAAGCGGATGCCG
GGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCA
TATGCGGTGTGAAATACCGCACAGATGCGTAAGGAGAAAATACCGCATCA
GGCGCCATTCGCCATTCAGGCTGCGCAACTGTTGGGAAGGGCGATCGGTG
CGGGCCTCTTCGCTATTACGCCAGCTGGCGAAAGGGGGATGTGCTGCAAG
GCGATTAAGTTGGGTAACGCCAGGGTTTTCCCAGTCACGACGTTGTAAAA
CGACGGCGCAAGGAAGCAGCCCAGTAGTAGGTTGAGGCCGTTGAGCACCG
CCGCCGCAAGGAATGGTGCATGCAAGGAGATGGCGCCCAACAGTCCCCCG
GCCACGGGGCCTGCCACCATACCCACGCCGAAACAAGCGCTCATGAGCCC
GAAGTGGCGAGCCCGATCTTCCCCATCGGTGATGTCGGCGATATAGGCGC
CAGCAACCGCACCTGTGGCGCCGGTGATGCCGGCCACGATGCGTCCGGCG
TAGAGGCGATTAGTCCAATTTGTTAAAGACAGGATATCAGTGGTCCAGGC
TCTAGTTTTGACTCAACAATATCACCAGCTGAAGCCTATAGAGTACGAGC
CATAGATAAAATAAAAGATTTTATTTAGTCTCCAGAAAAAGGGGGAA The MSCV FLIPi Puro2AGFP/Thy1.1-miR-FF construct comprises a sequence as follows (SEQ ID NO: 24):

TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGGAGACCCCTGCCT
AGGGACCACCGACCCCCCCGCCGGGAGGTAAGCTGGCCAGCGGTCGTTTC
GTGTCTGTCTCTGTCTTTGTGCGTGTTTGTGCCGGCATCTAATGTTTGCG
CCTGCGTCTGTACTAGTTAGCTAACTAGCTCTGTATCTGGCGGACCCGTG

GTGGAACTGACGAGTTCTGAACACCCGGCCGCAACCCTGGGAGACGTCCC
AGGGACTTTGGGGGCCGTTTTTGTGGCCCGACCTGAGGAAGGGAGTCGAT
GTGGAATCCGACCCCGTCAGGATATGTGGTTCTGGTAGGAGACGAGAACC
TAAAACAGTTCCCGCCTCCGTCTGATTTTTGCTTTCGGTTTGGAACCGAA
GCCGCGCGTCTTGTCTGCTGCAGCGCTGCAGCATCGTTCTGTGTTGTCTC
TGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCG
CTCACAACCAGTCGGTAGATGTCAAGAAGAGACGTTGGGTTACCTTCTGC
TCTGCAGAATGGCCAACCTTTAACGTCGGATGGCCGCGAGACGGCACCTT
TAACCGAGACCTCATCACCCAGGTTAAGATCAAGGTCTTTTCACCTGGCC
CGCATGGACACCCAGACCAGGTCCCCTACATCGTGACCTGGGAAGCCTTG
GCTTTTGACCCCCCTCCCTGGGTCAAGCCCTTTGTACACCCTAAGCCTCC
GCCTCCTCTTCCTCCATCCGCCCCGTCTCTCCCCCTTGAACCTCCTCGTT
CGACCCCGCCTCGATCCTCCCTTTATCCAGCCCTCACTCCTTCTCTAGGC
GCCGGAATTAGAtccataacttcgtataaggataccttatacgaagttat
ctcaggtaccGCCACCATGGTGGAGTACAAGCCCACGGTGCGCCTCGCCA
CCCGCGACGACGTCCCCAGGGCCGTACGCACCCTCGCCGCCGCGTTCGCC
GACTACCCCGCCACGCGCCACACCGTCGATCCGGACCGCCACATCGAGCG
GGTCACCGAGCTGCAAGAACTCTTCCTCACGCGCGTCGGGCTCGACATCG
GCAAGGTGTGGGTCGCGGACGACGGCGCCGCGGTGGCGGTCTGGACCACG
CCGGAGAGCGTCGAAGCGGGGGCGGTGTTCGCCGAGATCGGCCCGCGCAT
GGCCGAGTTGAGCGGTTCCCGGCTGGCCGCGCAGCAACAGATGGAAGGCC
TCCTGGCGCCGCACCGGCCCAAGGAGCCCGCGTGGTTCCTGGCCACCGTC
GGCGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTC
ACCGCCGACGTCGAGGTGCCCGAAGGACCGCGCACCTGGTGCATGACCCG
CAAGCCCGGTGCCAAACAGAAAATTGTGGCACCAGTGAAACAGACTTTGA
ATTTTGACCTTCTCAAGTTGGCGGGAGACGTCGAGTCCAACCCTGGGCCC
GGCCCGGTCGCCACCATGGTGAGCAAGGGCGAGGAGCTGTTCACCGGGGT
GGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTG
AAGTTCATCTGCACCACCGGCAAGCTGCCCGTGCCCTGGCCCACCCTCGT
GACCACCCTGACCTACGGCGTGCAGTGCTTCAGCCGCTACCCCGACCACA
TGAAGCAGCACGACTTCTTCAAGTCCGCCATGCCCGAAGGCTACGTCCAG
GAGCGCACCATCTTCTTCAAGGACGACGGCAACTACAAGACCCGCGCCGA
GGTGAAGTTCGAGGGCGACACCCTGGTGAACCGCATCGAGCTGAAGGGCA
TCGACTTCAAGGAGGACGGCAACATCCTGGGGCACAAGCTGGAGTACAAC
TACAACAGCCACAACGTCTATATCATGGCCGACAAGCAGAAGAACGGCAT
CAAGGTGAACTTCAAGATCCGCCACAACATCGAGGACGGCAGCGTGCAGC -continued TCGCCGACCACTACCAGCAGAACACCCCCATCGGCGACGGCCCCGTGCTG
CTGCCCGACAACCACTACCTGAGCACCCAGTCCGCCCTGAGCAAAGACCC
CAACGAGAAGCGCGATCACATGGTCCTGCTGGAGTTCGTGACCGCCGCCG
GATCACTCTCGGCATGGACGAGCTGTACAAGTAGtctagaagccataact
tcgtatagtacacattatacgaaGTTTATGCATACCTGGAGGAAAAAAA
AAGGGGAGAGTCAGGGgtttaaacgcattagtcttccaatgaaaaaagtg
atttaatttataccatttaattcagctttgtaaaaatgtatcaaagaga
tagcaaggtattcagtttagtaaacaagataattgctcctaaagtagcc
ccttgaattcCGAGGCAGTAGGCAGGCTCCCGCTGAATTGGAATCCTACA
TCTGTGGCTTCACTAGGATTCCAATTCACGGGAGCTCGCTCACTGTCAAC
AGCAATATACCTTctcgagccttctgttgggttaacctgaagaagtaatc
ccagcaagtgtttccaagatgtgcaggcaacgattctgtaaagtactgaa
gcctcattcaaacatagtatatgtgctgccgaagcgagcacttaacaagg
cttgcggccgctacttgtacagctcgtccatgccgagagtgatcccggcg
gcgCCACTCACCTGCAATTGGGCCGCTCACAGAGAAATGAAGTCCAGGGC
TTGGAGGAGGGAGAGGGAAAGCAGCAGCAGCAGCATCCAGGATGTGTTCT
GAACCAGCAGGCTTATGCCGCCACACTTGACCAGTTTGTCTCTATACACA
CTGATACTTTTATTGGAGCTCATGGGATTCGCGCCCGAGACTCGAAGCTC
ACAAAAGTAGTCGCCCTCATCCTTGGTGGTGAAGTTGGCTAGGGTAAGGA
CCTTGATATAGGGCTGGTTGGAGAGGGTGACGCGGGAGCGGTACGTGTGC
TCGGGTATCCCGAGGGTGCCTGAGAGCACGTGCTTCCTCTTCTCTCGGGT
CAGGCTGAACTCATGCTGGATGGAGTTATCCTTGGTGTTATTCTCATGGC
GGCAGTCCAGGCGAAGGTTTTGGTTCACCAGGCAGGCTGTCAGGCTGGTC
ACCTTCTGCCCTCGGGACACCTGCAAGACTGAGAGCAGGAGAGCGACGCT
GATGGCTGGGTTCATggtggcgaccggtataacttcgtataaggtatcct
atacgaagttatccattcaggctgtgctagcatcaatggcatggcacaaa
gcttagccataacttcgtataatgtgtactatacgaagttatcccgggtt
AAACGACCTGCAGCCAAGCTTATCGATAAAATAAAAGATTTTATTTAGTC
TCCAGAAAAAGGGGGGAATGAAAGACCCCACCTGTAGGTTTGGCAAGCTA
GCTTAAGTAACGCCATTTTGCAAGGCATGGAAAATACATAACTGAGAATA
GAGAAGTTCAGATCAAGGTTAGGAACAGAGAGACAGCAGAATATGGGCCA
AACAGGATATCTGTGGTAAGCAGTTCCTGCCCCGGCTCAGGGCCAAGAAC
AGATGGTCCCCAGATGCGGTCCCGCCCTCAGCAGTTTCTAGAGAACCATC
AGATGTTTCCAGGGTGCCCCAAGGACCTGAAAATGACCCTGTGCCTTATT
TGAACTAACCAATCAGTTCGCTTCTCGCTTCTGTTCGCGCGCTTCTGCTC
CCCGAGCTCAATAAAAGAGCCCACAACCCCTCACTCGGCGCGCCAGTCCT
CCGATAGACTGCGTCGCCCGGGTACCCGTGTATCCAATAAACCCTCTTGC
AGTTGCATCCGACTTGTGGTCTCGCTGTTCCTTGGGAGGGTCTCCTCTGA
GTGATTGACTACCCGTCAGCGGGGGTCTTTCATGGGTAACAGTTTCTTGA
AGTTGGAGAACAACATTCTGAGGGTAGGAGTCGAATATTAAGTAATCCTG
ACTCAATTAGCCACTGTTTTGAATCCACATACTCCAATACTCCTGAAATA -continued GTTCATTATGGACAGCGCAGAAGAGCTGGGGAGAATTAATTCGTAATCAT
GGTCATAGCTGTTTCCTGTGTGAAATTGTTATCCGCTCACAATTCCACAC
AACATACGAGCCGGAAGCATAAAGTGTAAAGCCTGGGGTGCCTAATGAGT
GAGCTAACTCACATTAATTGCGTTGCGCTCACTGCCCGCTTTCCAGTCGG
GAAACCTGTCGTGCCAGCTGCATTAATGAATCGGCCAACGCGCGGGGAGA
GGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGG
TAATACGGTTATCCACAGAATCAGGGGATAACGCAGGAAAGAACATGTGA
GCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTC
AAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGT
AACTATCGTCTTGAGTCCAACCCGGTAAGACACGACTTATCGCCACTGGC
AGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCT
TTGATCTTTTCTACGGGGTCTGACGCTCAGTGGAACGAAAACTCACGTTA
AGGGATTTTGGTCATGAGATTATCAAAAAGGATCTTCACCTAGATCCTTT
TAAATTAAAAATGAAGTTTTAAATCAATCTAAAGTATATATGAGTAAACT
TGGTCTGACAGTTACCAATGCTTAATCAGTGAGGCACCTATCTCAGCGAT
CTGTCTATTTCGTTCATCCATAGTTGCCTGACTCCCCGTCGTGTAGATAA
CTACGATACGGGAGGGCTTACCATCTGGCCCCAGTGCTGCAATGATACCG
CGAGACCCACGCTCACCGGCTCCAGATTTATCAGCAATAAACCAGCCAGC
CGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAAT
AGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAG
TTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTAT
GGCAGCACTGCATAATTCTCTTACTGTCATGCCATCCGTAAGATGCTTTT
CTGTGACTGGTGAGTACTCAACCAAGTCATTCTGAGAATAGTGTATGCGG
CGACCGAGTTGCTCTTGCCCGGCGTCAATACGGGATAATACCGCGCCACA
TAGTAGAACTTTAAAAGTGCTCATCATTGGAAAACGTTCTTCGGGGCGAA
AACTCTCAAGGATCTTACCGCTGTTGAGATCCAGTTCGATGTAACCCACT
CGTGCACCCAACTGATCTTCAGCATCTTTTACTTTCACCAGCGTTTCTGG -continued

```
GTGAGCAAAAACAGGAAGGCAAAATGCCGCAAAAAAGGGAATAAGGGCGA
CACGGAAATGTTGAATACTCATACTCTTCCTTTTTCAATATTATTGAAGC
ATTTATCAGGGTTATTGTCTCATGAGCGGATACATATTTGAATGTATTTA
GAAAAATAAACAAATAGGGGTTCCGCGCACATTTCCCCGAAAAGTGCCAC
CTGACGTCTAAGAAACCATTATTATCATGACATTAACCTATAAAAATAGG
CGTATCACGAGGCCCTTTCGTCTCGCGCGTTTCGGTGATGACGGTGAAAA
CCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGG
TGTCGGGGCTGGCTTAACTATGCGGCATCAGAGCAGATTGTACTGAGAGT
GCACCATATGCGGTGTGAAATACCGCACAGATGCGTAAGGAGAAAATACC
GCATCAGGCGCCATTCGCCATTCAGGCTGCGCAACTGTTGGGAAGGGCGA
TCGGTGCGGCCTCTTCGCTATTACGCCAGCTGGCGAAAGGGGGATGTGC
TGCAAGGCGATTAAGTTGGGTAACGCCAGGGTTTTCCCAGTCACGACGTT
GTAAAACGACGGCGCAAGGAAGCAGCCCAGTAGTAGGTTGAGGCCGTTGA
GCACCGCCGCCGCAAGGAATGGTGCATGCAAGGAGATGGCGCCCAACAGT
CCCCCGGCCACGGGGCCTGCCACCATACCCACGCCGAAACAAGCGCTCAT
GAGCCCGAAGTGGCGAGCCCGATCTTCCCCATCGGTGATGTCGGCGATAT
AGGCGCCAGCAACCGCACCTGTGGCGCCGGTGATGCCGGCCACGATGCGT
CCGGCGTAGAGGCGATTAGTCCAATTTGTTAAAGACAGGATATCAGTGGT
CCAGGCTCTAGTTTTGACTCAACAATATCACCAGCTGAAGCCTATAGAGT
ACGAGCCATAGATAAAATAAAAGATTTTATTTAGTCTCCAGAAAAAGGGG
GGAA
```

The MSCV FLIPi Puro2AGFP/Thy1.1-miR-p53 construct comprises a sequence as follows (SEQ ID NO: 25):

```
TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGGAGACCCCTGCCT
AGGGACCACCGACCCCCCGCCGGGAGGTAAGCTGGCCAGCGGTCGTTTC
GTGTCTGTCTCTGTCTTTGTGCGTGTTTGTGCCGGCATCTAATGTTTGCG
CCTGCGTCTGTACTAGTTAGCTAACTAGCTCTGTATCTGGCGGACCCGTG
GTGGAACTGACGAGTTCTGAACACCCGGCCGCAACCCTGGGAGACGTCCC
AGGGACTTTGGGGGCCGTTTTTGTGGCCCGACCTGAGGAAGGGAGTCGAT
```

-continued

```
GTGGAATCCGACCCCGTCAGGATATGTGGTTCTGGTAGGAGACGAGAACC
TAAAACAGTTCCCGCCTCCGTCTGAATTTTTGCTTTCGGTTTGGAACCGA
AGCCGCGCGTCTTGTCTGCTGCAGCGCTGCAGCATCGTTCTGTGTTGTCT
CTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATC
GCTCACAACCAGTCGGTAGATGTCAAGAAGAGACGTTGGGTTACCTTCTG
CTCTGCAGAATGGCCAACCTTTAACGTCGGATGGCCGCGAGACGGCACCT
TTAACCGAGACCTCATCACCCAGGTTAAGATCAAGGTCTTTTCACCTGGC
CCGCATGGACACCCAGACCAGGTCCCCTACATCGTGACCTGGGAAGCCTT
GGCTTTTGACCCCCCTCCCTGGGTCAAGCCCTTTGTACACCCTAAGCCTC
CGCCTCCTCTTCCTCCATCCGCCCCGTCTCTCCCCCTTGAACCTCCTCGT
TCGACCCCGCCTCGATCCTCCCTTTATCCAGCCCTCACTCCTTCTCTAGG
CGCCGGAATTAGAtccataacttcgtataggatacctt atacgaagttat
ctcaggtaccGCCACCATGGTGGAGTACAAGCCCACGGTGCGCCTCGCCA
CCCCGCGACGACGTCCCCAGGGCCGTACGCACCCTCGCCGCCGCGTTCGCC
GACTACCCCGCCACGCGCCACACCGTCGATCCGGACCGCCACATCGAGCG
GGTCACCGAGCTGCAAGAACTCTTCCTCACGCGCGTCGGGCTCGACATCG
GCAAGGTGTGGGTCGCGGACGACGGCGCCGCGGTGGCGGTCTGGACCACG
CCGGAGAGCGTCGAAGCGGGGGCGGTGTTCGCCGAGATCGGCCCGCGCAT
GGCCGAGTTGAGCCGGTTCCCGGCTGGCCGCGCAGCAACAGATGGAAGGC
CTCCTGGCCGCCGCACCGGCCCAAGGAGCCCGCGTGGTTCCTGGCCACCGT
CGGCGTCTCGCCCGACCACCAGGGCAAGGGTCTGGGCAGCCGCGTCGTGC
TCCCCGGAGTGGAGGCGGCCGAGCGCGCCGGGGTGCCCGCCTTCCTGGAG
ACCTCCGCGCCCCGCAACCTCCCCTTCTACGAGCGGCTCGGCTTCACCGT
CACCGCCGACGTCGAGGTGCCCGAAGGACCGCGCACCTGGTGCATGACCC
GCAAGCCCGGTGCCAAACAGAAAATTGTGGCACCAGTGAAACAGACTTTG
AATTTTGACCTTCTCAAGTTGGCGGGAGACGTCGAGTCCAACCCTGGGCC
CGGCCCGGTCGCCACCATGGTGAGCAAGGGCGAGGAGCTGTTCACCGGGG
TGGTGCCCATCCTGGTCGAGCTGGACGGCGACGTAAACGGCCACAAGTTC
AGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCG
TGACCACCCTGACCTACGGCGTGCAGTGCTTCAGCCGCTACCCCGACCAC
ATGAAGCAGCACGACTTCTTCAAGTCCGCCATGCCCGAAGGCTACGTCCA
GGAGCGCACCATCTTCTTCAAGGACGACGGCAACTACAAGACCCGCGCCG
AGGTGAAGTTCGAGGGCGACACCCTGGTGAACCGCATCGAGCTGAAGGGC
ATCGACTTCAAGGAGGACGGCAACATCCTGGGGCACAAGCTGGAGTACAA
CTACAACAGCCACAACGTCTATATCATGGCCGACAAGCAGAAGAACGGCA
TCAAGGTGAACTTCAAGATCCGCCACAACATCGAGGACGGCAGCGTGCAG
CTCGCCGACCACTACCAGCAGAACACCCCCATCGGCGACGGCCCCGTGCT
GCTGCCCGACAACCACTACCTGAGCACCCAGTCCGCCCTGAGCAAAGACC
CCAACGAGAAGCGCGATCACATGGTCCTGCTGGAGTTCGTGACCGCCGCC
```

-continued

GGGATCACTCTCGGCATGGACGAGCTGTACAAGTAGtctagaagccataa
cttcgtatagtacacattatacgaaGTTTATGCATACCTGGAGGAAAAAA
AAAAGGGGAGAGTCAGGGGTTTAAACGCATTAGTCTTCCAATTGAAAAAA
GTGATTTAATTTATACCATTTTAATTCAGCTTTGTAAAAATGTATCAAAG
AGATAGCAAGGTATTCAGTTTTAGTAAACAAGATAATTGCTCCTAAAGTA
GCCCCTTGAATTCCGAGGCAGTAGGCATCCACTACAAGTACATGTGTAAT
ACATCTGTGGCTTCACTATTACACATGTACTTGTAGTGGGCGCTCACTGT
CAACAGCAATATACCTTCTCGAGCCTTCTGTTGGGTTAACCTGAAGAAGT
AATCCCAGCAAGTGTTTCCAAGATGTGCAGGCAACGATTCTGTAAAGTAC
TGAAGCCTCATTCAAACATAGTATATGTGCTGCCGAAGCGAGCACTTAAC
AAGGCTTGCGGCCGCCCACTCACCTGCAATTGGGCCGCTCACAGAGAAAT
GAAGTCCAGGGCTTGGAGGAGGGAGGGGAAAGCAGCAGCAGCAGCATCC
AGGATGTGTTCTGAACCAGCAGGCTTATGCCGCCACACTTGACCAGTTTG
TCTCTATACACACTGATACTTTTATTGGAGCTCATGGGATTCGCGCCCGA
GACTCGAAGCTCACAAAAGTAGTCGCCCTCATCCTTGGTGGTGAAGTTGG
CTAGGGTAAGGACCTTGATATAGGGCTGGTTGGAGAGGGTGACGCGGGAG
CGGTACGTGTGCTCGGGTATCCCGAGGGTGCCTGAGAGCACGTGCTTCCT
CTTCTCTCGGGTCAGGCTGAACTCATGCTGGATGGAGTTATCCTTGGTGT
TATTCTCATGGCGGCAGTCCAGGCGAAGGTTTTGGTTCACCAGGCAGGCT
GTCAGGCTGGTCACCTTCTGCCCTCGGGACACCTGCAAGACTGAGAGCAG
GAGAGCGACGCTGATGGCTGGGTTCATggtggcgaccggtataacttcgt
ataaggtatcctatacgaagttatccattcaggctgtgctagcatcaatg
gcatggcacaaagcttagccataacttcgtataatgtgtactatacgaag
ttatcccgggttAAACGACCTGCAGCCAAGCTTATCGATAAAATAAAGA
TTTTATTTAGTCTCCAGAAAAAGGGGGGAATGAAAGACCCCACCTGTAGG
TTTGGCAAGCTAGCTTAAGTAACGCCATTTTGCAAGGCATGGAAAATACA
TAACTGAGAATAGAGAAGTTCAGATCAAGGTTAGGAACAGAGAGCAGCAG
AATATGGGCCAAACAGGATATCTGTGGTAAGCAGTTCCTGCCCCGGCTCA
GGGCCAAGAACAGATGGTCCCCAGATGCGGTCCCGCCCTCAGCAGTTTCT
AGAGAACCATCAGATGTTTCCAGGGTGCCCCAAGGACCTGAAAATGACCC
TGTGCCTTATTTGAACTAACCAATCAGTTCGCTTCTCGCTTCTGTTCGCG
CGCTTCTGCTCCCCGAGCTCAATAAAAGAGCCCACAACCCCTCACTCGGC
GCGCCAGTCCTCCGATAGACTGCGTCGCCCGGGTACCCGTGTATCCAATA
AACCCTCTTGCAGTTGCATCCGACTTGTGGTCTCGCTGTTCCTTGGGAGG
GTCTCCTCTGAGTGATTGACTACCCGTCAGCGGGGGTCTTTCATGGGTAA
CAGTTTCTTGAAGTTGGAGAACAACATTCTGAGGGTAGGAGTCGAATATT
AAGTAATCCTGACTCAATTAGCCACTGTTTTGAATCCACATACTCCAATA
CTCCTGAAATAGTTCATTATGGACAGCGCAGAAGAGCTGGGGAGAATTAA
TTCGTAATCATGGTCATAGCTGTTTCCTGTGTGAAATTGTTATCCGCTCA
CAATTCCACACAACATACGAGCCGGAAGCATAAAGTGTAAAGCCTGGGGT -continued GCCTAATGAGTGAGCTAACTCACATTAATTGCGTTGCGCTCACTGCCCGC
TTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTC
ACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAA
AGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAA
AAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGC
GCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCT
CAAGAAGATCCTTTGATCTTTTCTACGGGGTCTGACGCTCAGTGGAACGA
AAACTCACGTTAAGGGATTTTGGTCATGAGATTATCAAAAAGGATCTTCA
CCTAGATCCTTTTAAATTAAAAATGAAGTTTTAAATCAATCTAAAGTATA
TATGAGTAAACTTGGTCTGACAGTTACCAATGCTTAATCAGTGAGGCACC
TATCTCAGCGATCTGTCTATTTCGTTCATCCATAGTTGCCTGACTCCCCG
TCGTGTAGATAACTACGATACGGGAGGGCTTACCATCTGGCCCCAGTGCT
GCAATGATACCGCGAGACCCACGCTCACCGGCTCCAGATTTATCAGCAAT
AAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATC
ACTCATGGTTATGGCAGCACTGCATAATTCTCTTACTGTCATGCCATCCG
TAAGATGCTTTTCTGTGACTGGTGAGTACTCAACCAAGTCATTCTGAGAA
TAGTGTATGCGGCGACCGAGTTGCTCTTGCCCGGCGTCAATACGGGATAA
TACCGCGCCACATAGCAGAACTTTAAAAGTGCTCATCATTGGAAAACGTT
CTTCGGGGCGAAAACTCTCAAGGATCTTACCGCTGTTGAGATCCAGTTCG
ATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGG
GAATAAGGGCGACACGGAAATGTTGAATACTCATACTCTTCCTTTTTCAA
TATTATTGAAGCATTTATCAGGGTTATTGTCTCATGAGCGGATACATATT
TGAATGTATTTAGAAAAATAAACAAATAGGGGTTCCGCGCACATTTCCCC

```
GAAAAGTGCCACCTGACGTCTAAGAAACCATTATTATCATGACATTAACC
TATAAAAATAGGCGTATCACGAGGCCCTTTCGTCTCGCGCGTTTCGGTGA
TGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCG
GGTGTTGGCGGGTGTCGGGGCTGGCTTAACTATGCGGCATCAGAGCAGAT
TGTACTGAGAGTGCACCATATGCGGTGTGAAATACCGCACAGATGCGTAA
GGAGAAAATACCGCATCAGGCGCCATTCGCCATTCAGGCTGCGCAACTGT
TGGGAAGGGCGATCGGTGCGGGCCTCTTCGCTATTACGCCAGCTGGCGAA
AGGGGGATGTGCTGCAAGGCGATTAAGTTGGGTAACGCCAGGGTTTTCCC
AGTCACGACGTTGTAAAACGACGGCGCAAGGAAGCAGCCCAGTAGTAGGT
TGAGGCCGTTGAGCACCGCCGCCGCAAGGAATGGTGCATGCAAGGAGATG
GCGCCCAACAGTCCCCCGGCCACGGGGCCTGCCACCATACCCACGCCGAA
ACAAGCGCTCATGAGCCCGAAGTGGCGAGCCCGATCTTCCCCATCGGTGA
TGTCGGCGATATAGGCGCCAGCAACCGCACCTGTGGCGCCGGTGATGCCG
GCCACGATGCGTCCGGCGTAGAGGCGATTAGTCCAATTTGTTAAAGACAG
GATATCAGTGGTCCAGGCTCTAGTTTTGACTCAACAATATCACCAGCTGA
AGCCTATAGAGTACGAGCCATAGATAAAATAAAAGATTTTATTTAGTCTC
CAGAAAAAGGGGGGAA
```

The MSCV FLIPi Puro2AGFP/Thy1.1-miR-PTEN construct comprises a sequence as follows (seq id no: 26):

```
TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGGAGACCCCTGCCT
AGGGACCACCGACCCCCCCGGGAGGTAAGCTGGCCAGCGGTCGTTTCGTG
TCTGTCTCTGTCTTTGTGCGTGTTTGTGCCGGCATCTAATGTTTGCGCCT
GCGTCTGTACTAGTTAGCTAACTAGCTCTGTATCTGGCGGACCCGTGGTG
GAACTGACGAGTTCTGAACACCCGGCCGCAACCCTGGGAGACGTCCCAGG
GACTTTGGGGGCCGTTTTTGTGGCCCGACCTGAGGAAGGGAGTCGATGTG
GAATCCGACCCCGTCAGGATATGTGGTTCTGGTAGGAGACGAGAACCTAA
AACAGTTCCCGCCTCCGTCTGAATTTTTGCTTTCGGTTTGGAACCGAAGC
CGCGCGTCTTGTCTGCTGCAGCGCTGCAGCATCGTTCTGTGTTGTCTCTG
TCTGACTGTGTTTCTGTATTTGTCTGAAAATTAGGGCCAGACTGTTACCA
CTCCCTTAAGTTTGACCTTAGGTCACTGGAAAGATGTCGAGCGGATCGCT
CACAACCAGTCGGTAGATGTCAAGAAGAGACGTTGGGTTACCTTCTGCTC
TGCAGAATGGCCAACCTTTAACGTCGGATGGCCGCGAGACGGCACCTTTA
ACCGAGACCTCATCACCCAGGTTAAGATCAAGGTCTTTTCACCTGGCCCG
CATGGACACCCAGACCAGGTCCCCTACATCGTGACCTGGGAAGCCTTGGC
TTTTGACCCCCCTCCCTGGGTCAAGCCCTTTGTACACCCTAAGCCTCCGC
CTCCTCTTCCTCCATCCGCCCCGTCTCTCCCCCTTGAACCTCCTCGTTCG
ACCCCGCCTCGATCCTCCCTTTATCCAGCCCTCACTCCTTCTCTAGGCGC
CGGAATTAGAtccataacttcgtataggatacgttatacgaagttatctc
aggtaccGCCACCATGGTGGAGTACAAGCCCACGGTGCGCCTCGCCACCC
GCGACGACGTCCCCAGGGGCCGTACGCACCCTCGCCGCCGCGTTCGCCGA
CTACCCCGCCACGCGCCACACCGTCGATCCGGACCGCCACATCGAGCGGG
TCACCGAGCTGCAAGAACTCTTCCTCACGCGCGTCGGGCTCGACATCGGC
AAGGTGTGGGTCGCGGACGACGGCGCCGCGGTGGCGGTCTGGACCACGCC
GGAGAGCGTCGAAGCGGGGGCGGTGTTCGCCGAGATCGGCCCGCGCATGG
CCGAGTTGAGCGGTTCCCGGCTGGCCGCGCAGCAACAGATGGAAGGCCTC
CTGGCGCCGCACCGGCCCAAGGAGCCCGCGTGGTTCCTGGCCACCGTCGG
CGTCTCGCCCGACCACCAGGGCAAGGGTCTGGGCAGCGCCGTCGTGCTCC
CCGGAGTGGAGGCGGCCGAGCGCGCCGGGGTGCCCGCCTTCCTGGAGACC
TCCGCGCCCCGCAACCTCCCCTTCTACGAGCGGCTCGGCTTCACCGTCAC
CGCCGACGTCGAGGTGCCCGAAGGACCGCGCACCTGGTGCATGACCCGCA
AGCCCGGTGCCAAACAGAAAATTGTGGCACCAGTGAAACAGACTTTGAAT
TTTGACCTTCTCAAGTTGGCGGGAGACGTCGAGTCCAACCCTGGGCCCGG
CCCGGTCGCCACCATGGTGAGCAAGGGCGAGGAGCTGTTCACCGGGGTGG
TGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAA
GTTCATCTGCACCACCGGCAAGCTGCCCGTGCCCTGGCCCACCCTCGTGA
CCACCCTGACCTACGGCGTGCAGTGCTTCAGCCGCTACCCCGACCACATG
AAGCAGCACGACTTCTTCAAGTCCGCCATGCCCGAAGGCTACGTCCAGGA
GCGCACCATCTTCTTCAAGGACGACGGCAACTACAAGACCCGCGCCGAGG
TGAAGTTCGAGGGCGACACCCTGGTGAACCGCATCGAGCTGAAGGGCATC
GACTTCAAGGAGGACGGCAACATCCTGGGGCACAAGCTGGAGTACAACTA
CAACAGCCACAACGTCTATATCATGGCCGACAAGCAGAAGAACGGCATCA
AGGTGAACTTCAAGATCCGCCACAACATCGAGGACGGCAGCGTGCAGCTC
GCCGACCACTACCAGCAGAACACCCCCATCGGCGACGGCCCCGTGCTGCT
GCCCGACAACCACTACCTGAGCACCCAGTCCGCCCTGAGCAAAGACCCCA
ACGAGAAGCGCGATCACATGGTCCTGCTGGAGTTCGTGACCGCCGCCGGG
ATCACTCTCGGCATGGACGAGCTGTACAAGTAGtctagaagccataactt
cgtatagtacacattatacgaaGTTTATGCATACCTGGAGGAAAAAAAA
AGGGGAGAGTCAGGGGTTTAAACGCATTAGTCTTCCAATTGAAAAAGTG
```

```
ATTTAATTTATACCATTTTAATTCAGCTTTGTAAAAATGTATCAAAGAGA
TAGCAAGGTATTCAGTTTTAGTAAACAAGATAATTGCTCCTAAAGTAGCC
CCTTGAATTCCGAGGCAGTAGGCAAGGTGAAACTATACTTTACAAATACA
TCTGTGGCTTCACTATTTGTAAAGTATAGTTTCACCGCGCTCACTGTCAA
CAGCAATATACCTTCTCGAGCCTTCTGTTGGGTTAACCTGAAGAAGTAAT
CCCAGCAAGTGTTTCCAAGATGTGCAGGCAACGATTCTGTAAAGTACTGA
AGCCTCATTCAAACATAGTATATGTGCTGCCGAAGCGAGCACTTAACAAG
GCTTGCGGCCGCCCACTCACCTGCAATTGGGCCGCTCACAGAGAAATGAA
GTCCAGGGCTTGGAGGAGGGAGAGGGAAAGCAGCAGCAGCAGCATCCAGG
ATGTGTTCTGAACCAGCAGGCTTATGCCGCCACACTTGACCAGTTTGTCT
CTATACACACTGATACTTTTATTGGAGCTCATGGGATTCGCGCCCGAGAC
TCGAAGCTCACAAAAGTAGTCGCCCTCATCCTTGGTGGTGAAGTTGGCTA
GGGTAAGGACCTTGATATAGGGCTGGTTGGAGAGGGTGACGCGGGAGCGG
TACGTGTGCTCGGGTATCCCGAGGGTGCCTGAGAGCACGTGCTTCCTCTT
CTCTCGGGTCAGGCTGAACTCATGCTGGATGGAGTTATCCTTGGTGTTAT
TCTCATGGCGGCAGTCCAGGCGAAGGTTTTGGTTCACCAGGCAGGCTGTC
AGGCTGGTCACCTTCTGCCCTCGGGACACCTGCAAGACTGAGAGCAGGAG
AGCGACGCTGATGGCTGGGTTCATggtggcgaccggtataacttcgtata
aggtatcctatacgaagttatccattcaggctgtgctagcatcaatggca
tggcacaaagcttagccataacttcgtataatgtgtactatacgaagtta
tcccgggttAAACGACCTGCAGCCAAGCTTATCGATAAAATAAAGATTT
TATTTAGTCTCCAGAAAAAGGGGGAATGAAAGACCCCACCTGTAGGTTT
GGCAAGCTAGCCTTAAGTAACGCCATTTTGCAAGGCATGGAAAATACATAA
CTGAGAATAGAGAAGTTCAGATCAAGGTTAGGAACAGAGAGACAGCAGAA
TATGGGCCAAACAGGATATCTGTGGTAAGCAGTTCCTGCCCCGGCTCAGG
GCCAAGAACAGATGGTCCCCAGATGCGGTCCCGCCCTCAGCAGTTTCTAG
AGAACCATCAGATGTTTCCAGGGTGCCCCAAGGACCTGAAAATGACCCTG
TGCCTTATTTGAACTAACCAATCAGTTCGCTTCTCGCTTCTGTTCGCGCG
CTTCTGCTCCCCGAGCTCAATAAAAGAGCCCACAACCCCTCACTCGGCGC
GCCAGTCCTCCGATAGACTGCGTCGCCCGGGTACCCGTGTATCCAATAAA
CCCTCTTGCAGTTGCATCCGACTTGTGGTCTCGCTGTTCCTTGGGAGGGT
CTCCTCTGAGTGATTGACTACCCGTCAGCGGGGGTCTTTCATGGGTAACA
GTTTCTTGAAGTTGGAGAACAACATTCTGAGGGTAGGAGTCGAATATTAA
GTAATCCTGACTCAATTAGCCACTGTTTTGAATCCACATACTCCAATACT
CCTGAAATAGTTCATTATGGACAGCGCAGAAGAGCTGGGAGAATTAATT
CGTAATCATGGTCATAGCTGTTTCCTGTGTGAAATTGTTATCCGCTCACA
ATTCCACACAACATACGAGCCGGAAGCATAAAGTGTAAAGCCTGGGGTGC
CTAATGAGTGAGCTAACTCACATTAATTGCGTTGCGCTCACTGCCCGCTT
TCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACT CAAAGGCGGTAATACGGTTATCCACAGAATCAGGGGATAACGCAGGAAAG
AACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAA
ATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGC
CTTATCCGGTAACTATCGTCTTGAGTCCAACCCGGTAAGACACGACTTAT
CGCCACTGGCAGCAGCCACTGGTAACAGGATTAGCAGAGCGAGGTATGTA
GGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAA
AAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAA
ACTCACGTTAAGGGATTTTGGTCATGAGATTATCAAAAAGGATCTTCACC
TAGATCCTTTTAAATTAAAAATGAAGTTTTAAATCAATCTAAAGTATATA
TGAGTAAACTTGGTCTGACAGTTACCAATGCTTAATCAGTGAGGCACCTA
TCTCAGCGATCTGTCTATTTCGTTCATCCATAGTTGCCTGACTCCCCGTC
GTGTAGATAACTACGATACGGGAGGGCTTACCATCTGGCCCCAGTGCTGC
AATGATACCGCGAGACCCACGCTCACCGGCTCCAGATTTATCAGCAATAA
ACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTTCTGTGACTGGTGAGTACTCAACCAAGTCATTCTGAGAATA
GTGTATGCGGCGACCGAGTTGCTCTTGCCCGGCGTCAATACGGGATAATA
CCGCGCCACATAGCAGAACTTTAAAAGTGCTCATCATTGGAAAACGTTCT
TCGGGGCGAAAACTCTCAAGGATCTTACCGCTGTTGAGATCCAGTTCGAT
GTAACCCACTCGTGCACCCAACTGATCTTCAGCATCTTTTACTTTCACCA
GCGTTTCTGGGTGAGCAAAAACAGGAAGGCAAAATGCCGCAAAAAAGGGA
ATAAGGGCGACACGGAAATGTTGAATACTCATACTCTTCCTTTTTCAATA
TTATTGAAGCATTTATCAGGGTTATTGTCTCATGAGCGGATACATATTTG
AATGTATTTAGAAAAATAAACAAATAGGGGTTCCGCGCACATTTCCCCGA
AAAGTGCCACCTGACGTCTAAGAAACCATTATTATCATGACATTAACCTA
TAAAAATAGGCGTATCACGAGGCCCTTTCGTCTCGCGCGTTTCGGTGATG
ACGGTGAAAACCTCTGACACATGCAGCTCCCGGAGACGGTCACAGCTTGT
```

-continued

```
CTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTG
TACTGAGAGTGCACCATATGCGGTGTGAAATACCGCACAGATGCGTAAGG
AGAAAATACCGCATCAGGCGCCATTCGCCATTCAGGCTGCGCAACTGTTG
GGAAGGGCGATCGGTGCGGGCCTCTTCGCTATTACGCCAGCTGGCGAAAG
GGGGATGTGCTGCAAGGCGATTAAGTTGGGTAACGCCAGGGTTTTCCCAG
TCACGACGTTGTAAAACGACGGCGCAAGGAAGCAGCCCAGTAGTAGGTTG
AGGCCGTTGAGCACCGCCGCCGCAAGGAATGGTGCATGCAAGGAGATGGC
GCCCAACAGTCCCCCGGCCACGGGCCTGCCACCATACCCACGCCGAAAC
AAGCGCTCATGAGCCCGAAGTGGCGAGCCCGATCTTCCCCATCGGTGATG
TCGGCGATATAGGCGCCAGCAACCGCACCTGTGGCGCCGGTGATGCCGGC
CACGATGCGTCCGGCGTAGAGGCGATTAGTCAATTTGTTAAAGACAGGA
TATCAGTGGTCCAGGCTCTAGTTTTGACTCAACAATATCACCAGCTGAAG
CCTATAGAGTACGAGCCATAGATAAAATAAAAGATTTTATTTAGTCTCCA
GAAAAAGGGGGGAA
```

The MSCV FLIPi Puro2AGFP/Thy1.1-miR-Dbl (p53 & PTEN) construct comprises a sequence as follows (seq id no: 27):

```
TGAAAGACCCCACCTGTAGGTTTGGCAAGCTAGCTTAAGTAACGCCATTT
TGCAAGGCATGGAAAATACATAACTGAGAATAGAGAAGTTCAGATCAAGG
TTAGGAACAGAGAGACAGCAGAATATGGGCCAAACAGGATATCTGTGGTA
AGCAGTTCCTGCCCCGGCTCAGGGCCAAGAACAGATGGTCCCCAGATGCG
GTCCCGCCCTCAGCAGTTTCTAGAGAACCATCAGATGTTTCCAGGGTGCC
CCAAGGACCTGAAAATGACCCTGTGCCTTATTTGAACTAACCAATCAGTT
CGCTTCTCGCTTCTGTTCGCGCGCTTCTGCTCCCCGAGCTCAATAAAAGA
GCCCACAACCCCTCACTCGGCGCGCCAGTCCTCCGATAGACTGCGTCGCC
CGGGTACCCGTATTCCCAATAAAGCCTCTTGCTGTTTGCATCCGAATCGT
GGACTCGCTGATCCTTGGGAGGGTCTCCTCAGATTGATTGACTGCCCACC
TCGGGGGTCTTTCATTTGGAGGTTCCACCGAGATTTGGAGACCCCTGCCT
AGGGACCACCGACCCCCCGCCGGGAGGTAAGCTGGCCAGCGGTCGTTTC
GTGTCTGTCTCTGTCTTTGTGCGTGTTTGTGCCGGCATCTAATGTTTGCG
CCTGCGTCTGTACTAGTTAGCTAACTAGCTCTGTATCGGCGGACCCGTG
GTGGAACTGACGAGTTCTGAACACCCGGCCGCAACCCTGGGAGACGTCCC
AGGGACTTTGGGGGCCGTTTTTGTGGCCCGACCTGAGGAAGGGAGTCGAT
GTGGAATCCGACCCCGTCAGGATATGTGGTTCTGGTAGGAGACGAGAACC
TAAAACAGTTCCCGCCTCCGTCTGAATTTTTGCTTTCGGTTTGGAACCGA
AGCCGCGCGTCTTGTCTGCTGCAGCGCTGCAGCATCGTTCTGTGTTGTCT
CTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATC
GCTCACAACCAGTCGGTAGATGTCAAGAAGAGACGTTGGGTTACCTTCTG
CTCTGCAGAATGGCCAACCTTTAACGTCGGATGGCCGCGAGACGGCACCT
```

-continued

```
TTAACCGAGACCTCATCACCCAGGTTAAGATCAAGGTCTTTTCACCTGGC
CCGCATGGACACCCAGACCAGGTCCCCTACATCGTGACCTGGGAAGCCTT
GGCTTTTGACCCCCCTCCCTGGGTCAAGCCCTTTGTACACCCTAAGCCTC
CGCCTCCTCTTCCTCCATCCGCCCCGTCTCTCCCCCTTGAACCTCCTCGT
TCGACCCCGCCTCGATCCTCCCTTTATCCAGCCCTCACTCCTTCTCTAGG
CGCCGGAATTAGAtccataacttcgtataggatacCTTATACGAAGTTAT
ctcaggtaccGCCACCATGGTGGAGTACAAGCCCACGGTGCGCCTCGCCA
CCCGCGACGACGTCCCCAGGGCCGTACGCACCCTCGCCGCCGCGTTCGCC
GACTACCCCGCCACGCGCCACACCGTCGATCCGGACCGCCACATCGAGCG
GGTCACCGAGCTGCAAGAACTCTTCCTCACGCGCGTCGGGCTCGACATCG
GCAAGGTGTGGGTCGCGGACGACGGCGCCGCGGTGGCGGTCTGGACCACG
CCGGAGAGCGTCGAAGCGGGGGCGGTGTTCGCCGAGATCGGCCCGCGCAT
GGCCGAGTTGAGCGGTTCCCGGCTGGCCGCGCAGCAACAGATGGAAGGCC
TCCTGGCGCCGCACCGGCCCAAGGAGCCCGCGTGGTTCCTGGCCACCGTC
GGCGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTC
ACCGCCGACGTCGAGGTGCCCGAAGGACCGCGCACCTGGTGCATGACCCG
CAAGCCCGGTGCCAAACAGAAAATTGTGGCACCAGTGAAACAGACTTTGA
ATTTTGACCTTCTCAAGTTGGCGGGAGACGTCGAGTCCAACCCTGGGCCC
GGCCCGGTCGCCACCATGGTGAGCAAGGGCGAGGAGCTGTTCACCGGGGT
GGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTG
AAGTTCATCTGCACCACCGGCAAGCTGCCCGTGCCCTGGCCCACCCTCGT
GACCACCCTGACCTACGGCGTGCAGTGCTTCAGCCGCTACCCCGACCACA
TGAAGCAGCACGACTTCTTCAAGTCCGCCATGCCCGAAGGCTACGTCCAG
GAGCGCACCATCTTCTTCAAGGACGACGGCAACTACAAGACCCGCGCCGA
GGTGAAGTTCGAGGGCGACACCCTGGTGAACCGCATCGAGCTGAAGGGCA
TCGACTTCAAGGAGGACGGCAACATCCTGGGGCACAAGCTGGAGTACAAC
TACAACAGCCACAACGTCTATATCATGGCCGACAAGCAGAAGAACGGCAT
CAAGGTGAACTTCAAGATCCGCCACAACATCGAGGACGGCAGCGTGCAGC
TCGCCGACCACTACCAGCAGAACACCCCCATCGGCGACGGCCCCGTGCTG
CTGCCCGACAACCACTACCTGAGCACCCAGTCCGCCCTGAGCAAAGACCC
CAACGAGAAGCGCGATCACATGGTCCTGCTGGAGTTCGTGACCGCCGCCG
GGATCACTCTCGGCATGGACGAGCTGTACAAGTAGtctagaagccataac
ttcgtatagtacacattatacgaaGTTTATGCATACCTGGAGGAAAAAA
AAAGGGGAGAGTCAGGGGTTTAAACGCATTAGTCTTCCAATTGAAAAAAG
TGATTTAATTTATACCATTTTAATTCAGCTTTGTAAAAATGTATCAAAGA
GATAGCAAGGTATTCAGTTTTAGTAAACAAGATAATTGCTCCTAAAGTAG
CCCCTTGAATTCCGAGGCAGTAGGCAAGGTGAAACTATACTTTTACAAATA
```

```
CATCTGTGGCTTCACTATTTGTAAAGTATAGTTTCACCGCGCTCACTGTC
AACAGCAATATACCTTCTCGAGCCTTCTGTTGGGTTAACCTGAAGAAGTA
ATCCCAGCAAGTGTTTCCAAGATGTGCAGGCAACGATTCTGTAAAGTACT
GAAGCCTCATTCAAACATAGTATATGTGCTGCCGAAGCGAGCACTTAACA
AGGCTTGCATTTAAACGCATTAGTCTTCCAATTGAAAAAAGTGATTTAAT
TTATACCATTTTAATTCAGCTTTGTAAAAATGTATCAAAGAGATAGCAAG
GTATTCAGTTTTAGTAAACAAGATAATTGCTCCTAAAGTAGCCCCTTGAA
TTCCGAGGCAGTAGGCATCCACTACAAGTACATGTGTAATACATCTGTGG
CTTCACTATTACACATGTACTTGTAGTGGGCGCTCACTGTCAACAGCAAT
ATACCTTCTCGAGCCTTCTGTTGGGTTAACCTGAAGAAGTAATCCCAGCA
AGTGTTTCCAAGATGTGCAGGCAACGATTCTGTAAAGTACTGAAGCCTCA
TTCAAACATAGTATATGTGCTGCCGAAGCGAGCACTTAACAAGGCTTGCG
GCCGCCCACTCACCTGCAATTGGGCCGCTCACAGAGAAATGAAGTCCAGG
GCTTGGAGGAGGGAGAGGGAAAGCAGCAGCAGCAGCATCCAGGATGTGTT
CTGAACCAGCAGGCTTATGCCGCCACACTTGACCAGTTTGTCTCTATACA
CACTGATACTTTTATTGGAGCTCATGGGATTCGCGCCCGAGACTCGAAGC
TCACAAAAGTAGTCGCCCTCATCCTTGGTGGTGAAGTTGGCTAGGGTAAG
GACCTTGATATAGGGCTGGTTGGAGAGGGTGACGCGGGAGCGGTACGTGT
GCTCGGGTATCCCGAGGGTGCCTGAGAGCACGTGCTTCCTCTTCTCTCGG
GTCAGGCTGAACTCATGCTGGATGGAGTTATCCTTGGTGTTATTCTCATG
GCGGCAGTCCAGGCGAAGGTTTTGGTTCACCAGGCAGGCTGTCAGGCTGG
TCACCTTCTGCCCTCGGGACACCTGCAAGACTGAGAGCAGGAGAGCGACG
CTGATGGCTGGGTTCATggtggcgaccggtataacttcgtataaggtatc
ctatacgaagttatccattcaggctgtgctagcatcaatggcatggcaca
aagcttagccataacttcgtataatgtgtactatacgaagttatcccggg
ttAAACGACCTGCAGCCAAGCTTATCGATAAAATAAAAGATTTTATTTAG
TCTCCAGAAAAAGGGGGGAATGAAAGACCCCACCTGTAGGTTTGGCAAGC
TAGCTTAAGTAACGCCATTTTGCAAGGCATGGAAAATACATAACTGAGAA
TAGAGAAGTTCAGATCAAGGTTAGGAACAGAGAGACAGCAGAATATGGGC
CAAACAGGATATCTGTGGTAAGCAGTTCCTGCCCCGGCTCAGGGCCAAGA
ACAGATGGTCCCCAGATGCGGTCCCGCCCTCAGCAGTTTCTAGAGAACCA
TCAGATGTTTCCAGGGTGCCCCAAGGACCTGAAAATGACCCTGTGCCTTA
TTTGAACTAACCAATCAGTTCGCTTCTCGCTTCTGTTCGCGCGCTTCTGC
TCCCCGAGCTCAATAAAAGAGCCCACAACCCCTCACTCGGCGCGCCAGTC
CTCCGATAGACTGCGTCGCCCGGGTACCCGTGTATCCAATAAACCCTCTT
GCAGTTGCATCCGACTTGTGGTCTCGCTGTTCCTTGGGAGGGTCTCCTCT
GAGTGATTGACTACCCGTCAGCGGGGGTCTTTCATGGGTAACAGTTTCTT
GAAGTTGGAGAACAACATTCTGAGGGTAGGAGTCGAATATTAAGTAATCC
TGACTCAATTAGCCACTGTTTTGAATCCACATACTCCAATACTCCTGAAA
TAGTTCATTATGGACAGCGCAGAAGAGCTGGGGAGAATTAATTCGTAATC
ATGGTCATAGCTGTTTCCTGTGTGAAATTGTTATCCGCTCACAATTCCAC
ACAACATACGAGCCGGAAGCATAAAGTGTAAAGCCTGGGGTGCCTAATGA
GTGAGCTAACTCACATTAATTGCGTTGCGCTCACTGCCCGCTTTCCAGTC
GGGAAACCTGTCGTGCCAGCTGCATTAATGAATCGGCCAACGCGCGGGGA
GAGGCGGTTTGCGTATTGGGCGCTCTTCCGCTTCCTCGCTCACTGACTCG
CTGCGCTCGGTCGTTCGGCTGCGGCGAGCGGTATCAGCTCACTCAAAGGC
GGTAATACGGTTATCCACAGAATCAGGGGATAACGCAGGAAAGAACATGT
GAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACG
CTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGC
TGGGCTGTGTGCACGAACCCCCCGTTCAGCCCGACCGCTGCGCCTTATCC
GGTAACTATCGTCTTGAGTCCAACCCGGTAAGCACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACG
TTAAGGGATTTTGGTCATGAGATTATCAAAAAGGATCTTCACCTAGATCC
TTTTAAATTAAAAATGAAGTTTTAAATCAATCTAAAGTATATATGAGTAA
ACTTGGTCTGACAGTTACCAATGCTTAATCAGTGAGGCACCTATCTCAGC
GATCTGTCTATTTCGTTCATCCATAGTTGCCTGACTCCCCGTCGTGTAGA
TAACTACGATACGGGAGGGCTTACCATCTGGCCCCAGTGCTGCAATGATA
CCGCGAGACCCACGCTCACCGGCTCCAGATTTATCAGCAATAAACCAGCC
AGCCGGAAGGGCCGAGCGCAGAAGTGGTCCTGCAACTTTATCCGCCTCCA
TCCAGTCTATTAATTGTTGCCGGGAAGCTAGAGTAAGTAGTTCGCCAGTT
AATAGTTTGCGCAACGTTGTTGCCATTGCTACAGGCATCGTGGTGTCACG
CTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGT
TATGGCAGCACTGCATAATTCTCTTACTGTCATGCCATCCGTAAGATGCT
TTTCTGTGACTGGTGAGTACTCAACCAAGTCATTCTGAGAATAGTGTATG
CGGCGACCGAGTTGCTCTTGCCCGGCGTCAATACGGGATAATACCGCGCC
ACATAGCAGAACTTTAAAAGTGCTCATCATTGGAAAACGTTCTTCGGGGC
GAAAACTCTCAAGGATCTTACCGCTGTTGAGATCCAGTTCGATGTAACCC
ACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGG
CGACACGGAAATGTTGAATACTCATACTCTTCCTTTTTCAATATTATTGA
```

```
-continued
AGCATTTATCAGGGTTATTGTCTCATGAGCGGATACATATTTGAATGTAT

TTAGAAAAATAAACAAATAGGGGTTCCGCGCACATTTCCCCGAAAAGTGC

CACCTGACGTCTAAGAAACCATTATTATCATGACATTAACCTATAAAAAT

AGGCGTATCACGAGGCCCTTTCGTCTCGCGCGTTTCGGTGATGACGGTGA

AAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGC

GGGTGTCGGGGCTGGCTTAACTATGCGGCATCAGAGCAGATTGTACTGAG

AGTGCACCATATGCGGTGTGAAATACCGCACAGATGCGTAAGGAGAAAAT

ACCGCATCAGGCGCCATTCGCCATTCAGGCTGCGCAACTGTTGGGAAGGG

CGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGAC

GTTGTAAAACGACGGCGCAAGGAAGCAGCCCAGTAGTAGGTTGAGGCCGT

TGAGCACCGCCGCCGCAAGGAATGGTGCATGCAAGGAGATGGCGCCCAAC

AGTCCCCCGGCCACGGGGCCTGCCACCATACCCACGCCGAAACAAGCGCT

CATGAGCCCGAAGTGGCGAGCCCGATCTTCCCCATCGGTGATGTCGGCGA

TATAGGCGCCAGCAACCGCACCTGTGGCGCCGGTGATGCCGGCCACGATG

CGTCCGGCGTAGAGGCGATTAGTCCAATTTGTTAAAGACAGGATATCAGT

GGTCCAGGCTCTAGTTTTGACTCAACAATATCACCAGCTGAAGCCTATAG

AGTACGAGCCATAGATAAAATAAAAGATTTTATTTAGTCTCCAGAAAAAG

GGGGGAA.
```

The Tie2-Cre construct was as described in Kisanuki, Y.Y., et al. (2001) Dev Biol 230, 230-42. The CD19-Cre construct was as described in Rickert, R. C., Roes, J. & Rajewsky, K. (1997) Nucleic Acids Res 25, 1317-8. The Mox-Cre construct was as described in Tallquist M D; Soriano P. 2000. Genesis 26(2):113-5.

Reagents

Anti p53 antibody was provided by Andrea Ventura. Doxorubicin and doxycycline were obtained from Sigma.

Verification of Reporter Expression:

Reverse transcriptase-PCR assays were conducted, probing for efficient intron splicing from the FLIP vector and compared to PCR of genomic DNA. Primers were as follows:

```
Reverse primer (in vector):
                                       (SEQ ID NO: 9)
CCA GGA TTT ATA CAA GGA GGA GAA AAT GAA AGC Forward primer (in GFP):
                                      (SEQ ID NO: 10)
CTG AGC AAA GAC CCC AAC GAG AAG C
```

The PCR amplified only the transcript derived from FLIP vectors reversed by Cre activity.

Lewis Lung carcinoma cells (LL2) were transduced with pFLIP and probed for Thy 1.1 expression by FACS analysis following puromycin selection. Selected cells were also probed for GFP expression, prior to and following infection with MCSV-Cre.

Infectious viral particles were produced through standard lab methods. 293FT cells were transiently transfected with retroviral gag/pol and VSVg envelopes plasmids along with the viral vector. The supernatants were harvested at 48 hours and used to infect target cells in the presence of 4 ug/ml polybrene.

Northern Blot Analysis:

HEK293 cells were infected with retrovirus expressing an miR30 targeting firefly luciferase (FF), PTEN, p53, two tandem miR30 constructs targeting p53 and PTEN, or FLIP vector (Lanes 5-7). The FLIP vector contained the miR30 targeting PTEN or p53 in the antisense that was reversed by Cre expression. The intron pair contained the miR30 targeting PTEN or p53 flanked by synthetic consensus splice donor and splice acceptor sites. The blots were hybridized with a probe specific for the guide strand (sense probe) that mediates RNAi, or the antisense probe that is non-functional. The functional guide strand was only produced when the vector was flipped to the sense orientation.

HEK293 cells infected with FLIP retrovirus expressing miR-181a or miR-15b in the antisense that is reversed to the sense orientation by Cre expression were similarly evaluated. The intron vectors contained the miRNAs between consensus synthetic splice sites. The blots were hybridized with probes specific for miR181a or miR15b. The miRNA was only processed to the mature form when expressed in the sense orientation.

Probes utilized were as follows:

```
p53 sense probe (hybridizes to guide strand)
                                      (SEQ ID NO: 15)
5'-CCA CTA CAA GTA CAT GTG TA-3'.

p53 anti-sense probe
                                      (SEQ ID NO: 16)
5'-TAC ACA TGT ACT TGT AGT GG-3'.

PTEN sense probe
                                      (SEQ ID NO: 17)
5'-GGT GAA ACT ATA CTT TAC AA-3'.

PTEN anti-sense probe
                                      (SEQ ID NO: 18)
5'-TTG TAA AGT ATA GTT TCA CC-3'.

Mir-181a probe
                                      (SEQ ID NO: 19)
5'-ACT CAC CGA CAG CGT TGA ATG TT-3'.

Mir-15b probe
                                      (SEQ ID NO: 20)
5'-TGT AAA CCA TGA TGT GCT GCT A-3'.
```

In Vitro Knockdown Studies

The DC2.4 cell line was transduced with the pLB2 construct expressing a miR30 targeting alpha-4 integrin expression (SEQ ID NO: 2), with and without MCSV-Cre. Integrin expression was assessed by FACS analysis probing with anti-integrin alpha-4 conjugated to PE (Becton-Dickinson).

In Vivo Knockdown Studies

Murine embroyonic stem cells that express Cre from the VEGF-R2 (Flk1) locus, which turns on Cre expression about embryonic day 8 were infected with the pLB2 constructs, and selected with puromycin. Using tetraploid complementation, FLIP-infected ES cells were injected and embryos were generated, which were derived exclusively from pLB2-expressing ES cells.

Adult pLB2-FLIP males were also subsequently crossed with Mox-Cre females and embryos were removed at stage e9.5. Mox-Cre expressed very early in embryo (e2 or e3).

Bone marrow stem were purified by lineage depletion of marker positive cells and cultured for 8 days in STIF medium and angiopoietin-like-2 (Zhang et al.) On days 1 and 2, bone marrow stem cells were infected with FLIP retroviral supernatants and cultured for 4 days in the presence of puromycin.

Recipient mice were lethally irradiated and reconstituted with infected bone marrow stem cells and additional supporting cells derived from the spleen.

Bone marrow stem cells were also obtained from Cre-ERT2 mice (see Hayashi S, and McMahon A P. Dev Biol. 2002 Apr. 15; 244(2):305-18). Eight weeks after reconstitution, mice were treated with 2 mg/mouse tamoxifen to induce recombination of the vector. Five days later spleens were minced and sorted by MACS for Thy1.1+ cells. Purified cells were cultured for 4 hours in 5 ug/ml doxorubicin and lysed for SDS-PAGE.

Bone marrow stem cells were obtained from CD19-Cre mice, as well. After three months, mice appeared lethargic and were sacrificed, spleens obtained and analyzed (see Zhang C C, et al. Nat. Med. 2006 February; 12(2):240-5).

Example 1

Construction of Stable, Cre-lox Based Knockdown Constructs

A pFLIP cassette was constructed as schematically depicted in FIG. 1A. The construct may be expressed by a constitutive, tissue-specific, or inducible promoter. The mRNA expressed puromycin resistance and the surface marker Thy1.1 or GFP. The puromycin-Thy1.1, or -GFP construct, respectively, was translated as a fusion protein but generated two distinct polypeptides by virtue of the 2A peptide at the C-terminus of the puromycin resistance or GFP cassette, which resulted in the translation of two distinct polypeptide species from a single cistron.

As depicted in FIG. 1A, the green fluorescent protein (GFP) and a miR30 microRNA-based, RNAi construct were present in the anti-sense orientation in the 3' untranslated region of the mRNA. Upon addition of Cre recombinase, the puro-Thy1.1 cassette was deleted and the GFP-microRNA construct was reversed to the sense orientation, allowing expression of GFP and RNAi.

The vector expressed two markers, a drug selection and a surface marker. When Cre was introduced, the markers were deleted and expression of GFP and RNAi was induced. GFP and the RNAi were in antisense orientation until Cre-recombinase was active, at which point there was a "flip" to the sense orientation.

The vector containing the pFLIP cassette was referred to as pLB. The vector comprised a CMV promoter driving the RNA genome, a packaging signal (Psi), central polypurine tract (cPPT), antirepressor (Element #40) and scaffold attached region (SAR), an internal U6 and CMV promoter driving the FLIP cassette, with the GFP-miR30 in antisense orientation. The 3'LTR comprised a deletion of U3, and HIV U5 polyadenylation signal. For example, the pLB vector expressing a miR30 targeting firefly luciferase (SEQ ID NO: 7).

In one embodiment of this invention, a modified pLB vector was constructed, resulting in greater expression, the vector being schematically depicted in FIG. 1B, and referred to herein as pLB2.

In this embodiment of the modified vector (pLB2), the promoter driving the RNA genome was derived from RSV, as opposed to the former CMV. The packaging signal (Psi), central polypurine tract (cPPT), antirepressor (Element #40) and scaffold attached region (SAR) were unchanged.

The internal CMV promoter was replaced by Ubiquitin-C. The U6 promoter was removed and replaced with the FLIP cassette. The FLIP cassette maintained GFP-miR30 in the antisense orientation until reversed by Cre activity.

The 3'LTR was modified, as well: Deletions of the U3 resulted in self-inactivating vectors (SIN). The U3 in pLB has ~200 nucleotide deletion. The U3 in pLB2 has a 420 nucleotide deletion. The remaining nucleotides in U3 were the minimum required for integration (~25 nt) and another 20 nt that significantly improved polyadenylation of the integrated viral transcript. The HIV U5 was replaced by a Bovine Growth Hormone Polyadenylation signal.

Figure 1C:
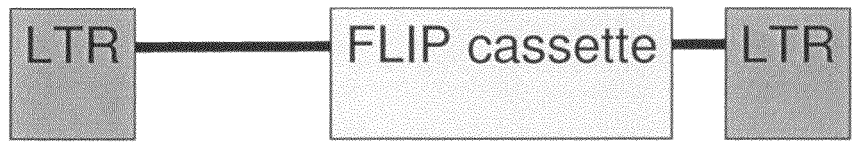
Figure 1C:

FIG. 1C schematically highlights differences between the MSCV and pLB2 vectors.

Figure 2A:
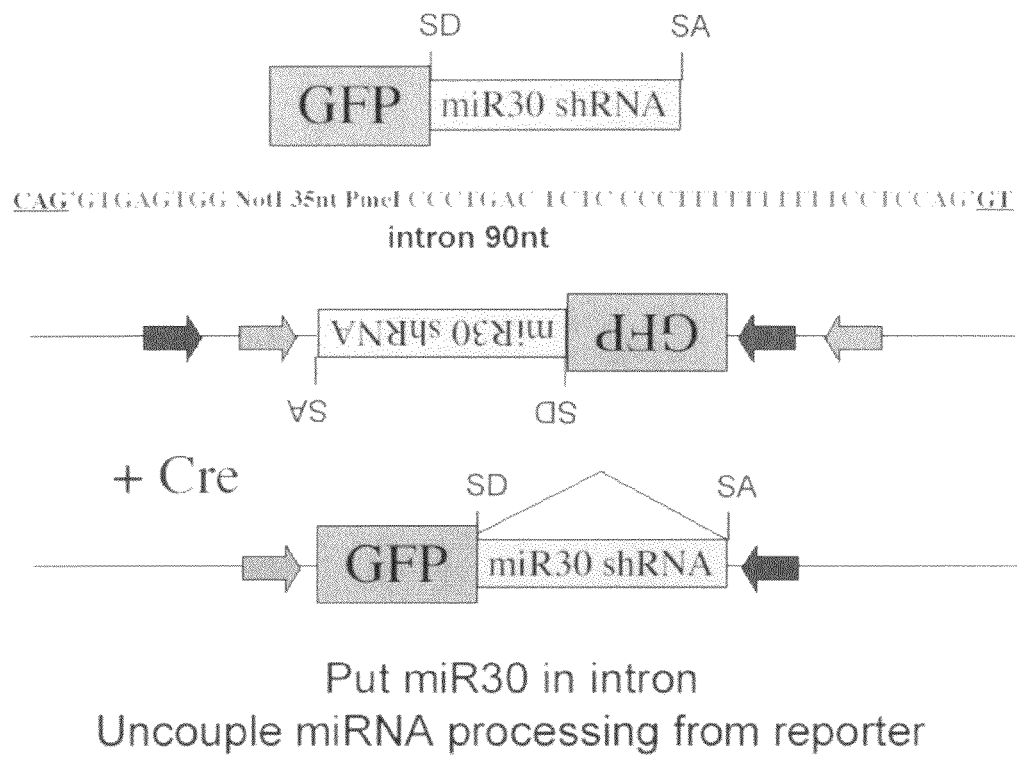
FIG. 2A depicts placement of the miR30 in an artificial intron by flanking the miR30 with consensus splice donor and splice acceptor sequences (in red) (SEQ ID NO: 28).
Figure 2B:
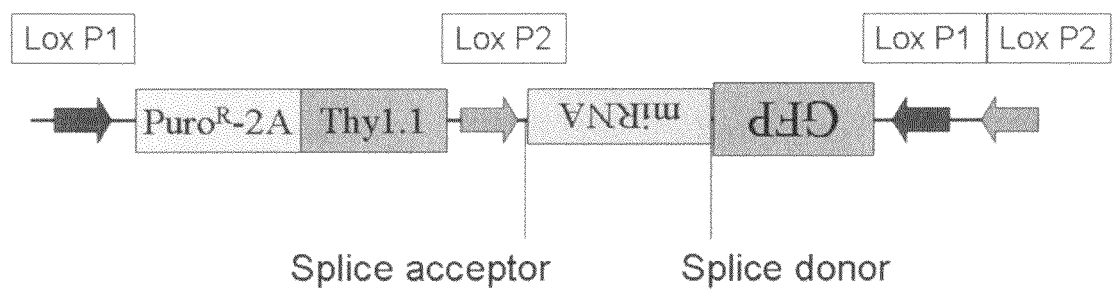
FIG. 2B is a schematic depiction of the FLIP vector comprising an miRNA in an intron.

In addition, the FLIP cassette was modified as well, in order to include a splice donor and splice acceptor flanking the miR30, such that the miR30 is contained within an artificial intron (FIG. 2A). By placing the miR30 in an intron, miRNA processing was uncoupled from reporter expression, such that the miR30 was spliced out of the transcript. FIG. 2B schematically depicts the FLIP vector comprising the miRNA in an intron.

The GFP-intron-miR30 is maintained in the antisense until reversed by Cre action on flanking loxP sites (purple and orange arrows). The intron cannot be maintained in the sense orientation of retro/lentiviruses, as the genome is RNA.

The intron follows the GFP (or other marker gene) within 30 nucleotides of the STOP codon so as to avoid nonsense-mediated decay of the transcript.

Example 2 pLB2 Constructs Demonstrate Enhanced Expression Following Cre-Mediated Recombination In order to determine whether efficient intron splicing from the FLIP vector occurred, cellular mRNA was assayed by reverse transcription PCR, and expression was compared to PCR of genomic DNA. PCR amplification of only the transcript derived from FLIP vectors occurred, which that been reversed by Cre activity (FIG. 3). Whereas constructs without an intron produced similarly sized products, PCR of mRNA derived from the intron-containing sample produced a significantly smaller fragment.

FACS analysis of marker expression was conducted on cells transduced with the pLB2 constructs and compared to pLB construct-mediated expression. FIG. 4 demonstrates that inclusion of the intron enhanced expression of reporter. While all the constructs, when exposed to Cre, and assayed by FACS produced GFP+ cells, inclusion in an intron increased expression.

Similarly, FIG. 5 demonstrates that placement of miR30 in an intron maintains its ability to "knock down" or diminish target gene expression. miR30 targeting integrin alpha-4 (surface protein) and assayed by FACS, following Cre expression (green plot), lowered surface alpha-4 expression by about 6-fold as compared to the FLIP vector without Cre (orange plot).

The miR30 constructs when placed in an intron produced greater expression of the miRNA, and enhanced targeted knockdown in vitro.

Functionally, placing the miR30 in an intron increased reporter expression. Such enhanced expression may be attributable to splicing being coupled to mRNA export from the nucleus to the cytoplasm and/or miR30 processing (cleavage and excision of the hairpin) and translation being mutually exclusive, as miR30 processing results in transcript destruction. By placing miR30 in an intron, the processing is uncoupled from translation.

Example 3

In Vivo pLB2 Expression

Figure 6:
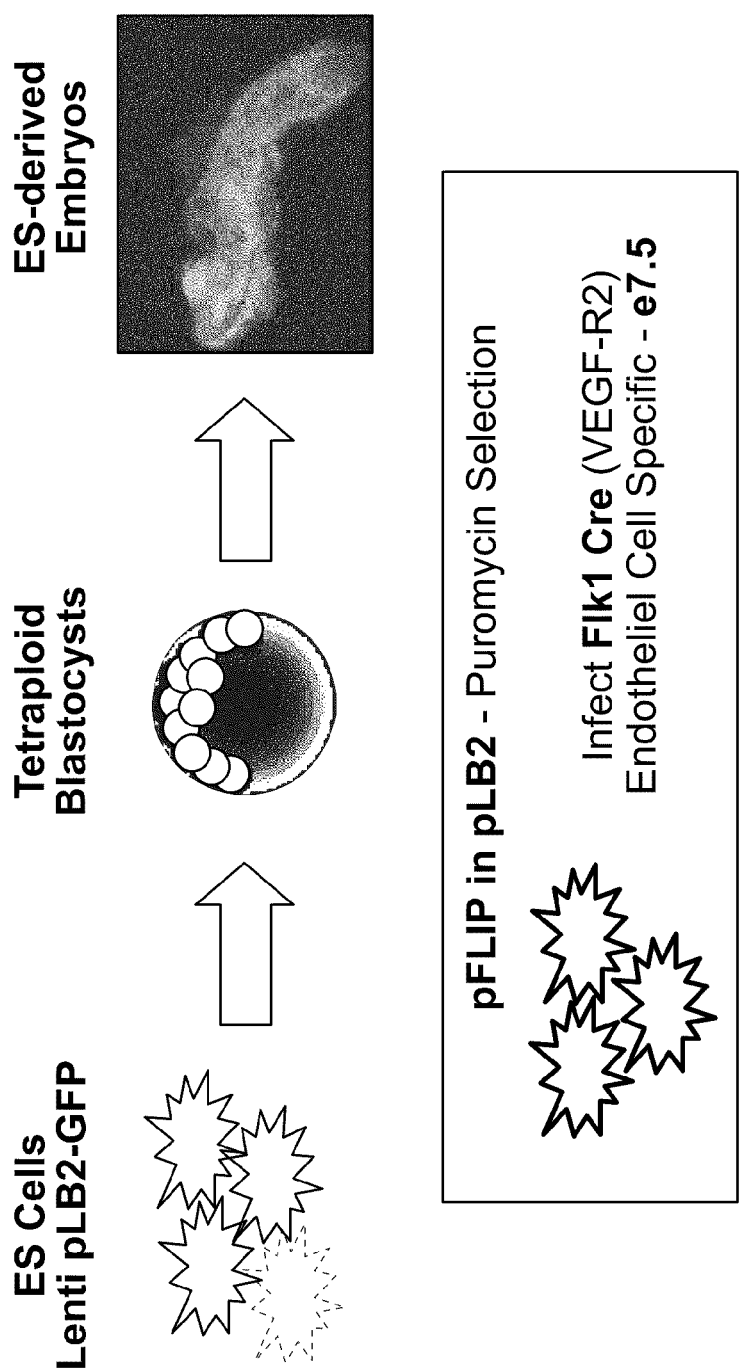
FIG. 6 schematically depicts the generation of mice transgenic for the vectors of this invention, with tissue-specific expression of such constructs. Embryonic Stem cells that express Cre from the VEGF-R2 (Flk1) locus, which turns on Cre expression about embryonic day 8 are infected with a vector of this invention and selected with puromycin. Using tetraploid complementation, the vector-infected ES cells are injected to blastocysts to generate embryos derived exclusively from the transduced ES cells. Fluorescence in the figure is background fluorescence, not Cre regulated.

A scheme for generating mice transgenic for pLB2 expression is presented in FIG. 6. Embryonic stem cells (ESC) that express Cre from the VEGF-R2 (Flk1) locus, which turns on Cre expression at about embryonic day 8 were infected with pLB2 containing the FLIP cassette, and transduced cells were selected with puromycin. Using tetraploid complementation, the pLB2-infected ES cells were injected to blastocysts, and generated embryos derived exclusively from the pLB2-infected ES cells.

Figure 7:
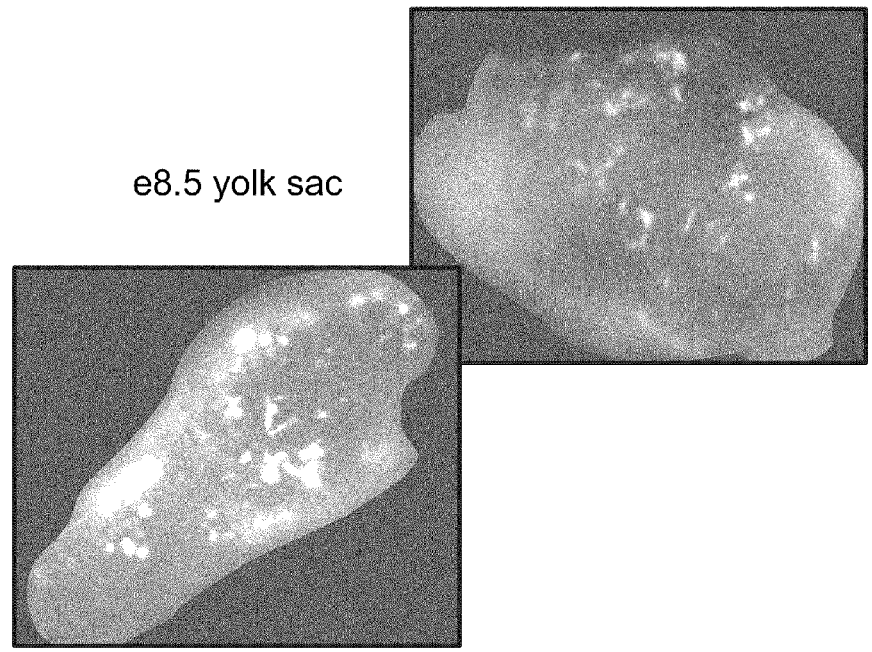
FIG. 7 demonstrates GFP expression in the yolk sacs of e8.5 embryos representing "blood islands", which are endothelial precursor cells and express Flk1 (and hence Cre) about 1 day before embryos were removed.

FIG. 7 demonstrates GFP expression in the yolk sacs of e8.5 embryos thus derived. As evident from the figure, cells that are "blood islands" represent the endothelial precursor cells, the only that express Flk1 (and hence Cre) about 1 day prior to embryo removal, and thus are "stained" by specific GFP expression.

Figure 8:
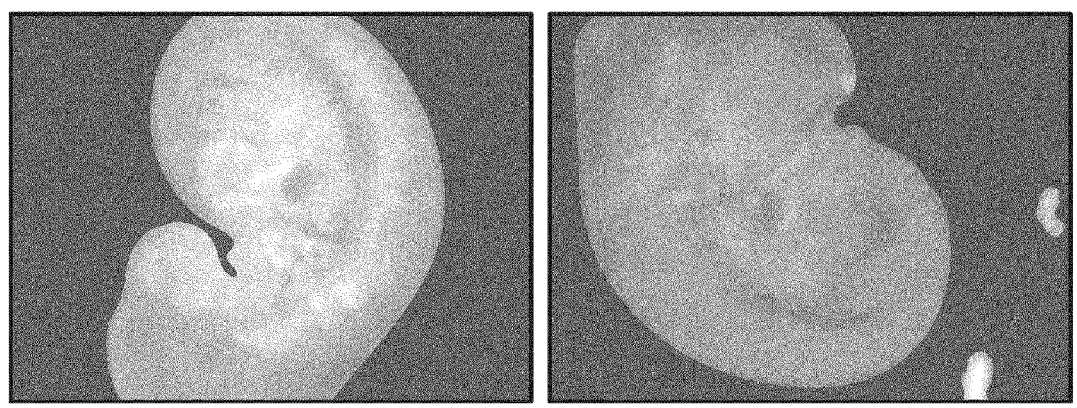
FIG. 8 demonstrates fluorescence in embryos derived at stage e9.5 from adult pLB2-FLIP transgenic males crossed to Mox-Cre females. Mox-Cre is expressed very early in embryos (e2 or e3). Embryos inheriting both the pLB2 vector and Cre exhibited GFP+ throughout (panel 1), as compared to embryos lacking Cre (panel 2).

Similarly, FIG. 8 demonstrates embryos derived at stage e9.5 from adult pLB2-FLIP transgenic males crossed to Mox-Cre females. Mox-Cre is expressed very early in embryos (e2 or e3). Embryos inheriting both the pLB2 vector and Cre exhibited GFP+ throughout, as compared to embryos lacking Cre.

The microRNA in antisense orientation was not processed to generate effective RNAi intermediates, nor did the antisense disrupt marker gene translation or virus production, indicating that the constructs provide for specific, controlled regulation of gene expression.

Example 4

Multiple Knockdowns with pLB2

Figure 9A:
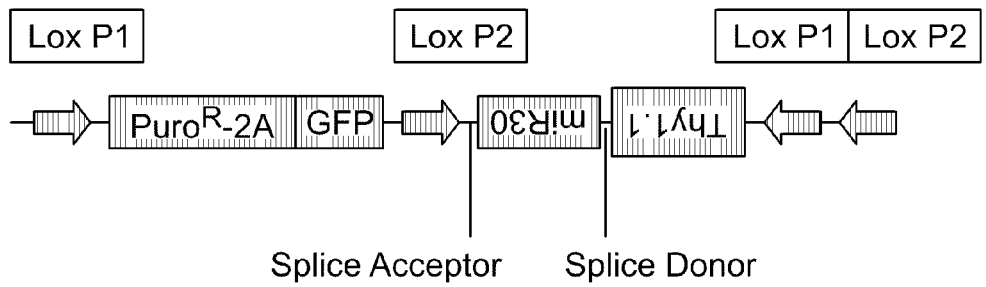
FIG. 9 presents multiple gene knockdowns. 9A schematically depicts how the miR30s can be concatamerized to knockdown more than 1 gene with a single vector.
FIG. 9B demonstrates immunoblot results of targeted knockdown of p53 and PTEN tumor suppressors using the scheme of FIG. 9A.
FIGS. 9C and 9D demonstrate Northern blot results of targeted knockdown of p53 and PTEN tumor suppressors.
FIG. 9E is a schematic depiction of a pFLIP construct in which GFP was replaced with the oncogene c-Myc.
FIG. 9F demonstrates immunoblot results of Cre-regulated expression of a c-Myc transgene. c-Myc expression was combined with targeted knockdown of p53, or PTEN expression, or p53/PTEN expression in an intron, which in turn allowed for the examination of oncogene-tumor suppressor interactions.
Figure 9A:
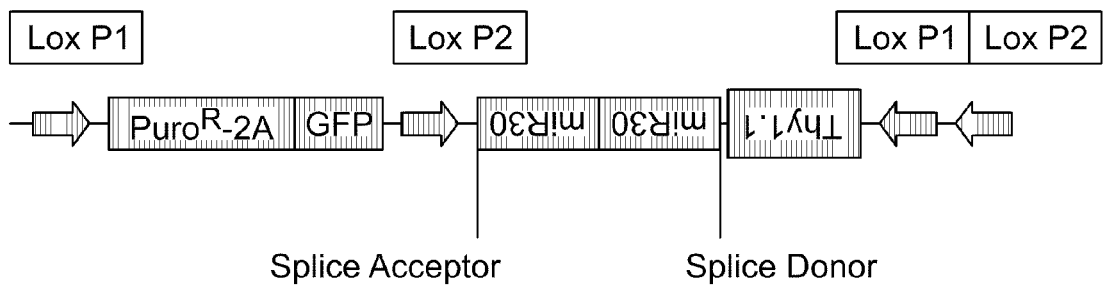
Figure 9A:
Figure 9B:
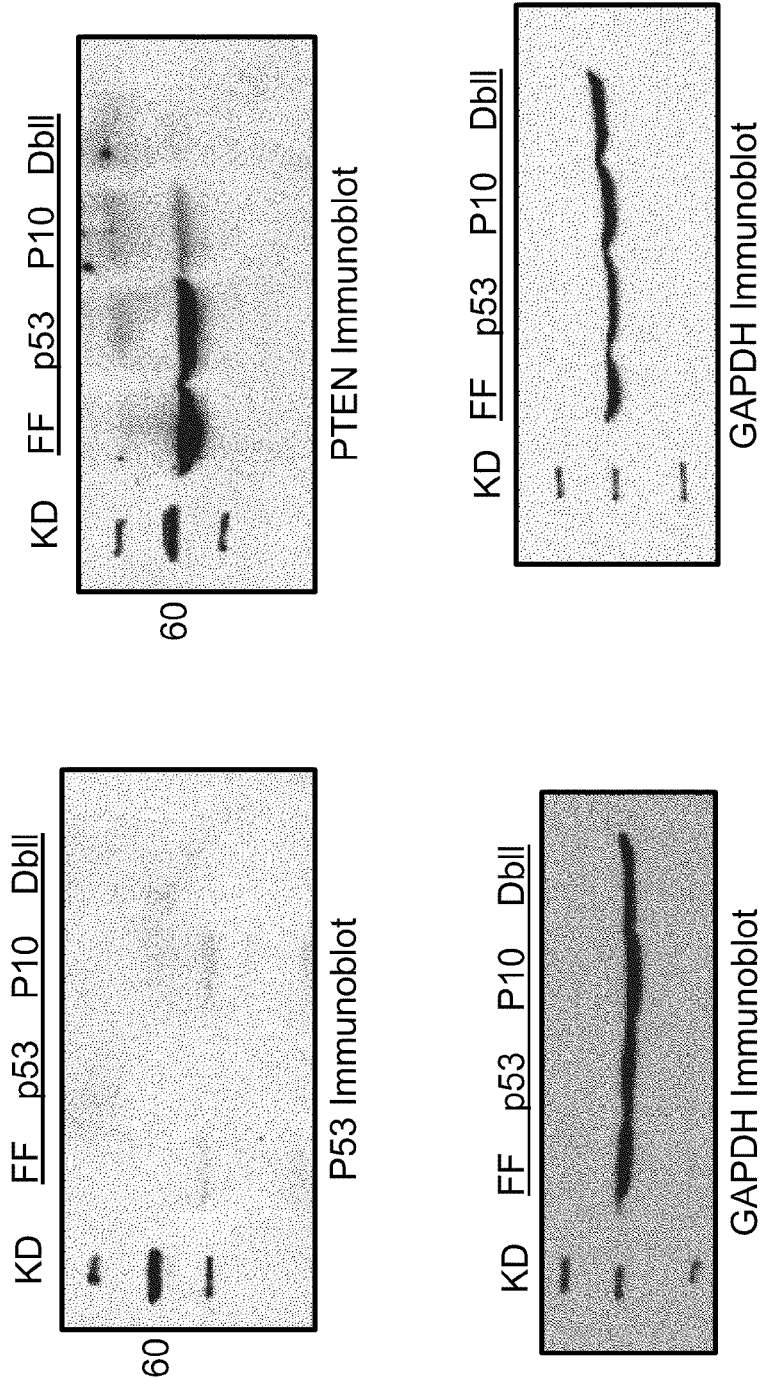

FIG. 9A presents a scheme for multiple gene knockdowns. The miR30s can be concatamerized to knockdown more than 1 gene with a single vector. FIG. 9B demonstrates targeted knockdown of p53 and PTEN tumor suppressors using the scheme of FIG. 9A. In this aspect, cooperative knockdown of related or suspected related gene products can be obtained.

Figure 9C:
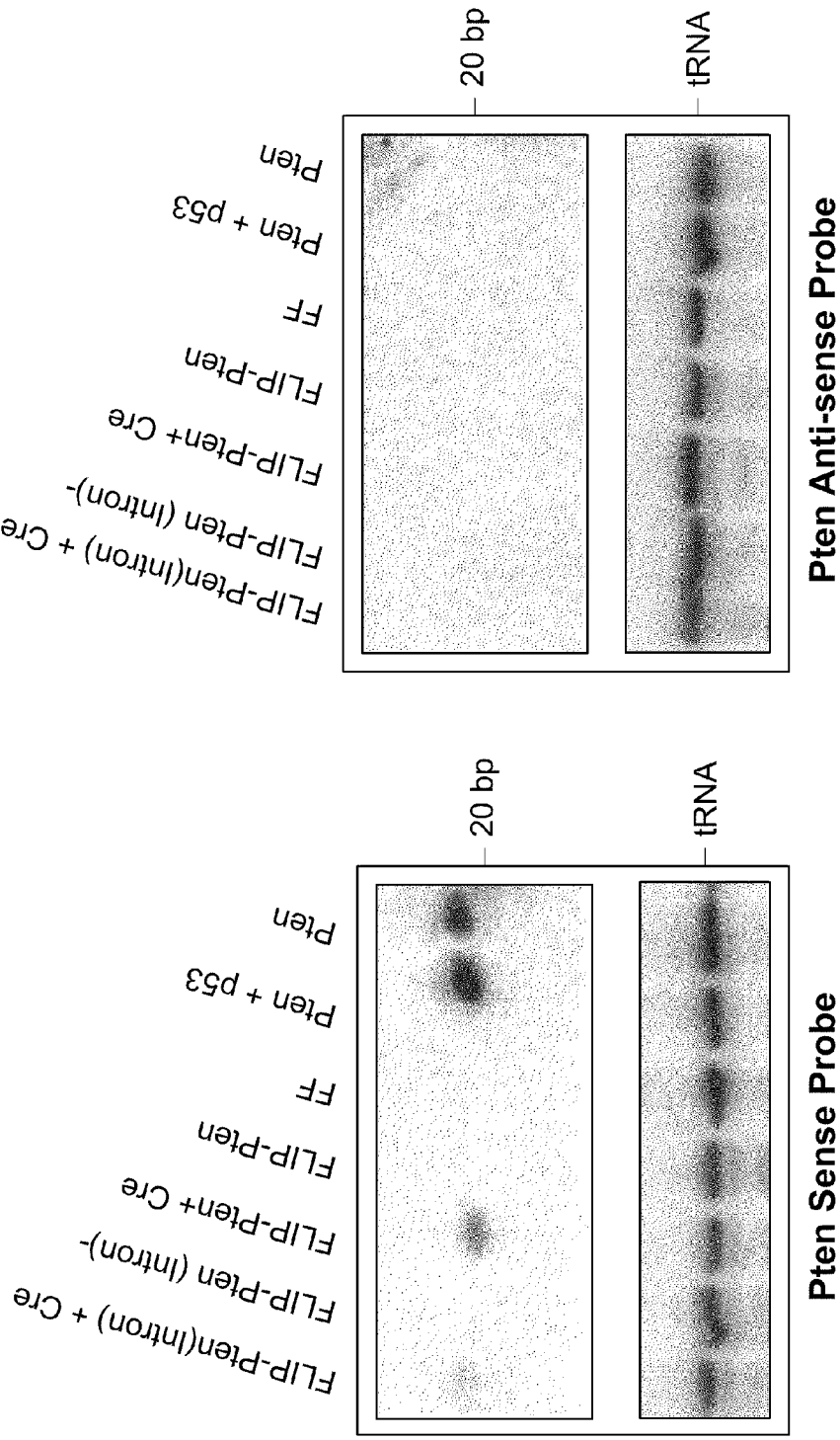
Figure 9D:
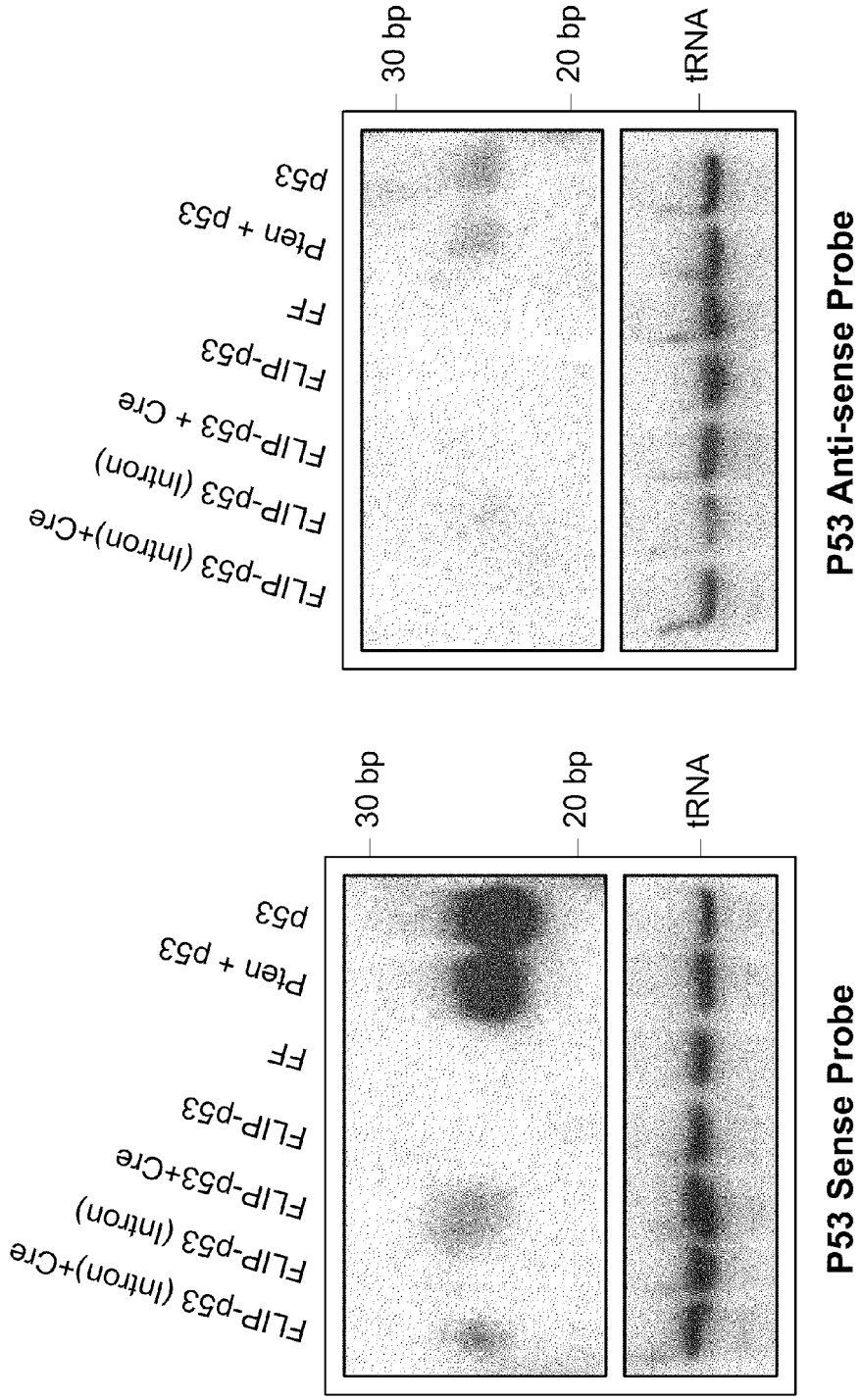

FIGS. 9C and 9D demonstrates targeted knockdown of p53 and PTEN tumor suppressors using the scheme of FIG. 9A respectively, as well, including comparative expression profiles of expression in an intron, or not.

Figure 9E:
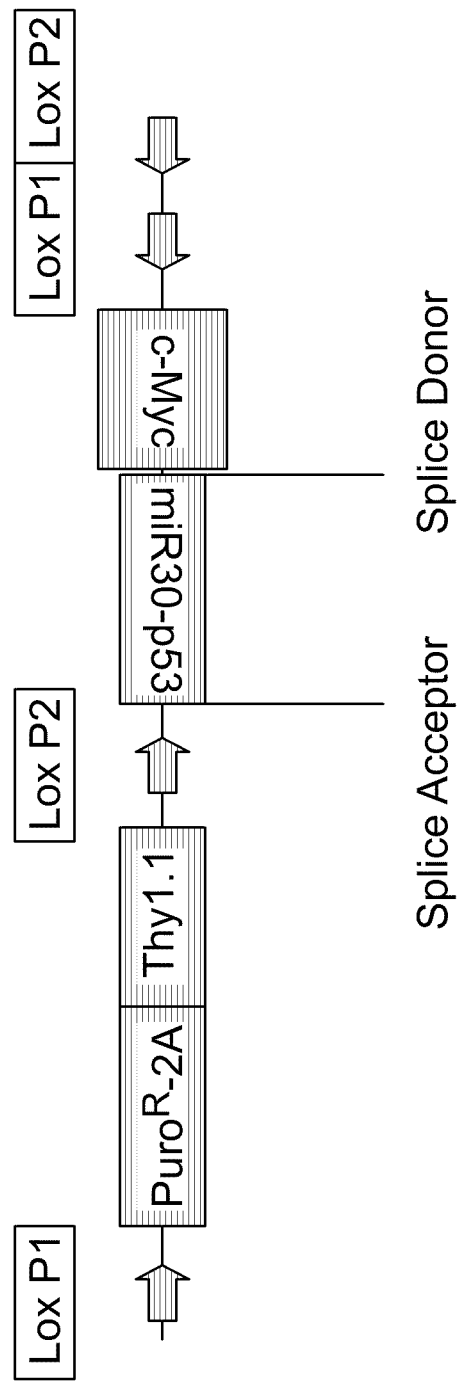
Figure 9F:
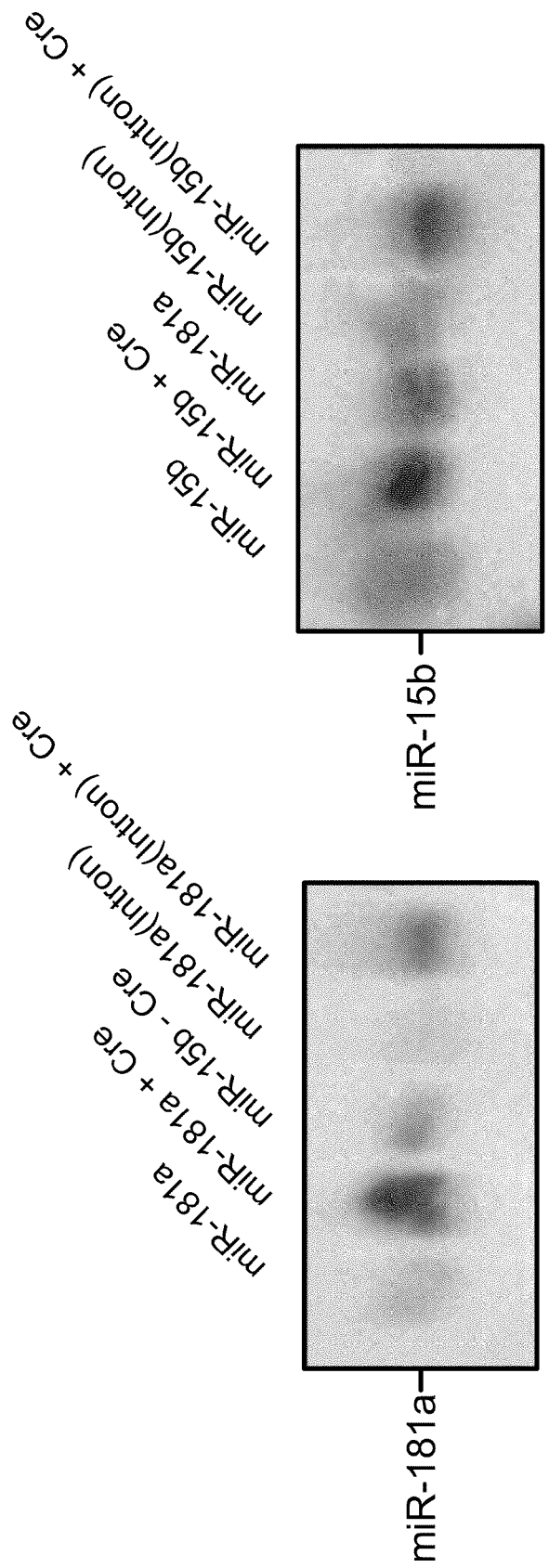

FIGS. 9E and F demonstrates a pFLIP construct in which GFP was replaced with the oncogene c-Myc. The immunoblot showed Cre-regulated expression of a c-Myc transgene incorporating an HA tag. Such a construct provided for the ability to combine c-Myc expression with targeted knockdown of p53, or PTEN expression, or p53/PTEN expression in an intron, which in turn allowed for the examination of oncogene-tumor suppressor interactions. The miRNAs expressed from the construct are endogenous (from the mouse genome), and mediate cellular differentiation by suppressing a set of genes. FIG. 9E further demonstrates, in one embodiment of the invention, the ability to regulate miRNA expression by flipping sense to antisense, a generally applicable method for gene regulation.

These constructs represent embodiments of the invention, whereby cooperative and/or antagonistic relationships can be instituted, evaluated, and/or used for therapy in complex diseases and/or conditions.

Example 5

Regulated Gene Expression in Hematopoietic Cells

In order to determine whether regulated expression could be accomplished in adult animals, bone marrow reconstitutions were conducted, using Cre-ER donor marrow infected with FLIP vector puro2AGFP/Thy1.1+miRNA(s). Three months post-transfer of infected bone marrow, mice were treated with tamoxifen (TMX). Peripheral blood leukocytes were collected 1 week after tamoxifen treatment and analyzed by fluorescent activated cell sorting (FACS) for changes in marker expression.

Figure 10A:
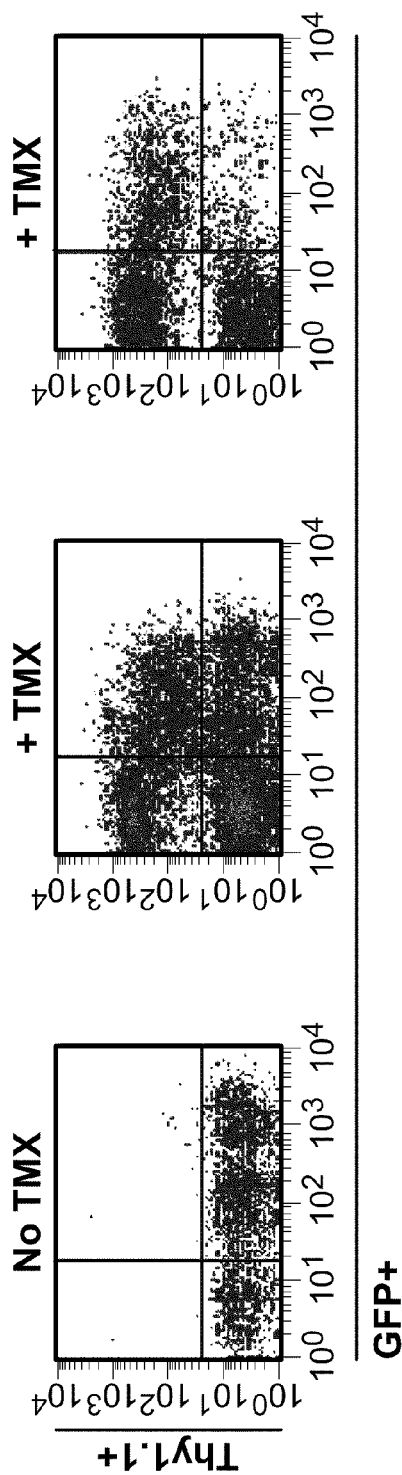
FIG. 10A plots results of a FACS analysis of PBLs detecting changes in surface marker expression following knockdown.
Figure 10B:
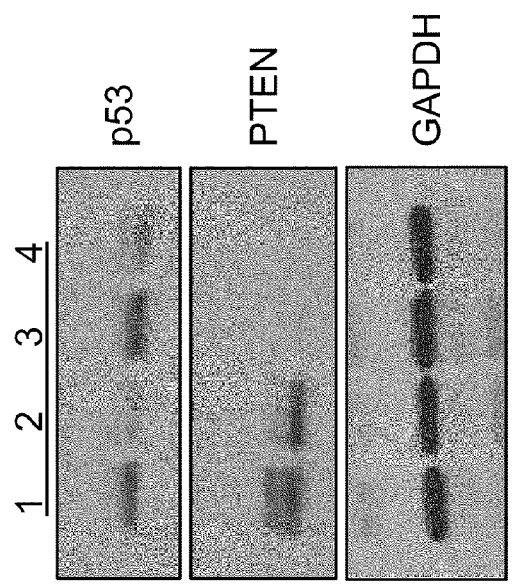
FIG. 10B presents immunoblots of spleen cells from mice reconstituted with Cre-ER donor marrow infected with FLIP vector puro2AGFP/Thy1.1+miRNA(s). Lane 1—FF luc knockdown, 2-p53 KD, 3—PTEN KD, 4-p53/PTEN KD.

Immunoblots of spleens of mice subjected to bone marrow reconstitution with Cre-ER donor marrow infected with FLIP vector puro2AGFP/Thy1.1+miRNA(s) were probed for the expression of the knocked down gene product as a measure of the ability to regulate expression. Three months post-transfer of infected bone marrow, mice were treated with tamoxifen and 1 week later spleens were harvested and sorted for Thy1.1+ cells (FIG. 10B). Each construct effectively resulted in reduced expression of the indicated gene product.

Figure 10C:
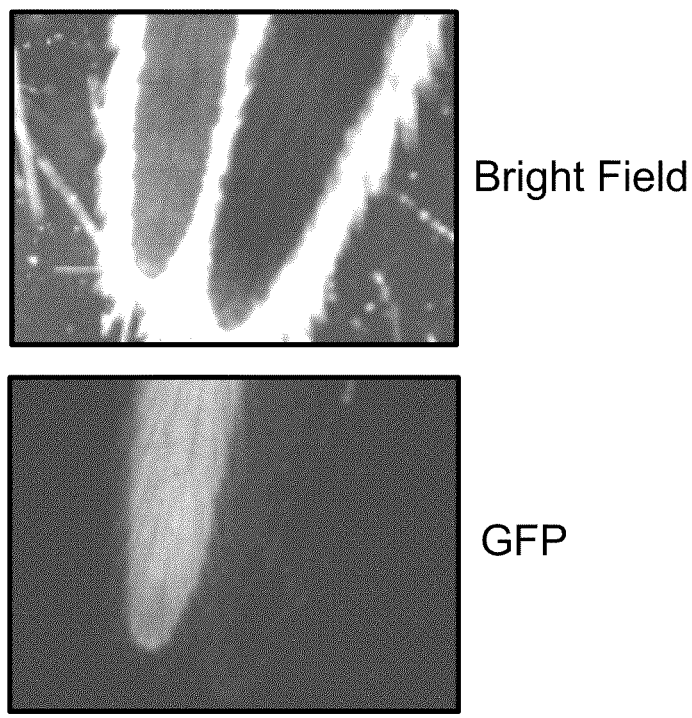
FIG. 10C is a photograph of tails of siblings of Lenti FLIP-p53 transgenic mouse crosses to Mox-Cre (early embryonic Cre).
Figure 10D:
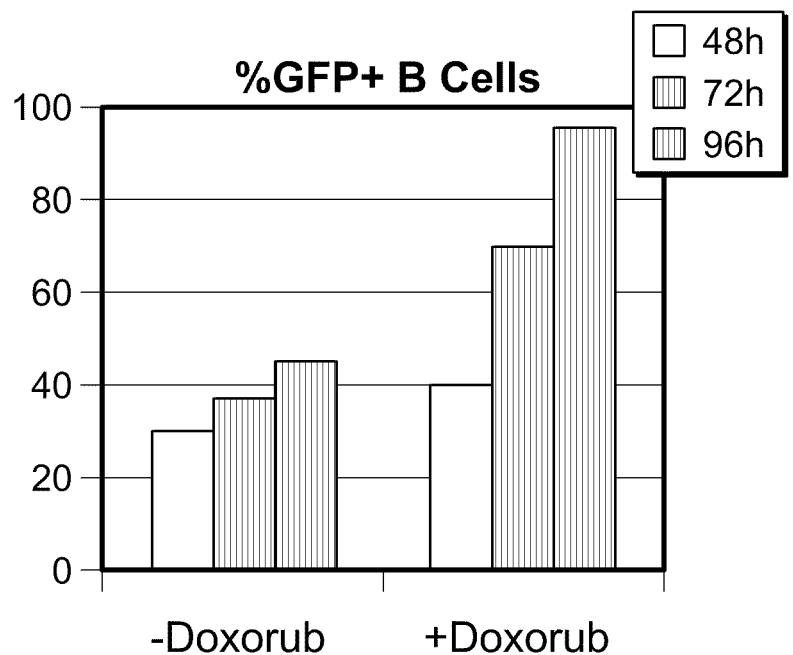
FIG. 10D plots the percent GFP positive B cells in doxorubicin treated versus untreated B cells in progeny of Lenti FLIP-p53 transgenic crossed to Tie2-Cre (hematopietic Cre).

Regulated expression was further evaluated in vivo, as well, via methods similar to those described in Example 4. Lenti FLIP-p53 transgenic mice were crossed to Mox-Cre males (FIG. 10C). Tails of the siblings were visualized, with animals expressing Cre failing to exhibit fluorescence. Similarly (FIG. 10D) lenti FLIP-p53 transgenic mice crossed to Tie2-Cre (hematopoietic Cre). B cells isolated, stimulated and cultured with or without Doxorubicin were evaluated for fluorescence. GFP+ cells expressed the p53 knockdown and exhibited a significant growth advantage in the presence of Doxorubicin.

Example 6

Tissue Specific Oncogene Expression

In order to determine whether tissue specific oncogene expression could be accomplished, mouse bone marrow reconstitutions with CD19-Cre (B cell Cre) donor marrow infected with FLIP vector puro2AGFP/c-Myc+miR-p53 was accomplished. Fourteen weeks post-transfer, spleens and lymph nodes of moribund mice were analyzed by FACS for marker expression (FIG. 11A). Spleen cells were cultured in vitro for 9 days prior to analysis by FACS. Similarly, spleen and lymph nodes were assessed for c-Myc expression by immunoblot (FIG. 11B), with both organs showing good expression of the oncogene.

Immunoblots of spleens of mice subjected to bone marrow reconstitution with Cre-ER It will be appreciated by persons skilled in the art that the present invention is not limited by what has been particularly shown and described herein above and that numerous modifications, all of which fall within the scope of

What is claimed is:

1. A vector comprising
   a. a first pair of loxP sequences inverted in orientation with respect to each other,
   b. a nucleic acid cassette comprising a first nucleic acid encoding
      (i) at least one nucleotide sequence that can form a hairpin structure comprising at least one miRNA agent, and
      (ii) miRNA sequences flanking the at least one nucleotide sequence, wherein the miRNA sequences flanking the at least one nucleotide sequence are derived from endogenous miRNA sequences that flank wild-type hairpin structures, and
   wherein the nucleic acid cassette is positioned in an antisense orientation between the first pair of loxP sequences,
   c. a second pair of loxP sequences distinct from the first pair of the loxP sequences, inverted in orientation with respect to each other, wherein the first pair of loxP sequences and the second pair of loxP sequences are configured such that flipping of the first pair results in excision of the sequences between the second pair.

2. The vector of claim 1, wherein the vector further comprises a second nucleic acid encoding a selectable marker in sense orientation, wherein the second nucleic acid is positioned between the first pair of loxP sequences.

3. The vector of claim of claim 2, wherein the nucleic acid cassette is 3' with regard to the second nucleic acid, and wherein a first loxP sequence of the second pair of loxP sequences is positioned between the second nucleic acid and the nucleic acid cassette, and a second loxP sequence of the second pair is positioned 3' with respect to the first pair of loxP sequences.

4. The vector of claim 3, wherein the nucleic acid cassette further comprises a third nucleic acid encoding a second selectable marker, wherein the third nucleic acid is in antisense orientation and fused in frame to the first nucleic acid sequence.

5. The vector of claim 1, wherein the first pair of loxP sequences comprises wild-type sequence.

6. The vector of claim 1, wherein the second pair of loxP sequences comprises a mutated loxP.

7. The vector of claim 1, wherein the first pair of loxP sequences comprises a loxP 5171 sequence.

8. The vector of claim 1, wherein the second pair of loxP sequences comprises a loxP 2272 sequence.

9. The vector of claim 2, wherein the second nucleic acid encodes two selectable markers fused in-frame with respect to each other.

10. A method of modulating gene expression in a cell, the method comprising:
    introducing into the cell the vector of claim 1; and
    inducing flipping of a first pair of loxP sequences contained within the vector thereby inverting a nucleic acid cassette contained within the vector from the antisense orientation to a sense orientation,
    wherein the inversion of the nucleic acid cassette allows processing of at least one nucleotide sequence encoded by the nucleic acid cassette into at least one functional miRNA agent.

11. The method of claim 10, further comprising:
    inducing flipping of a second pair of loxP sequences contained within the vector.

* * * * *